US012668617B2

(12) United States Patent
Martin

(10) Patent No.: US 12,668,617 B2
(45) Date of Patent: Jun. 30, 2026

(54) RECOMBINANT ADENO-ASSOCIATED VIRUS PRODUCTS AND METHODS FOR TREATING DYSTROGLYCANOPATHIES AND LAMININ-DEFICIENT MUSCULAR DYSTROPHIES

(71) Applicant: RESEARCH INSTITUTE AT NATIONWIDE CHILDREN'S HOSPITAL, Columbus, OH (US)

(72) Inventor: Paul Taylor Martin, Bexley, OH (US)

(73) Assignee: RESEARCH INSTITUTE AT NATIONWIDE CHILDREN'S HOSPITAL, Columbus, OH (US)

( * ) Notice: Subject to any disclaimer, the term of this patent is extended or adjusted under 35 U.S.C. 154(b) by 360 days.

(21) Appl. No.: 17/254,055

(22) PCT Filed: Jun. 18, 2019

(86) PCT No.: PCT/US2019/037769
§ 371 (c)(1),
(2) Date: Dec. 18, 2020

(87) PCT Pub. No.: WO2019/246125
PCT Pub. Date: Dec. 26, 2019

(65) Prior Publication Data
US 2024/0254181 A1     Aug. 1, 2024

Related U.S. Application Data

(60) Provisional application No. 62/686,522, filed on Jun. 18, 2018.

(51) Int. Cl.
| | |
|---|---|
| *C07K 14/485* | (2006.01) |
| *A61K 48/00* | (2006.01) |
| *A61P 21/00* | (2006.01) |
| *C07K 14/47* | (2006.01) |
| *C07K 14/78* | (2006.01) |
| *C12N 15/86* | (2006.01) |

(52) U.S. Cl.
CPC ........ *C07K 14/485* (2013.01); *A61K 48/0058* (2013.01); *A61P 21/00* (2018.01); *C07K 14/4707* (2013.01); *C07K 14/78* (2013.01); *C12N 15/86* (2013.01); *C07K 2319/00* (2013.01); *C12N 2750/14143* (2013.01); *C12N 2830/008* (2013.01)

(58) Field of Classification Search
CPC .. C07K 14/485; C07K 14/4707; C07K 14/78; C07K 2319/00; A61K 48/0058; A61P 21/00; C12N 15/86; C12N 2750/14143; C12N 2830/008
See application file for complete search history.

(56) References Cited

U.S. PATENT DOCUMENTS

| | | | |
|---|---|---|---|
| 5,173,414 A | 12/1992 | Lebkowski et al. | |
| 5,444,158 A * | 8/1995 | Engvall ................... | A61P 25/00 |
| | | | 530/413 |
| 5,658,776 A | 8/1997 | Flotte et al. | |
| 5,786,211 A | 7/1998 | Johnson | |
| 5,871,982 A | 2/1999 | Wilson et al. | |
| 6,258,595 B1 | 7/2001 | Gao et al. | |
| 6,566,118 B1 | 5/2003 | Atkinson et al. | |
| 9,434,928 B2 | 9/2016 | Mendell et al. | |
| 2011/0166081 A1 | 7/2011 | Campbell et al. | |

FOREIGN PATENT DOCUMENTS

| | | | | |
|---|---|---|---|---|
| WO | 95/13365 A1 | 5/1995 | | |
| WO | 95/13392 A1 | 5/1995 | | |
| WO | 96/17947 A1 | 6/1996 | | |
| WO | 97/06243 A1 | 2/1997 | | |
| WO | 97/08298 A1 | 3/1997 | | |
| WO | 97/09441 A2 | 3/1997 | | |
| WO | 97/21825 A1 | 6/1997 | | |
| WO | 98/09657 A2 | 3/1998 | | |
| WO | 99/11764 A2 | 3/1999 | | |
| WO | 01/83692 A2 | 11/2001 | | |
| WO | 02/53703 A2 | 7/2002 | | |
| WO | 2017/049031 A1 | 3/2017 | | |
| WO | 2017/181015 A1 | 10/2017 | | |
| WO | WO-2018151841 A1 * | 8/2018 | ............. | C07K 16/18 |

OTHER PUBLICATIONS

Chandler, L. A., et al., "Targeting tumor cells via EGF receptors: selective toxicity of an HBEGF-toxin fusion protein," Int J Cancer 78(1): 106-111. doi: 10.1002/(sici)1097-0215(19980925)78:1<106::aid-ijc17>3.0.co;2-9. (Year: 1988).*
Shaw, L., et al., "Laminin Polymerization and Inherited Disease: Lessons From Genetics," Front Genet 12:707087. doi: 10.3389/fgene.2021.707087. (Year: 2021).*
Yurchenco, P. D., et al., "Laminin-deficient muscular dystrophy: Molecular pathogenesis and structural repair strategies," Matrix Biol 71-72: 174-187. doi: 10.1016/j.matbio.2017.11.009. Epub Nov. 27, 2017. (Year: 2017).*
Ishihara, J., et al., "Laminin heparin-binding peptides bind to several growth factors and enhance diabetic wound healing," Nat Commun. Jun. 4, 2018;9(1):2163. doi: 10.1038/s41467-018-04525-w. (Year: 2018).*
GenBank Accession NM_001945.2, *Homo sapiens* heparin binding EGF like growth factor (HBEGF), mRNA. (Jul. 10, 2008) (Year: 2008).*
Mitamura, T., et al., "Structure-function analysis of the diphtheria toxin receptor toxin binding site by site-directed mutagenesis," J Biol Chem 272(43): 27084-27090. doi: 10.1074/jbc.272.43.27084. (Year: 1997).*

(Continued)

*Primary Examiner* — Tracy Vivlemore
*Assistant Examiner* — Eric J Rogers
(74) *Attorney, Agent, or Firm* — MARSHALL, GERSTEIN & BORUN LLP

(57) ABSTRACT

Products and methods for treating dystroglycanopathies and laminin-deficient muscular dystrophies are provided. In the methods, a protein including a linker domain, such as the heparin-binding domain of Heparin-Binding Epidermal Growth Factor-Like Growth Factor (HBEGF), is delivered to patients.

9 Claims, 61 Drawing Sheets

Specification includes a Sequence Listing.

(56)　　　　　　References Cited

OTHER PUBLICATIONS

GenBank Accession KJ891072, Synthetic construct *Homo sapiens* clone ccsbBroadEn_00466 HBEGF, DNA. (Year: 2015).*

Clark et al., A stable cell line carrying adenovirus-inducible rep and cap genes allows for infectivity titration of adeno-associated virus vectors, Gene. Therapy, 3(12):1124-1132 (1996).

Clark et al., Highly purified recombinant adeno-associated virus vectors are biologically active and free of detectable helper and wild-type viruses, Hum. Gene. Ther., 10(6):1031-1039 (1999).

Cserjesi et al., Myogenin induces the myocyte-specific enhancer binding factor MEF-2 independently of other muscle-specific gene products, Mol. Cell. Biol., 11(10):4854-4862 (1991).

De et al., High levels of persistent expression of alpha1-antitrypsin mediated by the nonhuman primate serotype rh.10 adeno-associated virus despite preexisting immunity to common human adeno-associated viruses, Mol. Ther., 13(1):67-76 (2006).

Gao et al., Clades of Adeno-associated Viruses Are Widely Disseminated in Human Tissues, J. Virol., 78:6381-6388 (2004).

Hermonat et al., Use of adeno-associated virus as a mammalian DNA cloning vector: transduction of neomycin resistance into mammalian tissue culture cells, Proc. Natl. Acad. Sci. U.S.A., 81(20):6466-6470 (1984).

International Application No. PCT/US19/37769, International Preliminary Report on Patentability, mailed Dec. 30, 2020.

International Application No. PCT/US19/37769, International Search Report and Written Opinion, mailed Sep. 16, 2019.

Johnson et al., Muscle creatine kinase sequence elements regulating skeletal and cardiac muscle expression in transgenic mice, Mol. Cell. Biol., 9(8):3393-3399 (1989).

Kanagawa et al., Impaired viability of muscle precursor cells in muscular dystrophy with glycosylation defects and amelioration of its severe phenotype by limited gene expression, Hum. Mol. Genet., 22(15):3003-3015 (2013).

Laughlin et al., Cloning of infectious adeno-associated virus genomes in bacterial plasmids, Gene., 23(1):65-73 (1983).

Lebkowski et al., Adeno-associated virus: a vector system for efficient introduction and integration of DNA into a variety of mammalian cell types, Mol. Cell. Biol., 8:349 (1988).

Mader et al., A steroid-inducible promoter for the controlled overexpression of cloned genes in eukaryotic cells, Proc. Natl. Acad Sci. USA, 90:5603-5607 (1993).

Marsic et al., Vector Design Tour de Force: Integrating Combinatorial and Rational Approaches to Derive Novel Adeno-associated Virus Variants, Molecular Therapy, 22(11):1900-1909 (2014).

McCarty, Self-complementary AAV vectors; advances and applications, Mol. Ther., 16(10):1648-1656 (2008).

McKee et al., Chimeric protein repair of laminin polymerization ameliorates muscular dystrophy phenotype, , Journal of Clinical Investigation, 127(3): 1075-1089 (2017).

McLaughlin et al., Adeno-associated virus general transduction vectors: analysis of proviral structures, J. Virol., 62(6):1963-73 (1988).

Meinen et al., Linker molecules between laminins and dystroglycan ameliorate laminin-[alpha]2-deficient muscular dystrophy at all disease stages, The Journal of Cell Biology JCB, 176(7) 979-993 (2007).

Mori et al., Two novel adeno-associated viruses from cynomolgus monkey: pseudotyping characterization of capsid protein, Virology, 330(2):375-383 (2004).

Muscat et al., Multiple 5'-flanking regions of the human alpha-skeletal actin gene synergistically modulate muscle-specific expression, Mol. Cell. Biol., 7(11):4089-4099 (1987).

Muzyczka, Use of Adeno-Associated Virus as a General Transduction Vector for Mammalian Cells, Curr. Topics in Microbiol and Immunol., 158:97-129 (1992).

Nonaka, Animal Models of Muscular Dystrophies, Lab. Anim. Sci., 48(1):8-17 (1998).

Paul et al., Increased Viral Titer Through Concentration of Viral Harvests from Retroviral Packaging Lines, Human Gene Therapy, 4(5):609-615 (1993).

Perrin et al., An experimental rabies vaccine produced with a new BHK-21 suspension cell culture process: use of serum-free medium and perfusion-reactor system, Vaccine, 13(13):1244-1250 (1995).

Qiao et al., Amelioration of Muscle and Nerve Pathology in LAMA2 Muscular Dystrophy by AAV9-Mini-Agrin, Molecular Therapy—Methods & Clinical Develop, 9:47-56 (2018).

Rabinowitz et al., Cross-packaging of a single adeno-associated virus (AAV) type 2 vector genome into multiple AAV serotypes enables transduction with broad specificity, J. Virol., 76(2):791-801 (2002).

Reinhard et al., Linker proteins restore basement membrane and correct LAMA2 in mice, Science Translational Medicine, 9(396): eaa14649 (2017).

Salva et al., Design of tissue-specific regulatory cassettes for high-level rAAV-mediated expression in skeletal and cardiac muscle, Mol. Ther., 15(2):320-329 (2007).

Samulski et al., Cloning of adeno-associated virus into pBR322: rescue of intact virus from the recombinant plasmid in human cells, Proc. Natl. Acad. Sci. U.S.A., 79(6):2077-2081 (1982).

Samulski et al., Helper-free stocks of recombinant adeno-associated viruses: normal integration does not require viral gene expression, J. Virol., 63(9):3822-3828 (1989).

Schenpp et al., Highly purified recombinant adeno-associated virus vectors. Preparation and quantitation, Methods Mol. Med., 69:427-443 (2002).

Semenza et al., Hypoxia-inducible nuclear factors bind to an enhancer element located 3' to the human erythropoietin gene, Proc. Natl. Acad. Sci. U.S.A., 88(13):5680-5684 (1991).

Senapathy et al., Molecular cloning of adeno-associated virus variant genomes and generation of infectious virus by recombination in mammalian cells, J. Biol. Chem., 259:4661-4666 (1984).

Srivastava et al., Nucleotide Sequence and Organization of the Adeno-Associated Virus 2 Genome, J. Virol., 45:555-564 (1983).

Tratschin et al., A human parvovirus, adeno-associated virus, as a eucaryotic vector: transient expression and encapsidation of the procaryotic gene for chloramphenicol acetyltransferase, Mol. Cell. Biol., 4(10):2072-2081 (1984).

Tratschin et al., Adeno-associated virus vector for high-frequency integration, expression, and rescue of genes in mammalian cells, Mol. Cell. Biol., 5(11):3251-3260 (1985).

Vannoy et al., Efficacy of Gene Therapy is Dependent on Disease Progression in Dystrophic Mice with Mutations in the FKRP Gene, Molecular Therapy—Methods & Clinical Develop Nature Publishing Group, 5:31-42 (2017).

Wang et al., Construction and analysis of compact muscle-specific promoters for AAV vectors, Gene. Therapy, 15(22):1489-1499 (2008).

Wang et al., Sustained correction of bleeding disorder in hemophilia B mice by gene therapy, Proc. Natl. Acad. Sci. USA, 96(7):3906-3910 (1999).

Weintraub et al., The myoD gene family: nodal point during specification of the muscle cell lineage, Science, 251:761-766 (1991).

Carter, Current Opinions in Biotechnology, 1533-1539 (1992).

Lee et al., Ocular abnormalities in Largemyd and Largevls mice, spontaneous models for muscle, eye, and brain diseases, Mol. Cell. Neurosci., 30(2):160-172 (2005).

Sframeli et al., Congenital muscular dystrophies in the UK population: Clinical and molecular spectrum of a large cohort diagnosed over a 12-year period, Neuromuscul Disord, 27(9):793-803 (2017).

Taniguchi-Ikeda et al., Mechanistic aspects of the formation of [alpha]-dystroglycan and therapeutic research for the treatment of [alpha]-dystroglycanopathy: A review, Molecular Aspects of Medicine, 51:115-124 (2016).

Yoon et al., A Method to Produce and Purify Full-Length Recombinant Alpha Dystroglycan: Analysis of N and O-Linked Monosaccharide Composition in CHO Cells with or without LARGE Overexpression, PLoS Curr. (2013).

Fukazawa, et al., Development of novel transactivation systems for cancer therapy, J. of Okayama Med. Assoc., 121(3): 157-162 (Dec. 2009).

(56) References Cited

OTHER PUBLICATIONS

Mekashi, Dual Functions of HB-EGF, Kagaku to Seibutsu, 39(10): 644-649, (2001).

* cited by examiner

A

B

C

A

HB-EGF (ending at heparin binding domain)-LAMA2 G1-G5

Figure 3 (Continued)

HB-EGF (complete soluble form)-LAMA2 G1-G5

Figure 4 (Continued)

```
5'  TGATGCTGTACGTGTGATTACATTCACTGGCTGCATGGGAGAAACATACTTTGACAACAA
o   +---+---+---+---+---+---+---+---+---+---+---+---+---+---+---+     960
o
2       D   A   V   R   V   I   T   F   T   G   C   M   G   E   T   Y   F   D   N   K
o
5'  ACCTATAGGTTTGTGGAATTTCCGAGAAAAAGAAGGTGACTGCAAAGGATGCACTGTCAG
o   +---+---+---+---+---+---+---+---+---+---+---+---+---+---+---+    1020
o
2       P   I   G   L   W   N   F   R   E   K   E   G   D   C   K   G   C   T   V   S
o
5'  TCCTCAGGTGGAAGATAGTGAGGGGACTATTCAATTTGATGGAGAAGGTTATGCATTGGT
o   +---+---+---+---+---+---+---+---+---+---+---+---+---+---+---+    1080
o
2       P   Q   V   E   D   S   E   G   T   I   Q   F   D   G   E   G   Y   A   L   V
o
5'  CAGCCGTCCCATTCGCTGGTACCCCAACATCTCCACTGTCATGTTCAAGTTCAGAACATT
o   +---+---+---+---+---+---+---+---+---+---+---+---+---+---+---+    1140
o
o
2       S   R   P   I   R   W   Y   P   N   I   S   T   V   M   F   K   F   R   T   F
o
5'  TTCTTCGAGTGCTCTTCTGATGTATCTTGCCACACGAGACCTGAGAGATTTCATGAGTGT
o   +---+---+---+---+---+---+---+---+---+---+---+---+---+---+---+    1200
o
2       S   S   S   A   L   L   M   Y   L   A   T   R   D   L   R   D   F   M   S   V
o
5'  GGAGCTCACTGATGGGCACATAAAAGTCAGTTACGATCTGGGCTCAGGAATGGCTTCCGT
o   +---+---+---+---+---+---+---+---+---+---+---+---+---+---+---+    1260
o
o
2       E   L   T   D   G   H   I   K   V   S   Y   D   L   G   S   G   M   A   S   V
o
5'  TGTCAGCAATCAAAACCATAATGATGGGAAATGGAAATCATTCACTCTGTCAAGAATTCA
o   +---+---+---+---+---+---+---+---+---+---+---+---+---+---+---+    1320
o
o
2       V   S   N   Q   N   H   N   D   G   K   W   K   S   F   T   L   S   R   I   Q
o
5'  AAAACAAGCCAATATATCAATTGTAGATATAGATACTAATCAGGAGGAGAATATAGCAAC
o   +---+---+---+---+---+---+---+---+---+---+---+---+---+---+---+    1380
o
2       K   Q   A   N   I   S   I   V   D   I   D   T   N   Q   E   E   N   I   A   T
o
5'  TTCGTCTTCTGGAAACAACTTTGGTCTTGACTTGAAAGCAGATGACAAAATATATTTTGG
o   +---+---+---+---+---+---+---+---+---+---+---+---+---+---+---+    1440
o
o
2       S   S   S   G   N   N   F   G   L   D   L   K   A   D   D   K   I   Y   F   G
o
```

Figure 4 (Continued)

```
5'  TGATTTTGCAACAGTTCAGCTGAGAAATGGATTGCCCTACTTCAGCTATGACTTGGGGAG
0   +++++|+++++|+++++|+++++|+++++|+++++|+++++|+++++|+++++|+++++|   2520
0
2       D  F  A  T  V  Q  L  R  N  G  L  P  Y  F  S  Y  D  L  G  S
0

5'  TGGGGACACCCACACCATGATCCCCACCAAAATCAATGATGGCCAGTGGCACAAGATTAA
0   +++++|+++++|+++++|+++++|+++++|+++++|+++++|+++++|+++++|+++++|   2580
0
2       G  D  T  H  T  M  I  P  T  K  I  N  D  G  Q  W  H  K  I  K
0

5'  GATAATGAGAAGTAAGCAAGAAGGAATTCTTTATGTAGATGGGGCTTCCAACAGAACCAT
0   +++++|+++++|+++++|+++++|+++++|+++++|+++++|+++++|+++++|+++++|   2640
0
2       I  M  R  S  K  Q  E  G  I  L  Y  V  D  G  A  S  N  R  T  I
0

5'  CAGTCCCAAAAAAGCCGACATCCTGGATGTCGTGGGAATGCTGTATGTTGGTGGGTTACC
0   +++++|+++++|+++++|+++++|+++++|+++++|+++++|+++++|+++++|+++++|   2700
0
2       S  P  K  K  A  D  I  L  D  V  V  G  M  L  Y  V  G  G  L  P
0

5'  CATCAACTACACTACCCGAAGAATTGGTCCAGTGACCTATAGCATTGATGGCTGCGTCAG
0   +++++|+++++|+++++|+++++|+++++|+++++|+++++|+++++|+++++|+++++|   2760
0
2       I  N  Y  T  T  R  R  I  G  P  V  T  Y  S  I  D  G  C  V  R
0

5'  GAATCTCCACATGGCAGAGGCCCCTGCCGATCTGGAACAACCCACCTCCAGCTTCCATGT
0   +++++|+++++|+++++|+++++|+++++|+++++|+++++|+++++|+++++|+++++|   2820
0
2       N  L  H  M  A  E  A  P  A  D  L  E  Q  P  T  S  S  F  H  V
0

5'  TGGGACATGTTTTGCAAATGCTCAGAGGGGAACATATTTTGACGGAACCGGTTTTGCCAA
0   +++++|+++++|+++++|+++++|+++++|+++++|+++++|+++++|+++++|+++++|   2880
0
2       G  T  C  F  A  N  A  Q  R  G  T  Y  F  D  G  T  G  F  A  K
0

5'  AGCAGTTGGTGGATTCAAAGTGGGATTGGACCTTCTTGTAGAATTTGAATTCCGCACAAC
0   +++++|+++++|+++++|+++++|+++++|+++++|+++++|+++++|+++++|+++++|   2940
0
2       A  V  G  G  F  K  V  G  L  D  L  L  V  E  F  E  F  R  T  T
0

5'  TACAACGACTGGAGTTCTTCTGGGGATCAGTAGTCAAAAAATGGATGGAATGGGTATTGA
0   +++++|+++++|+++++|+++++|+++++|+++++|+++++|+++++|+++++|+++++|   3000
0
2       T  T  T  G  V  L  L  G  I  S  S  Q  K  M  D  G  M  G  I  E
0
```

HB-EGF (ending at heparin binding domain)-LAMA2 G3-G5

HB-EGF (complete soluble form)-LAMA2 G3-G5

Figure 6 (Continued)

```
5' CCATGGACTTTGCAAGGCCTGTGTCCTTCAAAAATGCTGACATTGGTCCCTGTGCCCATCAGAAACTCCGTGAAGATGAA
                                                                                      880
   P  M  D  F  A  R  P  V  S  F  K  N  A  D  I  G  R  G  A  H  Q  K  L  R  E  D  E

5' GATGGAGCAGCTCCAGCTGAAATAGTTATCCAGCCTGAGCCAGTTCCCACCCCAGCCTTTCCTACGCCCACCCCAGTTCT
                                                                                      960
   D  G  A  A  P  A  E  I  V  I  Q  P  E  P  V  P  T  P  A  F  P  T  P  T  P  V  L

5' GACACATGGTCCTTGTGCTGCAGAATCAGAACCAGCTCTTTTGATAGGGAGCAAGCAGTTCGGGCTTTCAAGAAACAGTC
                                                                                      1040
                                                       a2LG4
   T  H  G  P  C  A  A  E  S  E  P  A  L  L  I  G  S  K  Q  F  G  L  S  R  N  S

5' ACATTGCAATTGCATTTGATGACACCAAAGTTAAAAACCGTCTCACAATTGAGTTGGAAGTAAGAACCGAAGCTGAATCC
                                                                                      1120
                                  a2LG4
   H  I  A  I  A  F  D  D  T  K  V  K  N  R  L  T  I  E  L  E  V  R  T  E  A  S

5' GGCTTGCTTTTTTACATGGCTCGCATCAATCATGCTGATTTTGCAACAGTTCAGCTGAGAAATGGATTGCCCTACTTCAG
                                                                                      1200
                                  a2LG4
   Q  L  L  F  Y  M  A  R  I  N  H  A  D  F  A  T  V  Q  L  R  N  G  L  P  Y  F  S

5' CTATGACTTGGGGAGTGGGGACACCCACACCATGATCCCCACCAAAATCAATGATGGCCAGTGGCACAAGATTAAGATAA
                                                                                      1280
                                  a2LG4
   Y  D  L  G  S  G  D  T  H  I  M  I  P  T  K  I  N  D  G  Q  W  H  K  I  K  I

5' TGAGAAGTAAGCAAGAAGGAATTCTTTATGTAGATGGGGCTTCCAACAGAACCATCAGTCCCAAAAAAGCCGACATCCTG
                                                                                      1360
                                  a2LG4
   M  R  S  K  Q  E  G  I  L  Y  V  D  G  A  S  N  R  T  I  S  P  K  K  A  D  I  L

5' GATGTCGTGGGAATGCTGTATGTTGGTGGGTTACCCATCAACTACACTACCCGAAGAATTGGTCCAGTGACCTATAGCAT
                                                                                      1440
                                  a2LG4
   D  V  V  G  M  L  Y  V  G  G  L  P  I  N  Y  T  T  R  R  I  G  P  V  T  Y  S  I

5' TGATCGGCTGCCGTCAGGAATCTCCACATGGCAGAGGCCCCTGCCGATCTCGGAACAACCCACCTCCAGCTTCCATGTTGGGA
                                                                                      1520
                                  a2LG4
   D  G  C  V  R  N  L  H  M  A  S  A  P  A  D  L  E  Q  P  T  S  S  F  H  V  G

5' CATGTTTTGCAAATGCTCAGAGGGGAACATATTTTGACGGAACCGGTTTTGCCAAAGCAGTTGGTGGATTCAAAGTGGGA
                                                                                      1600
   a2LG4              a2LG5
   T  C  F  A  N  A  Q  R  G  T  Y  F  D  G  T  G  F  A  K  A  V  G  G  F  K  V  G

5' TTGGACCTTCTTGTAGAATTTGAATTCCGCACAACTACAACGACTGGAGTTCTTCTGGGGATCAGTAGTCAAAAAATGGA
                                                                                      1680
                                  a2LG5
   L  D  L  L  V  E  F  R  T  T  T  T  G  V  L  L  G  I  S  S  Q  K  M  D

5' TGGAATGGGTATTGAAATGATTGATGAAAAGTTGATGTTTCATGTGGACAATGGTGCGGGCAGATTCACTGCTGTCTATG
                                                                                      1760
                                  a2LG5
   G  M  G  I  E  M  I  D  F  K  L  M  F  H  V  D  N  G  A  G  R  F  T  A  V  Y

5' ATGCTGGGGTTCCAGGGCATTTGTGTGATGGACAATGGCATAAAGTCACTGCCAACAAGATCAAACACCGCATTGAGCTC
                                                                                      1840
                                  a2LG5
   D  A  G  V  P  G  H  L  C  D  G  Q  W  H  K  V  I  A  N  K  I  K  H  R  I  E  L

5' ACAGTCGATGGGAACCAGGTGGAAGCCCAAAGCCCAAACCCAGCATCTACATCAGCTGACACAAATGACCCTGTGTTTGT
                                                                                      1920
                                  a2LG5
   T  V  D  G  N  Q  V  E  A  Q  S  P  N  P  A  S  T  S  A  D  T  N  D  P  V  F  V

5' TGGAGGCTTCCCAGATGACCTCAAGCAGTTTGGCCTAACAACCAGTATTCCGTTCCGAGGTTGCATCAGATCCCTGAAGC
                                                                                      2000
                                  a2LG5
   G  G  F  P  D  D  L  K  Q  F  G  L  T  T  S  I  P  F  R  G  C  I  R  S  L  K

5' TCACCAAAGGCACAGCAAGCCACTGGAGGTTAATTTTGCCAAGGCCCTGGAACTGAACTAGTGCGGCCGCAA
                                  a2LG5
   L  T  K  G  T  A  S  H  W  R  L  I  L  P  R  P  W  N  .  T  S  A  A  A
```

HB-EGF (ending at heparin binding domain)-DAG1 (native processed alpha DG gene)

HB-EGF (complete soluble form)-DAG1 (native processed alpha DG gene)

Figure 8 (Continued)

```
5'  TGACTCCACCACCACCACGACTCGCAGGCCAACCAAGAAACCACGGACACCCCGGCCAGT
    +---+---+---+---+---+---+---+---+---+---+---+---+---+---+---+   900
                              alpha-DG Mucin Domain
      D  S  T  T  T  T  R  P  T  K  K  P  R  T  P  R  P  V 5'  GCCCCGGGTCACCACCAAAGTTTCCATCACCAGATTGGAAACTGCCTCACCGCCTACTCG
    +---+---+---+---+---+---+---+---+---+---+---+---+---+---+---+   960
                              alpha-DG
    Mucin            C-Term
      P  R  V  T  T  K  V  S  I  T  R  L  E  T  A  S  P  P  T  R 5'  TATTCGCACCACCACCAGTGGAGTGCCCCGTGGCGGAGAACCCAACCAGCGCCCAGAGCT
    +---+---+---+---+---+---+---+---+---+---+---+---+---+---+---+  1020
                              alpha-DG
                              C-Term
      I  R  T  T  T  S  G  V  P  R  G  G  E  P  N  Q  R  P  E  L 5'  CAAGAACCATATTGACAGGGTAGATGCCTGGGTTGGCACCTACTTTGAGGTGAAGATCCC
    +---+---+---+---+---+---+---+---+---+---+---+---+---+---+---+  1080
                              alpha-DG
                              C-Term
      K  N  H  I  D  R  V  D  A  W  V  G  T  Y  F  E  V  K  I  P 5'  GTCAGACACTTTCTATGACCATGAGGACACCACCACTGACAAGCTGAAGCTGACCCTGAA
    +---+---+---+---+---+---+---+---+---+---+---+---+---+---+---+  1140
                              alpha-DG
                              C-Term
      S  D  T  F  Y  D  H  E  D  T  T  T  D  K  L  K  L  T  L  K 5'  ACTGCGGGAGCAGCAGCTGGTGGGCGAGAAGTCCTGGGTACAGTTCAACAGCAACAGCCA
    +---+---+---+---+---+---+---+---+---+---+---+---+---+---+---+  1200
                              alpha-DG
                              C-Term
      L  R  E  Q  Q  L  V  G  E  K  S  W  V  Q  F  N  S  N  S  Q 5'  GCTCATGTATGGCCTTCCCGACAGCAGCCACGTGGGCAAACACGAGTATTTCATGCATGC
    +---+---+---+---+---+---+---+---+---+---+---+---+---+---+---+  1260
                              alpha-DG
                              C-Term
      L  M  Y  G  L  P  D  S  S  H  V  G  K  H  E  Y  F  M  H  A
```

Wild Type dy/dy dy/dy
+ IV
rAAV9.HB.
LAMA2G1-G5

HBEGF-Green
Col(IV)-Red
DAPI-Blue

Figure 19

SEQ ID NO: 2 rAAV.CMV.HB.LAMA2(G1-G5)
Ampicillin Resistance Gene
ITRs
*CMV Promoter*
<u>*SV40 Enhancer*</u>
<u>HBEGF Signal Peptide</u>
<u>HBEGF Propeptide Domain</u>
<u>HBEGF Mature Peptide Domain</u>
<u>HBEGF HB Domain</u>
<u>LAMA2 G1-3</u>
<u>LAMA2 G3-5</u>
<u>SV40 PolyA Tail</u>

GCTCTTCCGCTTGGTCGCTCACTGACTCGCTGCGCTCGGTCGTTCGGCTGCGGCG
AGCGGTATCAGCTCACTCAAACCCGGTAATACGGTTATCCACAGAATCAGGGGA
TAACGCAGGAAAGAACATGTGAGCAAAAGGCCAGCAAAAGGCCAGGAACCGTA
AAAAGGCCGCGTTGCTGGCGTTTTTCCATAGGCTCCGCCCCCCTGACGAGCATCA
CAAAAATCGACGCTCAAGTCAGAGGTGGCGAAACCCGACAGGACTATAAAGATA
CCAGGCGTTTCCCCCTGGAAGCTCCCTCGTGCGCTCTCCTGTTCCGACCCTGCCGC
TTACCGGATACCTGTCCGCCTTTCTCCCTTCGGGAAGCGTGGCGCTTTCTCATAGC
TCACGCTGTAGGTATCTCAGTTCGGTGTAGGTCGTTCGCTCCAAGCTGGGCTGTG
TGCACGAACCCCCCGTTCAGCCCGACCGCTGCGCCTTATCCGGTAACTATCGTCT
TGAGTCCAACCCGGTAAGACACGACTTATCGCCACTGGCAGCAGCCACTGGTAA
CAGGATTAGCAGAGCGAGGTATGTACGCGGTGCTACAGAGTTCTTGAAGTGGTG
GCCTAACTACGGCTACACTAGAAGGACAGTATTTGGTATCTGCGCTCTGCTGAAG
CCAGTTACCTTCGGAAAAAGAGTTGGTAGCTCTTGATCCGGCAAACAAACCACC
GCTGGTAGCGGTGGTTTTTTTGTTTGCAAGCAGCAGATTACGCGCAGAAAAAAAG
GATCTCAAGAAGATCCTTTGATCTTTTCTACGGGGTCTGACGCTCAGTGGAACGA
AAACTCACGTTAAGGGATTTTGGTCATGAGATTATCAAAAAGGATCTTCACCTAG
ATCCTTTTAAATTAAAAATGAAGTTTTAAATCAATCTAAAGTATATATGAGTAAA
CTTGGTCTGACAGTTACCAATGCTTAATCAGTGAGGCACCTATCTCAGCGATCTG
TCTATTTCGTTCATCCATAGTTGCCTGACTCCCCGTCGTGTAGATAACTACGATAC
GGGAGGGCTTACCATCTGGCCCCAGTGCTGCAATGATACCGCGAGACCCACGCT
CACCGGCTCCAGATTTATCAGCAATAAACCAGCCAGCCGGAAGGGCCGAGCGCA
GAAGTGGTCCTGCAACTTTATCCGCCTCCATCCAGTCTATTAATTGTTGCCGGGA
AGCTAGAGTAAGTAGTTCGCCAGTTAATAGTTTGCGCAACGTTGTTGCCATTGCT
ACAGGCATCGTGGTGTCACGCTCGTCGTTTGGTATGGCTTCATTCAGCTCCGGTTC
CCAACGATCAAGGCGAGTTACATGATCCCCCATGTTGTGCAAAAAAGCGGTTAG
CTCCTTCGGTCCTCCGATCGTTGTCAGAAGTAAGTTGGCCGCAGTGTTATCACTC
ATGGTTATGGCAGCACTGCATAATTCTCTTACTGTCATGCCATCCGTAAGATGCTT
TTCTGTGACTGGTGAGTACTCAACCAAGTCATTCTGAGAATAGTGTATGCGGCGA
CCGAGTTGCTCTTGCCCGGCGTCAATACGGGATAATACCGCGCCACATAGCAGA
ACTTTAAAAGTGCTCATCATTGGAAAACGTTCTTCGGGGCGAAAACTCTCAAGGA
TCTTACCGCTGTTGAGATCCAGTTCGATGTAACCCACTCGTGCACCCAACTGATC
TTCAGCATCTTTTACTTTCACCAGCGTTTCTGGGTGAGCAAAAACAGGAAGGCAA

AATGCCGCAAAAAAGGGAATAAGGGCGACACGGAAATGTTGAATACTCATACTC
TTCCTTTTTCAATATTATTGAAGCATTTATCAGGGTTATTGTCTCATGAGCGGATA
CATATTTGAATGTATTTAGAAAAATAAACAAATAGGGGTTCCGCGCACATTTCCC
CGAAAAGTGCCACCTGACGTCTAAGAAACCATTATTATCATGACATTAACCTATA
AAAATAGGCGTATCACGAGGCCCTTTCGTCTCGCGCGTTTCGGTGATGACGGTGA
AAACCTCTGACACATGCAGCTCCCGGAGACGGTCACAGCTTGTCTGTAAGCGGAT
GCCGGGAGCAGACAAGCCCGTCAGGGCGCGTCAGCGGGTGTTGGCGGGTGTCGG
GGCTGGCTTAACTATGCGGCATCAGAGCAGATTGTACTGAGAGTGCACCATATGC
GGTGTGAAATACCGCACAGATGCGTAAGGAGAAAATACCGCATCAGGAACTTCC
AACATCCAATAAATCATACAGGCAAGGCAAAGAATTAGCAAAATTAAGCAATAA
AGCCTCAGAGCATAAAGCTAAATCGGTTGTACCAAAACATTATGACCCTGTAAT
ACTTTTGCGGGAGAAGCCTTTATTTCAACGCAAGGATAAAAATTTTTAGAACCCT
CATATATTTTAAATGCAATGCCTGAGTAATGTGTAGGTAAAGATTCAAACGGGTG
AGAAAGGCCGGAGACAGTCAAATCACCATCAATATGATATTCAACCGTTCTAGC
TGATAAATTCATGCCGGAGAGGGTAGCTATTTTTGAGAGGTCTCTACAAAGGCTA
TCAGGTCATTGCCTGAGAGTCTGGAGCAAACAAGAGAATCGATGAACGGTAATC
GTAAAACTAGCATGTCAATCATATGTACCCCGGTTGATAATCAGAAAAGCCCCA
AAAACAGGAAGATTGTATAAGCAAATATTTAAATTGTAAACGTTAATATTTTGTT
AAAATTCGCGTTAAATTTTGTTAAATCAGCTCATTTTTTAACCAATAGGCCGAA
ATCGGCAAAATCCCTTATAAATCAAAAGAATAGACCGAGATAGGGTTGAGTGTT
GTTCCAGTTTGGAACAAGAGTCCACTATTAAAGAACGTGGACTCCAACGTCAAA
GGGCGAAAAACCGTCTATCAGGGCGATGGCCCACTACGTGAACCATCACCCTAA
TCAAGTTTTTGGGGTCGAGGTGCCGTAAATCACTAAATCGGAACCCTAAAGGGA
GCCCCCGATTTAGAGCTTGACGGGGAAAGCCGGCGAACGTGGCGAGAAAGGAA
GGGAAGAAAGCGAAAGGAGCGGGCGCTAGGGCGCTGGCAAGTGTAGCGGTCAC
GCTGCGCGTAACCACCACACCCGCCGCGCTTAATGCGCCGCTACAGGGCGCGTA
CTATGGTTGCTTTGACGAGCACGTATAACGTGCTTTCCTCGTTAGAATCAGAGCG
GGAGCTAAACAGGAGGCCGATTAAAGGGATTTTAGACAGGAACGGTACGCCAGA
ATCCTGAGAAGTGTTTTTATAATCAGTGAGGCCACCGAGTAAAAGAGTCTGTCCA
TCACGCAAATTAACCGTTGTCGCAATACTTCTTTGATTAGTAATAACATCACTTGC
CTGAGTAGAAGAACTCAAACTATCGGCCTTGCTGGTAATATCCAGAACAATATTA
CCGCCAGCCATTGCAACAGGAAAAACGCTCATGGAAATACCTACATTTTGACGCT
CAATCGTCTGGAACTTCCATTCGCCATTCAGGCTGCGCAACTGTTGGGAAGGGCG
ATCGGTGCGGGCCTCTTCGCTATTACGCCAGCTGNNNNNNGCGCGCTCGCTCGC
TCACTGAGGCCGCCCGGGCAAAGCCCGGGCGTCGGGCGACCTTTGGTCGCC
CGGCCTCAGTGAGCGAGCGAGCGCGCAGAGAGGGAGTGGCCAACTCCATCA
CTAGGGGTTCCTTGTAGTTAATGATTAACCCGCCATGCTAATTATCTACGTA
GCCATGTCTAGGGT*CGTTACATAACTTACGGTAAATGGCCCGCCTGGCTGACCGCCC*
*AACGACCCCCGCCCATTGACGTCAATAATGACGTATGTTCCCATAGTAACGCCAATAGG*
*GACTTTCCATTGACGTCAATGGGTGGAGTATTTACGGTAAACTGCCCACTTGGCAGTAC*
*ATCAAGTGTATCATATGCCAAGTACGCCCCCTATTGACGTCAATGACGGTAAATGGCCC*
*GCCTGGCATTATGCCCAGTACATGACCTTATGGGACTTTCCTACTTGGCAGTACATCTA*
*CGTATTAGTCATCGCTATTACCATGGTGATGCGGTTTTGGCAGTACATCAATGGGCGTG*
*GATAGCGGTTTGACTCACGGGGATTTCCAAGTCTCCACCCCATTGACGTCAATGGGAG*
*TTTGTTTTGGCACCAAAATCAACGGGACTTTCCAAAATGTCGTAACAACTCCGCCCCAT*
*TGACGCAAATGGGCGGTAGGCGTGTACGGTGGGAGGTCTATATAAGCAGAGCTCGTTT*
*AGTGAACCGTCAGATCGCCTGGAGACGCCATCCACGCTGTTTTGACCTCCATAGAA*
GACACCGGGACCGATCCAGCCTCCGGAC*TCTAGAGGATCCGGTACTCGAGGAACTG*
*AAAAACCAGAAAGTTAACTGGTAAGTTTAGTCTTTTTGTCTTTTATTTCAGGTCCCGGAT*
*CCGGTGGTGGTGCAAATCAAAGAACTGCTCCTCAGTGGATGTTGCCTTTACTTCTAGG*

Figure 19 (Continued)

*CCTGTACGGAAGTGTTACTTCTGCTCTAAAAGCTGCGGAATTGTACCCGC*GGCCGCAC
CATGAAGCTGCTGCCGTCGGTGGTGCTGAAGCTCTTTCTGGCTGCAGTTCTCTCG
GCACTGGTGACTGGCGAGAGCCTGGAGCGGCTTCGGAGAGGGCTAGCTGCTG
GAACCAGCAACCCGGACCCTCCCACTGTATCCACGGACCAGCTGCTACCCC
TAGGAGGCGGCCGGGACCGGAAAGTCCGTGACTTGCAAGAGGCAGATCTGG
ACCTTTTGAGAGTCACTTTATCCTCCAAGCCACAAGCACTGGCCACACCAAA
CAAGGAGGAGCACGGGAAAAGAAAGAAGAAAGGCAAGGGGCTAGGGAAGAA
GAGGGACCCAAAAGTATCTGTGTCTTCAGGAGGTGACTGCATTCGAACATACAA
ACCAGAAATCAAGAAAGGAAGTTACAATAATATTGTTGTCAACGTAAAGACAGC
TGTTGCTGATAACCTCCTCTTTTATCTTGGAAGTGCCAAATTTATTGACTTTCTGG
CTATAGAAATGCGTAAAGGCAAAGTCAGCTTCCTCTGGGATGTTGGATCTGGAGT
TGGACGTGTAGAGTACCCAGATTTGACTATTGATGACTCATATTGGTACCGTATC
GTAGCATCAAGAACTGGGAGAAATGGAACTATTTCTGTGAGAGCCCTGGATGGA
CCCAAAGCCAGCATTGTGCCCAGCACACACCATTCGACGTCTCCTCCAGGGTACA
CGATTCTAGATGTGGATGCAAATGCAATGCTGTTTGTTGGTGGCCTGACTGGGAA
ATTAAAGAAGGCTGATGCTGTACGTGTGATTACATTCACTGGCTGCATGGGAGAA
ACATACTTTGACAACAAACCTATAGGTTTGTGGAATTTCCGAGAAAAAGAAGGT
GACTGCAAAGGATGCACTGTCAGTCCTCAGGTGGAAGATAGTGAGGGGACTATT
CAATTTGATGGAGAAGGTTATGCATTGGTCAGCCGTCCCATTCGCTGGTACCCCA
ACATCTCCACTGTCATGTTCAAGTTCAGAACATTTTCTTCGAGTGCTCTTCTGATG
TATCTTGCCACACGAGACCTGAGAGATTTCATGAGTGTGGAGCTCACTGATGGGC
ACATAAAAGTCAGTTACGATCTGGGCTCAGGAATGGCTTCCGTTGTCAGCAATCA
AAACCATAATGATGGGAAATGGAAATCATTCACTCTGTCAAGAATTCAAAAACA
AGCCAATATATCAATTGTAGATATAGATACTAATCAGGAGGAGAATATAGCAAC
TTCGTCTTCTGGAAACAACTTTGGTCTTGACTTGAAAGCAGATGACAAAATATAT
TTTGGTGGCCTGCCAACGCTGAGAAACTTGAGTATGAAAGCAAGGCCAGAAGTA
AATCTGAAGAAATATTCCGGCTGCCTCAAAGATATTGAAATTTCAAGAACTCCGT
ACAATATACTCAGTAGTCCCGATTATGTTGGTGTTACCAAAGGATGTTCCCTGGA
GAATGTTTACACAGTTAGCTTTCCTAAGCCTGGTTTTGTGGAGCTCTCCCCTGTGC
CAATTGATGTAGGAACAGAAATCAACCTGTCATTCAGCACCAAGAATGAGTCCG
GCATCATTCTTTTGGGAAGTGGAGGGACACCAGCACCACCTAGGAGAAAACGAA
GGCAGACTGGACAGGCCTATTATGTAATACTCCTCAACAGGGGCCGTCTGG
AAGTGCATCTCTCCACAGGGGCACGAACAATGAGGAAAATTGTCATCAGAC
CAGAGCCGAATCTGTTTCATGATGGAAGAGAACATTCCGTTCATGTAGAGCG
AACTAGAGGCATCTTTACAGTTCAAGTGGATGAAAACAGAAGATACATGCAA
AACCTGACAGTTGAACAGCCTATCGAAGTTAAAAAGCTTTTCGTTGGGGGTG
CTCCACCTGAATTTCAACCTTCCCCACTCAGAAATATTCCTCCTTTTGAAGG
CTGCATATGGAATCTTGTTATTAACTCTGTCCCCATGGACTTTGCAAGGCCT
GTGTCCTTCAAAAATGCTGACATTGGTCGCTGTGCCCATCAGAAACTCCGTG
AAGATGAAGATGGAGCAGCTCCAGCTGAAATAGTTATCCAGCTGAGCCAG
TTCCCACCCCAGCCTTTCCTACGCCCACCCCAGTTCTGACACATGGTCCTTG
TGCTGCAGAATCAGAACCAGCTCTTTTGATAGGGAGCAAGCAGTTCGGGCT
TTCAAGAAACAGTCACATTGCAATTGCATTTGATGACACCAAAGTTAAAAAC
CGTCTCACAATTGAGTTGGAAGTAAGAACCGAAGCTGAATCCGGCTTGCTTT
TTTACATGGCTCGCATCAATCATGCTGATTTTGCAACAGTTCAGCTGAGAAA
TGGATTGCCCTACTTCAGCTATGACTTGGGGAGTGGGGACACCCACACCAT
GATCCCCACCAAAATCAATGATGGCCAGTGGCACAAGATTAAGATAATGAG
AAGTAAGCAAGAAGGAATTCTTTATGTAGATGGGGCTTCCAACAGAACCATC
AGTCCCAAAAAGCCGACATCCTGGATGTCGTGGGAATGCTGTATGTTGGT
GGGTTACCCATCAACTACACTACCCGAAGAATTGGTCCAGTGACCTATAGCA

Figure 19 (Continued)

TTGATGGCTGCGTCAGGAATCTCCACATGGCAGAGGCCCCTGCCGATCTGG
AACAACCCACCTCCAGCTTCCATGTTGGGACATGTTTTGCAAATGCTCAGAG
GGGAACATATTTTGACGGAACCGGTTTTGCCAAAGCAGTTGGTGGATTCAAA
GTGGGATTGGACCTTCTTGTAGAATTTGAATTCCGCACAACTACAACGACTG
GAGTTCTTCTGGGGATCAGTAGTCAAAAAATGGATGGAATGGGTATTGAAAT
GATTGATGAAAGTTGATGTTTCATGTGGACAATGGTGCGGGCAGATTCACT
GCTGTCTATGATGCTGGGGTTCCAGGGCATTTGTGTGATGGACAATGGCAT
AAAGTCACTGCCAACAAGATCAAACACCGCATTGAGCTCACAGTCGATGGG
AACCAGGTGGAAGCCCAAAGCCCAAACCCAGCATCTACATCAGCTGACACA
AATGACCCTGTGTTTGTTGGAGGCTTCCCAGATGACCTCAAGCAGTTTGGCC
TAACAACCAGTATTCCGTTCCGAGGTTGCATCAGATCCCTGAAGCTCACCAA
AGGCACAGCAAGCCACTGGAGGTTAATTTTGCCAAGGCCCTGGAACTGAAC
TAGTGCGGCCGCGGGGATCCAGACATGATAAGATACATTGATGAGTTTGGACAA
ACCACAACTAGAATGCAGTGAAAAAAATGCTTTATTTGTGAAATTTGTGATGCTA
TTGCTTTATTTGTAACCATTATAAGCTGCAATAAACAAGTTAACAACAACAATTG
CATTCATTTTATGTTTCAGGTTCAGGGGGAGGTGTGGGAGGTTTTTTCGGATCCTC
TAGAGTCGACCACATGGCTACGTAGATAATTAGCATGGCGGGTTAATCATTA
ACTACAAGGAACCCCTAGTGATGGAGTTGGCCACTCCCTCTCTGCGCGCTC
GCTCGCTCACTGAGGCCGGGCGACCAAAGGTCGCCCGACGCCCGGGCTTTG
CCCGGGCGGCCTCAGTGAGCGAGCGAGCGCGCNNNNNNCAGCTGCATTAATG
AATCGGCCAACGCGCGGGGAGAGGCGGTTTGCGTATTGGG

SEQ ID NO: 4 pAAV.CMV.HBEGF.LAMA2(G1-G5)
Main Characteristics

Ampicillin Resistance Gene
ITRs
*CMV Promoter*
SV40 Enhancer
HBEGF Signal Peptide
HBEGF Propeptide Domain
HBEGF Mature Peptide Domain
HBEGF HB Domain
HBEGF EGF-Like Domain
LAMA2 G1-3
LAMA2 G3-5
SV40 PolyA Tail GCTCTTCCGCTTGGTCGCTCACTGACTCGCTGCGCTCGGTCGTTCGGCTGCGGCG
AGCGGTATCAGCTCACTCAAACCCGGTAATACGGTTATCCACAGAATCAGGGGA
TAACGCAGGAAAGAACATGTGAGCAAAAGGCCAGCAAAAGGCCAGGAACCGTA
AAAAGGCCGCGTTGCTGGCGTTTTTCCATAGGCTCCGCCCCCCTGACGAGCATCA
CAAAAATCGACGCTCAAGTCAGAGGTGGCGAAACCCGACAGGACTATAAAGATA
CCAGGCGTTTCCCCCTGGAAGCTCCCTCGTGCGCTCTCCTGTTCCGACCCTGCCGC
TTACCGGATACCTGTCCGCCTTTCTCCCTTCGGGAAGCGTGGCGCTTTCTCATAGC
TCACGCTGTAGGTATCTCAGTTCGGTGTAGGTCGTTCGCTCCAAGCTGGGCTGTG
TGCACGAACCCCCCGTTCAGCCCGACCGCTGCGCCTTATCCGGTAACTATCGTCT
TGAGTCCAACCCGGTAAGACACGACTTATCGCCACTGGCAGCAGCCACTGGTAA
CAGGATTAGCAGAGCGAGGTATGTACGCGGTGCTACAGAGTTCTTGAAGTGGTG
GCCTAACTACGGCTACACTAGAAGGACAGTATTTGGTATCTGCGCTCTGCTGAAG
CCAGTTACCTTCGGAAAAAGAGTTGGTAGCTCTTGATCCGGCAAACAAACCACC
GCTGGTAGCGGTGGTTTTTTTGTTTGCAAGCAGCAGATTACGCGCAGAAAAAAAG
GATCTCAAGAAGATCCTTTGATCTTTTCTACGGGGTCTGACGCTCAGTGGAACGA
AAACTCACGTTAAGGGATTTTGGTCATGAGATTATCAAAAAGGATCTTCACCTAG
ATCCTTTTAAATTAAAAATGAAGTTTTAAATCAATCTAAAGTATATATGAGTAAA
CTTGGTCTGACAGTTACCAATGCTTAATCAGTGAGGCACCTATCTCAGCGATCTG
TCTATTTCGTTCATCCATAGTTGCCTGACTCCCCGTCGTGTAGATAACTACGATAC
GGGAGGGCTTACCATCTGGCCCCAGTGCTGCAATGATACCGCGAGACCCACGCT
CACCGGCTCCAGATTTATCAGCAATAAACCAGCCAGCCGGAAGGGCCGAGCGCA
GAAGTGGTCCTGCAACTTTATCCGCCTCCATCCAGTCTATTAATTGTTGCCGGGA
AGCTAGAGTAAGTAGTTCGCCAGTTAATAGTTTGCGCAACGTTGTTGCCATTGCT
ACAGGCATCGTGGTGTCACGCTCGTCGTTTGGTATGGCTTCATTCAGCTCCGGTTC
CCAACGATCAAGGCGAGTTACATGATCCCCCATGTTGTGCAAAAAAGCGGTTAG
CTCCTTCGGTCCTCCGATCGTTGTCAGAAGTAAGTTGGCCGCAGTGTTATCACTC
ATGGTTATGGCAGCACTGCATAATTCTCTTACTGTCATGCCATCCGTAAGATGCTT
TTCTGTGACTGGTGAGTACTCAACCAAGTCATTCTGAGAATAGTGTATGCGGCGA
CCGAGTTGCTCTTGCCCGGCGTCAATACGGGATAATACCGCGCCACATAGCAGA ACTTTAAAAGTGCTCATCATTGGAAAACGTTCTTCGGGGCGAAAACTCTCAAGGA
TCTTACCGCTGTTGAGATCCAGTTCGATGTAACCCACTCGTGCACCCAACTGATC
TTCAGCATCTTTTACTTTCACCAGCGTTTCTGGGTGAGCAAAAACAGGAAGGCAA
AATGCCGCAAAAAAGGGAATAAGGGCGACACGGAAATGTTGAATACTCATACTC
TTCCTTTTTCAATATTATTGAAGCATTTATCAGGGTTATTGTCTCATGAGCGGATA
CATATTTGAATGTATTTAGAAAAATAAACAAATAGGGGTTCCGCGCACATTTCCC
CGAAAAGTGCCACCTGACGTCTAAGAAACCATTATTATCATGACATTAACCTATA
AAAATAGGCGTATCACGAGGCCCTTTCGTCTCGCGCGTTTCGGTGATGACGGTGA
AAACCTCTGACACATGCAGCTCCCGGAGACGGTCACAGCTTGTCTGTAAGCGGAT
GCCGGGAGCAGACAAGCCCGTCAGGGCGCGTCAGCGGGTGTTGGCGGGTGTCGG
GGCTGGCTTAACTATGCGGCATCAGAGCAGATTGTACTGAGAGTGCACCATATGC
GGTGTGAAATACCGCACAGATGCGTAAGGAGAAAATACCGCATCAGGAACTTCC
AACATCCAATAAATCATACAGGCAAGGCAAAGAATTAGCAAAATTAAGCAATAA
AGCCTCAGAGCATAAAGCTAAATCGGTTGTACCAAAACATTATGACCCTGTAAT
ACTTTTGCGGGAGAAGCCTTTATTTCAACGCAAGGATAAAAATTTTTAGAACCCT
CATATATTTTAAATGCAATGCCTGAGTAATGTGTAGGTAAAGATTCAAACGGGTG
AGAAAGGCCGGAGACAGTCAAATCACCATCAATATGATATTCAACCGTTCTAGC
TGATAAATTCATGCCGGAGAGGGTAGCTATTTTTGAGAGGTCTCTACAAAGGCTA
TCAGGTCATTGCCTGAGAGTCTGGAGCAAACAAGAGAATCGATGAACGGTAATC
GTAAAACTAGCATGTCAATCATATGTACCCCGGTTGATAATCAGAAAAGCCCCA
AAAACAGGAAGATTGTATAAGCAAATATTTAAATTGTAAACGTTAATATTTTGTT
AAAATTCGCGTTAAATTTTTGTTAAATCAGCTCATTTTTTAACCAATAGGCCGAA
ATCGGCAAAATCCCTTATAAATCAAAAGAATAGACCGAGATAGGGTTGAGTGTT
GTTCCAGTTTGGAACAAGAGTCCACTATTAAAGAACGTGGACTCCAACGTCAAA
GGGCGAAAAACCGTCTATCAGGGCGATGGCCCACTACGTGAACCATCACCCTAA
TCAAGTTTTTTGGGGTCGAGGTGCCGTAAATCACTAAATCGGAACCCTAAAGGGA
GCCCCCGATTTAGAGCTTGACGGGGAAAGCCGGCGAACGTGGCGAGAAAGGAA
GGGAAGAAAGCGAAAGGAGCGGGCGCTAGGGCGCTGGCAAGTGTAGCGGTCAC
GCTGCGCGTAACCACCACACCCGCCGCGCTTAATGCGCCGCTACAGGGCGCGTA
CTATGGTTGCTTTGACGAGCACGTATAACGTGCTTTCCTCGTTAGAATCAGAGCG
GGAGCTAAACAGGAGGCCGATTAAAGGGATTTTAGACAGGAACGGTACGCCAGA
ATCCTGAGAAGTGTTTTTATAATCAGTGAGGCCACCGAGTAAAAGAGTCTGTCCA
TCACGCAAATTAACCGTTGTCGCAATACTTCTTTGATTAGTAATAACATCACTTGC
CTGAGTAGAAGAACTCAAACTATCGGCCTTGCTGGTAATATCCAGAACAATATTA
CCGCCAGCCATTGCAACAGGAAAAACGCTCATGGAAATACCTACATTTTGACGCT
CAATCGTCTGGAACTTCCATTCGCCATTCAGGCTGCGCAACTGTTGGGAAGGGCG
ATCGGTGCGGGCCTCTTCGCTATTACGCCAGCTGNNNNNGCGCGCTCGCTCGC
TCACTGAGGCCGCCCGGGCAAAGCCCGGGCGTCGGCGACCTTTGGTCGCC
CGGCCTCAGTGAGCGAGCGAGCGCGCAGAGAGGGAGTGGCCAACTCCATCA
CTAGGGGTTCCTTGTAGTTAATGATTAACCCGCCATGCTAATTATCTACGTA
GCCATGTCTAGGGT*CGTTACATAACTTACGGTAAATGGCCCGCCTGGCTGACCGCCC*
*AACGACCCCCGCCCATTGACGTCAATAATGACGTATGTTCCCATAGTAACGCCAATAGG*
*GACTTTCCATTGACGTCAATGGGTGGAGTATTTACGGTAAACTGCCCACTTGGCAGTAC*
*ATCAAGTGTATCATATGCCAAGTACGCCCCCTATTGACGTCAATGACGGTAAATGGCCC*
*GCCTGGCATTATGCCCAGTACATGACCTTATGGGACTTTCCTACTTGGCAGTACATCTA*
*CGTATTAGTCATCGCTATTACCATGGTGATGCGGTTTTGGCAGTACATCAATGGGCGTG*
*GATAGCGGTTTGACTCACGGGGATTTCCAAGTCTCCACCCCATTGACGTCAATGGGAG*
*TTTGTTTTGGCACCAAAATCAACGGGACTTTCCAAAATGTCGTAACAACTCCGCCCCAT*
*TGACGCAAATGGGCGGTAGGCGTGTACGGTGGGAGGTCTATATAAGCAGAGCTCGTTT*
*AGTGAACCGTCAGATCGCCTGGAGACGCCATCCACGCTGTTTTGACCTCCATAGAA*

Figure 20 (Continued)

GACACCGGGACCGATCCAGCCTCCGGAC*TCTAGAGGATCCGGTACTCGAGGAACTG*
*AAAAACCAGAAAGTTAACTGGTAAGTTTAGTCTTTTTGTCTTTTATTTCAGGTCCCGGAT*
*CCGGTGGTGGTGCAAATCAAAGAACTGCTCCTCAGTGGATGTTGCCTTTACTTCTAGG*
*CCTGTACGGAAGTGTTACTTCTGCTCTAAAAGCTGCGGAATTGTACCCGCGGCCGCAC*
CATGAAGCTGCTGCCGTCGGTGGTGCTGAAGCTCTTTCTGGCTGCAGTTCTCTCG
GCACTGGTGACTGGCGAGAGCCTGGAGCGGCTTCGGAGAGGGCTAGCTGCTG
GAACCAGCAACCCGGACCCTCCCACTGTATCCACGGACCAGCTGCTACCCC
TAGGAGGCGGCCGGGACCGGAAAGTCCGTGACTTGCAAGAGGCAGATCTGG
ACCTTTTGAGAGTCACTTTATCCTCCAAGCCACAAGCACTGGCCACACCAAA
CAAGGAGGAGCACGGGAAAAGAAAGAAGAAAGGCAAGGGGCTAGGGAAGAA
GAGGGACCCATGTCTTCGGAAATACAAGGACTTCTGCATCCATGGAGAATGC
AAATATGTGAAGGAGCTCCGGGCTCCCTCCTGCATCTGCCACCCGGGTTAC
CATGGAGAGAGGTGTCATGGGCTGAGCCTCCCAAAAGTATCTGTGTCTTCAG
GAGGTGACTGCATTCGAACATACAAACCAGAAATCAAGAAAGGAAGTTACAATA
ATATTGTTGTCAACGTAAAGACAGCTGTTGCTGATAACCTCCTCTTTTATCTTGGA
AGTGCCAAATTTATTGACTTTCTGGCTATAGAAATGCGTAAAGGCAAAGTCAGCT
TCCTCTGGGATGTTGGATCTGGAGTTGGACGTGTAGAGTACCCAGATTTGACTAT
TGATGACTCATATTGGTACCGTATCGTAGCATCAAGAACTGGGAGAAATGGAAC
TATTTCTGTGAGAGCCCTGGATGGACCCAAAGCCAGCATTGTGCCCAGCACACAC
CATTCGACGTCTCCTCCAGGGTACACGATTCTAGATGTGGATGCAAATGCAATGC
TGTTTGTTGGTGGCCTGACTGGGAAATTAAAGAAGGCTGATGCTGTACGTGTGAT
TACATTCACTGGCTGCATGGGAGAAACATACTTTGACAACAAACCTATAGGTTTG
TGGAATTTCCGAGAAAAAGAAGGTGACTGCAAAGGATGCACTGTCAGTCCTCAG
GTGGAAGATAGTGAGGGGACTATTCAATTTGATGGAGAAGGTTATGCATTGGTC
AGCCGTCCCATTCGCTGGTACCCCAACATCTCCACTGTCATGTTCAAGTTCAGAA
CATTTTCTTCGAGTGCTCTTCTGATGTATCTTGCCACACGAGACCTGAGAGATTTC
ATGAGTGTGGAGCTCACTGATGGGCACATAAAAGTCAGTTACGATCTGGGCTCA
GGAATGGCTTCCGTTGTCAGCAATCAAAACCATAATGATGGGAAATGGAAATCA
TTCACTCTGTCAAGAATTCAAAAACAAGCCAATATATCAATTGTAGATATAGATA
CTAATCAGGAGGAGAATATAGCAACTTCGTCTTCTGGAAACAACTTTGGTCTTGA
CTTGAAAGCAGATGACAAAATATATTTTGGTGGCCTGCCAACGCTGAGAAACTTG
AGTATGAAAGCAAGGCCAGAAGTAAATCTGAAGAAATATTCCGGCTGCCTCAAA
GATATTGAAATTTCAAGAACTCCGTACAATATACTCAGTAGTCCCGATTATGTTG
GTGTTACCAAAGGATGTTCCCTGGAGAATGTTTACACAGTTAGCTTTCCTAAGCC
TGGTTTTGTGGAGCTCTCCCCTGTGCCAATTGATGTAGGAACAGAAATCAACCTG
TCATTCAGCACCAAGAATGAGTCCGGCATCATTCTTTTGGGAAGTGGAGGGACAC
CAGCACCACCTAGGAGAAAACGAAGGCAGACTGGACAGGCCTATTATGTAAT
ACTCCTCAACAGGGGCCGTCTGGAAGTGCATCTCTCCACAGGGGCACGAAC
AATGAGGAAAATTGTCATCAGACCAGAGCCGAATCTGTTTCATGATGGAAGA
GAACATTCCGTTCATGTAGAGCGAACTAGAGGCATCTTTACAGTTCAAGTGG
ATGAAAACAGAAGATACATGCAAAACCTGACAGTTGAACAGCCTATCGAAGT
TAAAAAGCTTTTCGTTGGGGGTGCTCCACCTGAATTTCAACCTTCCCCACTC
AGAAATATTCCTCCTTTTGAAGGCTGCATATGGAATCTTGTTATTAACTCTGT
CCCCATGGACTTTGCAAGGCCTGTGTCCTTCAAAAATGCTGACATTGGTCGC
TGTGCCCATCAGAAACTCCGTGAAGATGAAGATGGAGCAGCTCCAGCTGAA
ATAGTTATCCAGCCTGAGCCAGTTCCCACCCCAGCCTTTCCTACGCCCACCC
CAGTTCTGACACATGGTCCTTGTGCTGCAGAATCAGAACCAGCTCTTTTGAT
AGGGAGCAAGCAGTTCGGGCTTTCAAGAAACAGTCACATTGCAATTGCATTT
GATGACACCAAAGTTAAAAACCGTCTCACAATTGAGTTGGAAGTAAGAACCG
AAGCTGAATCCGGCTTGCTTTTTTACATGGCTCGCATCAATCATGCTGATTT

Figure 20 (Continued)

TGCAACAGTTCAGCTGAGAAATGGATTGCCCTACTTCAGCTATGACTTGGGG
AGTGGGGACACCCACACCATGATCCCCACCAAAATCAATGATGGCCAGTGG
CACAAGATTAAGATAATGAGAAGTAAGCAAGAAGGAATTCTTTATGTAGATG
GGGCTTCCAACAGAACCATCAGTCCCAAAAAAGCCGACATCCTGGATGTCG
TGGGAATGCTGTATGTTGGTGGGTTACCCATCAACTACACTACCCGAAGAAT
TGGTCCAGTGACCTATAGCATTGATGGCTGCGTCAGGAATCTCCACATGGCA
GAGGCCCCTGCCGATCTGGAACAACCCACCTCCAGCTTCCATGTTGGGACA
TGTTTTGCAAATGCTCAGAGGGGAACATATTTTGACGGAACCGGTTTTGCCA
AAGCAGTTGGTGGATTCAAAGTGGGATTGGACCTTCTTGTAGAATTTGAATT
CCGCACAACTACAACGACTGGAGTTCTTCTGGGGATCAGTAGTCAAAAAATG
GATGGAATGGGTATTGAAATGATTGATGAAAGTTGATGTTTCATGTGGACA
ATGGTGCGGGCAGATTCACTGCTGTCTATGATGCTGGGGTTCCAGGGCATT
TGTGTGATGGACAATGGCATAAAGTCACTGCCAACAAGATCAAACACCGCAT
TGAGCTCACAGTCGATGGGAACCAGGTGGAAGCCCAAAGCCCAAACCCAGC
ATCTACATCAGCTGACACAAATGACCCTGTGTTTGTTGGAGGCTTCCCAGAT
GACCTCAAGCAGTTTGGCCTAACAACCAGTATTCCGTTCCGAGGTTGCATCA
GATCCCTGAAGCTCACCAAAGGCACAGCAAGCCACTGGAGGTTAATTTTGC
CAAGGCCCTGGAACTGAACTAGTGCGGCCGCGGGGATCCAGACATGATAAGAT
ACATTGATGAGTTTGGACAAACCACAACTAGAATGCAGTGAAAAAAATGCTTTA
TTTGTGAAATTTGTGATGCTATTGCTTTATTTGTAACCATTATAAGCTGCAATAAA
CAAGTTAACAACAACAATTGCATTCATTTTATGTTTCAGGTTCAGGGGGAGGTGT
GGGAGGTTTTTTCGGATCCTCTAGAGTCGACCACATGGCTACGTAGATAATTAG
CATGGCGGGTTAATCATTAACTACAAGGAACCCCTAGTGATGGAGTTGGCC
ACTCCCTCTCTGCGCGCTCGCTCGCTCACTGAGGCCGGGCGACCAAAGGTC
GCCCGACGCCCGGGCTTTGCCCGGGCGGCCTCAGTGAGCGAGCGAGCGCG
CNNNNNNCAGCTGCATTAATGAATCGGCCAACGCGCGGGGAGAGGCGGTTTGCG
TATTGGGCMG

SEQ ID NO: 6 pAAV.CMV.HB.LAMA2(G3-G5)

Main Characteristics
Ampicillin Resistance Gene
ITRs
*CMV Promoter*
SV40 Enhancer
HBEGF Signal Peptide
HBEGF Propeptide Domain
HBEGF Mature Peptide Domain
HBEGF HB Domain
LAMA2 G3-G5
SV40 PolyA Tail GCTCTTCCGCTTGGTCGCTCACTGACTCGCTGCGCTCGGTCGTTCGGCTGCGGCG
AGCGGTATCAGCTCACTCAAACCCGGTAATACGGTTATCCACAGAATCAGGGGA
TAACGCAGGAAAGAACATGTGAGCAAAAGGCCAGCAAAAGGCCAGGAACCGTA
AAAAGGCCGCGTTGCTGGCGTTTTTCCATAGGCTCCGCCCCCCTGACGAGCATCA
CAAAAATCGACGCTCAAGTCAGAGGTGGCGAAACCCGACAGGACTATAAAGATA
CCAGGCGTTTCCCCCTGGAAGCTCCCTCGTGCGCTCTCCTGTTCCGACCCTGCCGC
TTACCGGATACCTGTCCGCCTTTCTCCCTTCGGGAAGCGTGGCGCTTTCTCATAGC
TCACGCTGTAGGTATCTCAGTTCGGTGTAGGTCGTTCGCTCCAAGCTGGGCTGTG
TGCACGAACCCCCCGTTCAGCCCGACCGCTGCGCCTTATCCGGTAACTATCGTCT
TGAGTCCAACCCGGTAAGACACGACTTATCGCCACTGGCAGCAGCCACTGGTAA
CAGGATTAGCAGAGCGAGGTATGTACGCGGTGCTACAGAGTTCTTGAAGTGGTG
GCCTAACTACGGCTACACTAGAAGGACAGTATTTGGTATCTGCGCTCTGCTGAAG
CCAGTTACCTTCGGAAAAAGAGTTGGTAGCTCTTGATCCGGCAAACAAACCACC
GCTGGTAGCGGTGGTTTTTTTGTTTGCAAGCAGCAGATTACGCGCAGAAAAAAAG
GATCTCAAGAAGATCCTTTGATCTTTTCTACGGGGTCTGACGCTCAGTGGAACGA
AAACTCACGTTAAGGGATTTTGGTCATGAGATTATCAAAAAGGATCTTCACCTAG
ATCCTTTTAAATTAAAAATGAAGTTTTAAATCAATCTAAAGTATATATGAGTAAA
CTTGGTCTGACAGTTACCAATGCTTAATCAGTGAGGCACCTATCTCAGCGATCTG
TCTATTTCGTTCATCCATAGTTGCCTGACTCCCCGTCGTGTAGATAACTACGATAC
GGGAGGGCTTACCATCTGGCCCCAGTGCTGCAATGATACCGCGAGACCCACGCT
CACCGGCTCCAGATTTATCAGCAATAAACCAGCCAGCCGGAAGGGCCGAGCGCA
GAAGTGGTCCTGCAACTTTATCCGCCTCCATCCAGTCTATTAATTGTTGCCGGGA
AGCTAGAGTAAGTAGTTCGCCAGTTAATAGTTTGCGCAACGTTGTTGCCATTGCT
ACAGGCATCGTGGTGTCACGCTCGTCGTTTGGTATGGCTTCATTCAGCTCCGGTTC
CCAACGATCAAGGCGAGTTACATGATCCCCCATGTTGTGCAAAAAAGCGGTTAG
CTCCTTCGGTCCTCCGATCGTTGTCAGAAGTAAGTTGGCCGCAGTGTTATCACTC
ATGGTTATGGCAGCACTGCATAATTCTCTTACTGTCATGCCATCCGTAAGATGCTT
TTCTGTGACTGGTGAGTACTCAACCAAGTCATTCTGAGAATAGTGTATGCGGCGA CCGAGTTGCTCTTGCCCGGCGTCAATACGGGATAATACCGCGCCACATAGCAGA
ACTTTAAAAGTGCTCATCATTGGAAAACGTTCTTCGGGGCGAAAACTCTCAAGGA
TCTTACCGCTGTTGAGATCCAGTTCGATGTAACCCACTCGTGCACCCAACTGATC
TTCAGCATCTTTTACTTTCACCAGCGTTTCTGGGTGAGCAAAAACAGGAAGGCAA
AATGCCGCAAAAAAGGGAATAAGGGCGACACGGAAATGTTGAATACTCATACTC
TTCCTTTTTCAATATTATTGAAGCATTTATCAGGGTTATTGTCTCATGAGCGGATA
CATATTTGAATGTATTTAGAAAAATAAACAAATAGGGGTTCCGCGCACATTTCCC
CGAAAAGTGCCACCTGACGTCTAAGAAACCATCGTTACATAACTTACGGTATATT
ATCATGACATTAACCTATAAAAATAGGCGTATCACGAGGCCCTTTCGTCTCGCGC
GTTTCGGTGATGACGGTGAAAACCTCTGACACATGCAGCTCCCGGAGACGGTCA
CAGCTTGTCTGTAAGCGGATGCCGGGAGCAGACAAGCCCGTCAGGGCGCGTCAG
CGGGTGTTGGCGGGTGTCGGGGCTGGCTTAACTATGCGGCATCAGAGCAGATTGT
ACTGAGAGTGCACCATATGCGGTGTGAAATACCGCACAGATGCGTAAGGAGAAA
ATACCGCATCAGGAACTTCCAACATCCAATAAATCATACAGGCAAGGCAAAGAA
TTAGCAAAATTAAGCAATAAAGCCTCAGAGCATAAAGCTAAATCGGTTGTACCA
AAAACATTATGACCCTGTAATACTTTTGCGGGAGAAGCCTTTATTTCAACGCAAG
GATAAAAATTTTTAGAACCCTCATATATTTTAAATGCAATGCCTGAGTAATGTGT
AGGTAAAGATTCAAACGGGTGAGAAAGGCCGGAGACAGTCAAATCACCATCAAT
ATGATATTCAACCGTTCTAGCTGATAAATTCATGCCGGAGAGGGTAGCTATTTTT
GAGAGGTCTCTACAAAGGCTATCAGGTCATTGCCTGAGAGTCTGGAGCAAACAA
GAGAATCGATGAACGGTAATCGTAAAACTAGCATGTCAATCATATGTACCCCGG
TTGATAATCAGAAAAGCCCCAAAAACAGGAAGATTGTATAAGCAAATATTTAAA
TTGTAAACGTTAATATTTTGTTAAAATTCGCGTTAAATTTTGTTAAATCAGCTCA
TTTTTTAACCAATAGGCCGAAATCGGCAAAATCCCTTATAAATCAAAAGAATAGA
CCGAGATAGGGTTGAGTGTTGTTCCAGTTTGGAACAAGAGTCCACTATTAAAGAA
CGTGGACTCCAACGTCAAAGGGCGAAAAACCGTCTATCAGGGCGATGGCCCACT
ACGTGAACCATCACCCTAATCAAGTTTTTTGGGGTCGAGGTGCCGTAAATCACTA
AATCGGAACCCTAAAGGGAGCCCCCGATTTAGAGCTTGACGGGGAAAGCCGGCG
AACGTGGCGAGAAAGGAAGGGAAGAAAGCGAAAGGAGCGGGCGCTAGGGCGCT
GGCAAGTGTAGCGGTCACGCTGCGCGTAACCACCACACCCGCCGCGCTTAATGC
GCCGCTACAGGGCGCGTACTATGGTTGCTTTGACGAGCACGTATAACGTGCTTTC
CTCGTTAGAATCAGAGCGGGAGCTAAACAGGAGGCCGATTAAAGGGATTTTAGA
CAGGAACGGTACGCCAGAATCCTGAGAAGTGTTTTTATAATCAGTGAGGCCACC
GAGTAAAAGAGTCTGTCCATCACGCAAATTAACCGTTGTCGCAATACTTCTTTGA
TTAGTAATAACATCACTTGCCTGAGTAGAAGAACTCAAACTATCGGCCTTGCTGG
TAATATCCAGAACAATATTACCGCCAGCCATTGCAACAGGAAAAACGCTCATGG
AAATACCTACATTTTGACGCTCAATCGTCTGGAACTTCCATTCGCCATTCAGGCT
GCGCAACTGTTGGGAAGGGCGATCGGTGCGGGCCTCTTCGCTATTACGCCAGCTG
NNNNNGCGCTCGCTCGCTCACTGAGGCCGCCCGGGCAAAGCCCGGGCG
TCGGGCGACCTTTGGTCGCCCGGCCTCAGTGAGCGAGCGAGCGCGCAGAGA
GGGAGTGGCCAACTCCATCACTAGGGGTTCCTTGTAGTTAATGATTAACCCG
CCATGCTAATTATCTACGTAGCCATGTCTAGGT*CGTTACATAACTTACGGTAAAT*
*GGCCCGCCTGGCTGACCGCCCAACGACCCCCGCCCATTGACGTCAATAATGACGTAT*
*GTTCCCATAGTAACGCCAATAGGGACTTTCCATTGACGTCAATGGGTGGAGTATTTACG*

Figure 21 (Continued)

*GTAAACTGCCCACTTGGCAGTACATCAAGTGTATCATATGCCAAGTACGCCCCCTATTG*
*ACGTCAATGACGGTAAATGGCCCGCCTGGCATTATGCCCAGTACATGACCTTATGGGA*
*CTTTCCTACTTGGCAGTACATCTACGTATTAGTCATCGCTATTACCATGGTGATGCGGTT*
*TTGGCAGTACATCAATGGGCGTGGATAGCGGTTTGACTCACGGGGATTTCCAAGTCTC*
*CACCCCATTGACGTCAATGGGAGTTTGTTTTGGCACCAAAATCAACGGGACTTTCCAAA*
*ATGTCGTAACAACTCCGCCCCATTGACGCAAATGGGCGGTAGGCGTGTACGGTGGGA*
*GGTCTATATAAGCAGAGCTCGTTTAGTGAACCGTCAGATCGCCTGGAGACGCCATCC*
ACGCTGTTTTGACCTCCATAGAAGACACCGGGACCGATCCAGCCTCCGGAC*TCTA*
*GAGGATCCGGTACTCGAGGAACTGAAAAACCAGAAAGTTAACTGGTAAGTTTAGTCTTT*
*TTGTCTTTTATTTCAGGTCCCGGATCCGGTGGTGGTGCAAATCAAAGAACTGCTCCTCA*
*GTGGATGTTGCCTTTACTTCTAGGCCTGTACGGAAGTGTTACTTCTGCTCTAAAAGCTG*
*CGGAATTGTACCCGCGGCCGCACC*ATGAAGCTGCTGCCGTCGGTGGTGCTGAAGC
TCTTTCTGGCTGCAGTTCTCTCGGCACTGGTGACTGGCGAGAGCCTGGAGCGGC
TTCGGAGAGGGCTAGCTGCTGGAACCAGCAACCCGGACCCTCCCACTGTAT
CCACGGACCAGCTGCTACCCCTAGGAGGCGGCCGGGACCGGAAAGTCCGTG
ACTTGCAAGAGGCAGATCTGGACCTTTTGAGAGTCACTTTATCCTCCAAGCC
ACAAGCACTGGCCACACCAAACAAGGAGGAGCACGGGAAAAGAAAGAAGAA
AGGCAAGGGGCTAGGGAAGAAGAGGGACCCACAGACTGGACAGGCCTATTATG
TAATACTCCTCAACAGGGGCCGTCTGGAAGTGCATCTCTCCACAGGGGCACGAA
CAATGAGGAAAATTGTCATCAGACCAGAGCCGAATCTGTTTCATGATGGAAGAG
AACATTCCGTTCATGTAGAGCGAACTAGAGGCATCTTTACAGTTCAAGTGGATGA
AAACAGAAGATACATGCAAAACCTGACAGTTGAACAGCCTATCGAAGTTAAAAA
GCTTTTCGTTGGGGGTGCTCCACCTGAATTTCAACCTTCCCCACTCAGAAATATTC
CTCCTTTTGAAGGCTGCATATGGAATCTTGTTATTAACTCTGTCCCCATGGACTTT
GCAAGGCCTGTGTCCTTCAAAAATGCTGACATTGGTCGCTGTGCCCATCAGAAAC
TCCGTGAAGATGAAGATGGAGCAGCTCCAGCTGAAATAGTTATCCAGCCTGAGC
CAGTTCCCACCCCAGCCTTTCCTACGCCCACCCCAGTTCTGACACATGGTCCTTGT
GCTGCAGAATCAGAACCAGCTCTTTTGATAGGGAGCAAGCAGTTCGGGCTTTCAA
GAAACAGTCACATTGCAATTGCATTTGATGACACCAAAGTTAAAAACCGTCTCAC
AATTGAGTTGGAAGTAAGAACCGAAGCTGAATCCGGCTTGCTTTTTTACATGGCT
CGCATCAATCATGCTGATTTTGCAACAGTTCAGCTGAGAAATGGATTGCCCTACT
TCAGCTATGACTTGGGGAGTGGGGACACCCACACCATGATCCCCACCAAAATCA
ATGATGGCCAGTGGCACAAGATTAAGATAATGAGAAGTAAGCAAGAAGGAATTC
TTTATGTAGATGGGGCTTCCAACAGAACCATCAGTCCCAAAAAAGCCGACATCCT
GGATGTCGTGGGAATGCTGTATGTTGGTGGGTTACCCATCAACTACACTACCCGA
AGAATTGGTCCAGTGACCTATAGCATTGATGGCTGCGTCAGGAATCTCCACATGG
CAGAGGCCCCTGCCGATCTGGAACAACCCACCTCCAGCTTCCATGTTGGGACATG
TTTTGCAAATGCTCAGAGGGGAACATATTTTGACGGAACCGGTTTTGCCAAAGCA
GTTGGTGGATTCAAAGTGGGATTGGACCTTCTTGTAGAATTTGAATTCCGCACAA
CTACAACGACTGGAGTTCTTCTGGGGATCAGTAGTCAAAAAATGGATGGAATGG
GTATTGAAATGATTGATGAAAGTTGATGTTTCATGTGGACAATGGTGCGGGCAG
ATTCACTGCTGTCTATGATGCTGGGGTTCCAGGGCATTTGTGTGATGGACAATGG
CATAAAGTCACTGCCAACAAGATCAAACACCGCATTGAGCTCACAGTCGATGGG
AACCAGGTGGAAGCCCAAAGCCCAAACCCAGCATCTACATCAGCTGACACAAAT

Figure 21 (Continued)

GACCCTGTGTTTGTTGGAGGCTTCCCAGATGACCTCAAGCAGTTTGGCCTAACAA
CCAGTATTCCGTTCCGAGGTTGCATCAGATCCCTGAAGCTCACCAAAGGCACAGC
AAGCCACTGGAGGTTAATTTTGCCAAGGCCCTGGAACTGAACTAGTGCGGCCGC
GGGGATCCAGACATGATAAGATACATTGATGAGTTTGGACAAACCACAACTAGA
ATGCAGTGAAAAAAATGCTTTATTTGTGAAATTTGTGATGCTATTGCTTTATTTGT
AACCATTATAAGCTGCAATAAACAAGTTAACAACAACAATTGCATTCATTTTATG
TTTCAGGTTCAGGGGGAGGTGTGGGAGGTTTTTTCGGATCCTCTAGAGTCGACCA
CATGGCTACGTAGATAATTAGCATGGCGGGTTAATCATTAACTACAAGGAAC
CCCTAGTGATGGAGTTGGCCACTCCCTCTCTGCGCGCTCGCTCGCTCACTGA
GGCCGGGCGACCAAAGGTCGCCCGACGCCCGGGCTTTGCCCGGGCGGCCT
CAGTGAGCGAGCGAGCGCGCNNNNNNCAGCTGCATTAATGAATCGGCCAACG
CGCGGGGAGAGGCGGTTTGCGTATTGGGC

SEQ ID NO: 8 pAAV.CMV.HBEGF.LAMA2(G3-G5)

Main Characteristics
Ampicillin Resistance Gene
ITRs
*CMV Promoter*
SV40 Enhancer
HBEGF Signal Peptide
HBEGF Propeptide Domain
HBEGF Mature Peptide Domain
HBEGF HB Domain
HBEGF EGF-Like Domain
LAMA2 G3-5
SV40 PolyA Tail GCTCTTCCGCTTGGTCGCTCACTGACTCGCTGCGCTCGGTCGTTCGGCTGCGGCG
AGCGGTATCAGCTCACTCAAACCCGGTAATACGGTTATCCACAGAATCAGGGGA
TAACGCAGGAAAGAACATGTGAGCAAAAGGCCAGCAAAAGGCCAGGAACCGTA
AAAAGGCCGCGTTGCTGGCGTTTTTCCATAGGCTCCGCCCCCCTGACGAGCATCA
CAAAAATCGACGCTCAAGTCAGAGGTGGCGAAACCCGACAGGACTATAAAGATA
CCAGGCGTTTCCCCCTGGAAGCTCCCTCGTGCGCTCTCCTGTTCCGACCCTGCCGC
TTACCGGATACCTGTCCGCCTTTCTCCCTTCGGGAAGCGTGGCGCTTTCTCATAGC
TCACGCTGTAGGTATCTCAGTTCGGTGTAGGTCGTTCGCTCCAAGCTGGGCTGTG
TGCACGAACCCCCCGTTCAGCCCGACCGCTGCGCCTTATCCGGTAACTATCGTCT
TGAGTCCAACCCGGTAAGACACGACTTATCGCCACTGGCAGCAGCCACTGGTAA
CAGGATTAGCAGAGCGAGGTATGTACGCGGTGCTACAGAGTTCTTGAAGTGGTG
GCCTAACTACGGCTACACTAGAAGGACAGTATTTGGTATCTGCGCTCTGCTGAAG
CCAGTTACCTTCGGAAAAAGAGTTGGTAGCTCTTGATCCGGCAAACAAACCACC
GCTGGTAGCGGTGGTTTTTTTGTTTGCAAGCAGCAGATTACGCGCAGAAAAAAAG
GATCTCAAGAAGATCCTTTGATCTTTTCTACGGGGTCTGACGCTCAGTGGAACGA
AAACTCACGTTAAGGGATTTTGGTCATGAGATTATCAAAAAGGATCTTCACCTAG
ATCCTTTTAAATTAAAAATGAAGTTTTAAATCAATCTAAAGTATATATGAGTAAA
CTTGGTCTGACAGTTACCAATGCTTAATCAGTGAGGCACCTATCTCAGCGATCTG
TCTATTTCGTTCATCCATAGTTGCCTGACTCCCCGTCGTGTAGATAACTACGATAC
GGGAGGGCTTACCATCTGGCCCCAGTGCTGCAATGATACCGCGAGACCCACGCT
CACCGGCTCCAGATTTATCAGCAATAAACCAGCCAGCCGGAAGGGCCGAGCGCA
GAAGTGGTCCTGCAACTTTATCCGCCTCCATCCAGTCTATTAATTGTTGCCGGGA
AGCTAGAGTAAGTAGTTCGCCAGTTAATAGTTTGCGCAACGTTGTTGCCATTGCT
ACAGGCATCGTGGTGTCACGCTCGTCGTTTGGTATGGCTTCATTCAGCTCCGGTTC
CCAACGATCAAGGCGAGTTACATGATCCCCCATGTTGTGCAAAAAAGCGGTTAG
CTCCTTCGGTCCTCCGATCGTTGTCAGAAGTAAGTTGGCCGCAGTGTTATCACTC
ATGGTTATGGCAGCACTGCATAATTCTCTTACTGTCATGCCATCCGTAAGATGCTT
TTCTGTGACTGGTGAGTACTCAACCAAGTCATTCTGAGAATAGTGTATGCGGCGA
CCGAGTTGCTCTTGCCCGGCGTCAATACGGGATAATACCGCGCCACATAGCAGA
ACTTTAAAAGTGCTCATCATTGGAAAACGTTCTTCGGGGCGAAAACTCTCAAGGA
TCTTACCGCTGTTGAGATCCAGTTCGATGTAACCCACTCGTGCACCCAACTGATC

```
TTCAGCATCTTTTACTTTCACCAGCGTTTCTGGGTGAGCAAAAACAGGAAGGCAA
AATGCCGCAAAAAAGGGAATAAGGGCGACACGGAAATGTTGAATACTCATACTC
TTCCTTTTTCAATATTATTGAAGCATTTATCAGGGTTATTGTCTCATGAGCGGATA
CATATTTGAATGTATTTAGAAAAATAAACAAATAGGGGTTCCGCGCACATTTCCC
CGAAAAGTGCCACCTGACGTCTAAGAAACCATTATTATCATGACATTAACCTATA
AAAATAGGCGTATCACGAGGCCCTTTCGTCTCGCGCGTTTCGGTGATGACGGTGA
AAACCTCTGACACATGCAGCTCCCGGAGACGGTCACAGCTTGTCTGTAAGCGGAT
GCCGGGAGCAGACAAGCCCGTCAGGGCGCGTCAGCGGGTGTTGGCGGGTGTCGG
GGCTGGCTTAACTATGCGGCATCAGAGCAGATTGTACTGAGAGTGCACCATATGC
GGTGTGAAATACCGCACAGATGCGTAAGGAGAAAATACCGCATCAGGAACTTCC
AACATCCAATAAATCATACAGGCAAGGCAAAGAATTAGCAAAATTAAGCAATAA
AGCCTCAGAGCATAAAGCTAAATCGGTTGTACCAAAAACATTATGACCCTGTAAT
ACTTTTGCGGGAGAAGCCTTTATTTCAACGCAAGGATAAAAATTTTAGAACCCT
CATATATTTTAAATGCAATGCCTGAGTAATGTGTAGGTAAAGATTCAAACGGGTG
AGAAAGGCCGGAGACAGTCAAATCACCATCAATATGATATTCAACCGTTCTAGC
TGATAAATTCATGCCGGAGAGGGTAGCTATTTTTGAGAGGTCTCTACAAAGGCTA
TCAGGTCATTGCCTGAGAGTCTGGAGCAAACAAGAGAATCGATGAACGGTAATC
GTAAAACTAGCATGTCAATCATATGTACCCCGGTTGATAATCAGAAAAGCCCCA
AAAACAGGAAGATTGTATAAGCAAATATTTAAATTGTAAACGTTAATATTTTGTT
AAAATTCGCGTTAAATTTTGTTAAATCAGCTCATTTTTTAACCAATAGGCCGAA
ATCGGCAAAATCCCTTATAAATCAAAGAATAGACCGAGATAGGGTTGAGTGTT
GTTCCAGTTTGGAACAAGAGTCCACTATTAAAGAACGTGGACTCCAACGTCAAA
GGGCGAAAAACCGTCTATCAGGGCGATGGCCCACTACGTGAACCATCACCCTAA
TCAAGTTTTTTGGGGTCGAGGTGCCGTAAATCACTAAATCGGAACCCTAAAGGGA
GCCCCCGATTTAGAGCTTGACGGGGAAAGCCGGCGAACGTGGCGAGAAAGGAA
GGGAAGAAAGCGAAAGGAGCGGGCGCTAGGGCGCTGGCAAGTGTAGCGGTCAC
GCTGCGCGTAACCACCACACCCGCCGCGCTTAATGCGCCGCTACAGGGCGCGTA
CTATGGTTGCTTTGACGAGCACGTATAACGTGCTTTCCTCGTTAGAATCAGAGCG
GGAGCTAAACAGGAGGCCGATTAAAGGGATTTTAGACAGGAACGGTACGCCAGA
ATCCTGAGAAGTGTTTTTATAATCAGTGAGGCCACCGAGTAAAAGAGTCTGTCCA
TCACGCAAATTAACCGTTGTCGCAATACTTCTTTGATTAGTAATAACATCACTTGC
CTGAGTAGAAGAACTCAAACTATCGGCCTTGCTGGTAATATCCAGAACAATATTA
CCGCCAGCCATTGCAACAGGAAAAACGCTCATGGAAATACCTACATTTTGACGCT
CAATCGTCTGGAACTTCCATTCGCCATTCAGGCTGCGCAACTGTTGGGAAGGGCG
ATCGGTGCGGGCCTCTTCGCTATTACGCCAGCTGNNNNNNGCGCGCTCGCTCGC
TCACTGAGGCCGCCCGGGCAAAGCCCGGGCGTCGGGCGACCTTTGGTCGCC
CGGCCTCAGTGAGCGAGCGAGCGCGCAGAGAGGGAGTGGCCAACTCCATCA
CTAGGGGTTCCTTGTAGTTAATGATTAACCCGCCATGCTAATTATCTACGTA
GCCATGTCTAGGGTCGTTACATAACTTACGGTAAATGGCCCGCCTGGCTGACCGCCC
AACGACCCCCGCCCATTGACGTCAATAATGACGTATGTTCCCATAGTAACGCCAATAGG
GACTTTCCATTGACGTCAATGGGTGGAGTATTTACGGTAAACTGCCCACTTGGCAGTAC
ATCAAGTGTATCATATGCCAAGTACGCCCCCTATTGACGTCAATGACGGTAAATGGCCC
GCCTGGCATTATGCCCAGTACATGACCTTATGGGACTTTCCTACTTGGCAGTACATCTA
CGTATTAGTCATCGCTATTACCATGGTGATGCGGTTTTGGCAGTACATCAATGGGCGTG
GATAGCGGTTTGACTCACGGGGATTTCCAAGTCTCCACCCCATTGACGTCAATGGGAG
TTTGTTTTGGCACCAAAATCAACGGGACTTTCCAAAATGTCGTAACAACTCCGCCCCAT
TGACGCAAATGGGCGGTAGGCGTGTACGGTGGGAGGTCTATATAAGCAGAGCTCGTTT
AGTGAACCGTCAGATCGCCTGGAGACGCCATCCACGCTGTTTTGACCTCCATAGAA
GACACCGGGACCGATCCAGCCTCCGGACTCTAGAGGATCCGGTACTCGAGGAACTG
AAAAACCAGAAAGTTAACTGGTAAGTTTAGTCTTTTTGTCTTTTATTTCAGGTCCCGGAT
```

Figure 22 (Continued)

*CCGGTGGTGGTGCAAATCAAAGAACTGCTCCTCAGTGGATGTTGCCTTTACTTCTAGG*
*CCTGTACGGAAGTGTTACTTCTGCTCTAAAAGCTGCGGAATTGTACCCGCGGCCGCAC*
CATGAAGCTGCTGCCGTCGGTGGTGCTGAAGCTCTTTCTGGCTGCAGTTCTCTCG
GCACTGGTGACTGGCGAGAGCCTGGAGCGGCTTCGGAGAGGGCTAGCTGCTG
GAACCAGCAACCCGGACCCTCCCACTGTATCCACGGACCAGCTGCTACCCC
TAGGAGGCGGCCGGGACCGGAAAGTCCGTGACTTGCAAGAGGCAGATCTGG
ACCTTTTGAGAGTCACTTTATCCTCCAAGCCACAAGCACTGGCCACACCAAA
CAAGGAGGAGCACGGGAAAAGAAAGAAGAAAGGCAAGGGGCTAGGGAAGAA
GAGGGACCCATGTCTTCGGAAATACAAGGACTTCTGCATCCATGGAGAATGC
AAATATGTGAAGGAGCTCCGGGCTCCCTCCTGCATCTGCCACCCGGGTTAC
CATGGAGAGAGGTGTCATGGGCTGAGCCTCCCACAGACTGGACAGGCCTATT
ATGTAATACTCCTCAACAGGGGCCGTCTGGAAGTGCATCTCTCCACAGGGGCACG
AACAATGAGGAAAATTGTCATCAGACCAGAGCCGAATCTGTTTCATGATGGAAG
AGAACATTCCGTTCATGTAGAGCGAACTAGAGGCATCTTTACAGTTCAAGTGGAT
GAAAACAGAAGATACATGCAAAACCTGACAGTTGAACAGCCTATCGAAGTTAAA
AAGCTTTTCGTTGGGGGTGCTCCACCTGAATTTCAACCTTCCCCACTCAGAAATA
TTCCTCCTTTTGAAGGCTGCATATGGAATCTTGTTATTAACTCTGTCCCATGGAC
TTTGCAAGGCCTGTGTCCTTCAAAAATGCTGACATTGGTCGCTGTGCCCATCAGA
AACTCCGTGAAGATGAAGATGGAGCAGCTCCAGCTGAAATAGTTATCCAGCCTG
AGCCAGTTCCCACCCCAGCCTTTCCTACGCCCACCCCAGTTCTGACACATGGTCC
TTGTGCTGCAGAATCAGAACCAGCTCTTTTGATAGGGAGCAAGCAGTTCGGGCTT
TCAAGAAACAGTCACATTGCAATTGCATTTGATGACACCAAAGTTAAAAACCGTC
TCACAATTGAGTTGGAAGTAAGAACCGAAGCTGAATCCGGCTTGCTTTTTTACAT
GGCTCGCATCAATCATGCTGATTTTGCAACAGTTCAGCTGAGAAATGGATTGCCC
TACTTCAGCTATGACTTGGGGAGTGGGGACACCCACACCATGATCCCCACCAAA
ATCAATGATGGCCAGTGGCACAAGATTAAGATAATGAGAAGTAAGCAAGAAGG
AATTCTTTATGTAGATGGGGCTTCCAACAGAACCATCAGTCCCAAAAAAGCCGAC
ATCCTGGATGTCGTGGGAATGCTGTATGTTGGTGGGTTACCCATCAACTACACTA
CCCGAAGAATTGGTCCAGTGACCTATAGCATTGATGGCTGCGTCAGGAATCTCCA
CATGGCAGAGGCCCCTGCCGATCTGGAACAACCCACCTCCAGCTTCCATGTTGGG
ACATGTTTTGCAAATGCTCAGAGGGGAACATATTTTGACGGAACCGGTTTTGCCA
AAGCAGTTGGTGGATTCAAAGTGGGATTGGACCTTCTTGTAGAATTTGAATTCCG
CACAACTACAACGACTGGAGTTCTTCTGGGGATCAGTAGTCAAAAAATGGATGG
AATGGGTATTGAAATGATTGATGAAAGTTGATGTTTCATGTGGACAATGGTGCG
GGCAGATTCACTGCTGTCTATGATGCTGGGGTTCCAGGGCATTTGTGTGATGGAC
AATGGCATAAAGTCACTGCCAACAAGATCAAACACCGCATTGAGCTCACAGTCG
ATGGGAACCAGGTGGAAGCCCAAAGCCCAAACCCAGCATCTACATCAGCTGACA
CAAATGACCCTGTGTTTGTTGGAGGCTTCCCAGATGACCTCAAGCAGTTTGGCCT
AACAACCAGTATTCCGTTCCGAGGTTGCATCAGATCCCTGAAGCTCACCAAAGGC
ACAGCAAGCCACTGGAGGTTAATTTTGCCAAGGCCCTGGAACTGAACTAGTGCG
GCCGCGGGGATCCAGACATGATAAGATACATTGATGAGTTTGGACAAACCACAA
CTAGAATGCAGTGAAAAAAATGCTTTATTTGTGAAATTTGTGATGCTATTGCTTT
ATTTGTAACCATTATAAGCTGCAATAAACAAGTTAACAACAACAATTGCATTCAT
TTTATGTTTCAGGTTCAGGGGGAGGTGTGGGAGGTTTTTTCGGATCCTCTAGAGT
CGACCACATGGCTACGTAGATAATTAGCATGGCGGGTTAATCATTAACTACAAG
GAACCCCTAGTGATGGAGTTGGCCACTCCCTCTCTGCGCGCTCGCTCGCTCACTG
AGGCCGGGCGACCAAAGGTCGCCCGACGCCCGGGCTTTGCCCGGGCGGCCTCAG
TGAGCGAGCGAGCGCGCNNNNNNCAGCTGCATTAATGAATCGGCCAACGCGCGG
GGAGAGGCGGTTTGCGTATTGGGC

<center>Figure 22 (Continued)</center>

Figure 23

SEQ ID NO: 10 pAAV.CMV.HB.DAG1a

Main Characteristics
Ampicillin Resistance Gene
ITRs
*CMV Promoter*
SV40 Enhancer
HBEGF Signal Peptide
HBEGF Propeptide Domain
HBEGF Mature Peptide Domain
HBEGF HB Domain
DAG1a
SV40 PolyA Tail GCTCTTCCGCTTGGTCGCTCACTGACTCGCTGCGCTCGGTCGTTCGGCTGCGGCG
AGCGGTATCAGCTCACTCAAACCCGGTAATACGGTTATCCACAGAATCAGGGGA
TAACGCAGGAAAGAACATGTGAGCAAAAGGCCAGCAAAAGGCCAGGAACCGTA
AAAAGGCCGCGTTGCTGGCGTTTTTCCATAGGCTCCGCCCCCCTGACGAGCATCA
CAAAAATCGACGCTCAAGTCAGAGGTGGCGAAACCCGACAGGACTATAAAGATA
CCAGGCGTTTCCCCCTGGAAGCTCCCTCGTGCGCTCTCCTGTTCCGACCCTGCCGC
TTACCGGATACCTGTCCGCCTTTCTCCCTTCGGGAAGCGTGGCGCTTTCTCATAGC
TCACGCTGTAGGTATCTCAGTTCGGTGTAGGTCGTTCGCTCCAAGCTGGGCTGTG
TGCACGAACCCCCCGTTCAGCCCGACCGCTGCGCCTTATCCGGTAACTATCGTCT
TGAGTCCAACCCGGTAAGACACGACTTATCGCCACTGGCAGCAGCCACTGGTAA
CAGGATTAGCAGAGCGAGGTATGTACGCGGTGCTACAGAGTTCTTGAAGTGGTG
GCCTAACTACGGCTACACTAGAAGGACAGTATTTGGTATCTGCGCTCTGCTGAAG
CCAGTTACCTTCGGAAAAAGAGTTGGTAGCTCTTGATCCGGCAAACAAACCACC
GCTGGTAGCGGTGGTTTTTTTGTTTGCAAGCAGCAGATTACGCGCAGAAAAAAAG
GATCTCAAGAAGATCCTTTGATCTTTTCTACGGGGTCTGACGCTCAGTGGAACGA
AAACTCACGTTAAGGGATTTTGGTCATGAGATTATCAAAAAGGATCTTCACCTAG
ATCCTTTTAAATTAAAAATGAAGTTTTAAATCAATCTAAAGTATATATGAGTAAA
CTTGGTCTGACAGTTACCAATGCTTAATCAGTGAGGCACCTATCTCAGCGATCTG
TCTATTTCGTTCATCCATAGTTGCCTGACTCCCCGTCGTGTAGATAACTACGATAC
GGGAGGGCTTACCATCTGGCCCCAGTGCTGCAATGATACCGCGAGACCCACGCT
CACCGGCTCCAGATTTATCAGCAATAAACCAGCCAGCCGGAAGGGCCGAGCGCA
GAAGTGGTCCTGCAACTTTATCCGCCTCCATCCAGTCTATTAATTGTTGCCGGGA
AGCTAGAGTAAGTAGTTCGCCAGTTAATAGTTTGCGCAACGTTGTTGCCATTGCT
ACAGGCATCGTGGTGTCACGCTCGTCGTTTGGTATGGCTTCATTCAGCTCCGGTTC
CCAACGATCAAGGCGAGTTACATGATCCCCCATGTTGTGCAAAAAAGCGGTTAG
CTCCTTCGGTCCTCCGATCGTTGTCAGAAGTAAGTTGGCCGCAGTGTTATCACTC
ATGGTTATGGCAGCACTGCATAATTCTCTTACTGTCATGCCATCCGTAAGATGCTT
TTCTGTGACTGGTGAGTACTCAACCAAGTCATTCTGAGAATAGTGTATGCGGCGA
CCGAGTTGCTCTTGCCCGGCGTCAATACGGGATAATACCGCGCCACATAGCAGA
ACTTTAAAAGTGCTCATCATTGGAAAACGTTCTTCGGGGCGAAAACTCTCAAGGA
TCTTACCGCTGTTGAGATCCAGTTCGATGTAACCCACTCGTGCACCCAACTGATC TTCAGCATCTTTTACTTTCACCAGCGTTTCTGGGTGAGCAAAAACAGGAAGGCAA
AATGCCGCAAAAAAGGGAATAAGGGCGACACGGAAATGTTGAATACTCATACTC
TTCCTTTTTCAATATTATTGAAGCATTTATCAGGGTTATTGTCTCATGAGCGGATA
CATATTTGAATGTATTTAGAAAAATAAACAAATAGGGGTTCCGCGCACATTTCCC
CGAAAAGTGCCACCTGACGTCTAAGAAACCATTATTATCATGACATTAACCTATA
AAAATAGGCGTATCACGAGGCCCTTTCGTCTCGCGCGTTTCGGTGATGACGGTGA
AAACCTCTGACACATGCAGCTCCCGGAGACGGTCACAGCTTGTCTGTAAGCGGAT
GCCGGGAGCAGACAAGCCCGTCAGGGCGCGTCAGCGGGTGTTGGCGGGTGTCGG
GGCTGGCTTAACTATGCGGCATCAGAGCAGATTGTACTGAGAGTGCACCATATGC
GGTGTGAAATACCGCACAGATGCGTAAGGAGAAAATACCGCATCAGGAACTTCC
AACATCCAATAAATCATACAGGCAAGGCAAAGAATTAGCAAAATTAAGCAATAA
AGCCTCAGAGCATAAAGCTAAATCGGTTGTACCAAAAACATTATGACCCTGTAAT
ACTTTTGCGGGAGAAGCCTTTATTTCAACGCAAGGATAAAAATTTTAGAACCCT
CATATATTTTAAATGCAATGCCTGAGTAATGTGTAGGTAAAGATTCAAACGGGTG
AGAAAGGCCGGAGACAGTCAAATCACCATCAATATGATATTCAACCGTTCTAGC
TGATAAATTCATGCCGGAGAGGGTAGCTATTTTTGAGAGGTCTCTACAAAGGCTA
TCAGGTCATTGCCTGAGAGTCTGGAGCAAACAAGAGAATCGATGAACGGTAATC
GTAAAACTAGCATGTCAATCATATGTACCCCGGTTGATAATCAGAAAAGCCCCA
AAAACAGGAAGATTGTATAAGCAAATATTTAAATTGTAAACGTTAATATTTGTT
AAAATTCGCGTTAAATTTTGTTAAATCAGCTCATTTTTTAACCAATAGGCCGAA
ATCGGCAAAATCCCTTATAAATCAAAGAATAGACCGAGATAGGGTTGAGTGTT
GTTCCAGTTTGGAACAAGAGTCCACTATTAAAGAACGTGGACTCCAACGTCAAA
GGGCGAAAAACCGTCTATCAGGGCGATGGCCCACTACGTGAACCATCACCCTAA
TCAAGTTTTTTGGGGTCGAGGTGCCGTAAATCACTAAATCGGAACCCTAAAGGGA
GCCCCCGATTTAGAGCTTGACGGGGAAAGCCGGCGAACGTGGCGAGAAAGGAA
GGGAAGAAAGCGAAAGGAGCGGGCGCTAGGGCGCTGGCAAGTGTAGCGGTCAC
GCTGCGCGTAACCACCACACCCGCCGCGCTTAATGCGCCGCTACAGGGCGCGTA
CTATGGTTGCTTTGACGAGCACGTATAACGTGCTTTCCTCGTTAGAATCAGAGCG
GGAGCTAAACAGGAGGCCGATTAAAGGGATTTTAGACAGGAACGGTACGCCAGA
ATCCTGAGAAGTGTTTTTATAATCAGTGAGGCCACCGAGTAAAAGAGTCTGTCCA
TCACGCAAATTAACCGTTGTCGCAATACTTCTTTGATTAGTAATAACATCACTTGC
CTGAGTAGAAGAACTCAAACTATCGGCCTTGCTGGTAATATCCAGAACAATATTA
CCGCCAGCCATTGCAACAGGAAAAACGCTCATGGAAATACCTACATTTTGACGCT
CAATCGTCTGGAACTTCCATTCGCCATTCAGGCTGCGCAACTGTTGGGAAGGGCG
ATCGGTGCGGGCCTCTTCGCTATTACGCCAGCTGNNNNNNGCGCGCTCGCTCGC
TCACTGAGGCCGCCCGGGCAAAGCCCGGGCGTCGGGCGACCTTTGGTCGCC
CGGCCTCAGTGAGCGAGCGAGCGCGCAGAGAGGGAGTGGCCAACTCCATCA
CTAGGGGTTCCTTGTAGTTAATGATTAACCCGCCATGCTAATTATCTACGTA
GCCATG*TCTAGGGTCGTTACATAACTTACGGTAAATGGCCCGCCTGGCTGACCGCCC*
*AACGACCCCCGCCCATTGACGTCAATAATGACGTATGTTCCCATAGTAACGCCAATAGG*
*GACTTTCCATTGACGTCAATGGGTGGAGTATTTACGGTAAACTGCCCACTTGGCAGTAC*
*ATCAAGTGTATCATATGCCAAGTACGCCCCCTATTGACGTCAATGACGGTAAATGGCCC*
*GCCTGGCATTATGCCCAGTACATGACCTTATGGGACTTTCCTACTTGGCAGTACATCTA*
*CGTATTAGTCATCGCTATTACCATGGTGATGCGGTTTTGGCAGTACATCAATGGGCGTG*
*GATAGCGGTTTGACTCACGGGGATTTCCAAGTCTCCACCCCATTGACGTCAATGGGAG*
*TTTGTTTTGGCACCAAAATCAACGGGACTTTCCAAAATGTCGTAACAACTCCGCCCCAT*
*TGACGCAAATGGGCGGTAGGCGTGTACGGTGGGAGGTCTATATAAGCAGAGCTCGTTT*
*AGTGAACCGTCAGATCGCCTGGAGACGCCATCCACGCTGTTTTGACCTCCATAGAA*
*GACACCGGGACCGATCCAGCCTCCGGAC*<ins>*TCTAGAGGATCCGGTACTCGAGGAACTG*</ins>
<ins>*AAAAACCAGAAAGTTAACTGGTAAGTTTAGTCTTTTTGTCTTTTATTTCAGGTCCCGGAT*</ins>

Figure 23 (Continued)

*CCGGTGGTGGTGCAAATCAAAGAACTGCTCCTCAGTGGATGTTGCCTTTACTTCTAGG*
*CCTGTACGGAAGTGTTACTTCTGCTCTAAAAGCTGCGGAATTGTACCCGCGGCCGCAC*
CATGAAGCTGCTGCCGTCGGTGGTGCTGAAGCTCTTTCTGGCTGCAGTTCTCTCG
GCACTGGTGACTGGCGAGAGCCTGGAGCGGCTTCGGAGAGGGCTAGCTGCTG
GAACCAGCAACCCGGACCCTCCCACTGTATCCACGGACCAGCTGCTACCCC
TAGGAGGCGGCCGGGACCGGAAAGTCCGTGACTTGCAAGAGGCAGATCTGG
ACCTTTTGAGAGTCACTTTATCCTCCAAGCCACAAGCACTGGCCACACCAAA
CAAGGAGGAGCACGGGAAAAGAAAGAAGAAAGGCAAGGGGCTAGGGAAGAA
GAGGGACCCACAGATCCATGCTACACCCACACCTGTCACTGCCATTGGGCCCCCA
ACCACGGCTATCCAGGAGCCCCCATCCAGGATCGTGCCAACCCCCACATCTCCAG
CCATTGCTCCTCCAACAGAGACCATGGCTCCTCCAGTCAGGGATCCTGTTCCTGG
GAAACCCACGGTCACCATCCGGACTCGAGGCGCCATTATTCAAACCCCAACCCTA
GGCCCCATCCAGCCTACTCGGGTGTCAGAAGCTGGCACCACAGTTCCTGGCCAGA
TTCGCCCAACGATGACCATTCCTGGCTATGTGGAGCCTACTGCAGTTGCTACCCC
TCCCACAACCACCACCAAGAAGCCACGAGTATCCACACCAAAACCAGCAACGCC
TTCAACTGACTCCACCACCACCACGACTCGCAGGCCAACCAAGAAACCACGGAC
ACCCCGGCCAGTGCCCCGGGTCACCACCAAAGTTTCCATCACCAGATTGGAAACT
GCCTCACCGCCTACTCGTATTCGCACCACCACCAGTGGAGTGCCCCGTGGCGGAG
AACCCAACCAGCGCCCAGAGCTCAAGAACCATATTGACAGGGTAGATGCCTGGG
TTGGCACCTACTTTGAGGTGAAGATCCCGTCAGACACTTTCTATGACCATGAGGA
CACCACCACTGACAAGCTGAAGCTGACCCTGAAACTGCGGGAGCAGCAGCTGGT
GGGCGAGAAGTCCTGGGTACAGTTCAACAGCAACAGCCAGCTCATGTATGGCCT
TCCCGACAGCAGCCACGTGGGCAAACACGAGTATTTCATGCATGCCACAGACAA
GGGGGGGCCTGTCGGCTGTGGATGCCTTCGAGATCCACGTCCACAGGCGCCCCCA
AGGGGATAGGGCTCCTGCAAGGTTCAAGGCCAAGTTTGTGGGTGACCCGGCACT
GGTGTTGAATGACATCCACAAGAAGATTGCCTTGGTAAAGAAACTGGCCTTCGCC
TTTGGAGACCGAAACTGTAGCACCATCACCCTGCAGAATATCACCCGGGGCTAA
ACTAGTGCGGCCGCGGGGATCCAGACATGATAAGATACATTGATGAGTTTGGAC
AAACCACAACTAGAATGCAGTGAAAAAAATGCTTTATTTGTGAAATTTGTGATGC
TATTGCTTTATTTGTAACCATTATAAGCTGCAATAAACAAGTTAACAACAACAAT
TGCATTCATTTTATGTTTCAGGTTCAGGGGGAGGTGTGGGAGGTTTTTTCGGATCC
TCTAGAGTCGACCACATGGCTACGTAGATAATTAGCATGCGGGTTAATCATT
AACTACAAGGAACCCCTAGTGATGGAGTTGGCCACTCCCTCTGCGCGCTC
GCTCGCTCACTGAGGCCGGGCGACCAAAGGTCGCCCGACGCCCGGGCTTTG
CCCGGGCGGCCTCAGTGAGCGAGCGAGCGCGCNNNNNCAGCTGCATTAATG
AATCGGCCAACGCGCGGGGAGAGGCGGTTTGCGTATTGGGC

SEQ ID NO: 12 pAAV.CMV.HBEGF.DAG1

Main Characteristics
Ampicillin Resistance Gene
ITRs
*CMV Promoter*
*SV40 Enhancer*
HBEGF Signal Peptide
HBEGF Propeptide Domain
HBEGF Mature Peptide Domain
HBEGF HB Domain
HBEGF EGF-Like Domain
DAG1a
SV40 PolyA Tail GCTCTTCCGCTTGGTCGCTCACTGACTCGCTGCGCTCGGTCGTTCGGCTGCGGCG
AGCGGTATCAGCTCACTCAAACCCGGTAATACGGTTATCCACAGAATCAGGGGA
TAACGCAGGAAAGAACATGTGAGCAAAAGGCCAGCAAAAGGCCAGGAACCGTA
AAAAGGCCGCGTTGCTGGCGTTTTTCCATAGGCTCCGCCCCCCTGACGAGCATCA
CAAAAATCGACGCTCAAGTCAGAGGTGGCGAAACCCGACAGGACTATAAAGATA
CCAGGCGTTTCCCCCTGGAAGCTCCCTCGTGCGCTCTCCTGTTCCGACCCTGCCGC
TTACCGGATACCTGTCCGCCTTTCTCCCTTCGGGAAGCGTGGCGCTTTCTCATAGC
TCACGCTGTAGGTATCTCAGTTCGGTGTAGGTCGTTCGCTCCAAGCTGGGCTGTG
TGCACGAACCCCCCGTTCAGCCCGACCGCTGCGCCTTATCCGGTAACTATCGTCT
TGAGTCCAACCCGGTAAGACACGACTTATCGCCACTGGCAGCAGCCACTGGTAA
CAGGATTAGCAGAGCGAGGTATGTACGCGGTGCTACAGAGTTCTTGAAGTGGTG
GCCTAACTACGGCTACACTAGAAGGACAGTATTTGGTATCTGCGCTCTGCTGAAG
CCAGTTACCTTCGGAAAAAGAGTTGGTAGCTCTTGATCCGGCAAACAAACCACC
GCTGGTAGCGGTGGTTTTTTTGTTTGCAAGCAGCAGATTACGCGCAGAAAAAAAG
GATCTCAAGAAGATCCTTTGATCTTTTCTACGGGGTCTGACGCTCAGTGGAACGA
AAACTCACGTTAAGGGATTTTGGTCATGAGATTATCAAAAAGGATCTTCACCTAG
ATCCTTTTAAATTAAAAATGAAGTTTTAAATCAATCTAAAGTATATATGAGTAAA
CTTGGTCTGACAGTTACCAATGCTTAATCAGTGAGGCACCTATCTCAGCGATCTG
TCTATTTCGTTCATCCATAGTTGCCTGACTCCCCGTCGTGTAGATAACTACGATAC
GGGAGGGCTTACCATCTGGCCCCAGTGCTGCAATGATACCGCGAGACCCACGCT
CACCGGCTCCAGATTTATCAGCAATAAACCAGCCAGCCGGAAGGGCCGAGCGCA
GAAGTGGTCCTGCAACTTTATCCGCCTCCATCCAGTCTATTAATTGTTGCCGGGA
AGCTAGAGTAAGTAGTTCGCCAGTTAATAGTTTGCGCAACGTTGTTGCCATTGCT
ACAGGCATCGTGGTGTCACGCTCGTCGTTTGGTATGGCTTCATTCAGCTCCGGTTC
CCAACGATCAAGGCGAGTTACATGATCCCCCATGTTGTGCAAAAAAGCGGTTAG
CTCCTTCGGTCCTCCGATCGTTGTCAGAAGTAAGTTGGCCGCAGTGTTATCACTC
ATGGTTATGGCAGCACTGCATAATTCTCTTACTGTCATGCCATCCGTAAGATGCTT
TTCTGTGACTGGTGAGTACTCAACCAAGTCATTCTGAGAATAGTGTATGCGGCGA
CCGAGTTGCTCTTGCCCGGCGTCAATACGGGATAATACCGCGCCACATAGCAGA
ACTTTAAAAGTGCTCATCATTGGAAAACGTTCTTCGGGGCGAAAACTCTCAAGGA TCTTACCGCTGTTGAGATCCAGTTCGATGTAACCCACTCGTGCACCCAACTGATC
TTCAGCATCTTTTACTTTCACCAGCGTTTCTGGGTGAGCAAAAACAGGAAGGCAA
AATGCCGCAAAAAAGGGAATAAGGGCGACACGGAAATGTTGAATACTCATACTC
TTCCTTTTTCAATATTATTGAAGCATTTATCAGGGTTATTGTCTCATGAGCGGATA
CATATTTGAATGTATTTAGAAAAATAAACAAATAGGGGTTCCGCGCACATTTCCC
CGAAAAGTGCCACCTGACGTCTAAGAAACCATTATTATCATGACATTAACCTATA
AAAATAGGCGTATCACGAGGCCCTTTCGTCTCGCGCGTTTCGGTGATGACGGTGA
AAACCTCTGACACATGCAGCTCCCGGAGACGGTCACAGCTTGTCTGTAAGCGGAT
GCCGGGAGCAGACAAGCCCGTCAGGGCGCGTCAGCGGGTGTTGGCGGGTGTCGG
GGCTGGCTTAACTATGCGGCATCAGAGCAGATTGTACTGAGAGTGCACCATATGC
GGTGTGAAATACCGCACAGATGCGTAAGGAGAAAATACCGCATCAGGAACTTCC
AACATCCAATAAATCATACAGGCAAGGCAAAGAATTAGCAAAATTAAGCAATAA
AGCCTCAGAGCATAAAGCTAAATCGGTTGTACCAAAAACATTATGACCCTGTAAT
ACTTTTGCGGGAGAAGCCTTTATTTCAACGCAAGGATAAAAATTTTTAGAACCCT
CATATATTTTAAATGCAATGCCTGAGTAATGTGTAGGTAAAGATTCAAACGGGTG
AGAAAGGCCGGAGACAGTCAAATCACCATCAATATGATATTCAACCGTTCTAGC
TGATAAATTCATGCCGGAGAGGGTAGCTATTTTTGAGAGGTCTCTACAAAGGCTA
TCAGGTCATTGCCTGAGAGTCTGGAGCAAACAAGAGAATCGATGAACGGTAATC
GTAAAACTAGCATGTCAATCATATGTACCCCGGTTGATAATCAGAAAAGCCCCA
AAAACAGGAAGATTGTATAAGCAAATATTTAAATTGTAAACGTTAATATTTTGTT
AAAATTCGCGTTAAATTTTGTTAAATCAGCTCATTTTTTAACCAATAGGCCGAA
ATCGGCAAAATCCCTTATAAATCAAAAGAATAGACCGAGATAGGGTTGAGTGTT
GTTCCAGTTTGGAACAAGAGTCCACTATTAAAGAACGTGGACTCCAACGTCAAA
GGGCGAAAAACCGTCTATCAGGGCGATGGCCCACTACGTGAACCATCACCCTAA
TCAAGTTTTTTGGGGTCGAGGTGCCGTAAATCACTAAATCGGAACCCTAAAGGGA
GCCCCCGATTTAGAGCTTGACGGGGAAAGCCGGCGAACGTGGCGAGAAAGGAA
GGGAAGAAAGCGAAAGGAGCGGGCGCTAGGGCGCTGGCAAGTGTAGCGGTCAC
GCTGCGCGTAACCACCACACCCGCCGCGCTTAATGCGCCGCTACAGGGCGCGTA
CTATGGTTGCTTTGACGAGCACGTATAACGTGCTTTCCTCGTTAGAATCAGAGCG
GGAGCTAAACAGGAGGCCGATTAAAGGGATTTTAGACAGGAACGGTACGCCAGA
ATCCTGAGAAGTGTTTTTATAATCAGTGAGGCCACCGAGTAAAAGAGTCTGTCCA
TCACGCAAATTAACCGTTGTCGCAATACTTCTTTGATTAGTAATAACATCACTTGC
CTGAGTAGAAGAACTCAAACTATCGGCCTTGCTGGTAATATCCAGAACAATATTA
CCGCCAGCCATTGCAACAGGAAAAACGCTCATGGAAATACCTACATTTTGACGCT
CAATCGTCTGGAACTTCCATTCGCCATTCAGGCTGCGCAACTGTTGGGAAGGGCG
ATCGGTGCGGGCCTCTTCGCTATTACGCCAGCTGNNNNNNGCGCGCTCGCTCGC
TCACTGAGGCCGCCCGGGCAAAGCCCGGGCGTCGGGCGACCTTTGGTCGCC
CGGCCTCAGTGAGCGAGCGAGCGCGCAGAGAGGGAGTGGCCAACTCCATCA
CTAGGGGTTCCTTGTAGTTAATGATTAACCCGCCATGCTAATTATCTACGTA
GCCATG*TCTAGGGTCGTTACATAACTTACGGTAAATGGCCCGCCTGGCTGACCGCCC*
*AACGACCCCCGCCCATTGACGTCAATAATGACGTATGTTCCCATAGTAACGCCAATAGG*
*GACTTTCCATTGACGTCAATGGGTGGAGTATTTACGGTAAACTGCCCACTTGGCAGTAC*
*ATCAAGTGTATCATATGCCAAGTACGCCCCCTATTGACGTCAATGACGGTAAATGGCCC*
*GCCTGGCATTATGCCCAGTACATGACCTTATGGGACTTTCCTACTTGGCAGTACATCTA*
*CGTATTAGTCATCGCTATTACCATGGTGATGCGGTTTTGGCAGTACATCAATGGGCGTG*
*GATAGCGGTTTGACTCACGGGGATTTCCAAGTCTCCACCCCATTGACGTCAATGGGAG*
*TTTGTTTTGGCACCAAAATCAACGGGACTTTCCAAAATGTCGTAACAACTCCGCCCCAT*
*TGACGCAAATGGGCGGTAGGCGTGTACGGTGGGAGGTCTATATAAGCAGAGCTCGTTT*
*AGTGAACCGTCAGATCGCCTGGAGACGCCATCCACGCTGTTTTGACCTCCATAGAA*
GACACCGGGACCGATCCAGCCTCCGGAC<u>*TCTAGAGGATCCGGTACTCGAGGAACTG*</u>

Figure 24 (Continued)

*AAAAACCAGAAAGTTAACTGGTAAGTTTAGTCTTTTTGTCTTTTATTTCAGGTCCCGGAT*
*CCGGTGGTGGTGCAAATCAAAGAACTGCTCCTCAGTGGATGTTGCCTTTACTTCTAGG*
*CCTGTACGGAAGTGTTACTTCTGCTCTAAAAGCTGCGGAATTGTACCCGCGGCCGCAC*
CATGAAGCTGCTGCCGTCGGTGGTGCTGAAGCTCTTTCTGGCTGCAGTTCTCTCG
GCACTGGTGACTGGCGAGAGCCTGGAGCGGCTTCGGAGAGGGCTAGCTGCTG
GAACCAGCAACCCGGACCCTCCCACTGTATCCACGGACCAGCTGCTACCCC
TAGGAGGCGGCCGGGACCGGAAAGTCCGTGACTTGCAAGAGGCAGATCTGG
ACCTTTTGAGAGTCACTTTATCCTCCAAGCCACAAGCACTGGCCACACCAAA
CAAGGAGGAGCACGGGAAAAGAAAGAAGAAAGGCAAGGGGCTAGGGAAGAA
GAGGGACCCATGTCTTCGGAAATACAAGGACTTCTGCATCCATGGAGAATGC
AAATATGTGAAGGAGCTCCGGGCTCCCTCCTGCATCTGCCACCCGGGTTAC
CATGGAGAGAGGTGTCATGGGCTGAGCCTCCCACAGATCCATGCTACACCCA
CACCTGTCACTGCCATTGGGCCCCCAACCACGGCTATCCAGGAGCCCCCATCCAG
GATCGTGCCAACCCCCACATCTCCAGCCATTGCTCCTCCAACAGAGACCATGGCT
CCTCCAGTCAGGGATCCTGTTCCTGGGAAACCCACGGTCACCATCCGGACTCGAG
GCGCCATTATTCAAACCCCAACCCTAGGCCCCATCCAGCCTACTCGGGTGTCAGA
AGCTGGCACCACAGTTCCTGGCCAGATTCGCCCAACGATGACCATTCCTGGCTAT
GTGGAGCCTACTGCAGTTGCTACCCCTCCCACAACCACCACCAAGAAGCCACGA
GTATCCACACCAAAACCAGCAACGCCTTCAACTGACTCCACCACCACCACGACTC
GCAGGCCAACCAAGAAACCACGGACACCCCGGCCAGTGCCCCGGGTCACCACCA
AAGTTTCCATCACCAGATTGGAAACTGCCTCACCGCCTACTCGTATTCGCACCAC
CACCAGTGGAGTGCCCCGTGGCGGAGAACCCAACCAGCGCCCAGAGCTCAAGAA
CCATATTGACAGGGTAGATGCCTGGGTTGGCACCTACTTTGAGGTGAAGATCCCG
TCAGACACTTTCTATGACCATGAGGACACCACCACTGACAAGCTGAAGCTGACCC
TGAAACTGCGGGAGCAGCAGCTGGTGGGCGAGAAGTCCTGGGTACAGTTCAACA
GCAACAGCCAGCTCATGTATGGCCTTCCCGACAGCAGCCACGTGGGCAAACACG
AGTATTTCATGCATGCCACAGACAAGGGGGGCCTGTCGGCTGTGGATGCCTTCGA
GATCCACGTCCACAGGCGCCCCCAAGGGGATAGGGCTCCTGCAAGGTTCAAGGC
CAAGTTTGTGGGTGACCCGGCACTGGTGTTGAATGACATCCACAAGAAGATTGCC
TTGGTAAAGAAACTGGCCTTCGCCTTTGGAGACCGAAACTGTAGCACCATCACCC
TGCAGAATATCACCCGGGGCTAAACTAGTGCGGCCGCGGGGATCCAGACATGAT
AAGATACATTGATGAGTTTGGACAAACCACAACTAGAATGCAGTGAAAAAAATG
CTTTATTTGTGAAATTTGTGATGCTATTGCTTTATTTGTAACCATTATAAGCTGCA
ATAAACAAGTTAACAACAACAATTGCATTCATTTTATGTTTCAGGTTCAGGGGGA
GGTGTGGGAGGTTTTTTCGGATCCTCTAGAGTCGACCACATGGCTACGTAGATA
ATTAGCATGGCGGGTTAATCATTAACTACAAGGAACCCCTAGTGATGGAGTT
GGCCACTCCCTCTCTGCGCGCTCGCTCGCTCACTGAGGCCGGGCGACCAAA
GGTCGCCCGACGCCCGGGCTTTGCCCGGGCGGCCTCAGTGAGCGAGCGAG
CGCGCNNNNNCAGCTGCATTAATGAATCGGCCAACGCGCGGGGAGAGGCGGT
TTGCGTATTGGGC

Figure 24 (Continued)

RECOMBINANT ADENO-ASSOCIATED VIRUS PRODUCTS AND METHODS FOR TREATING DYSTROGLYCANOPATHIES AND LAMININ-DEFICIENT MUSCULAR DYSTROPHIES

This application is a national phase application of International Application No. PCT/US19/37769, filed on Jun. 18, 2019, which claims priority benefit to U.S. Provisional Patent Application No. 62/686,522, filed Jun. 18, 2018, which are incorporated by reference herein in their entirety.

This invention was made with government support under AR070604 awarded by The National Institutes of Health. The government has certain rights in the invention.

Incorporation By Reference of Material Submitted Electronically

This application contains, as a separate part of the disclosure, a Sequence Listing in computer-readable form which is incorporated by reference in its entirety and identified as follows: Filename: 53147A_RevisedSeqListing.txt; Size: 203,853 bytes; Created: Dec. 3, 2024.

FIELD OF THE INVENTION

Products and methods for treating dystroglycanopathies and laminin-deficient muscular dystrophies are provided. In the methods, a protein including a linker domain, such as the heparin-binding domain of Heparin-Binding Epidermal Growth Factor-Like Growth Factor (HBEGF), is delivered to patients. This linker protein assists in targeting a transgene to the extracellular matrix (ECM) of a muscle cell.

BACKGROUND

Muscular dystrophies (MDs) are a group of genetic diseases. The group is characterized by progressive weakness and degeneration of the skeletal muscles that control movement. Some forms of MD develop in infancy or childhood, while others may not appear until middle age or later. The disorders differ in terms of the distribution and extent of muscle weakness (some forms of MD also affect cardiac muscle), the age of onset, the rate of progression, and the pattern of inheritance.

Congenital muscular dystrophy (CMD) describes a group of MDs in which the loss of muscle structural components results in neonatal hypotonia and progressive skeletal muscle weakness. These disorders are often associated with significant extramuscular complications, including brain and eye developmental defects, cognitive impairment, seizures, and respiratory and cardiac abnormalities, requiring regular medical management by a multidisciplinary team. The estimated incidence of CMD is 1 in 21,500 live births worldwide. Despite the gravity of these disorders, there are currently no approved and effective therapies. Dystroglycanopathies and merosin-deficient CMD Type 1A (MDC1A) are two of the most common forms of CMD [Sframcli et al., *Neuromuscul Disord.*, 27 (9): 793-803 (2017)].

Dystroglycanopathies are caused by mutations in any of eighteen or more genes required for glycosylating α-dystroglycan. Proper glycosylation allows α-dystroglycan to bind components of the extracellular matrix (ECM). α-Dystroglycan, in turn, anchors to the sarcolemma by binding β-dystroglycan, a transmembrane protein. The number of susceptible genes makes impossible the development of a single gene-replacement therapy for dystroglycanopathy.

Examples of dystroglycanopathies include the following. Walker-Warburg Syndrome (WWS) involves genetic mutations in B3GLNT2, B4GAT1, DAG1, FKRP, FKTN, GMPPB, ISPD, or LARGE. Muscle Eye Brain disease (MEB) involves genetic mutations in B3GLNT2, B4GAT1, DAG1, FKRP, FKTN, GMPPB, ISPD, or LARGE. Fukuyama CMD involves mutations in the FKTN gene. A group of congenital muscular dystrophies with cognitive impairment results from mutations in FKRP, LARGE, POMT1, POMT2, or POMGNT1. A group of CMDs without cognitive impairment are a result of genetic mutations in FKRP or FKTN. Limb Girdle Muscular Dystrophies LGMD 2I, 2K, 2M, 2N and 20 are associated with glycosylation abnormalities involving genetic mutations in FKRP, FKTN, POMGNT1, POMT1, or POMT2. Limb Girdle Muscular Dystrophies LGMD 2T and 2U are respectively a result of genetic mutations in GMPPB and ISPD. Other mutated genes in dystroglycanopathies include DOLK, DPM1, DPM2, DPM3, GTDC2/AG061, TMEM5, and SK196.

MDC1A is caused by mutations in the LAMA2 gene, encoding the key ECM protein, laminin-α2, which binds glycosylated α-dystroglycan at the sarcolemma. The full LAMA2 gene is over 9,000 base pairs in length.

A study by Reinhard and colleagues [Reinhard et al., Sci Transl Med., 9(396), (2017)] involved germline expression of fused domains from laminin-α4 and mini-agrin to incompletely ameliorate disease symptoms in the dyW/dyW mouse model of MDC1A.

Adeno-associated virus (AAV) is a replication-deficient parvovirus, the single-stranded DNA genome of which is about 4.7 kb in length including two 145 nucleotide inverted terminal repeat (ITRs). There are multiple serotypes of AAV. The nucleotide sequences of the genomes of AAV serotypes are known. For example, the complete genome of AAV-1 is provided in GenBank Accession No. NC_002077; the complete genome of AAV-2 is provided in GenBank Accession No. NC_001401 and Srivastava et al., J. Virol., 45:555-564 (1983); the complete genome of AAV-3 is provided in GenBank Accession No. NC_1829; the complete genome of AAV-4 is provided in GenBank Accession No. NC_001829; the AAV-5 genome is provided in GenBank Accession No. AF085716; the complete genome of AAV-6 is provided in GenBank Accession No. NC_00 1862; at least portions of AAV-7 and AAV-8 genomes are provided in GenBank Accession Nos. AX753246 and AX753249, respectively; the AAV-9 genome is provided in Gao et al., J. Virol., 78:6381-6388 (2004); the AAV-10 genome is provided in *Mol. Ther.*, 13 (1): 67-76 (2006); the AAV-11 genome is provided in Virology, 330 (2): 375-383 (2004); portions of the AAV-12 genome are provided in Genbank Accession No. DQ813647; portions of the AAV-13 genome are provided in Genbank Accession No. EU285562. The sequence of the AAV rh.74 genome is provided in see U.S. Pat. No. 9,434,928, incorporated herein by reference. Cis-acting sequences directing viral DNA replication (rep), encapsidation/packaging and host cell chromosome integration are contained within the AAV ITRs. Three AAV promoters (named p5, p19, and p40 for their relative map locations) drive the expression of the two AAV internal open reading frames encoding rep and cap genes. The two rep promoters (p5 and p19), coupled with the differential splicing of the single AAV intron (at nucleotides 2107 and 2227), result in the production of four rep proteins (rep 78, rep 68, rep 52, and rep 40) from the rep gene. Rep proteins possess multiple enzymatic properties that are ultimately responsible for replicating the viral genome. The cap gene is expressed from the p40 promoter and it encodes the three capsid proteins VP1, VP2, and VP3. Alternative splicing and non-consensus translational start sites are responsible for the production of the three related capsid proteins. A single consensus polyadenylation site is located at map position 95 of the AAV genome. The life cycle and genetics of AAV are reviewed in Muzyczka, *Current Topics in Microbiology and Immunology*, 158:97-129 (1992).

AAV possesses unique features that make it attractive as a vector for delivering foreign DNA to cells, for example, in gene therapy. AAV infection of cells in culture is noncytopathic, and natural infection of humans and other animals is silent and asymptomatic. Moreover, AAV infects many mammalian cells allowing the possibility of targeting many different tissues in vivo. Moreover, AAV transduces slowly dividing and non-dividing cells, and can persist essentially for the lifetime of those cells as a transcriptionally active nuclear episome (extrachromosomal element). The AAV proviral genome is inserted as cloned DNA in plasmids, which makes construction of recombinant genomes feasible. Furthermore, because the signals directing AAV replication and genome encapsidation are contained within the ITRs of the AAV genome, some or all of the internal approximately 4.3 kb of the genome (encoding replication and structural capsid proteins, rep-cap) may be replaced with foreign DNA. To generate AAV vectors, the rep and cap proteins may be provided in trans. Another significant feature of AAV is that it is an extremely stable and hearty virus. It easily withstands the conditions used to inactivate adenovirus (56° to 65° C. for several hours), making cold preservation of AAV less critical. AAV may even be lyophilized. Finally, AAV-infected cells are not resistant to superinfection.

There remains a need in the art for treatments for CMDs such as dystroglycanopathies and MDC1A.

SUMMARY

Provided herein are methods and products for treatment of CMDs such as dystroglycanopathies and laminin-deficient muscular dystrophies. The products include therapeutic proteins and rAAV encoding a disclosed therapeutic protein.

A polynucleotide is provided encoding a protein comprising:
- a) a first domain comprising the heparin-binding domain of Heparin-Binding Epidermal Growth Factor-Like Growth Factor (HBEGF), and a second domain comprising the G1-G5 domain of the human laminin alpha 2 (LAMA2) gene;
- b) a first domain comprising the heparin-binding domain of HBEGF and the EGF-like domain of HBEGF, and a second domain comprising the G1-G5 domain of the human LAMA2 gene;
- c) a first domain comprising the heparin-binding domain of HBEGF, and a second domain comprising the G3-G5 domain of the human LAMA2 gene;
- d) a first domain comprising the heparin-binding domain of HBEGF and the EGF-like domain of HBEGF, and a second domain comprising the G3-G5 domain of the human LAMA2 gene,
- c) a first domain comprising the heparin-binding domain of HBEGF and a second domain comprising DAG1alpha or
- f) a first domain comprising the heparin-binding domain of HBEGF and the EGF-like domain of HBEGF, and a second domain comprising DAG1alpha.

In one embodiment, the provided polynucleotides encode a protein, wherein the first domain of the protein is encoded by the nucleotide sequence of SEQ ID NO: 13 or SEQ ID NO: 14, and the second the second domain of the protein is encoded by the nucleotide sequence of SEQ ID NO: 15, SEQ ID NO: 16 or SEQ ID NO: 17.

For example, the provided polynucleotides comprises the nucleotide sequence of SEQ ID NO: 13 and SEQ ID NO: 15, or comprise the nucleotide sequence of SEQ ID NO: 13 and SEQ ID NO: 16, or comprise the nucleotide sequence of SEQ ID NO: 14 and SEQ ID NO: 15, or comprise the nucleotide sequence of SEQ ID NO: 14 and SEQ ID NO: 16, or comprise the nucleotide sequence of SEQ ID NO: 13 and SEQ ID NO: 17 or comprise the nucleotide sequence of SEQ ID NO: 14 and SEQ ID NO: 17.

In one embodiment, the provided polynucleotides comprise one of the following: i) the nucleotide sequence set forth in FIG. 3, ii) a nucleotide sequence comprising nucleotides 14 to 3235 set out in FIG. 3, iii) the nucleotide sequence of SEQ ID NO: 1, or iv) a nucleotide sequence encoding the amino acid sequence of SEQ ID NO: 19.

In another embodiment, the provided polynucleotides comprise one of the following: i) the nucleotide sequence set forth in FIG. 4, ii) a nucleotide sequence comprising nucleotides 14 to 3361 set forth in FIG. 4, iii) the nucleotide sequence of SEQ ID NO: 3 or iv) a nucleotide sequence encoding the amino acid sequence of SEQ ID NO: 20.

In a further embodiment, the provided polynucleotides comprise one of the following: i) the nucleotide sequence set forth in FIG. 5, ii) a nucleotide sequence comprising nucleotides 14 to 1930 set forth in FIG. 5, iii) the nucleotide sequence of SEQ ID NO: 5 or iv) a nucleotide sequence encoding the amino acid sequence of SEQ ID NO: 21.

In another embodiment, the provided polynucleotides comprise one of the following: i) the nucleotide sequence set forth in FIG. 6, ii) a nucleotide sequence comprising nucleotides 14 to 2056 set forth in FIG. 6, iii) the nucleotide sequence of SEQ ID NO: 7 or iv) a nucleotide sequence encoding the amino acid sequence of SEQ ID NO: 22.

In an embodiment, the provided polynucleotides comprise one of the following: i) the nucleotide sequence set forth in FIG. 7, ii) a nucleotide sequence comprising nucleotides 14 to 1360 set forth in FIG. 7, iii) the nucleotide sequence of SEQ ID NO: 9 or iv) a nucleotide sequence encoding the amino acid sequence of SEQ ID NO: 23.

In another embodiment, the provided polynucleotides comprise one of the following: i) the nucleotide sequence set forth in FIG. 8, ii) a nucleotide sequence comprising nucleotides 14-1486 set forth in FIG. 8, iii) the nucleotide sequence of SEQ ID NO: 11 or iv) a nucleotide sequence encoding the amino acid sequence of SEQ ID NO: 24.

Therapeutic proteins encoded by any of the provided polynucleotides are also provided. For example, the provided proteins comprise the amino acid sequence of SEQ ID NO: 19, SEQ ID NO: 20, SEQ ID NO: 21, SEQ ID NO: 22, SEQ ID NO: 23 or SEQ ID NO: 24.

In addition, the disclosure provides recombinant host cells comprising any of the polynucleotide described herein. In exemplary embodiments, the host cells, the polynucleotides are operatively linked to a transcriptional control element and these host cells express any of the polynucleotides disclosed herein. For example, the host cells are Chinese hamster ovary (CHO) cell or human HEK293 cell.

Further provided are recombinant adeno-associate virus (rAAV), wherein the genome of the rAAV comprises any of the polynucleotide described herein. For example, provided are rAAV, wherein the genome of the rAAV comprises a polynucleotide sequence of SEQ ID NO: 1, SEQ ID NO: 3, SEQ ID NO: 5, SEQ ID NO: 7, SEQ ID NO: 9 or SEQ ID NO: 11. In exemplary embodiments, the rAAV genome further comprises a muscle-specific transcriptional control element, such as a CMV promoter (SEQ ID NO: 18), MCK, NHCK, LAMA2 or tMCK. Any of the rAAV described herein comprise the AAV9, AAV10, AAVrh74, AAV8 or AAV6 capsid.

Also provided are rAAV, wherein the genome of the rAAV comprises nucleotides 3590 to 8215 of SEQ ID NO: 2, nucleotides 3590 to 8341 of SEQ ID NO: 4, nucleotides 3609 to 6929 of SEQ ID NO: 6, nucleotides 3590 to 7036 of SEQ ID NO: 8, nucleotides 3590 to 6340 of SEQ ID NO: 10, nucleotides 3590 to 6049 of SEQ ID NO: 12, the nucleotide sequence set out in FIG. 13, or the nucleotide sequence set out in FIG. 14.

rAAV particles comprising any of the rAAV described herein are also provided. The disclosure also provides for compositions comprising any of the polynucleotides disclosed herein, any of the rAAV disclosed herein, any of the rAAV particles disclosed herein or any of the proteins disclosed herein.

Provided are methods for treating a laminin-deficient muscular dystrophy comprising administering to a patient in need thereof a rAAV, wherein the genome of the rAAV comprises a polynucleotide encoding a protein comprising:
  a) a first domain comprising the heparin-binding domain of HBEGF, and a second domain comprising the G1-G5 domain of the human LAMA2 gene;
  b) a first domain comprising the heparin-binding domain of HBEGF and the EGF-like domain of HBEGF, and a second domain comprising the G1-G5 domain of the human LAMA2 gene;
  c) a first domain comprising the heparin-binding domain of HBEGF, and a second domain comprising the G3-G5 domain of the human LAMA2 gene; or
  d) a first domain comprising the heparin-binding domain of HBEGF and the EGF-like domain of HBEGF, and a second domain comprising the G3-G5 domain of the human LAMA2 gene.

For example, the methods of treating a laminin-deficient muscular dystrophy comprise administering to a patient in need thereof any of the following: any of the polynucleotides disclosed herein which encode a protein comprising LAMA2 (G1-G5) or LAMA2 (G3-G5) as the second domain, any of the rAAV or rAAV particles disclosed herein which comprise a polynucleotide encoding a protein comprising LAMA2 (G1-G5) or LAMA2 (G3-G5) as the second domain.

Further provided are methods for treating a laminin-deficient muscular dystrophy comprising administering to a patient in need thereof a protein comprising:
  a) a first domain comprising the heparin-binding domain of HBEGF, and a second domain comprising the G1-G5 domain of the human LAMA2 gene;
  b) a first domain comprising the heparin-binding domain of HBEGF and the EGF-like domain of HBEGF, and a second domain comprising the G1-G5 domain of the human LAMA2 gene;
  c) a first domain comprising the heparin-binding domain of HBEGF, and a second domain comprising the G3-G5 domain of the human LAMA2 gene; or
  d) a first domain comprising the heparin-binding domain of HBEGF and the EGF-like domain of HBEGF, and a second domain comprising the G3-G5 domain of the human LAMA2 gene.

For example, the methods for treating a treating laminin-deficient muscular dystrophy comprise administering a protein to a patient in need thereof, wherein the protein comprises the amino acid sequence of SEQ ID NO: 19, SEQ ID NO: 20, SEQ ID NO: 21 or SEQ ID NO: 22.

Also provided are compositions for treating a laminin-deficient muscular dystrophy comprising a rAAV, wherein the genome of the rAAV comprises a polynucleotide encoding a protein comprising:
  a) a first domain comprising the heparin-binding domain of HBEGF, and a second domain comprising the G1-G5 domain of the human LAMA2 gene;
  b) a first domain comprising the heparin-binding domain of HBEGF and the EGF-like domain of HBEGF, and a second domain comprising the G1-G5 domain of the human LAMA2 gene;
  c) a first domain comprising the heparin-binding domain of HBEGF, and a second domain comprising the G3-G5 domain of the human LAMA2 gene; or
  d) a first domain comprising the heparin-binding domain of HBEGF and the EGF-like domain of HBEGF, and a second domain comprising the G3-G5 domain of the human LAMA2 gene.

For example, the compositions for treating a laminin-deficient muscular dystrophy comprise any of the following: any of the polynucleotides disclosed herein which encode a protein comprising LAMA2 (G1-G5) or LAMA2 (G3-G5) as the second domain, any of the rAAV or rAAV particles disclosed herein which comprise a polynucleotide encoding a protein comprising LAMA2 (G1-G5) or LAMA2 (G3-G5) as the second domain.

Further provided are compositions for treating laminin-deficient muscular dystrophies comprising a protein comprising:
  a) a first domain comprising the heparin-binding domain of HBEGF, and a second domain comprising the G1-G5 domain of the human LAMA2 gene;
  b) a first domain comprising the heparin-binding domain of HBEGF and the EGF-like domain of HBEGF, and a second domain comprising the G1-G5 domain of the human LAMA2 gene;
  c) a first domain comprising the heparin-binding domain of HBEGF, and a second domain comprising the G3-G5 domain of the human LAMA2 gene; or
  d) a first domain comprising the heparin-binding domain of HBEGF and the EGF-like domain of HBEGF, and a second domain comprising the G3-G5 domain of the human LAMA2 gene.

For example, the compositions for treating a treating laminin-deficient muscular dystrophy comprise a protein, wherein the protein comprises the amino acid sequence of SEQ ID NO: 19, SEQ ID NO: 20, SEQ ID NO: 21 or SEQ ID NO: 22.

The disclosure also provides for a use of a rAAV for the preparation of a medicament for treating a laminin-deficient muscular dystrophy in a patient in need thereof, wherein the genome of the rAAV comprises a polynucleotide encoding a protein comprising:
  a) a first domain comprising the heparin-binding domain of HBEGF, and a second domain comprising the G1-G5 domain of the human LAMA2 gene;
  b) a first domain comprising the heparin-binding domain of HBEGF and the EGF-like domain of HBEGF, and a second domain comprising the G1-G5 domain of the human LAMA2 gene;
  c) a first domain comprising the heparin-binding domain of HBEGF, and a second domain comprising the G3-G5 domain of the human LAMA2 gene; or
  d) a first domain comprising the heparin-binding domain of HBEGF and the EGF-like domain of HBEGF, and a second domain comprising the G3-G5 domain of the human LAMA2 gene.

For example, the disclosure also provides for use of any of the following: any of the polynucleotides disclosed herein which encode a protein comprising LAMA2 (G1-G5) or LAMA2 (G3-G5) as the second domain, any of the rAAV or rAAV particles disclosed herein which comprise a poly-nucleotide encoding a protein comprising LAMA2 (G1-G5) or LAMA2 (G3-G5) as the second domain for the prepara-tion of a medicament for treating a laminin-deficient mus-cular dystrophy in a patient in need thereof.

Further provided are use of a protein for the preparation of a medicament for treating a laminin-deficient muscular dystrophy in a patient in need thereof, wherein the protein comprises:
  a) a first domain comprising the heparin-binding domain of HBEGF, and a second domain comprising the G1-G5 domain of the human LAMA2 gene;
  b) a first domain comprising the heparin-binding domain of HBEGF and the EGF-like domain of HBEGF, and a second domain comprising the G1-G5 domain of the human LAMA2 gene;
  c) a first domain comprising the heparin-binding domain of HBEGF, and a second domain comprising the G3-G5 domain of the human LAMA2 gene; or
  d) a first domain comprising the heparin-binding domain of HBEGF and the EGF-like domain of HBEGF, and a second domain comprising the G3-G5 domain of the human LAMA2 gene.

For example, the disclosure also provides for use of a protein for the preparation of a medicament for treating a treating laminin-deficient muscular dystrophy in a patient in need thereof, wherein the protein comprises the amino acid sequence of SEQ ID NO: 19, SEQ ID NO: 20, SEQ ID NO: 21 or SEQ ID NO: 22.

Also provided are methods for treating a dystroglycan-opathy comprising administering to a patient in need thereof a rAAV, wherein the genome of the rAAV comprises a polynucleotide encoding a protein comprising:
  a) a first domain comprising the heparin-binding domain of HBEGF and a second domain comprising DAG1alpha or
  b) a first domain comprising the heparin-binding domain of HBEGF and the EGF-like domain of HBEGF, and a second domain comprising DAG1alpha.

For example, the methods of treating a dystroglycanopa-thy comprising administering to a patient in need thereof any of the following: any of the polynucleotides disclosed herein which encode a protein comprising DAG1alpha as the second domain, any of the rAAV or rAAV particles disclosed herein which comprise a polynucleotide encoding a protein comprising DAG1alpha as the second domain.

Still further provided are methods for treating a dystro-glycanopathy comprising administering to a patient in need thereof a protein comprising:
  a) a first domain comprising the heparin-binding domain of HBEGF and a second domain comprising DAG1alpha or
  b) a first domain comprising the heparin-binding domain of HBEGF and the EGF-like domain of HBEGF, and a second domain comprising DAG1alpha.

For example, the methods for treating a dystroglycanopa-thy comprising administering a protein to a patient in need thereof, wherein the protein comprises the amino acid sequence of SEQ ID NO: 23 or SEQ ID NO: 24.

Also provided are compositions for treating a dystrogly-canopathy comprising a rAAV, wherein the genome of the rAAV comprises a polynucleotide encoding a protein com-prising:

a) a first domain comprising the heparin-binding domain of HBEGF and a second domain comprising DAG1alpha or
  b) a first domain comprising the heparin-binding domain of HBEGF and the EGF-like domain of HBEGF, and a second domain comprising DAG1alpha.

For example, the disclosure provides compositions for treating a dystroglycanopathy comprising any of the follow-ing: any of the polynucleotides disclosed herein which encode a protein comprising DAG1alpha as the second domain, or any of the rAAV or rAAV particles disclosed herein which comprise a polynucleotide encoding a protein comprising DAG1alpha as the second domain.

Still further provided are compositions for treating a dystroglycanopathy comprising a protein comprising:
  a) a first domain comprising the heparin-binding domain of HBEGF and a second domain comprising DAG1alpha or
  b) a first domain comprising the heparin-binding domain of HBEGF and the EGF-like domain of HBEGF, and a second domain comprising DAG1alpha.

For example, the compositions for treating a dystrogly-canopathy comprise a protein wherein the protein comprises the amino acid sequence of SEQ ID NO: 23 or SEQ ID NO: 24.

Also provided is use of a rAAV for the preparation of a medicament for treating a dystroglycanopathy in a patient in need thereof, wherein the genome of the rAAV comprises a polynucleotide encoding a protein comprising:
  a) a first domain comprising the heparin-binding domain of HBEGF and a second domain comprising DAG1alpha or
  b) a first domain comprising the heparin-binding domain of HBEGF and the EGF-like domain of HBEGF, and a second domain comprising DAG1alpha.

For example, the disclosure provides for use of any of the following: any of the polynucleotides disclosed herein which encode a protein comprising DAG1alpha as the second domain or any of the rAAV or rAAV particles disclosed herein which comprise a polynucleotide encoding a protein comprising DAG1alpha as the second domain, for the preparation of a medicament for treating a dystrogly-canopathy in a patient in need thereof.

Still further provided is a use of a protein for the prepa-ration of a medicament for treating a dystroglycanopathy in a patient in need thereof, wherein the protein comprises:
  a) a first domain comprising the heparin-binding domain of HBEGF and a second domain comprising DAG1alpha or
  b) a first domain comprising the heparin-binding domain of HBEGF and the EGF-like domain of HBEGF, and a second domain comprising DAG1alpha.

For example, the disclosure provides a use of a protein for the preparation of a medicament for treating a dystrogly-canopathy in a patient in need thereof, wherein the protein comprises the amino acid sequence of SEQ ID NO: 23 or SEQ ID NO: 24.

In methods, uses or composition for treating laminin-deficient muscular dystrophy provided, the laminin-deficient muscular dystrophy may be, for example, MDC1A.

In any of the methods, uses or compositions for treating a dystroglycanopathy, the dystroglycanopathy may be, for example, Walker Warburg syndrome, Muscle Eye Brain disease, Fukuyama Congenital Muscular Dystrophy, MDC1C, MDC1D, LGMD2I, LGMD2K, LGMD2M, LGMD2N, LGMD2O, LGMD2P, LGMD2T or LGMD2U.

Examples of the provided proteins are described in Table 1.

TABLE 1

| Therapeutic protein | Linker/ Laminin | FIG. | Encoded by nucleotide in FIG. or SEQ ID NO: | Protein SEQ ID NO: | Plasmid SEQ ID No:/FIG. |
|---|---|---|---|---|---|
| HB-LAMA2 (G1-G5) | Ending after HB domain | 3 | 14 to 3235 of FIG. 3 SEQ ID NO: 1 | 19 | SEQ ID NO: 2 FIG. 19 |
| HBEGF-LAMA2 (G1-G5) | Complete soluble form HBEGF | 4 | 14 to 3361 of FIG. 4 SEQ ID NO: 3 | 20 | SEQ ID NO: 4 FIG. 20 |
| HB-LAMA2 (G3-G5) | Ending after HB domain | 5 | 14 to 1930 of FIG. 5 SEQ ID NO: 5 | 21 | SEQ ID NO: 6 FIG. 21 |
| HBEGF-LAMA2 (G3-G5) | Complete soluble form HBEGF | 6 | 14 to 2056 of FIG. 6 SEQ ID NO: 7 | 22 | SEQ ID NO: 8 FIG. 22 |
| HB-DAG1 | Ending after HB domain | 7 | 14 to 1360 of FIG. 7 SEQ ID NO: 9 | 23 | SEQ ID NO: 10 FIG. 23 |
| HBEGF-DAG1 | Complete soluble form HBEGF | 8 | 14-1486 of FIG. 8 SEQ ID NO: 11 | 24 | SEQ ID NO: 12 FIG. 24 |

Figure 15:
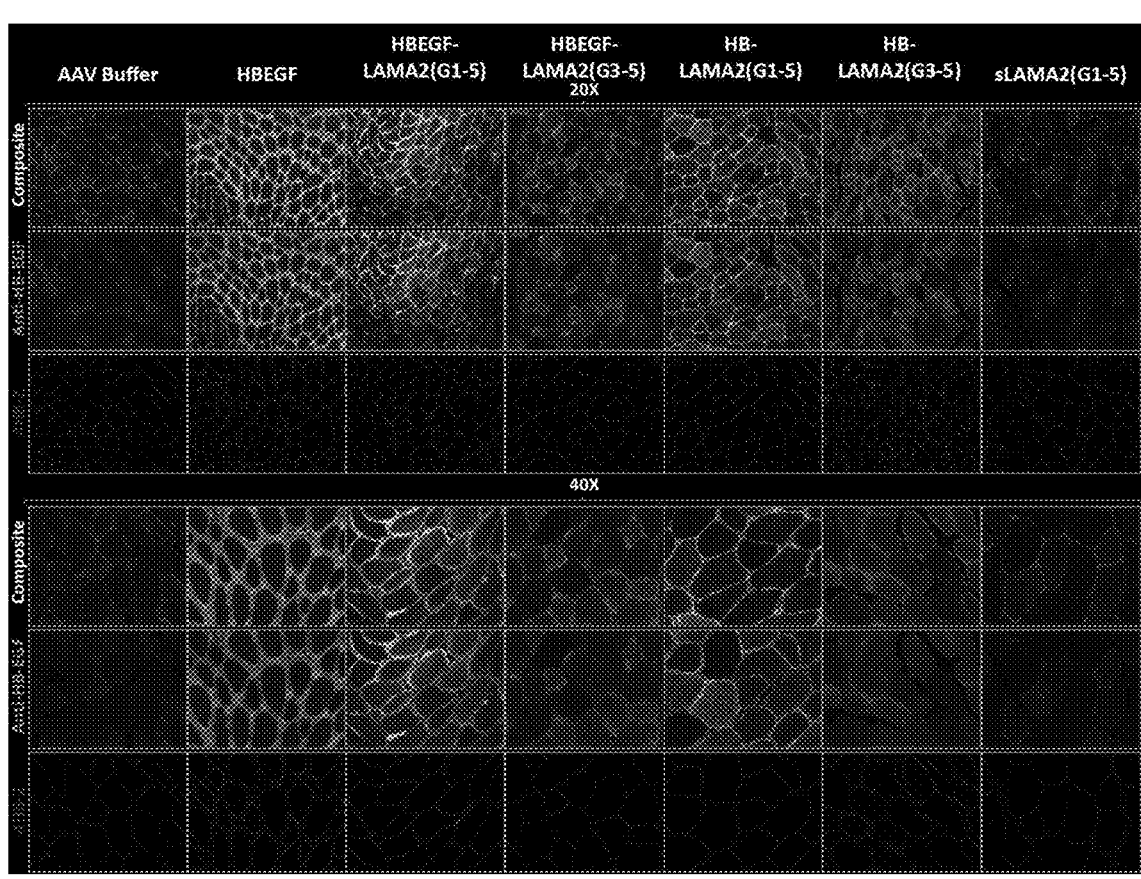

FIG. 15 provides immunohistochemical staining for HB-EGF and LG5 (denoted in figure as 4H8-2) after intramuscular injection of rAAV9.CMV vectors containing HBEGF, HBEGF.LAMA2 (G1-G5), HBEGF.LAMA2 (G3-G5), HB.LAMA2 (G1-G5), HB.LAMA2 (G3-G5), or LAMA2 (G1-G5) in wild type mice. Mock injected mice (buffer alone) are shown as a negative control. 4H8-2 is an anti-laminin antibody to show muscle cells in the sections.

Figure 16:
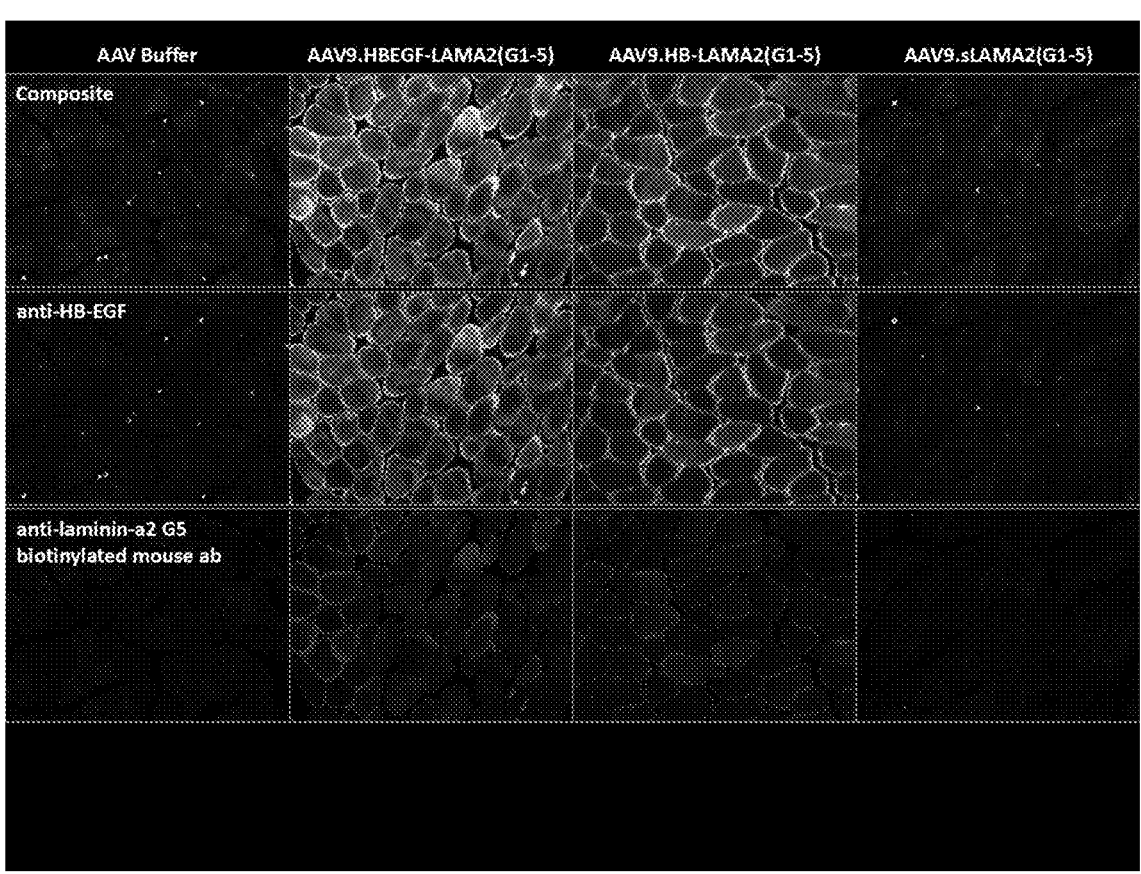

FIG. 16 provides immunohistochemistry staining for HB-EGF and Laminin Globular Domain (LG5) in muscles injected IM with rAAV9.HBEGF-LAMA2 (G1-G5), HB-LAMA2 (G1-G5), or LAMA2 (G1-G5). The lower panels below show staining for secondary antibody alone.

Figure 17:
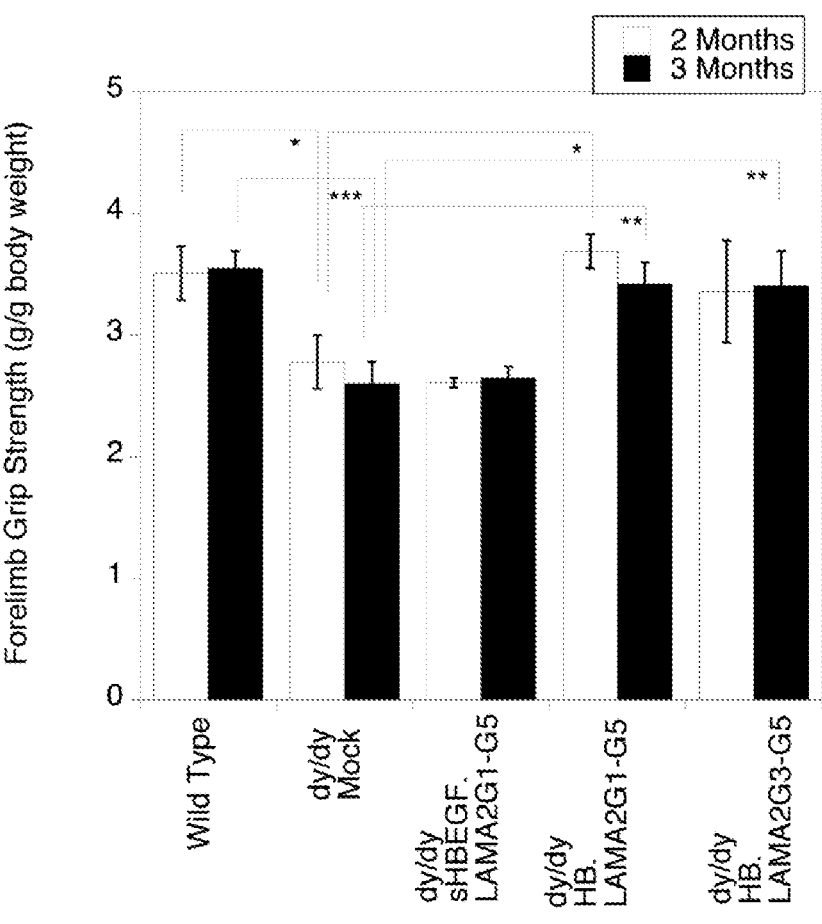

FIG. 17 is a graph demonstrating that rAAV9.CMV.HB.LAMA (G1-G5) prevented loss of muscle strength in dy/dy mice. Mice were injected IV with $1 \times 10^{12}$ vg of rAAV9.CMV vectors containing HBEGF.LAMA2 (G1-G5), HB.LAMA2 (G1-G5), or HB.LAMA2 (G3-G5). Mice were compared to mock-injected dy/dy disease controls and wild type normal controls at 2 months and 3 months post-injection. Mixed (50:50) female:male genders were used in all groups. Errors are SEM for n=12 (wild type and dy/dy mock), 6 (SHB-EGF.LAMA2G1-G5 and HB.LAMA2G1-G5) or 5 (HB.LAMA2G3-G5) animals per group, with five measures averaged per data point. *p<0.05, p<0.01, *p<0.001

Figure 18:
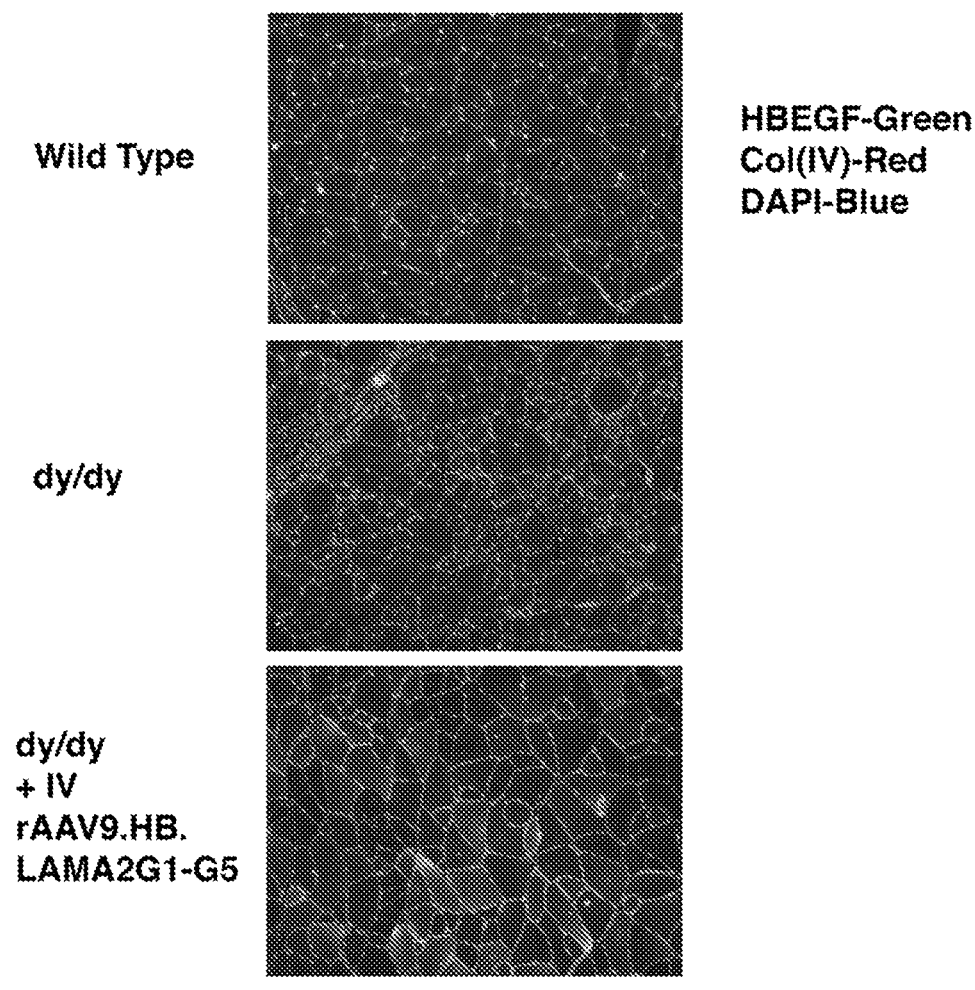

FIG. 18 provides immunohistochemistry staining for HB-EGF and LG5 to demonstrate expression of HB.LAMA2 (G1-G5) in dy/dy muscle (triceps) at 4 months of age after IV injection at P1. Muscle sections from the triceps muscle of 4-month old wild type and dy/dy mice, either mock-injected or injected with $1 \times 10^{12}$ vg rAAV9.CMV.HB-LAMA2 (G1-G5) were stained with antibodies specific to HBEGF (green), to recognize transgenic protein, and to collagen IV (Col (IV), red), to recognize all muscle cells. DAPI is added in blue to stain nuclei. Merged tricolor images are shown.

FIG. 19 provides the plasmid sequence of pAAV.CMV.HB.LAMA1(G1-G5) (SEQ ID NO: 2), the rAAV genome corresponds to nucleotides 3590 to 8215.

FIG. 20 provides the plasmid sequence of pAAV.CMV.HBEGF LAMA2 (G1-G5) (SEQ ID NO:4), the rAAV genome corresponds to nucleotides 3590-8341.

FIG. 21 provides the plasmid sequence of pAAV.CMV.HB LAMA2 (G3-G5) (SEQ ID NO: 6), the rAAV genome corresponds to nucleotides 36909-6929.

FIG. 22 provides the plasmid sequence of pAAV.CMV.HBEGF.LAMA2 (G3-G5) (SEQ ID NO: 8), the rAAV genome corresponds to nucleotides 3590-7036.

FIG. 23 provides the plasmid sequence of pAAV.CMV.HB.DAG1 (alpha) (SEQ ID NO: 10), the rAAV genome corresponds to nucleotides, the rAAV genome corresponds to nucleotides 3590 to 6340.

FIG. 24 provides the plasmid sequence of pAAV.CMV.HB.DAG1 (alpha) (SEQ ID NO: 12), the rAAV genome corresponds to nucleotides 3590-6049.

DETAILED DESCRIPTION

Methods and products are provided herein for treatment of dystroglycanopathies (including, but not limited to, Walker Warburg syndrome, Muscle Eye Brain disease, Fukuyama Congenital Muscular Dystrophy, MDC1C, MDC1D, LGMD2I, LGMD2K, LGMD2M, LGMD2N, LGMD2O, LGMD2P, LGMD2T and LGMD2U) and laminin-deficient muscular dystrophies (including, but not limited to, MDC1A) which utilize the lysine-rich heparin-binding domain of HBEGF. Heparin sulfate proteoglycans are abundant in the extracellular matrix (ECM) and, as shown herein, the overexpression of HBEGF in muscle leads to localization of HBEGF in the muscle ECM. In methods described herein, the membrane anchoring defects in dystroglycanopathies and laminin-deficient muscular dystrophies are treated using the heparin-binding domain of HBEGF as a "linker" domain in therapeutic proteins.

Figure 1:
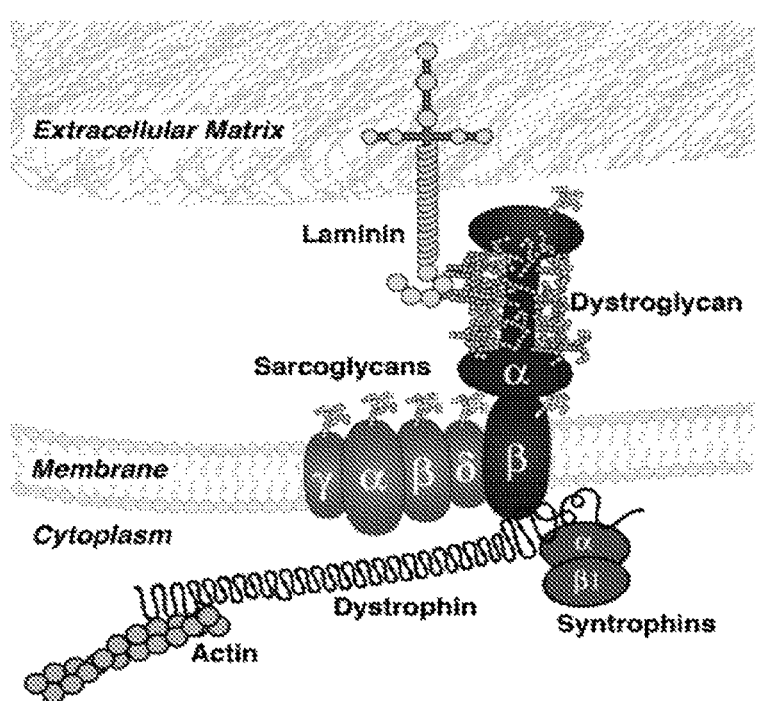
FIG. 1A depicts the dystrophin-associated glycoprotein (DAG) complex.
FIG. 1B shows a dystroglycan is not only abnormally glycosylated in dystroglycanopathies, which removes its normal laminin binding function, but α dystroglycan protein is reduced in diseased muscles.
FIG. 1C shows therapeutic proteins described herein will allow a dystroglycan to link to the muscle membrane by binding to β dystroglycan, which is present in normal amounts, and link to the ECM, even without its proper ECM-binding glycans, via binding of HBEGF to heparin sulfate proteoglycans of the ECM. This will reconstitute the lost linkages of α dystroglycan to the ECM and to the muscle membrane. Use of methods described herein providing these therapeutic proteins is indicated for treatment of all 18-plus genetic forms of dystroglycanopathies, making the methods powerful alternatives to gene replacement strategies in which each dystroglycanopathy would require development of a different gene therapy.
Figure 1:
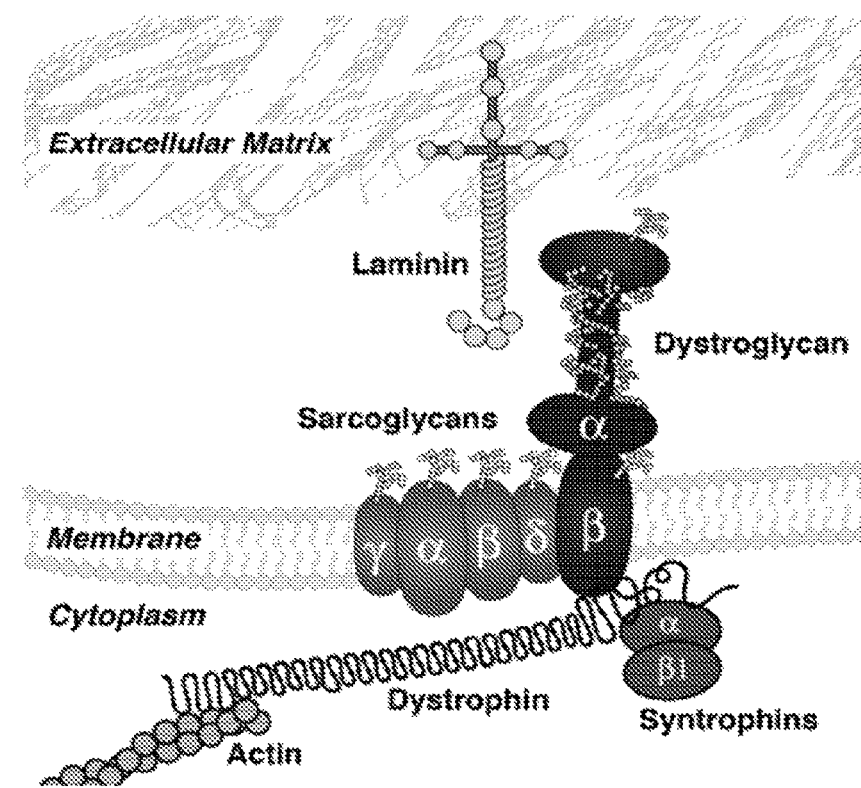
Figure 1:
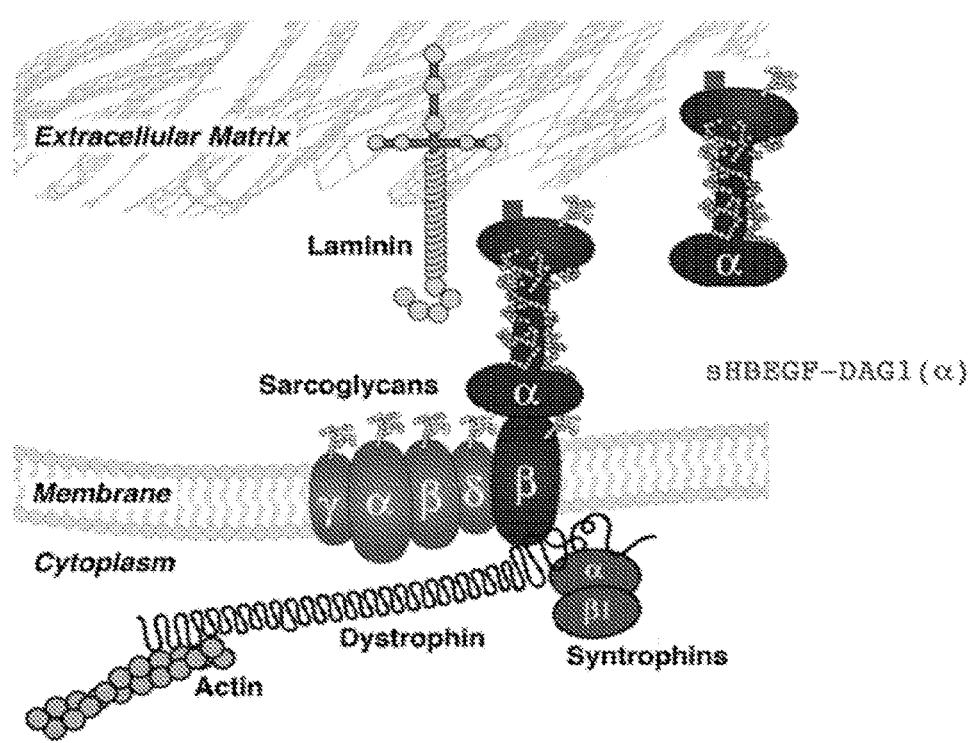
Figure 2:
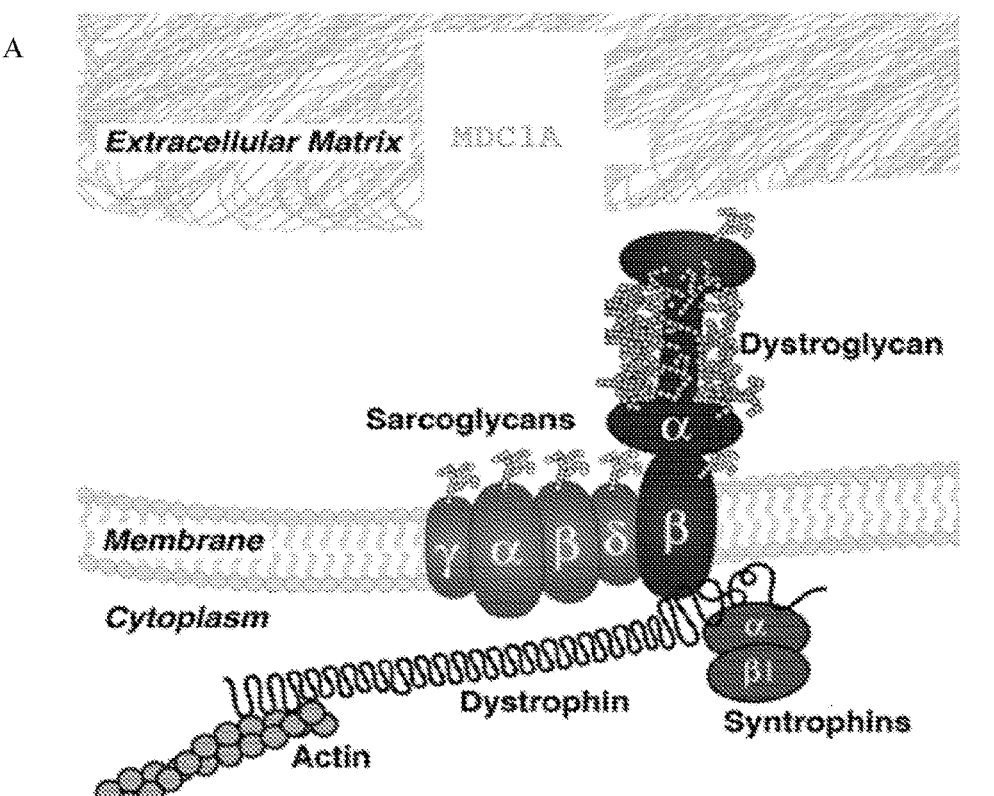
FIG. 2A depicts MDC1A is caused by loss of function mutations in the LAMA2 gene, which encodes laminin α2, an extracellular matrix (ECM) protein that surrounds each muscle cell in the body. LAMA2 is required for muscle cell adherence to the ECM and for muscle membrane stability.
FIG. 2B shows therapeutic proteins described herein can anchor the LAMA2 G1-G5 domains to the ECM where the LAMA2 G1-G5 domains would normally be present, so the LAMA2 G1-G5 domains can function as they do in native laminin α2. Use of methods described herein providing these therapeutic proteins is thus indicated for MDC1A.
Figure 3:
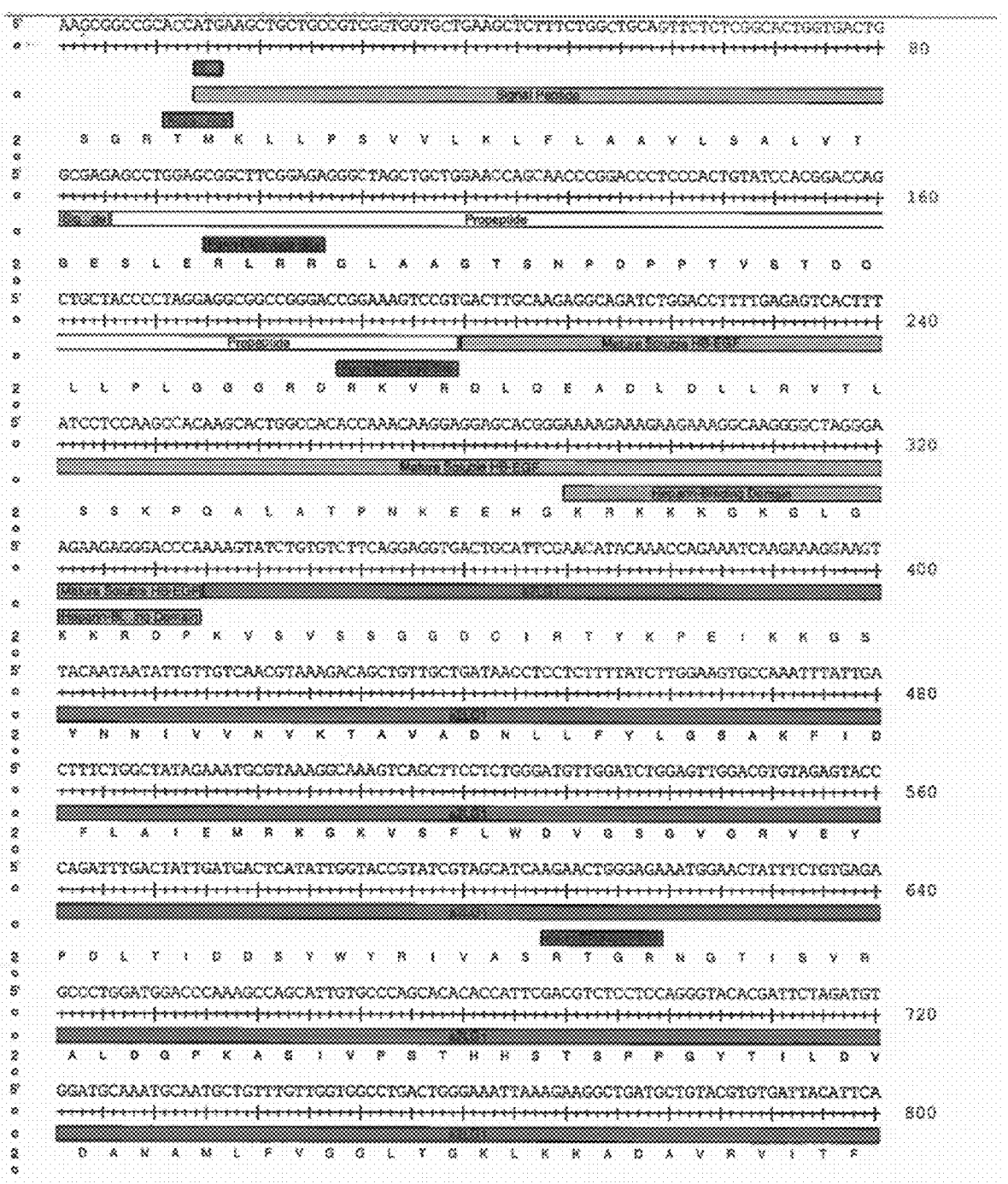
FIG. 3 shows the polynucleotide sequence encoding a therapeutic protein HB-EGF (ending at heparin binding domain)-LAMA2 G1-G5. The therapeutic protein is encoded by nucleotides of the invention comprises nucleotides 14 to 3235, which also correspond to SEQ ID NO: 1. The plasmid sequence provided in FIG. 3 is set out as SEQ ID NO: 27. The amino acid sequence provided in FIG. 3 is set out as SEQ ID NO: 33, and further comprises a terminal peptide at the C-terminus as set out in SEQ ID NO: 39.
Figure 3:
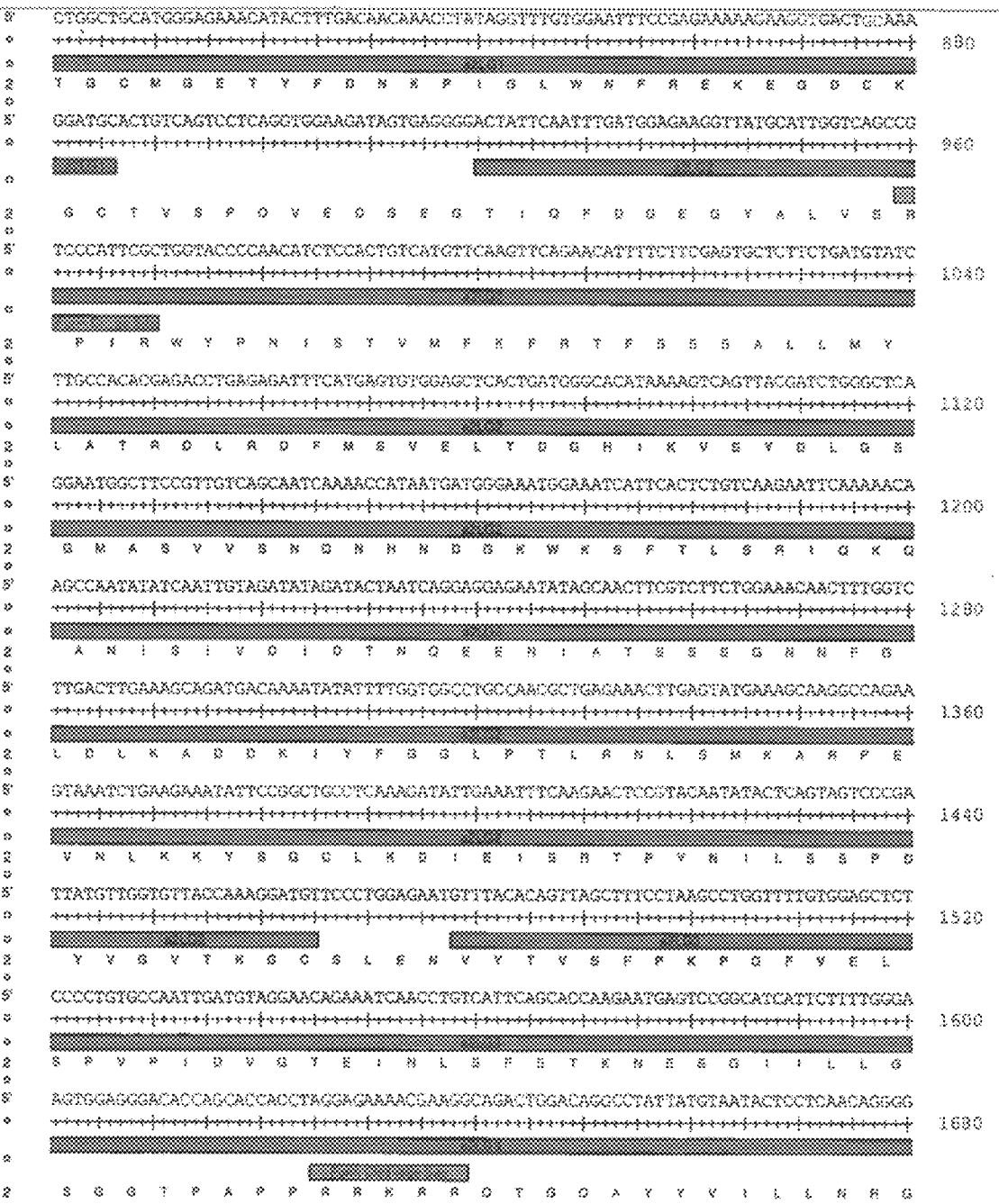
Figure 3:
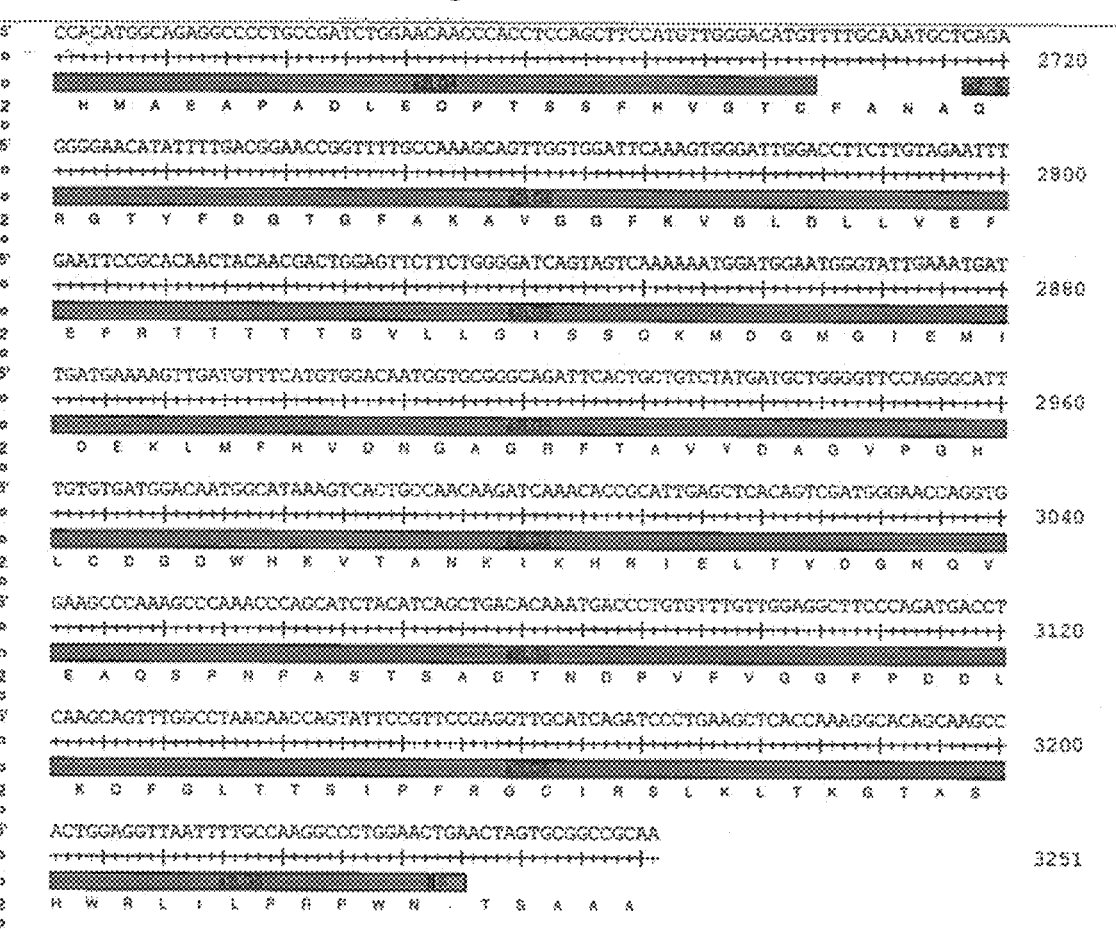
Figure 4:
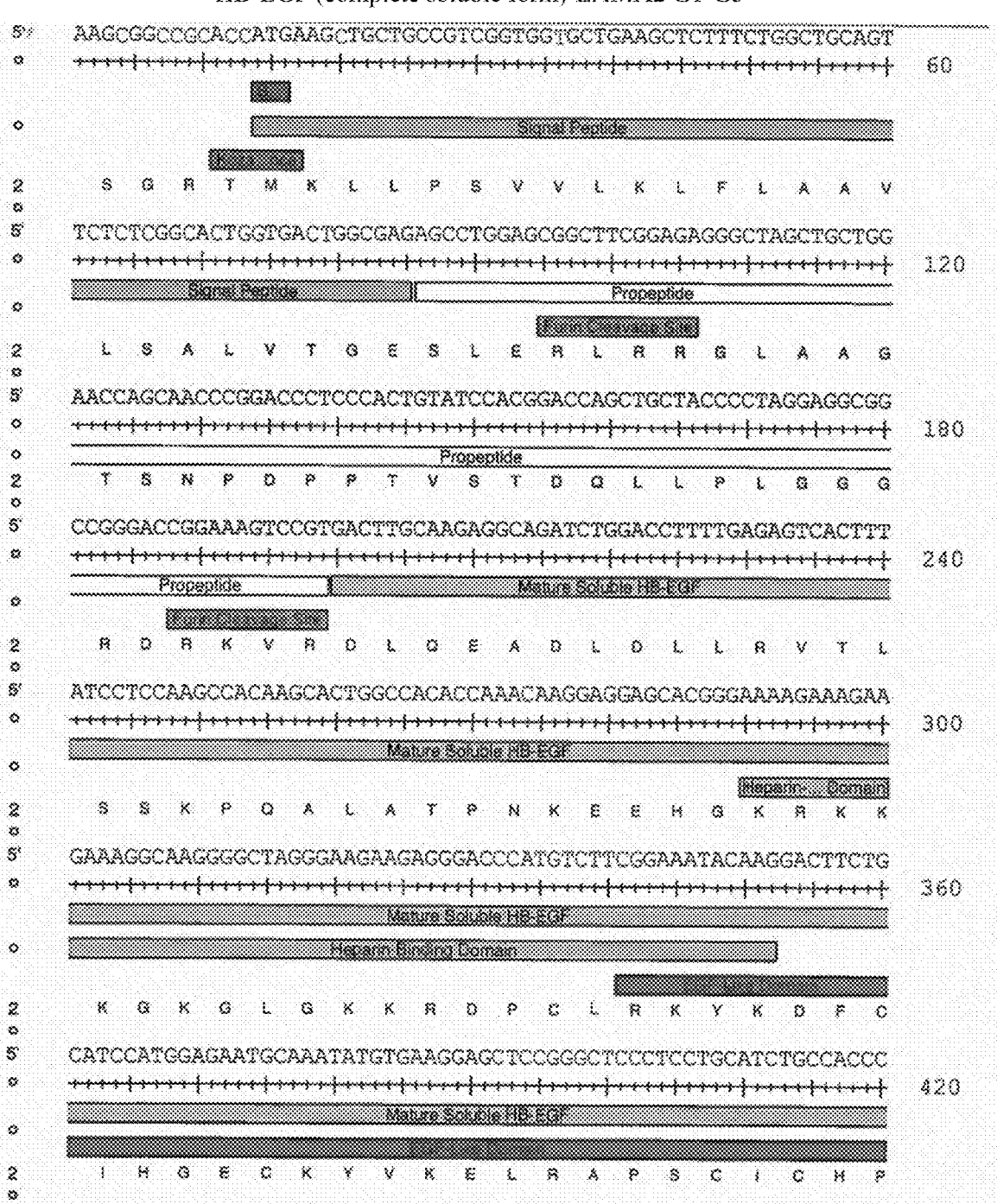
FIG. 4 shows the polynucleotide sequence encoding a therapeutic protein HB-EGF (complete soluble form)-LAMA2 G1-G5. The therapeutic protein is encoded by nucleotides of the invention comprises nucleotides 14 to 3361, which also correspond to SEQ ID NO: 3. The plasmid sequence provided in FIG. 4 is set out as SEQ ID NO: 28. The amino acid sequence provided in FIG. 4 is set out as SEQ ID NO: 34, and further comprises a terminal peptide at the C-terminus as set out in SEQ ID NO: 39.
Figure 4:
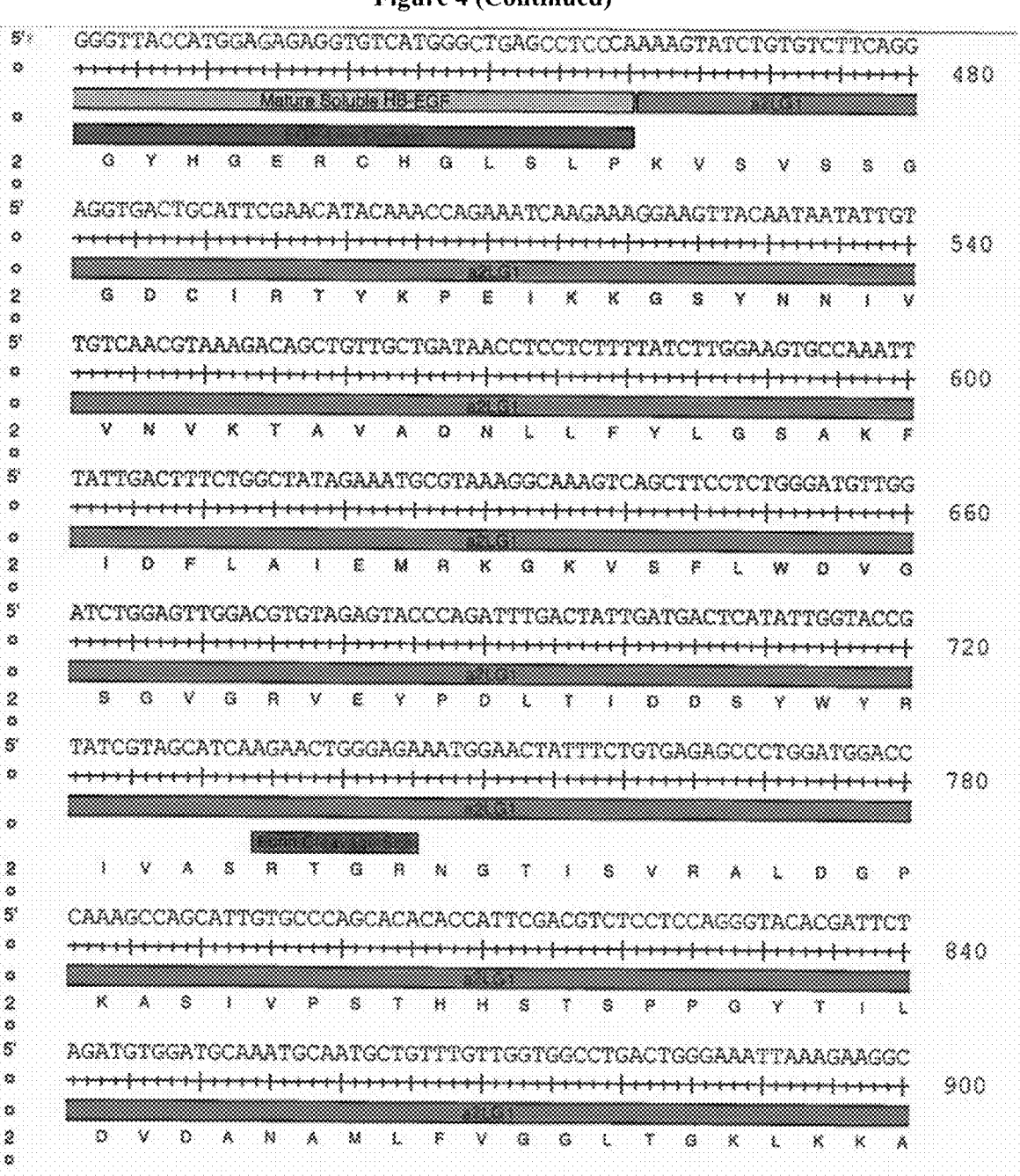
Figure 4:
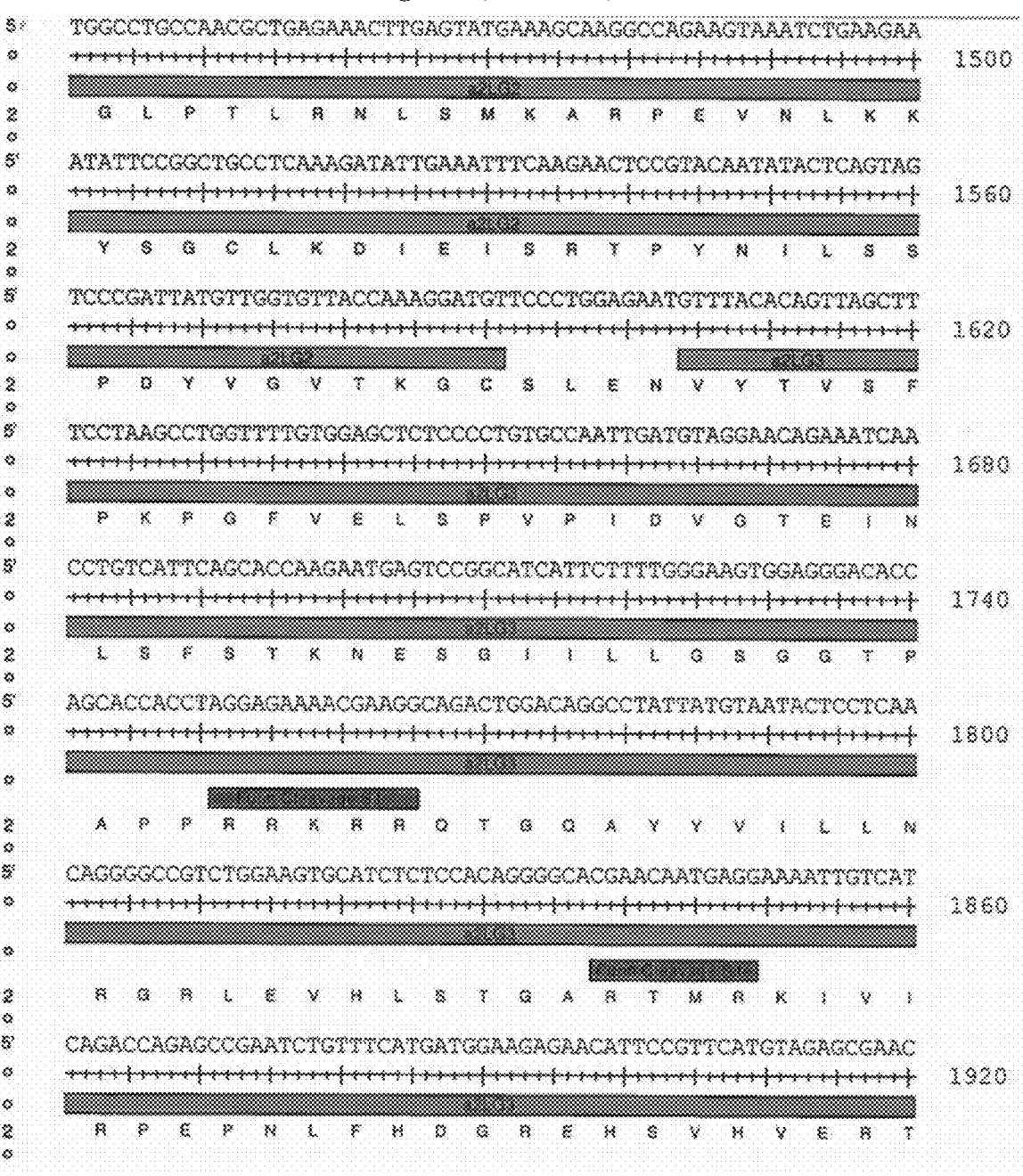
Figure 4:
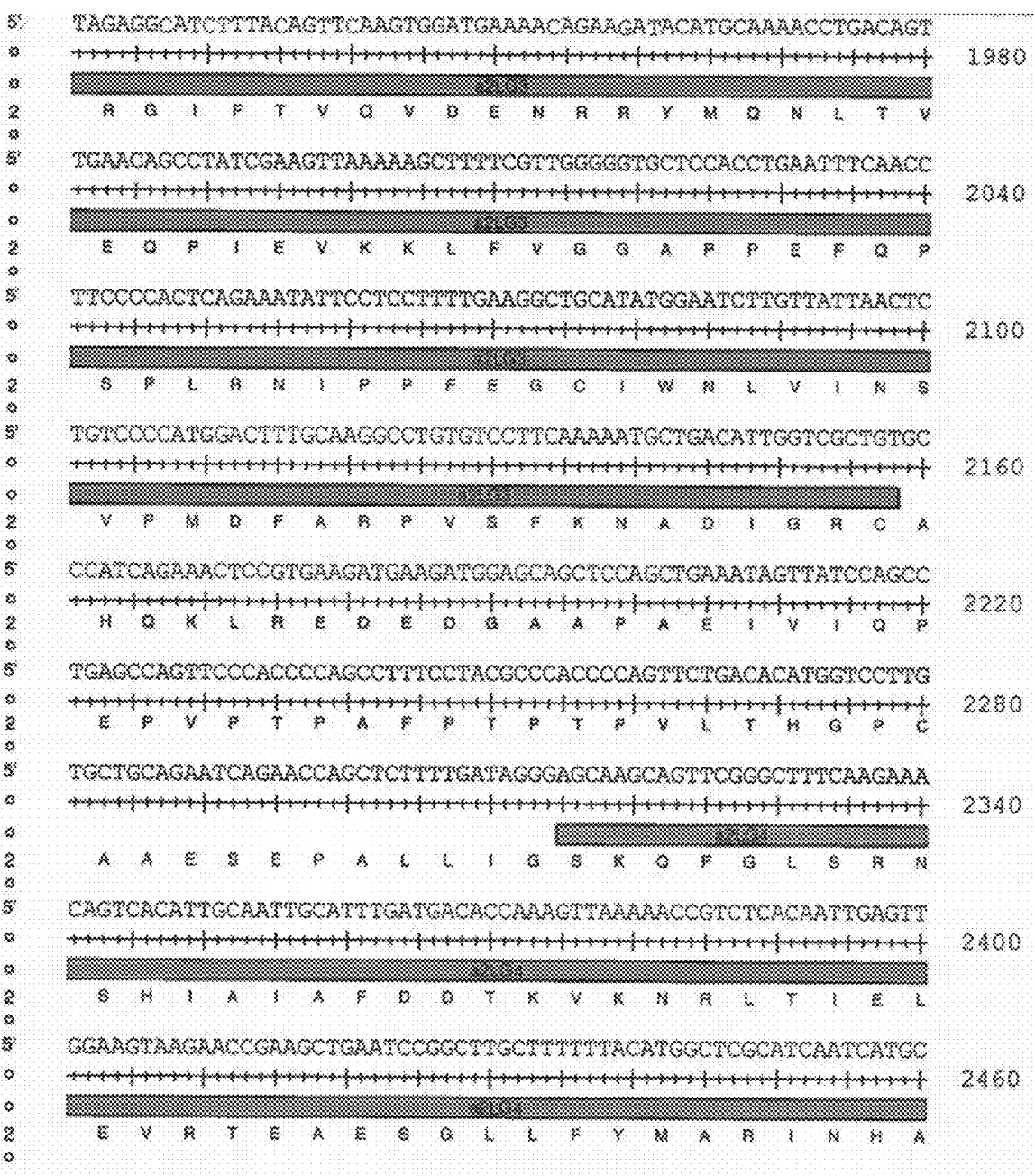
Figure 4:
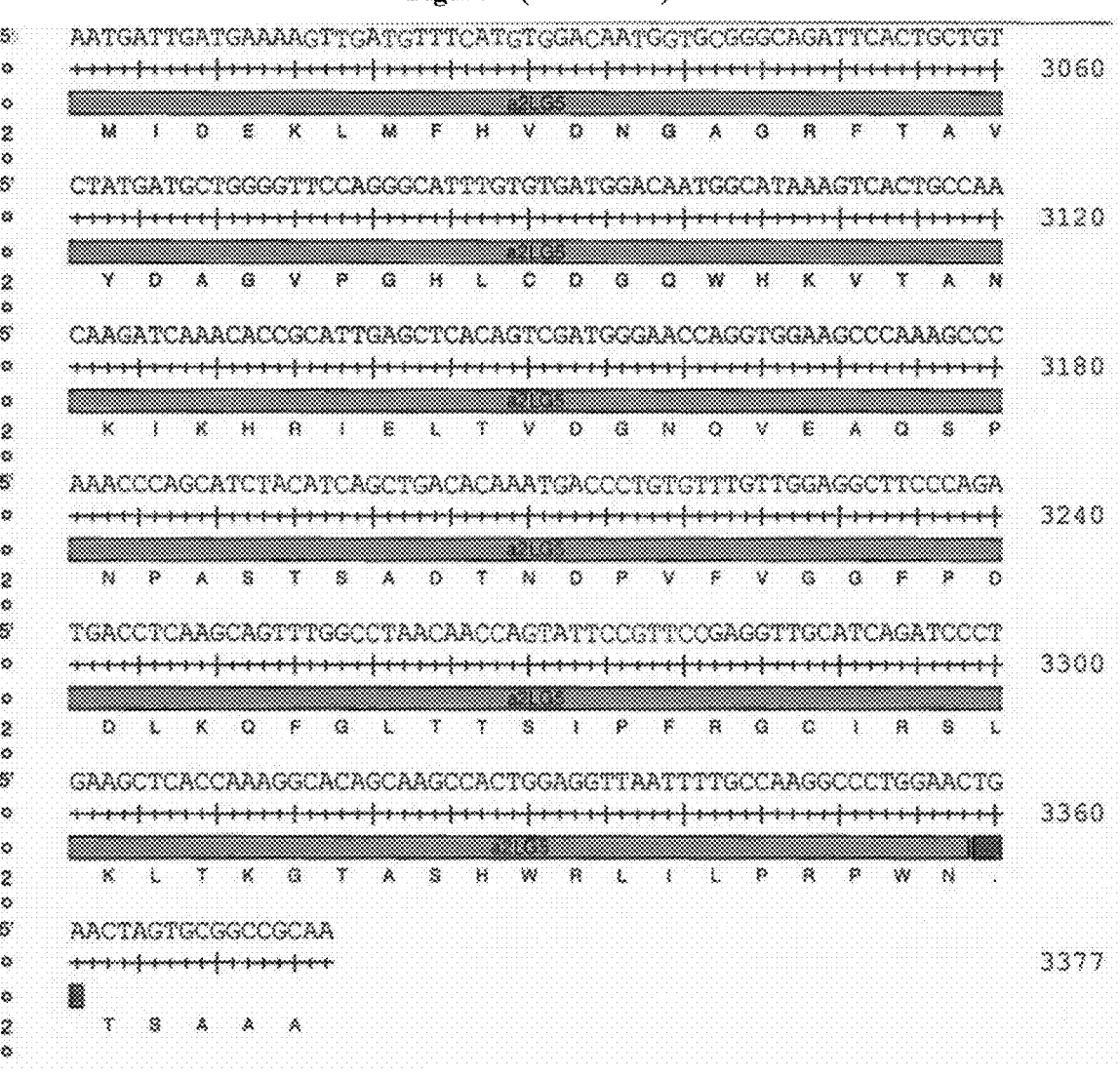

Here, the term "HBEGF" refers to the entire HBEGF sequence up to and including the bioactive EGF domain, but lacking the transmembrane domain, which thereby allows HBEGF secretion (FIG. 4). The HBEGF fragment contains four domains from the HBEGF gene, the signal peptide, which allows entry into the secretory pathway, the prepro-peptide, which allows folding and stabilization of the protein, the heparin binding domain, which allows for increased interaction with the extracellular matrix, and the bioactive EGF domain, which allows for HBEGF signaling. In the proteins disclosed herein, the coding sequence for these domains are then then linked to laminin alpha 2 or dystroglycan coding sequences. A second "HB" fragment is also used (FIG. 3). The HB fragment only contains 3 of the four domains found in HBEGF: the signal peptide, the pre-propeptide, and the heparin binding domain (and so HB lacks the bioactive EGF domain). When linked to laminin alpha 2 or dystroglycan protein fragments, the HB domain allows for increased association with the ECM but without increasing EGF or HBEGF signaling.

The HBEGF or HB linker domain targets a protein to the extracellular matrix of a cell and acts to anchor this protein to the extracellular domain of a cell, such as a muscle cell. Polynucleotides encoding therapeutic proteins are delivered to a patient (for example, delivery by a recombinant AAV encoding the therapeutic proteins), or the therapeutic proteins are delivered to a patient.

For example, for all of the dystroglycanopathies, a coding sequence for HBEGF heparin-binding domain is fused to a coding sequence for α-dystroglycan, creating a polynucleotide encoding the therapeutic protein HBEGF-DAG1(α). In addition to α-dystroglycan hypoglycosylation, α-dystroglycan protein levels are reduced in dystroglycanopathies. In methods described herein, the HBEGF domain of HBEGF-DAG1(α) binds the ECM heparin sulfate proteoglycans, while the α-dystroglycan domain binds β-dystroglycan, linking the sarcolemma to the ECM despite hypoglycosylation in the dystroglycanopathies. Four examples of such HBEGF-DAG1 (a) therapeutic proteins are: HB-EGF (ending at heparin binding domain)-LAMA2 G1-G5 (encoded by the polynucleotide of FIG. 3), HB-EGF (complete soluble form)-LAMA2 G1-G5 (encoded by the polynucleotide of FIG. 4), HB-EGF (ending at heparin binding domain)-LAMA2 G3-G5 (encoded by the polynucleotide of FIG. 5), and HB-EGF (complete soluble form)-LAMA2 G3-G5 (encoded by the polynucleotide of FIG. 6).

The term "complete soluble form" herein indicates the therapeutic protein comprises the HBEGF heparin-binding and EGF-like domains, but not the transmembrane portion of HBEGF. The combination of the HBEGF heparin-binding and EGF-like domains of HBEGF corresponds to the cleaved, active, soluble isoform of HBEGF. This term is referred to as 'HBEGF" herein.

The term "ending at heparin binding domain" herein indicates that that therapeutic protein comprises only HBEGF heparin-binding domain and does not comprise the EGF-like domain or the transmembrane portion of HBEGF. This term is abbreviated as 'HB' herein.

Figure 7:
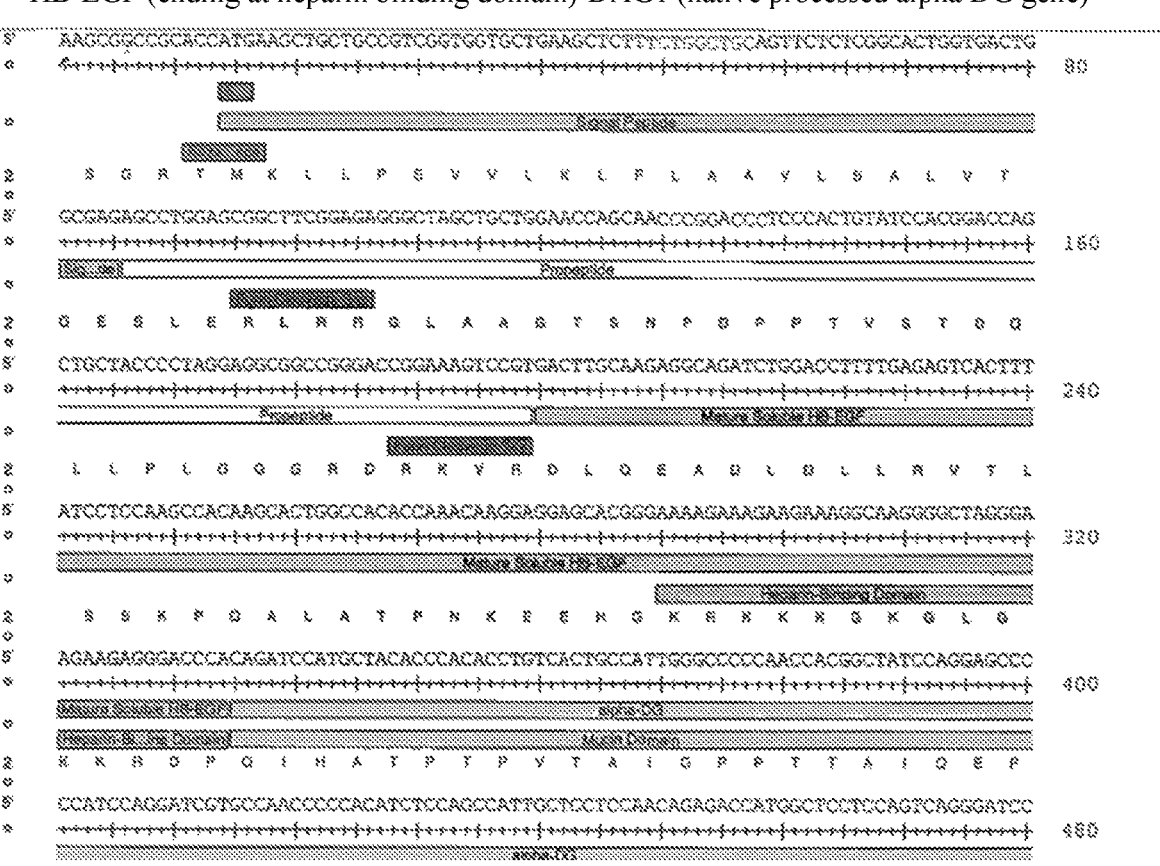
FIG. 7 shows the polynucleotide sequence encoding a therapeutic protein HB-EGF (ending at heparin binding domain)-DAG1 (native processed alpha DG gene). The therapeutic protein is encoded by nucleotides of the invention comprises nucleotides 14 to 1360, which also correspond to SEQ ID NO: 9. The plasmid sequence provided in FIG. 7 is set out as SEQ ID NO: 31. The amino acid sequence provided in FIG. 7 is set out as SEQ ID NO: 37, and further comprises a terminal peptide at the C-terminus as set out in SEQ ID NO: 39.
Figure 7:
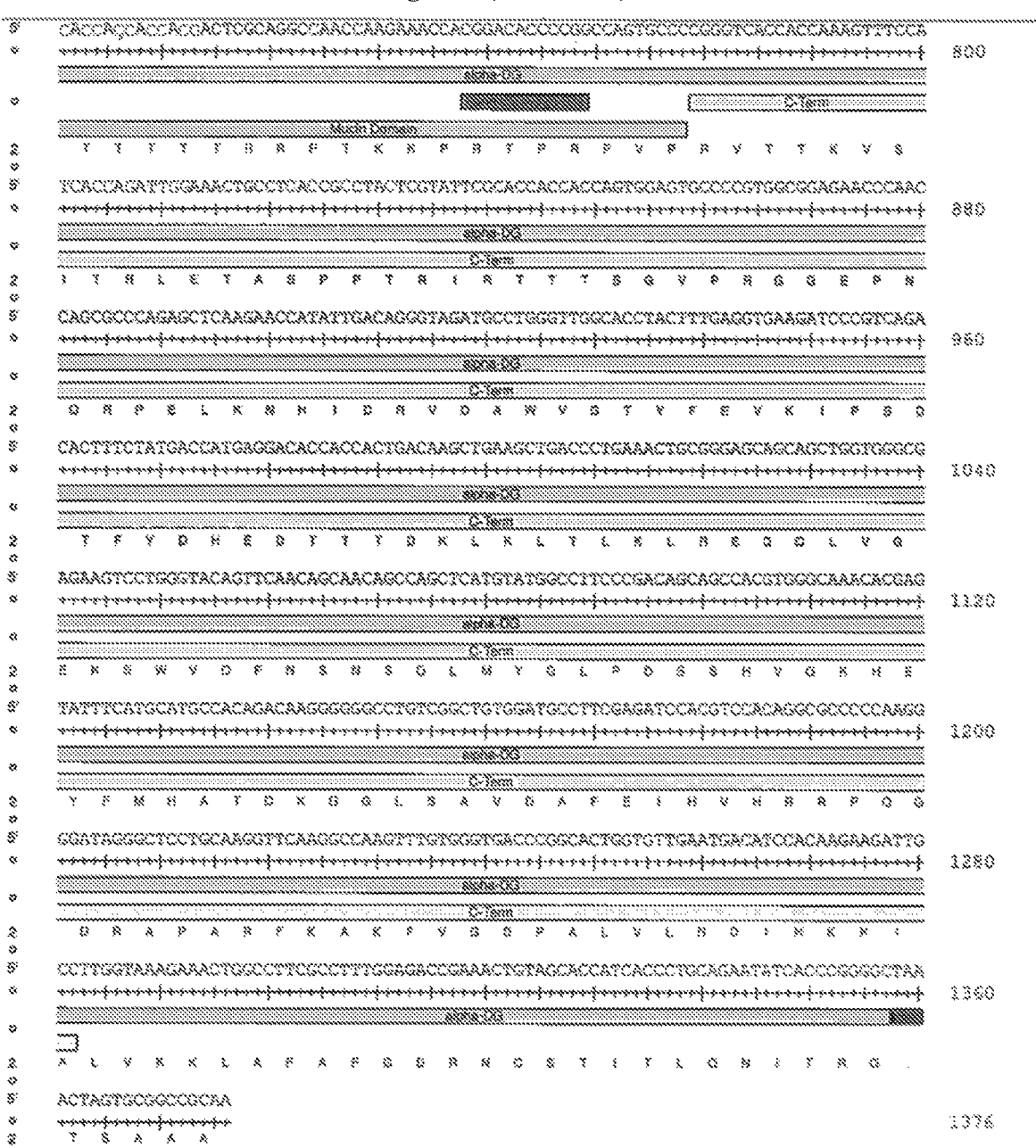
Figure 8:
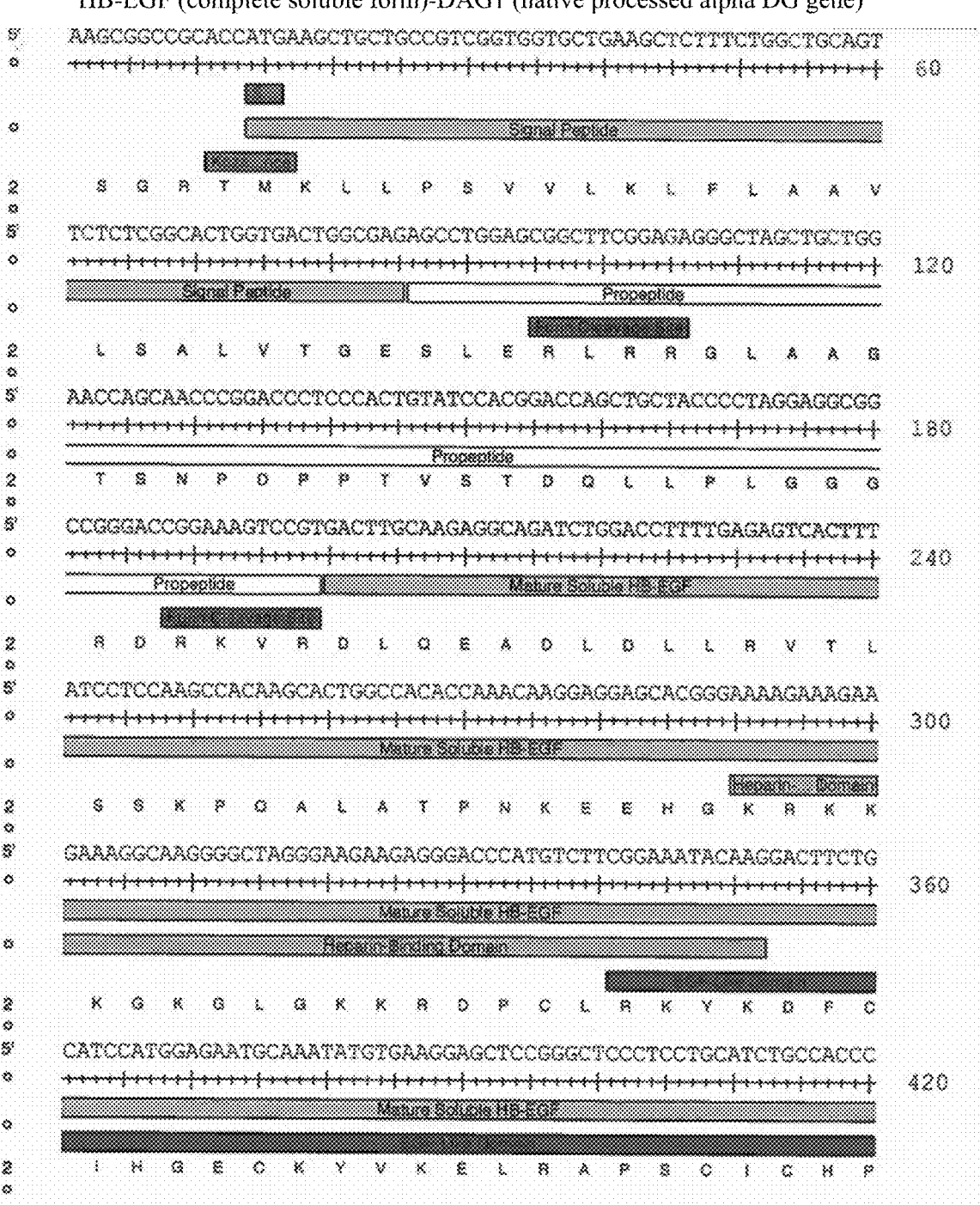
FIG. 8 shows the polynucleotide sequence encoding a therapeutic protein HB-EGF (complete soluble form)-DAG1 (native processed alpha DG gene). The therapeutic protein is encoded by nucleotides of the invention comprises nucleotides 14 to 1486, which also correspond to SEQ ID NO: 11. The plasmid sequence provided in FIG. 8 is set out as SEQ ID NO: 32. The amino acid sequence provided in FIG. 8 is set out as SEQ ID NO: 38, and further comprises a terminal peptide at the C-terminus as set out in SEQ ID NO: 39.
Figure 8:
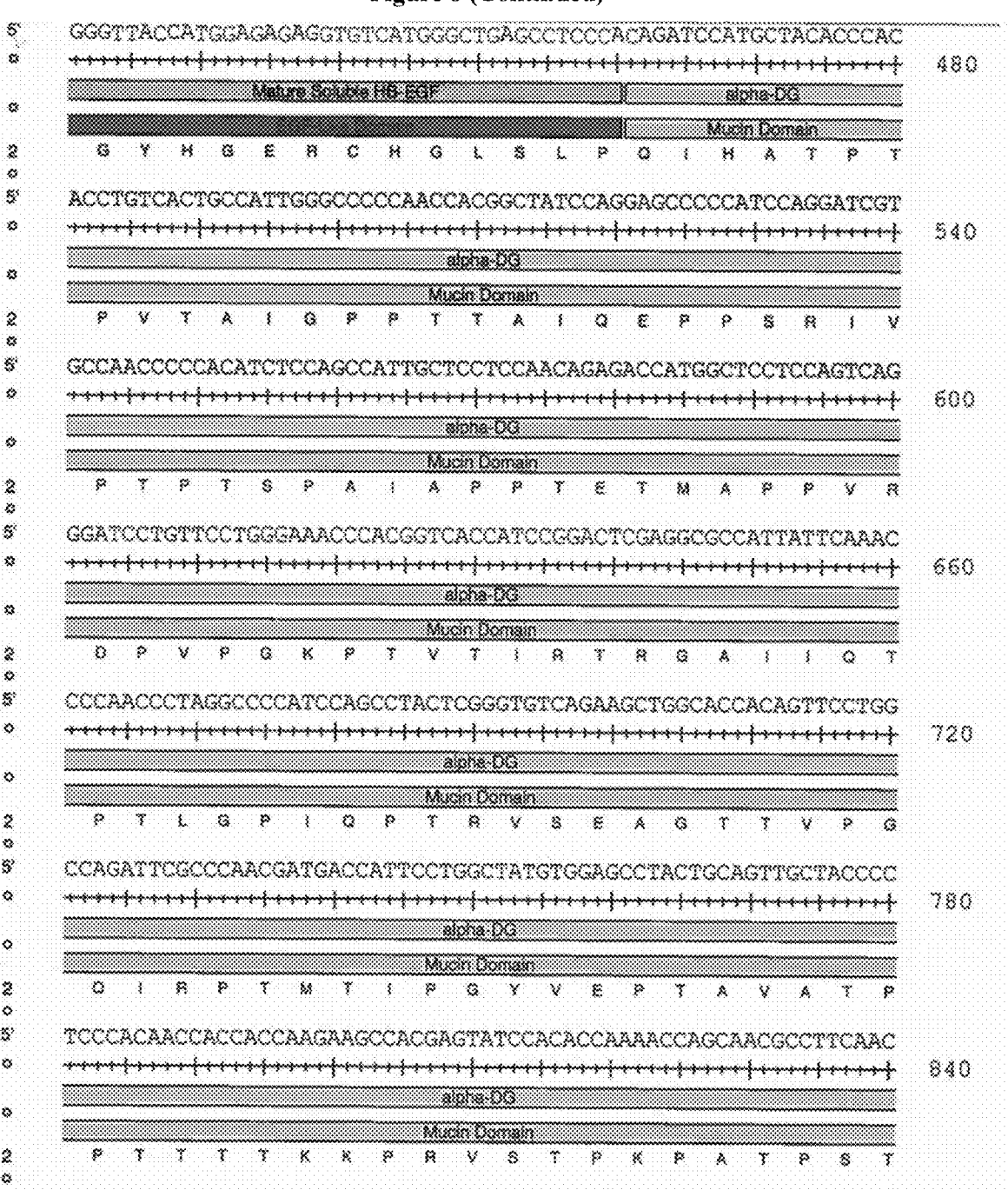
Figure 8:
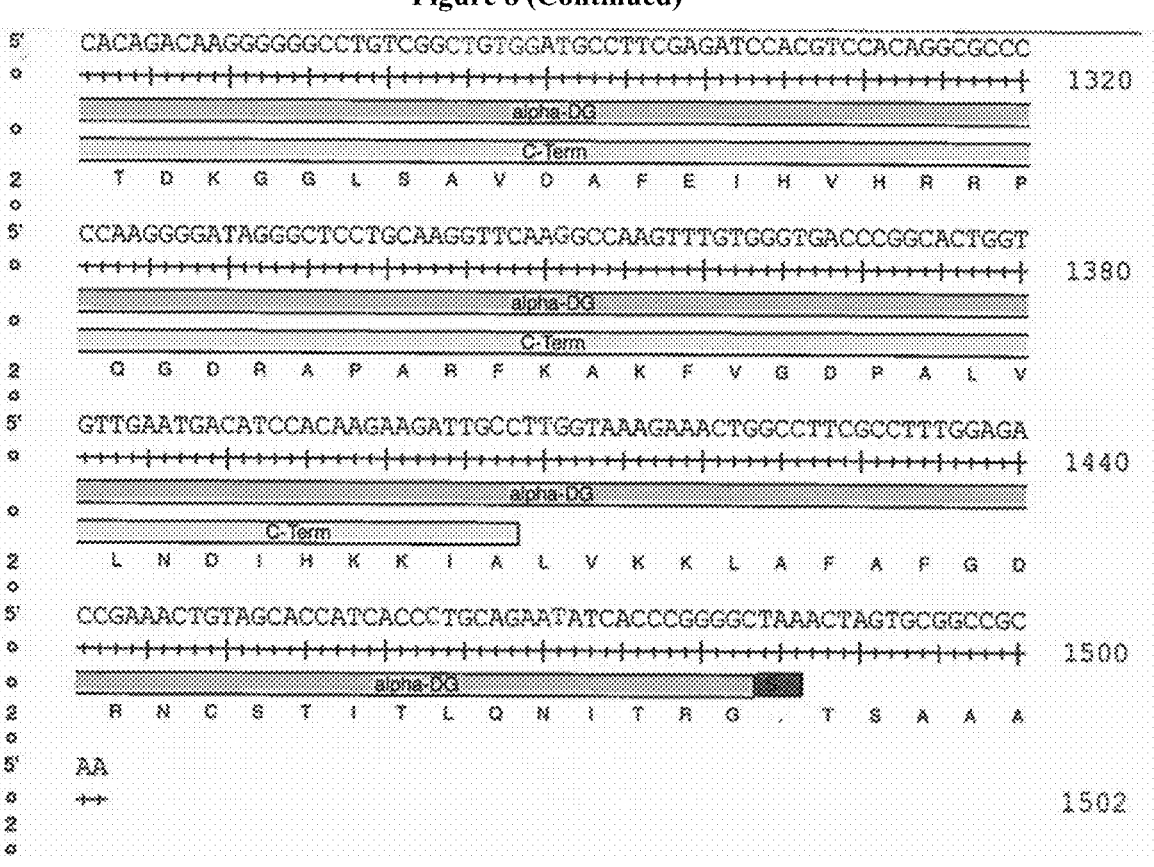

For example, for laminin-deficient muscular dystrophies such as MDC1A, a coding sequence for HBEGF heparin-binding domain is fused to a coding sequence for the globular (G) domains 1-5 of laminin-α2, creating a polynucleotide encoding the therapeutic protein HBEGF-LAMA2 (G1-5). The laminin-α2 G domains bind glycosylated α-dystroglycan and also integrins at the sarcolemma, and are encoded by a part of the LAMA2 gene. In methods described herein, the HBEGF domain of HBEGF-LAMA2 (G1-5) binds the ECM heparin sulfate proteoglycans, while the G domains bind α-dystroglycan, linking the sarcolemma to the ECM despite the absence of full-length laminin-α2 in MDC1A. Two examples of such HBEGF-LAMA2 (G1-5) therapeutic proteins are:

HB-EGF (ending at heparin binding domain)-DAG1 (native processed alpha DG gene) (encoded by the polynucleotide of FIG. 7) and HB-EGF (complete soluble form)-DAG1 (native processed alpha DG gene) (encoded by the polynucleotide of FIG. 8).

Furthermore, both dystroglycanopathies and laminin-deficient muscular dystrophies (such as MDC1A) are associated with reduced muscle regeneration and, in embodiments of methods described herein wherein the therapeutic proteins comprise a HBEGF heparin-binding domain and HBEGF EGF-like domain, patients also benefit from trophic signaling of the HBEGF EGF-like domain of the therapeutic proteins which results in the alteration of expression of genes including Pax7, MyOD, Myogenin and Myh3 increasing myogenesis and muscle regeneration.

Thus, polynucleotides are provided encoding the therapeutic proteins. Embodiments include a polynucleotide comprising the polynucleotide sequence set forth in FIG. 3, 4, 5, 6, 7 or 8. Other embodiments include a polynucleotide encoding the same amino acid sequence as the polynucleotide sequence set forth in FIG. 3, 4, 5, 6, 7 or 8. Still other embodiments include a polynucleotide comprising a polynucleotide consisting of the polynucleotide sequence set forth in FIG. 3, 4, 5, 6, 7 or 8.

In one embodiment, the provided polynucleotides comprise one of the following: i) the nucleotide sequence set forth in FIG. 3, ii) a nucleotide sequence comprising nucleotides 14 to 3235 set out in FIG. 3, iii) the nucleotide sequence of SEQ ID NO: 1, or iv) a nucleotide sequence encoding the amino acid sequence of SEQ ID NO: 19.

In another embodiment, the provided polynucleotides comprise one of the following: i) the nucleotide sequence set forth in FIG. 4, ii) a nucleotide sequence comprising nucleotides 14 to 3361 set forth in FIG. 4, iii) the nucleotide sequence of SEQ ID NO: 3 or iv) a nucleotide sequence encoding the amino acid sequence of SEQ ID NO: 20.

Figure 5:
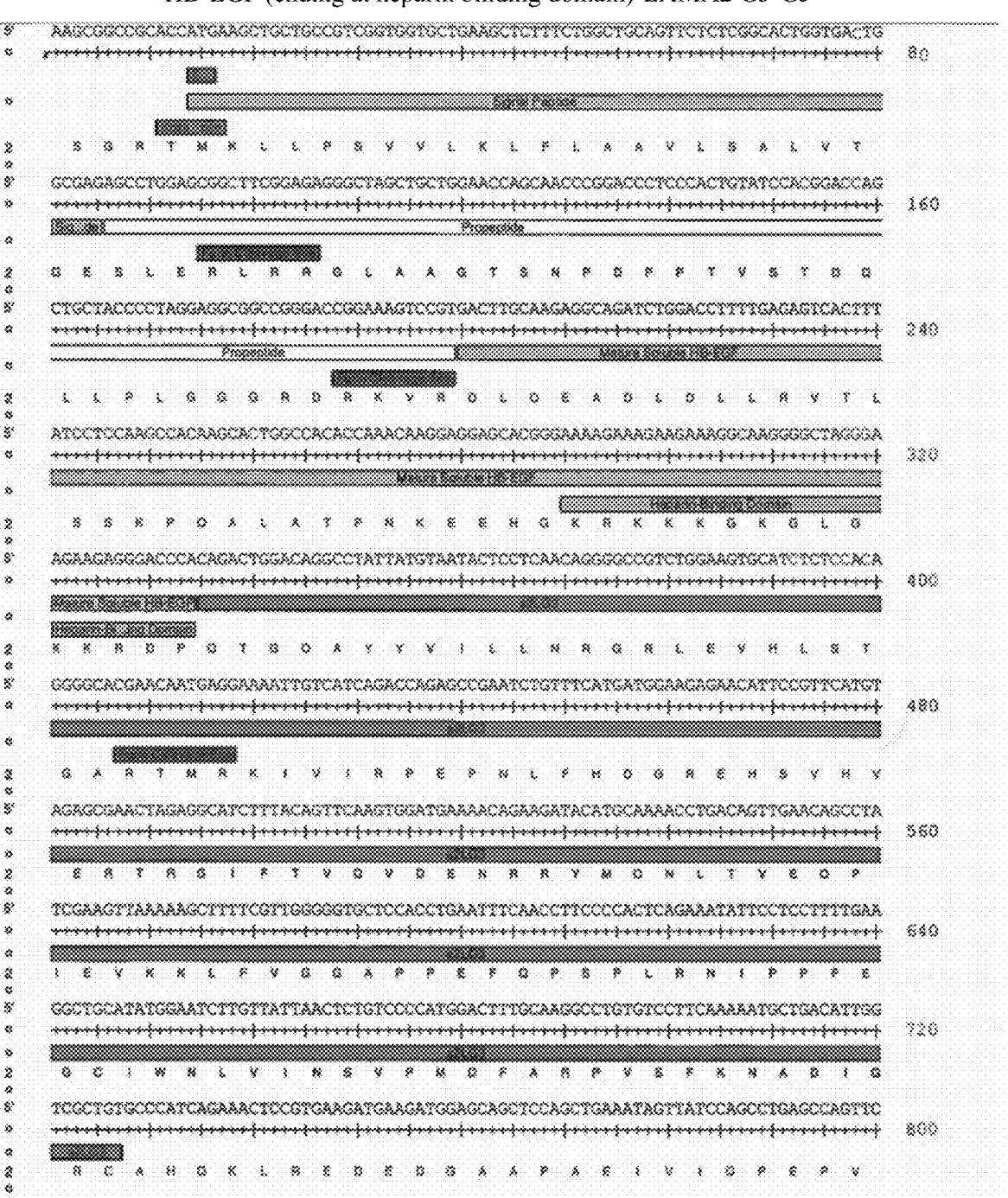
FIG. 5 shows the polynucleotide sequence encoding a therapeutic protein HB-EGF (ending at heparin binding domain)-LAMA2 G3-G5. The therapeutic protein is encoded by nucleotides of the invention comprises nucleotides 14 to 1930, which also correspond to SEQ ID NO: 5. The plasmid sequence provided in FIG. 5 is set out as SEQ ID NO: 29. The amino acid sequence provided in FIG. 5 is set out as SEQ ID NO: 35, and further comprises a terminal peptide at the C-terminus as set out in SEQ ID NO: 39.
Figure 5:
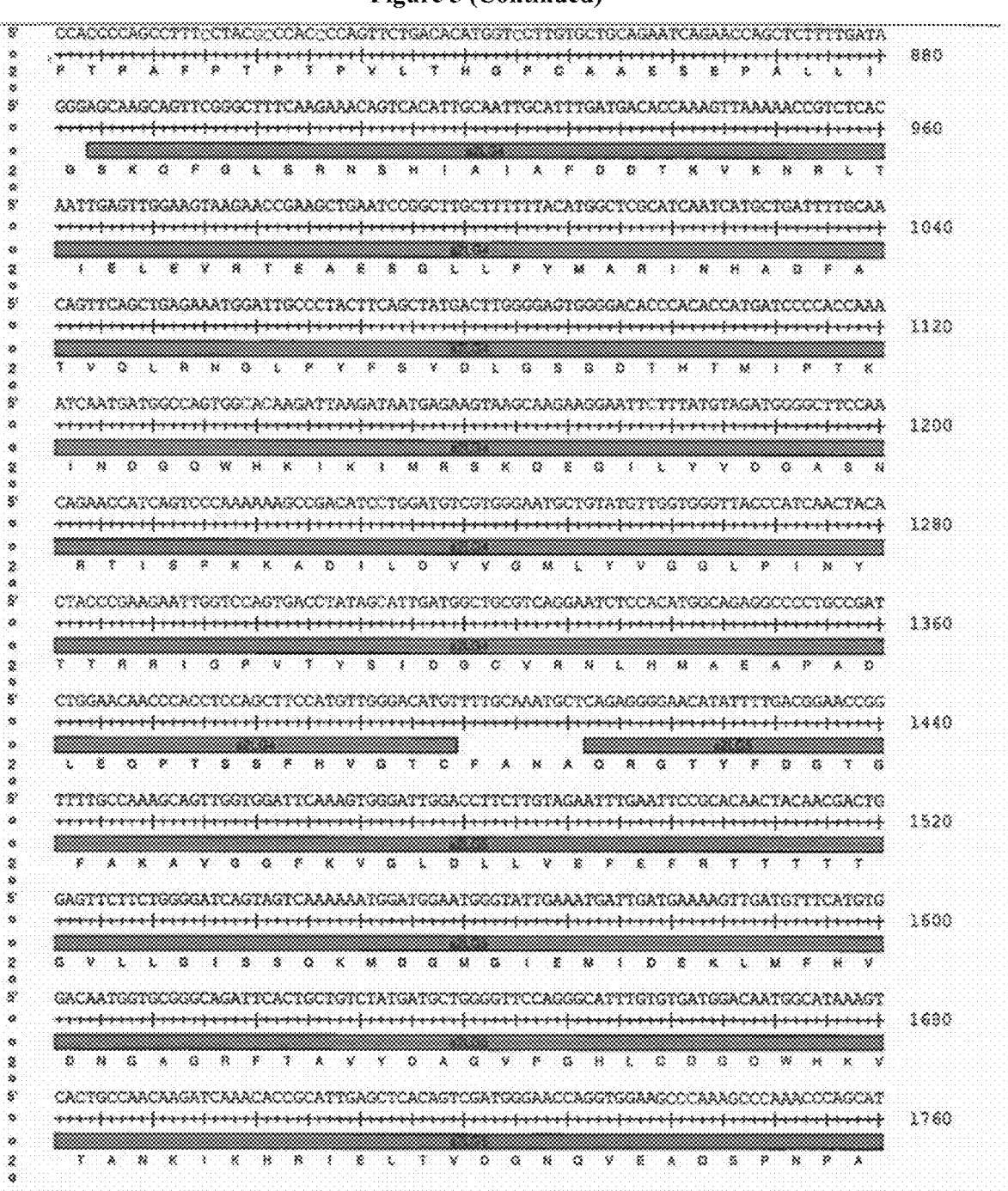
Figure 5:
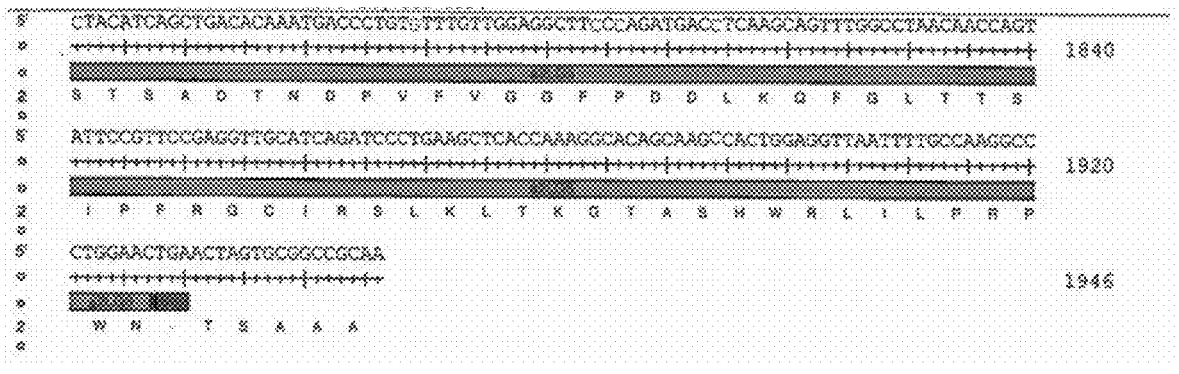

In a further embodiment, the provided polynucleotides comprise one of the following: i) the nucleotide sequence set forth in FIG. 5, ii) a nucleotide sequence comprising nucleotides 14 to 1930 set forth in FIG. 5, iii) the nucleotide sequence of SEQ ID NO: 5 or iv) a nucleotide sequence encoding the amino acid sequence of SEQ ID NO: 21.

Figure 6:
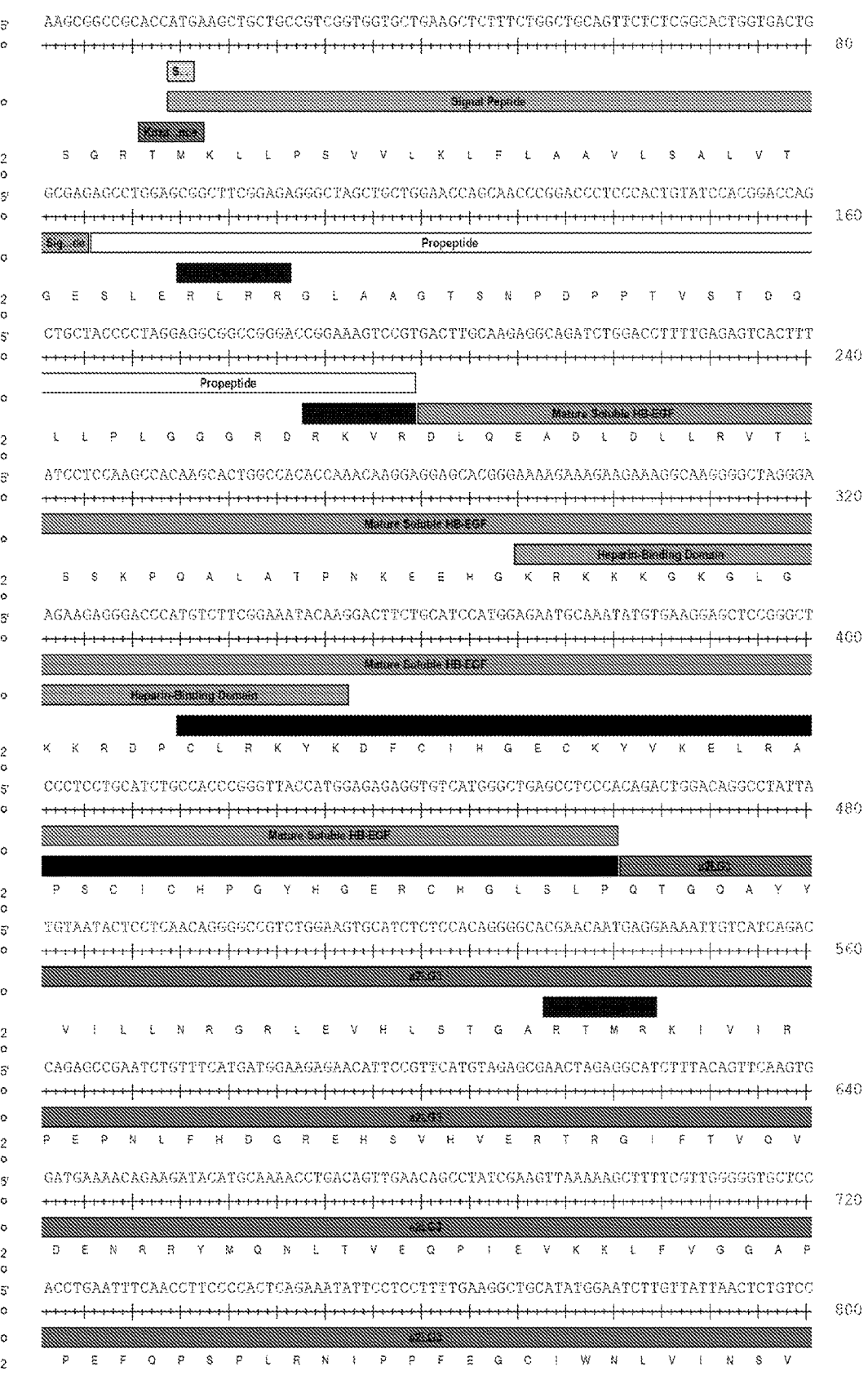
FIG. 6 shows the polynucleotide sequence encoding a therapeutic protein HB-EGF (complete soluble form)-LAMA2 G3-G5. The therapeutic protein is encoded by nucleotides of the invention comprises nucleotides 14 to 2056, which also correspond to SEQ ID NO: 7. The plasmid sequence provided in FIG. 6 is set out as SEQ ID NO: 30. The amino acid sequence provided in FIG. 6 is set out as SEQ ID NO: 36, and further comprises a terminal peptide at the C-terminus as set out in SEQ ID NO: 39.

In another embodiment, the provided polynucleotides comprise one of the following: i) the nucleotide sequence set forth in FIG. 6, ii) a nucleotide sequence comprising nucleotides 14 to 2056 set forth in FIG. 6, iii) the nucleotide sequence of SEQ ID NO: 7 or iv) a nucleotide sequence encoding the amino acid sequence of SEQ ID NO: 22.

In an embodiment, the provided polynucleotides comprise one of the following: i) the nucleotide sequence set forth in FIG. 7, ii) a nucleotide sequence comprising nucleotides 14 to 1360 set forth in FIG. 7, iii) the nucleotide sequence of SEQ ID NO: 9 or iv) a nucleotide sequence encoding the amino acid sequence of SEQ ID NO: 23.

In another embodiment, the provided polynucleotides comprise one of the following: i) the nucleotide sequence set forth in FIG. 8, ii) a nucleotide sequence comprising nucleotides 14-1486 set forth in FIG. 8, iii) the nucleotide sequence of SEQ ID NO: 11 or iv) a nucleotide sequence encoding the amino acid sequence of SEQ ID NO: 24.

Other polynucleotides provided include, but are not limited to, a polynucleotide that encodes an amino acid variant of a therapeutic polypeptide which retains the binding activity of the therapeutic protein, which polynucleotide has a nucleotide sequence at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to the protein-coding nucleotide sequence set out in FIG. 3, 4, 5, 6, 7 or 8 or the nucleotide sequence of any of the provided polynucleotides.

Also provided herein are polynucleotides that encode an amino acid variant of a therapeutic polypeptide which retains the binding activity of the therapeutic protein, which polynucleotide hybridizes under stringent conditions to the protein-coding nucleotide sequence set out in FIG. 3, 4, 5, 6, 7 or 8, or the complement thereof or the nucleotide sequence of any of the provided polynucleotides. The term "stringent" is used to refer to conditions that are commonly understood in the art as stringent. Hybridization stringency is principally determined by temperature, ionic strength, and the concentration of denaturing agents such as formamide. Examples of stringent conditions for hybridization and washing are 0.015 M sodium chloride, 0.0015 M sodium citrate at 65-68° C. or 0.015 M sodium chloride, 0.0015M sodium citrate, and 50% formamide at 42° C. See Sambrook et al., Molecular Cloning: A Laboratory Manual, $2^{nd}$ Ed., Cold Spring Harbor Laboratory, (Cold Spring Harbor, N.Y. 1989).

"Retains the binding activity" is contemplated herein to mean that the amino acid variant of the therapeutic protein encoded by a polynucleotide competes for binding with a therapeutic protein encoded by the nucleotide sequence set out in FIG. 3, 4, 5, or 6 to heparin sulfate proteoglycans and β-dystroglycan; or for binding with a therapeutic protein encoded by the nucleotide sequence set out in FIG. 7 or 8 to heparin sulfate proteoglycans and α-dystroglycan; or a therapeutic protein comprising the amino acid sequence of SEQ ID NO: 19, SEQ ID NO: 20, SEQ ID NO: 21 SEQ ID NO: 22, SEQ ID NO: 23 OR SEQ ID NO: 24 to heparin sulfate proteoglycans and α-dystroglycan.

Recombinant expression vectors comprising one or more of the polynucleotides described herein are also provided. Recombinant AAV genomes comprising a polynucleotide described herein are also provided.

In expression vectors or recombinant AAV genomes described herein, the polynucleotide encoding the therapeutic protein is operatively linked to transcriptional control elements (including, but not limited to, promoters, enhancers and/or introns), specifically transcriptional control elements functional in target cells of interest. For example, suitable promoters for use with mammalian host cells are well known and include, but are not limited to, those obtained from the genomes of viruses such as polyoma virus, fowlpox virus, adenovirus (such as Adenovirus 2), bovine papilloma virus, avian sarcoma virus, cytomegalovirus, retroviruses, hepatitis-B virus, and Simian Virus 40 (SV40). Other suitable mammalian promoters include heterologous mammalian promoters, for example, heat-shock promoters and the actin promoter. Also for example, AAV delivery methods may comprise transducing muscle or liver cells using muscle-specific transcriptional control elements, including, but not limited to, those derived from the actin and myosin gene families, such as from the myoD gene family [See Weintraub et al., *Science,* 251:761-766 (1991)], the myocyte-specific enhancer binding factor MEF-2 [Cserjesi and Olson, *Mol Cell Biol,* 11:4854-4862 (1991)], control elements derived from the human skeletal actin gene [Muscat et al., *Mol Cell Biol,* 7:4089-4099 (1987)], muscle creatine kinase sequence elements [See Johnson et al., *Mol Cell Biol,* 9:3393-3399 (1989)] and the murine creatine kinase enhancer (mCK) element, control elements derived from the skeletal fast-twitch troponin C gene, the slow-twitch cardiac troponin C gene and the slow-twitch troponin I gene: hypoxia-inducible nuclear factors [Semenza et al., *Proc Natl Acad Sci USA,* 88:5680-5684 (1991)], steroid-inducible elements and promoters including the glucocorticoid response element (GRE) [Mader and White, *Proc. Natl. Acad. Sci. USA,* 90:5603-5607 (1993)], the tMCK promoter [see Wang et al., *Gene Therapy,* 15:1489-1499 (2008)], hybrid α-myosin heavy chain enhancer-/MCK enhancer-promoter (MHCK7) promoter [Salva et al. *Mol Ther,* 15:320-329 (2007), the CK6 promoter [see Wang et al., supra] and other control elements. Thus, one example of a muscle-specific transcriptional control element is the tMCK promoter. An example of a liver-specific promoter is LSP [Wang and Verma, *Proc. Natl. Acad. Sci. USA,* 96, 3906-3910 (1999)]. As another promoter example, for production of the therapeutic proteins in recombinant host cells, the promoter may be a constitutive promoter such as the cytomegalous virus (CMV) promoter. Another example is LAMA2.

For the expression of therapeutic proteins described herein, provided are expression systems and constructs in the form of plasmids, expression vectors, transcription or expression cassettes that comprise at least one polynucleotide as described herein are also provided, as well host cells comprising such expression systems or constructs. As used herein, "vector" means any molecule or entity (e.g., polynucleotide, plasmid, bacteriophage or virus) suitable for use to transfer protein coding information into a host cell. Examples of vectors include, but are not limited to, plasmids, viral vectors, non-episomal mammalian vectors and expression vectors, for example, recombinant expression vectors. Expression vectors, such as recombinant expression vectors, are useful for transformation of a host cell.

Host cells are provided into which an expression vector, such as a recombinant expression vector, has been introduced. A host cell can be any prokaryotic cell (for example, *E. coli*) or eukaryotic cell (for example, yeast, insect, or mammalian cells (e.g., CHO cells)). Expression vectors can be introduced into prokaryotic or eukaryotic cells via conventional transformation or transfection techniques. For stable transfection of mammalian cells, a gene that encodes a selectable marker (e.g., for resistance to antibiotics) is generally introduced into the host cells along with the gene of interest. Preferred selectable markers include those which confer resistance to drugs, such as G418, hygromycin and methotrexate. Cells stably transfected with the introduced polynucleotide can be identified by drug selection, among other methods. Methods for introduction of heterologous polynucleotides into mammalian cells are well known in the art and include, but are not limited to, dextran-mediated transfection, calcium phosphate precipitation, polybrene mediated transfection, protoplast fusion, electroporation, encapsulation of the polynucleotide(s) in liposomes, mixing nucleic acid with positively-charged lipids, and direct microinjection of the DNA into nuclei.

The method selected will in part be a function of the type of host cell to be used. These methods and other suitable methods are well known to the skilled artisan, and are set forth, for example, in Sambrook et al., Molecular Cloning: A Laboratory Manual, 3rd ed., Cold Spring Harbor Laboratory Press, Cold Spring Harbor, N.Y. (2001).

A host cell, when cultured under appropriate conditions, synthesizes protein that can be subsequently collected from the culture medium (if the host cell secretes it into the medium) or directly from the host cell producing it (if it is not soluble). The selection of an appropriate host cell will depend upon various factors, such as desired expression levels, polypeptide modifications that are desirable or necessary for activity (such as glycosylation or phosphorylation) and case of folding into a biologically active molecule. As one example, Chinese hamster ovary cells overexpressing LARGE (CHO-LARGE cells) [Yoon et al., A Method to Produce and Purify Full-Length Recombinant Alpha Dystroglycan: Analysis of N- and O-Linked Monosaccharide Composition in CHO Cells with or without LARGE Overexpression, PLOS Curr. (2013 Jan. 2)] are contemplated for use in producing glycosylated therapeutic proteins described herein.

Mammalian cell lines available as hosts for expression are well known in the art and include, but are not limited to, immortalized cell lines available from the American Type Culture Collection (ATCC), including but not limited to Chinese hamster ovary (CHO) cells, CHO-LARGE cells, HEK293 cells, HeLa cells, baby hamster kidney (BHK) cells, monkey kidney cells (COS), human hepatocellular carcinoma cells (e.g., Hep G2), and other cell lines standard in the art.

The rAAV genomes provided herein lack AAV rep and cap DNA. Recombinant AAV genomes provided herein comprise a polynucleotide encoding a therapeutic protein as described above and one or more AAV ITRs flanking the polynucleotide. AAV DNA in the rAAV genomes may be from any AAV serotype for which a recombinant virus can be derived including, but not limited to, AAV serotypes AAV-1, AAV-2, AAV-3, AAV-4, AAV-5, AAV-6, AAV-7, AAV-8, AAV-9, AAV-10, AAV-11, AAV-12, AAV-13 and AAV rh.74. Other types of rAAV variants, for example rAAV with capsid mutations, are also contemplated. See, for example, Marsic et al., Molecular Therapy, 22 (11): 1900-1909 (2014). As noted in the Background section above, the nucleotide sequences of the genomes of various AAV serotypes are known in the art. To promote skeletal muscle specific expression, AAV1, AAV5, AAV6, AAV8 or AAV9 may be used.

DNA plasmids are provided that comprise rAAV genomes. The DNA plasmids are transferred to cells permissible for infection with a helper virus of AAV (including, but not limited to, adenovirus, E1-deleted adenovirus or herpesvirus) for assembly of the rAAV genome into infectious viral particles. Techniques to produce rAAV particles, in which an AAV genome to be packaged, rep and cap genes, and helper virus functions are provided to a cell are standard in the art. Production of rAAV requires that the following components are present within a single cell (denoted herein as a packaging cell): a rAAV genome, AAV rep and cap genes separate from (i.e., not in) the rAAV genome, and helper virus functions. The AAV ITRs and rep and cap genes may be from any AAV serotype for which recombinant virus can be derived and may be from a different AAV serotype than the rAAV genome ITRs, including, but not limited to, AAV serotypes AAV-1, AAV-2, AAV-3, AAV-4, AAV-5, AAV-6, AAV-7, AAV-8, AAV-9, AAV-10, AAV-11, AAV-12, AAV-13 and AAV rh.74. Production of pseudotyped rAAV is disclosed in, for example, WO 01/83692 which is incorporated by reference herein in its entirety.

A method of generating a packaging cell is to create a cell line that stably expresses all the necessary components for AAV particle production. For example, a plasmid (or multiple plasmids) comprising a rAAV genome lacking AAV rep and cap genes, AAV rep and cap genes separate from the rAAV genome, and a selectable marker, such as a neomycin resistance gene, are integrated into the genome of a cell. AAV genomes have been introduced into bacterial plasmids by procedures such as GC tailing (Samulski et al., 1982, Proc. Natl. Acad. S6. USA, 79:2077-2081), addition of synthetic linkers containing restriction endonuclease cleavage sites (Laughlin et al., 1983, Gene, 23:65-73) or by direct, blunt-end ligation (Senapathy & Carter, 1984, J. Biol. Chem., 259:4661-4666). The packaging cell line is then infected with a helper virus such as adenovirus. The advantages of this method are that the cells are selectable and are suitable for large-scale production of rAAV. Other examples of suitable methods employ adenovirus or baculovirus rather than plasmids to introduce rAAV genomes and/or rep and cap genes into packaging cells.

General principles of rAAV production are reviewed in, for example, Carter, *Current Opinions in Biotechnology*, 1533-1539 (1992); and Muzyczka, *Curr. Topics in Microbial. And Immunol.*, 158:97-129 (1992). Various approaches are described in Ratschin et al., *Mol. Cell. Biol.*, 4:2072 (1984); Hermonat et al., *Proc. Natl. Acad. Sci. USA*, 81:6466 (1984); Tratschin et al., *Mol. Cell. Biol.*, 5:3251 (1985); Mclaughlin et al., *J. Virol.*, 62:1963 (1988); Lebkowski et al., *Mol. Cell. Biol.*, 7:349 (1988); Samulski et al., *J. Virol.*, 63:3822-3828 (1989); U.S. Pat. No. 5,173,414; WO 95/13365 and corresponding U.S. Pat. No. 5,658,776; WO 95/13392; WO 96/17947; PCT/US98/18600; WO 97/09441 (PCT/US96/14423); WO 97/08298 (PCT/US96/13872); WO 97/21825 (PCT/US96/20777); WO 97/06243 (PCT/FR96/01064); WO 99/11764; Perrin et al., Vaccine, 13:1244-1250 (1995); Paul et al., *Human Gene Therapy*, 4:609-615 (1993); Clark et al., *Gene Therapy* 3:1124-1132 (1996); U.S. Pat. Nos. 5,786,211; 5,871,982; 6,258,595; and McCarty, *Mol. Ther.*, 16 (10): 1648-1656 (2008). The foregoing documents are hereby incorporated by reference in their entirety herein, with particular emphasis on those sections of the documents relating to rAAV production.

The invention thus provides packaging cells that produce infectious rAAV. In one embodiment packaging cells may be stably transformed cancer cells such as HeLa cells, 293 cells and PerC.6 cells (a cognate 293 line). In another embodiment, packaging cells are cells that are not transformed cancer cells, such as low passage 293 cells (human fetal kidney cells transformed with E1 of adenovirus), MRC-5 cells (human fetal fibroblasts), WI-38 cells (human fetal fibroblasts), Vero cells (monkey kidney cells) and FRhL-2 cells (rhesus fetal lung cells).

Recombinant AAV, which herein are replication-deficient, infectious, encapsidated viral particles (rAAV), comprise a rAAV genome. A rAAV encodes a therapeutic protein described herein. The rAAV genomes lack AAV rep and cap DNA, that is, there is no AAV rep or cap DNA between the ITRs of the rAAV genomes.

The rAAV may be purified by methods standard in the art such as by column chromatography or cesium chloride gradients. Methods for purifying rAAV vectors from helper virus are known in the art and include methods disclosed in, for example, Clark et al., *Hum. Gene Ther.*, 10 (6): 1031-1039 (1999); Schenpp and Clark, *Methods Mol. Med.*, 69:427-443 (2002); U.S. Pat. No. 6,566,118; and WO 98/09657.

In another embodiment, the invention contemplates compositions comprising rAAV or therapeutic protein described herein. Compositions of the invention comprise rAAV or therapeutic protein in a pharmaceutically acceptable carrier. The compositions may also comprise other ingredients such as diluents and adjuvants. Acceptable carriers, diluents and adjuvants are nontoxic to recipients and are preferably inert at the dosages and concentrations employed, and include buffers such as phosphate, citrate, or other organic acids; antioxidants such as ascorbic acid; low molecular weight polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, pluronics or polyethylene glycol (PEG).

Titers of rAAV to be administered in methods described herein will vary depending, for example, on the particular rAAV, the mode of administration, the treatment goal, the individual, and the cell type(s) being targeted, and may be determined by methods standard in the art. Titers of rAAV may range from about $1 \times 10^{10}$, about $1 \times 10^{11}$, about $1 \times 10^{12}$, about $1 \times 10^{13}$ to about $1 \times 10^{14}$ or more DNase resistant particles (DRP) per ml. Dosages may also be expressed in units of viral genomes (vg) as understood in the art.

Methods of transducing a target cell with rAAV, in vivo or in vitro, are contemplated by the invention. The in vivo methods comprise the step of administering an effective dose, or effective multiple doses, of a composition comprising a rAAV described herein to an animal (including a human patient) in need thereof.

Dosages and the frequency of administration of therapeutic proteins described herein may vary according to such factors as the route of administration, the particular therapeutic protein administered, and the size and general condition of the patient. Appropriate dosages can be determined by procedures known in the pertinent art, e.g., in clinical trials that may involve dose escalation studies. In view of these factors, a typical dose for a therapeutic protein described herein may range from about 0.1 pg/kg to up to about 30 mg/kg or more. Further, a dose may range from 0.1 pg/kg up to about 30 mg/kg, from 1 μg/kg up to about 30 mg/kg, from 10 μg/kg up to about 10 mg/kg, from about 0.1 mg/kg to 5 mg/kg, or from about 0.3 mg/kg to 3 mg/kg.

Methods of treating a patient with a therapeutic protein described herein are thus also provided. The methods comprise the step of administering an effective dose, or effective multiple doses, of a composition comprising a therapeutic protein described herein to an animal (including a human patient) in need thereof.

If the dose is administered prior to development of a disorder/disease, the administration is prophylactic. If the dose is administered after the development of a disorder/ disease, the administration is therapeutic. An "effective dose" is a dose that alleviates (eliminates or reduces) at least one symptom associated with the disorder/disease state being treated, that slows or prevents progression to a disorder/disease state, that slows or prevents progression of a disorder/disease state, that diminishes the extent of disease, that results in remission (partial or total) of disease, and/or that prolongs survival. Methods described herein result in one or more of improved ambulation time, limb grip strength, decreased muscle pathology, and decreased neural pathology in a treated patient. Other endpoints achieved by methods described herein are one or more of increased muscle fiber size, decreased number of small oxidative fibers, correction of muscle atrophy, increased muscular force, and increased muscle regeneration in the treated patient. Dystroglycanopathies and laminin-deficient muscular dystrophies are contemplated for prevention or treatment according to methods of the invention.

Combination therapies are also contemplated by the invention. Combination therapies as used herein includes both simultaneous treatment, or sequential treatments. Combinations of methods described herein with standard medical treatments are specifically contemplated, as are combinations with novel therapies.

Administration of an effective dose of the compositions of rAAV or therapeutic protein may be by routes standard in the art including, but not limited to, intramuscular, intraparenteral, intravenous, intrathecal, oral, buccal, nasal, pulmonary, intracranial, intraosseous, intraocular, rectal, or vaginal. Route(s) of administration and serotype(s) of AAV components of the rAAV (in particular, the AAV ITRs and capsid protein) of the invention may be chosen and/or matched by those skilled in the art taking into account the infection and/or disease state being treated and the target cells/tissue(s) that are to express the therapeutic proteins.

In particular, actual administration of rAAV of the present invention may be accomplished by using any physical method that will transport the rAAV recombinant vector into the target tissue of an animal. Administration according to the invention includes, but is not limited to, injection into muscle, the bloodstream and/or directly into the liver. Simply resuspending a rAAV in phosphate buffered saline or lactated Ringer's solution has been demonstrated to be sufficient to provide a vehicle useful for muscle tissue expression, and there are no known restrictions on the carriers or other components that can be co-administered with the rAAV (although compositions that degrade DNA should be avoided in the normal manner with rAAV). Capsid proteins of a rAAV may be modified so that the rAAV is targeted to a particular target tissue of interest such as muscle. See, for example, WO 02/053703, the disclosure of which is incorporated by reference herein. Pharmaceutical compositions can be prepared as injectable formulations or as topical formulations to be delivered to the muscles by transdermal transport. Numerous formulations for both intramuscular injection and transdermal transport have been previously developed and can be used in the practice of the invention. The rAAV can be used with any pharmaceutically acceptable carrier for case of administration and handling.

For purposes of intramuscular injection, solutions of rAAV or therapeutic protein in an adjuvant such as sesame or peanut oil or in aqueous propylene glycol can be employed, as well as sterile aqueous solutions. Such aqueous solutions can be buffered, if desired, and the liquid diluent first rendered isotonic with saline or glucose. Solutions of rAAV as a free acid (DNA contains acidic phosphate groups) or a pharmacologically acceptable salt can be prepared in water suitably mixed with a surfactant such as hydroxpropylcellulose. A dispersion of rAAV can also be prepared in glycerol, liquid polyethylene glycols and mixtures thereof and in oils. Under ordinary conditions of storage and use, these preparations contain a preservative to prevent the growth of microorganisms. In this connection, the sterile aqueous media employed are all readily obtainable by standard techniques well-known to those skilled in the art.

The pharmaceutical forms of rAAV or therapeutic protein suitable for systemic (e.g., intravenous) injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating actions of microorganisms such as bacteria and fungi. The carrier can be a solvent or dispersion medium containing, for example, water, ethanol, polyol (for example, glycerol, propylene glycol, liquid polyethylene glycol and the like), suitable mixtures thereof, and vegetable oils. The proper fluidity can be maintained, for example, by the use of a coating such as lecithin, by the maintenance of the required particle size in the case of a dispersion and by the use of surfactants. The prevention of the action of microorganisms can be brought about by various antibacterial and antifungal agents, for example, parabens, chlorobutanol, phenol, sorbic acid, thimerosal and the like. In many cases it will be preferable to include isotonic agents, for example, sugars or sodium chloride. Prolonged absorption of the injectable compositions can be brought about by use of agents delaying absorption, for example, aluminum monostearate and gelatin.

Sterile injectable solutions are prepared by incorporating rAAV in the required amount in the appropriate solvent with various other ingredients enumerated above, as required, followed by filter sterilization. Generally, dispersions are prepared by incorporating the sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique that yield a powder of the active ingredient plus any additional desired ingredient from the previously sterile-filtered solution thereof.

Transduction with rAAV may also be carried out in vitro. In one embodiment, desired target muscle cells are removed from the subject, transduced with rAAV and reintroduced into the subject. Alternatively, syngeneic or xenogeneic muscle cells can be used where those cells will not generate an inappropriate immune response in the subject.

Suitable methods for the transduction and reintroduction of transduced cells into a subject are known in the art. In one embodiment, cells can be transduced in vitro by combining rAAV with muscle cells, e.g., in appropriate media, and screening for those cells harboring the DNA of interest using conventional techniques such as Southern blots and/or PCR, or by using selectable markers. Transduced cells can then be formulated into pharmaceutical compositions, and the composition introduced into the subject by various techniques, such as by intramuscular, intravenous, subcutaneous and intraperitoneal injection, or by injection into smooth and cardiac muscle, using e.g., a catheter.

Transduction of cells with rAAV of the invention results in sustained expression of a therapeutic protein described herein. The present invention thus provides methods of administering rAAV which express a therapeutic protein described herein to a patient, preferably a human being. These methods include transducing tissues (including, but not limited to, tissues such as muscle, organs such as liver and brain, and glands such as salivary glands) with one or more rAAV of the present invention.

Muscle tissue is an attractive target for in vivo DNA delivery, because it is not a vital organ and is easy to access. The invention contemplates sustained expression of therapeutic protein described herein from transduced muscle cells.

By "muscle cell" or "muscle tissue" is meant a cell or group of cells derived from muscle of any kind [for example, skeletal muscle and smooth muscle (e.g., from the digestive tract, urinary bladder, blood vessels or cardiac tissue)]. Such muscle cells may be differentiated or undifferentiated, such as myoblasts, myocytes, myotubes, cardiomyocytes and cardiomyoblasts.

The term "transduction" is used to refer to the administration/delivery of therapeutic protein to a recipient cell either in vivo or in vitro, via a rAAV of the invention resulting in expression of therapeutic protein by the recipient cell.

Thus, methods are provided herein of administering an effective dose (or doses administered essentially simultaneously or doses given at intervals) of rAAV that encode a therapeutic protein described herein to a patient in need thereof.

Methods are also provided herein of administering an effective dose (or doses administered essentially simultaneously or doses given at intervals) of a therapeutic protein described herein to a patient in need thereof.

EXAMPLES

Aspects and embodiments of the invention are illustrated by the following examples. Example 1 describes constructs encoding therapeutic proteins of the disclosure. Example 2 describes recombinant expression of the therapeutic proteins in cultured host cells. Example 3 describes experiments demonstrating heparin-binding domain targets LAMA2 (g1-G50 to the muscle of wild type mice. Example 4 describes experiments to demonstrate efficacy of AAV-mediated HBEGF-LAMA2 (G1-5) expression in reducing symptoms and pathology in the dy$^W$/dy$^W$ mouse model of MDC1A. Example 5 describes experiments to demonstrate efficacy of AAV-mediated HBEGF-DAG1 (a) expression in reducing symptoms and pathology in the mouse models of dystroglycanopathy. Example 6 describes properties of (domains of) sHBEGF contemplated herein as useful for its application as a linker domain in therapeutic proteins described herein and as a trophic factor in various methods described herein.

Example 1

Constructs Encoding Therapeutic Proteins

Six exemplary DNA constructs encoding therapeutic proteins including an HBEGF EGF domain were generated as follows:

HB-EGF (ending at heparin binding domain)-LAMA2 G1-G5 (encoded by the polynucleotide of FIG. 3),
HB-EGF (complete soluble form)-LAMA2 G1-G5 (encoded by the polynucleotide of FIG. 4), HB-EGF (ending at heparin binding domain)-LAMA2 G3-G5 (encoded by the polynucleotide of FIG. 5),
HB-EGF (complete soluble form)-LAMA2 G3-G5 (encoded by the polynucleotide of FIG. 6),
HB-EGF (ending at heparin binding domain)-DAG1 (native processed alpha DG gene) (encoded by the polynucleotide of FIG. 7), and
HB-EGF (complete soluble form)-DAG1 (native processed alpha DG gene) (encoded by the polynucleotide of FIG. 8).

The constructs were expressed from plasmids in CHO cells. CHO cells were transfected with plasmids containing one of the constructs or mock-transfected (–).

The transfected CHO cells were stained with antibodies against HB-EGF, dystroglycan, or laminin-α2 G5 domain. Results are shown in FIG. 9A. Also, culture media was collected from each plate 48 hours post-transfection and cell lysis was performed. Heparin-agarose pull-down was performed on both cell lysate and culture media and loaded in Western blot along with whole cell lysate. Results are shown in FIG. 9B.

Example 2

Recombinant Expression of Therapeutic Proteins in Cultured Host Cells

The constructs of Example 1 were also subcloned into a plasmid to produce AAV9 vectors encoding the therapeutic proteins.

AAV vectors carrying one of the therapeutic genes of Example 1 under the transcriptional control of the cytomegalovirus (CMV) promoter were produced.

rAAV vectors were produced by a modified cross-packaging approach whereby the AAV type 2 vector genome can be packaged into multiple AAV capsid serotypes [Rabinowitz et al., *J Virol.* 76 (2): 791-801 (2002)]. Production was accomplished using a standard three plasmid DNA/CaPO4 precipitation method using HEK293 cells. HEK293 cells were maintained in DMEM supplemented with 10% fetal bovine serum (FBS) and penicillin and streptomycin. The production plasmids were: (i) plasmids encoding the therapeutic proteins, (ii) rep2-capX modified AAV helper plasmids encoding cap serotype 9 isolate, and (iii) an adenovirus type 5 helper plasmid (pAdhelper) expressing adenovirus E2A, E4 ORF6, and VA I/II RNA genes. A quantitative PCR-based titration method was used to determine an encapsidated vector genome (vg) titer utilizing a Prism 7500 Taqman detector system (PE Applied Biosystems). [Clark et al., *Hum Gene Ther.* 10 (6): 1031-1039 (1999)]. A final titer (vg ml$^{-1}$) was determined by quantitative reverse transcriptase PCR using the specific primers and probes utilizing a Prism 7500 Real-time detector system (PE Applied Biosystems, Grand Island, NY, USA). Aliquoted viruses were kept at –80° C. until use.

TABLE 2

| AAV construct | Membrane linker (first domain) | Second Domain | Denoted herein as | SEQ ID NO: | rAAV genome nt's |
|---|---|---|---|---|---|
| rAAV.CMV.HB.LAMA2(G1-G5) | Heparin binding domain only | Laminin alpha 2 G1-G5 | HB-LAMA2 (G1-G5) | 2 | Nt. 3590-8215 |

TABLE 2-continued

| AAV construct | Membrane linker (first domain) | Second Domain | Denoted herein as | SEQrAAV ID genome NO: nt's |
|---|---|---|---|---|
| rAAV9.CMV. HBEGF.LAMA2 (G1-G5) | Complete soluble form | Laminin alpha 2 G1-G5 | HBEGF-LAMA2 (G1-G5) | 4 Nt. 3590-8341 |
| rAAV.CMV.HB. LAMA2(G3-G5) | Heparin binding domain only | Laminin alpha 2 G3-G5 | HB-LAMA2 (G3-G5) | 6 Nt. 3609-6929 |
| rAAV.CMV. HBEGF.LAMA2 (G3-G5) | Complete soluble form | Laminin alpha 2 G3-G5 | HBEGF-LAMA2 (G3-G5) | 8 Nt. 3590-7036 |
| rAAV.CMV.HB. DAG1 | Heparin binding domain only | DAG1 | HB-DAG1 | 10 Nt. 3590 to 6340 |
| rAAV.CMV. HBEGF.DAG1 | Complete soluble form | DAG1 | HBEGF. DAG1 | 12 Nt. 3590 to 6049 |

Example 3

Heparin-Binding Domain Targets LAMA2 (G1-G5) to the Muscle in Wild Type Mice

Wild type mice were injected intramuscularly in the gastrocnemius muscle with $5 \times 10^{11}$ vg pf rAAV9.CMV vectors containing HBEGF, HBEGF.LAMA2 (G1-G5), HBEGF.LAMA2 (G3-G5), HB.LAMA2 (G1-G5), HB.LAMA2 (G3-G5), or LAMA2 (G1-G5) (see Table 2). Cells were stained with antibody specific to human HB-EGF or recombinant G5 domain of LAMA2. Mock injected mice (buffer alone) are shown as a negative control. 4H8-2 is an anti-laminin antibody to show muscle cells in the sections.

As shown in FIG. 15, HBEGF and HBEGF.LAMA2 (G1-G5) reduced muscle growth and/or induced mild muscle atrophy, much as we had previously shown for overexpression of HBEGF, while IM injection of rAAV9.CMV.HB.LAMA2 (G1-G5) lead to secretion and localization of LAMA2 (G1-G5) protein in the extracellular matrix. In addition, HB. LAMA2 (G1-G5)-expressing muscles appeared larger than normal wild type muscles. HB.LAMA2 (G3-G5) showed lower overall protein staining than HB.LAMA2 (G1-G5). The ECM targeting function of the HB domain of HBEGF allows for secretion and targeting of LAMA2 (G1-G5) protein to the muscle extracellular matrix. By contrast, expression of LAMA2 (G1-G5) without the HB domain led to very poor protein production and no detectable ECM localization. Thus, the constructs comprising the HB domain alone, rather than the full HB-EGF domain serves the purpose of targeting LAMA2 (G1-G5) to the muscle ECM, and successfully does so without having the negative consequences of EGF signaling, as this construct has the EGF domain from HBEGF deleted.

The pre-pro peptide portion of HBEGF, which is still present in the HB construct, may also improve protein folding and/or expression for LAMA2 (G1-G5) relative to LAMA2 (G1-G5) alone, which only contains the signal peptide from HBEGF. Last, HB.LAMA2 (G1-G5), when localized appropriately, may improve muscle growth, even in normal muscles.

FIG. 16 shows staining of HBEGF.LAMA2 (G1-G5), HB.LAMA2 (G1-G5) and LAMA2 (G1-G5) using an antibody to human HBEGF protein and an antibody to the G5 domain of human LAMA2. This data confirmed that expression of LAMA2 (G1-G5) alone leads to very poor protein production in muscle, while inclusion of the HB domain improves expression for LAMA2 (G1-G5), which was visualized with an anti-laminin antibody as well as an HBEGF antibody.

Example 4

Efficacy of AAV9-Mediated HBEGF-LAMA2 (G1-5) Expression in Reducing Symptoms and Pathology in the $dy^W/dy^W$ Mouse Model of MDC1A $dy^W/dy^W$ mice [Nonaka, *Lab Anim Sci.*, 48 (1): 8-17 (1998)] have a loss-of-function mutation in Lama2, resulting in impaired laminin-$\alpha 2$ production, similar to MDC1A pathogenesis. $Dy^W/dy^W$ mice have decreased size, grip strength, and lifespan compared to wild-type mice. They display muscle atrophy, dystrophic muscle pathology, and severely impaired ambulation by three months of age. As such, these mice are an appropriate and robust model for testing MDC1A therapy.

To demonstrate the therapeutic efficacy of the LAMA2 expressing rAAV genomes provided in Example 2, 8 $dy^W/dy^W$ pups were injected intravenously through the facial vein at postnatal day 1 with either a low dose, $10^{11}$ viral genomes (vg), or a high dose, $10^{12}$ vg, rAAV9.CMV.HBEGF.LAMA2 (G1-G5), or rAAV9.CMV.HB.LAMA2 (G1-G5) or rAAV.CMV.HB.LAMA2(G3-G5). Mock injections of AAV buffer in control $dy^W/dy^W$ pups were also performed.

At 2 and at 3 months post-injection, grip strength in the forelimb muscles was analyzed (FIG. 17). At 4 months of age, the mice were euthanized and limb muscles were dissected and analyzed for expression of recombinant protein. As shown in FIG. 17, both HB.LAMA2 (G3-G5) and HB.LAMA2 (G1-G5) prevented loss of grip strength in dy/dy mice, showing a significant change from mock-treated dy/dy mice and bringing strength values to within the range seen in untreated wild type mice of the same age. Thus, both HB.LAMA2 (G3-G5) and HB.LAMA2 (G1-G5) show a therapeutic effect in the dy/dy model for MDC1A. In this experiment, HB.LAMA2 (G3-G5) did not reach significance at 2 months relative to mock-treated dy/dy mice, while HB.LAMA2 (G1-G5) did.

The role of transgene expression in preventing muscle pathology by comparing the percentage of myofibers with central nuclei, myofiber diameter and area, and variance in myofiber diameter in treated dy/dy mice was also analyzed. Muscle pathology intransgene-expressing myofibers was compared to the same pathology measures in non-expressing myofibers using the triceps muscle. This experiment demonstrated that expression of HB.LAMA2 (G1-G5) increased muscle size. An example of staining showing such changes is shown in FIG. 18. When quantified across all muscles, the average cross-sectional muscle area was 2328 $mm^2$ in expressing myofibers versus 1082 $mm^2$ in nonexpressing myofibers (n=4 muscles each with 400 myofibers analyzed per muscle), which was a two-fold average increase in muscle size with treatment. The variance in myofiber diameter index (Diameter SD/Mean X1000) was reduced from 620 in non-expressing muscles to 431 in expressing muscles (250 or lower is considered normal), and the percentage of myofibers with central nuclei, an indicator of a cycle of muscle degeneration and regeneration, was reduced from 28% in non-expressing myofibers to 14% in expressing ones (n=2 each).

While not reduced to zero pathology, it is important to remember that AAV requires 3-4 weeks to achieve maximal gene expression, so some pathology will develop in these animals prior to when therapeutic transgene expression occurs. In all such experiments, the average level of muscle transduction was 26±1% (n=4 triceps muscles analyzed, 400 fibers each). The take home from these pathological measures is that HB-LAMA2 (G1-G5) not only appears to prevent, at least in part, muscle damage in dy/dy muscles, but it also increases muscle growth back to, and perhaps beyond, wild type levels.

Example 5

Efficacy of AAV-Mediated HBEGF-DAG1(α) Expression in Reducing Symptoms and Pathology in Mouse Models of Dystroglycanopathy Mice lacking dystroglycan or the α-dystroglycan-glycosylating enzyme, fukutin, encoded by the Fktn gene, are embryonic lethal, and cannot be used to study dystroglycanopathy therapy. Myf5Cre-Fktn$^{loxP}$ mice [Kanagawa et al., *Hum Mol Genet.*, 22(15): 3003-3015 (2013)], in which Fktn deletion is restricted to skeletal muscle are used to demonstrate efficacy. Myf5Cre-Fktn$^{loxP}$ mice have decreased body weight, grip strength, and lifespan compared to wild-type mice. They also display dystrophic muscle pathology.

To demonstrate the therapeutic efficacy of rAAV9.CMV.HBEGF-DAG1(α) in the Myf5Cre-Fktn$^{loxP}$ mouse model, the same injection protocol and assessments are performed as described in Example 3.

Another mouse model of dystroglycanopathy the Large-vls mouse mutant (Lee et al., Mol. Cell. Neurosci. 30:160-172, 2005). Several Large vls mice were IM injected with 1×10$^{12}$ vg rAAV9.CMV.HB-DAG1 IV via the facial vein at P1. The tests of grip strength of these mice suggest potential improvement. Of the 4-7 animals analyzed per group at 2 months, forelimb grip strength is reduced from 4.7±0.2 g/g in wild type to 3.8±0.1 g/g in untreated Large vls mice (p=0.0005), while pAAV9.CMV.HB-DAG1(α) treatment of Large vls mice (IV with 1×10$^{12}$ vg at P1) showed improvement in grip strength, to 4.4±0.3 g/g (p=0.06 versus mock-treated Large vls). This data is very close to significance, and a significant difference may be achieved with additional measures.

Example 6 sHBEGF as a Linker Protein and Trophic Factor

Figure 10:
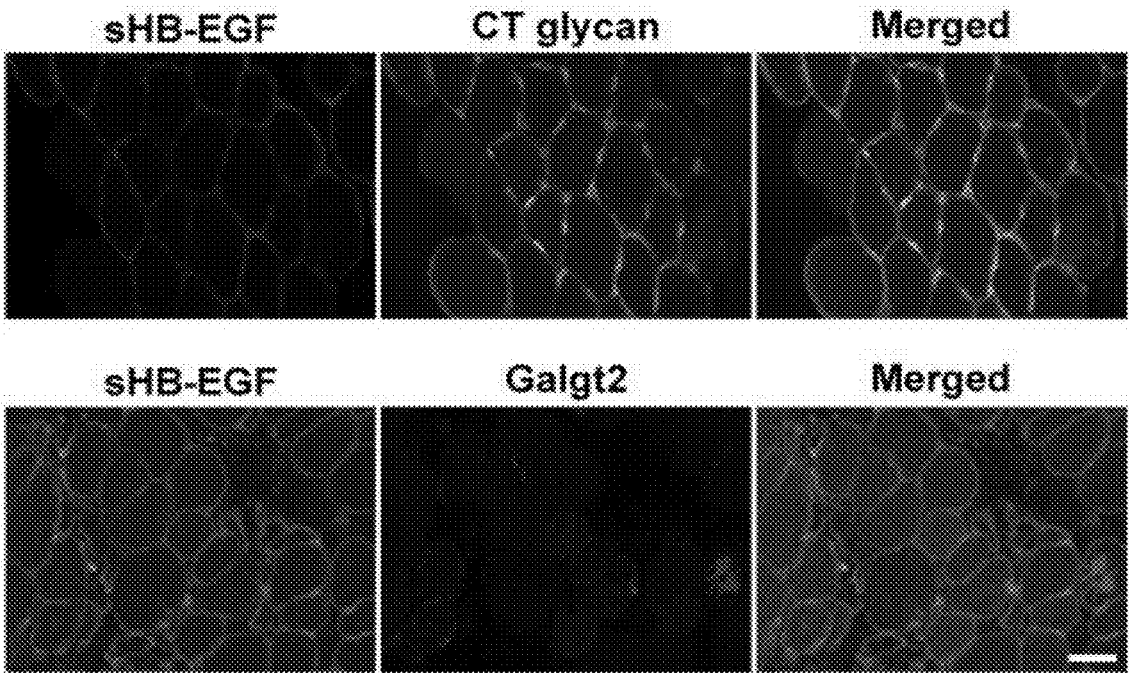
FIG. 10 shows that sHB-EGF can be secreted from muscles and stick to the extracellular matrix.
Figure 11:
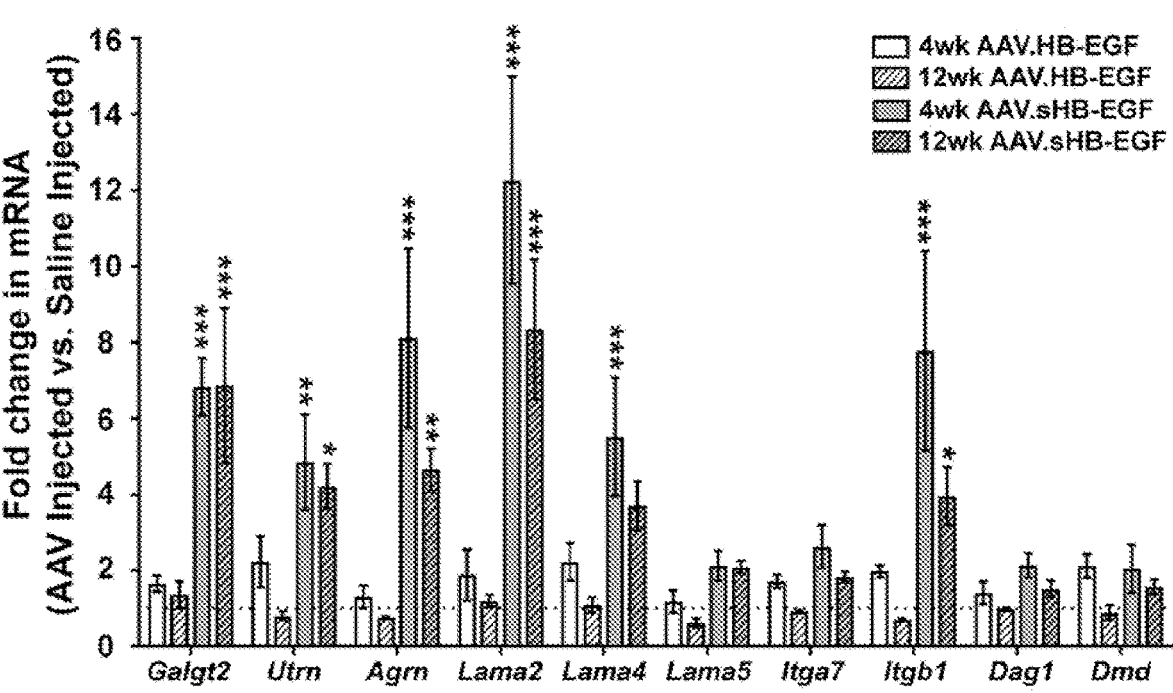
FIG. 11 shows that sHB-EGF induces expression of therapeutic surrogate muscular dystrophy genes. Full length HBEGF does not induce therapeutic gene expression.
Figure 12:
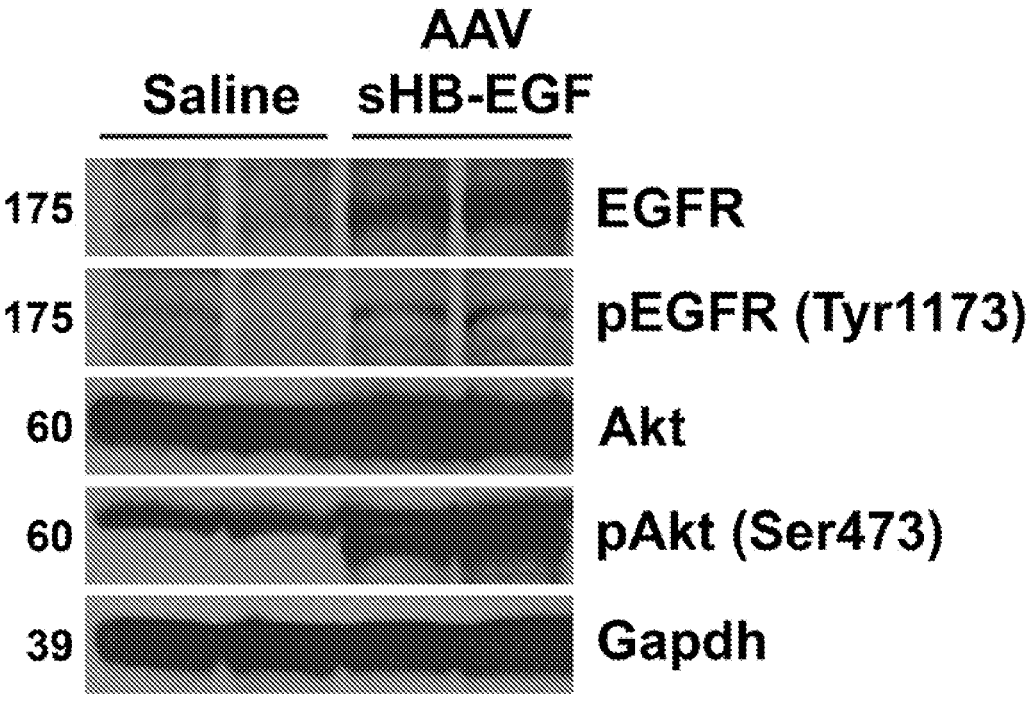
FIG. 12 shows that sHB-EGF induces Akt tyrosine kinase cascade in skeletal muscle and can stimulate muscle growth and regeneration.
Figure 13:
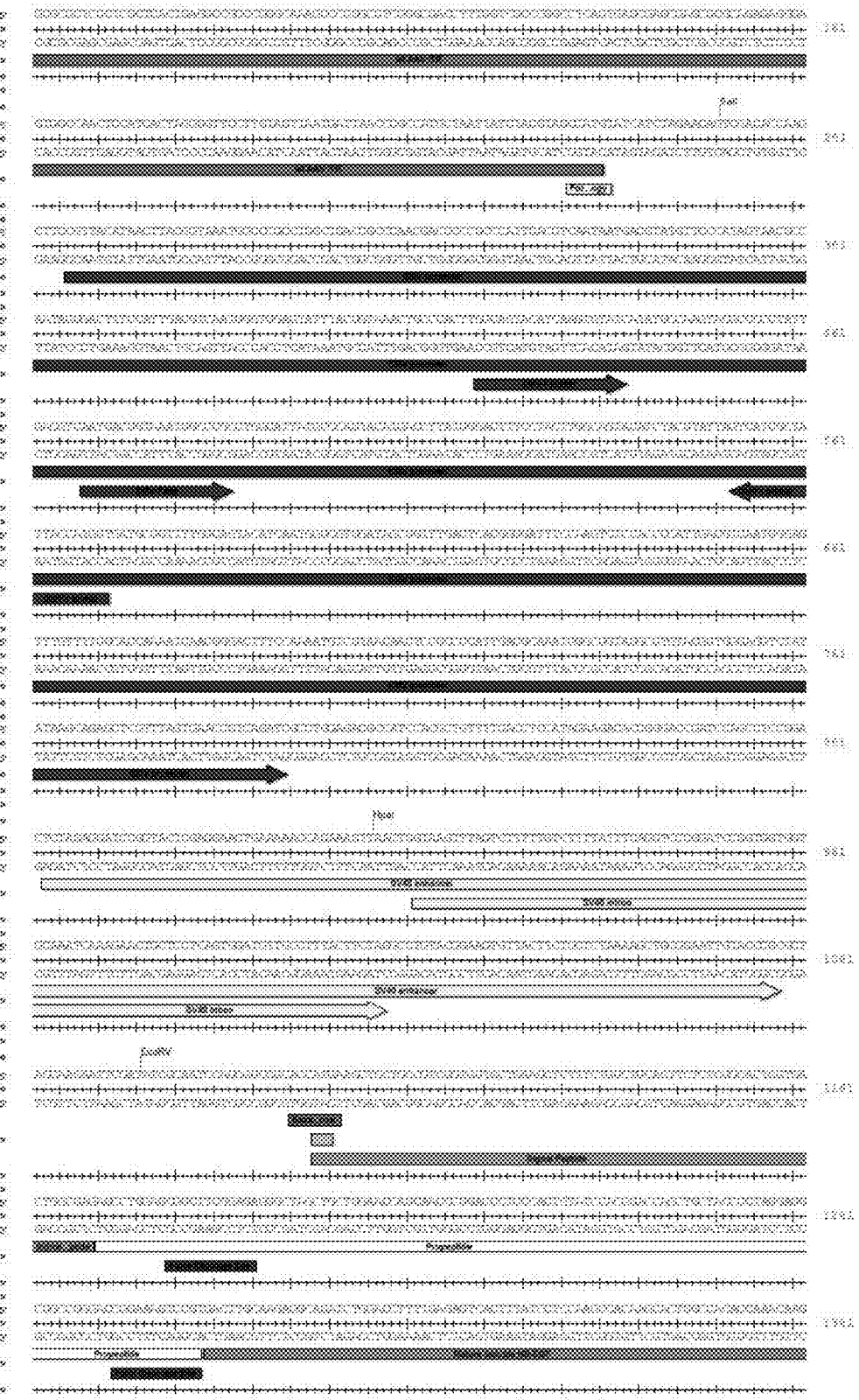
FIG. 13 shows an exemplary rAAV genome encoding the therapeutic protein HB-EGF (complete soluble form)-LAMA2 G1-G5. The 5' to 3' depicted sequence (top) corresponds to SEQ ID NO: 25, and the 3' to 5' depicted sequence (bottom) corresponds to SEQ ID NO: 40.
Figure 13:
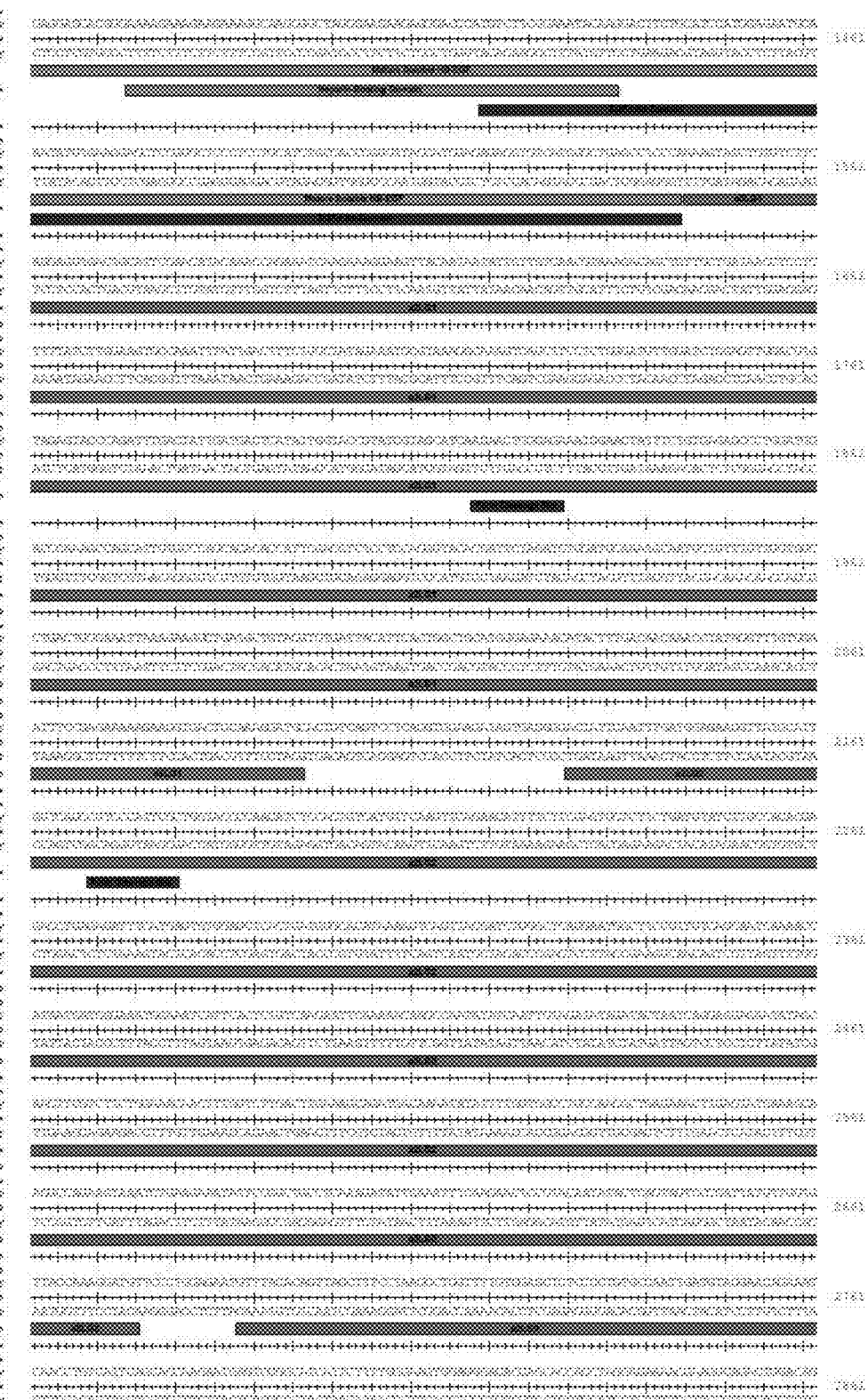
Figure 13:
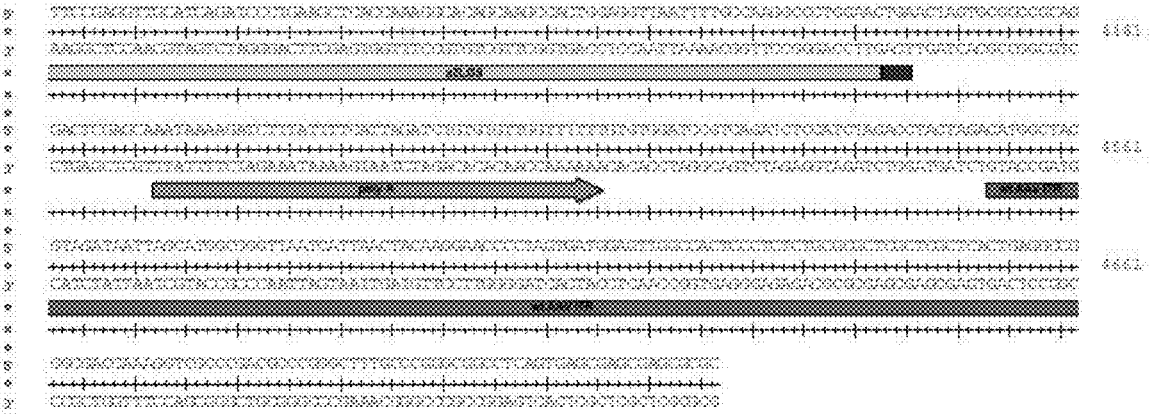
Figure 14:
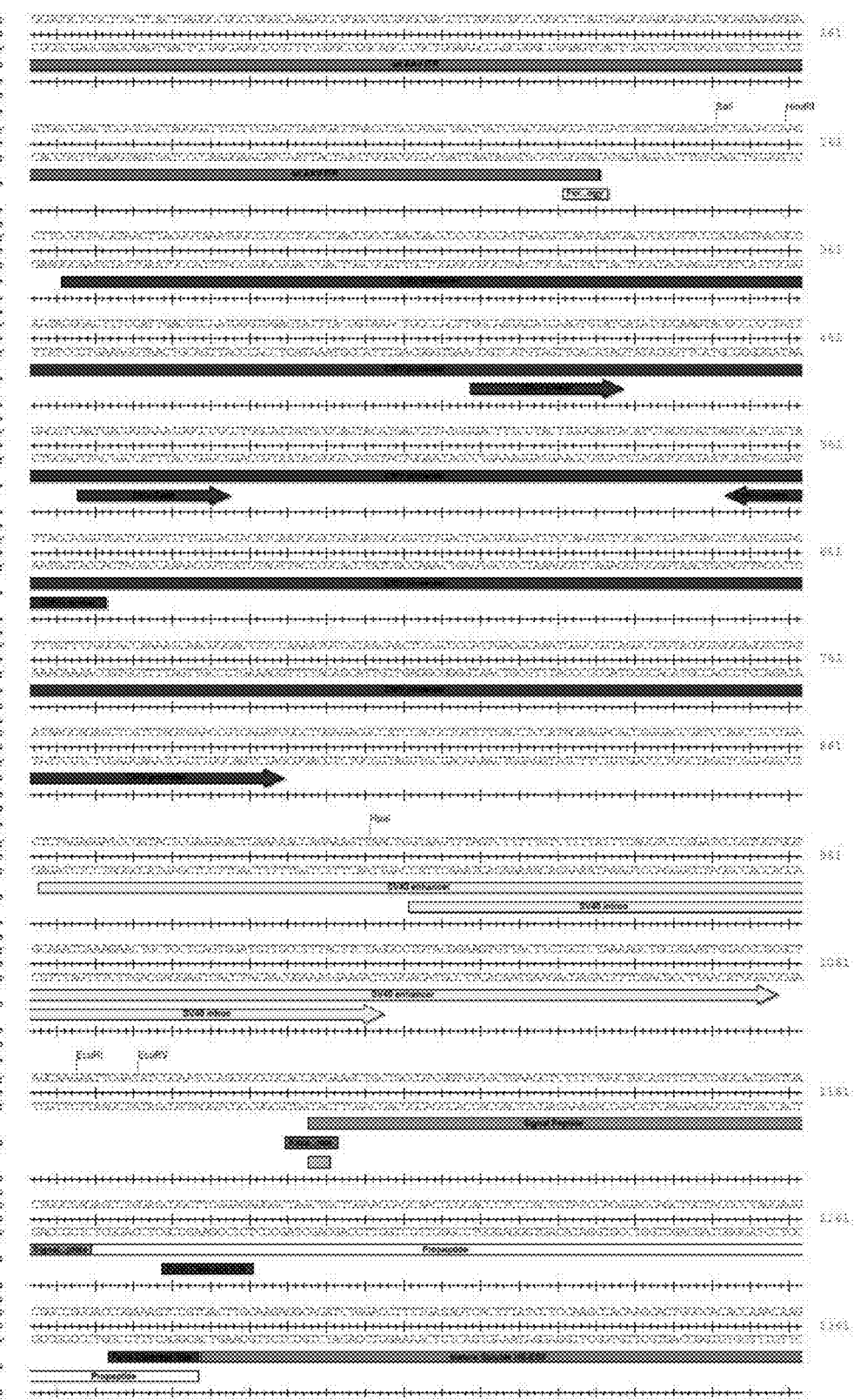
FIG. 14 shows an exemplary rAAV genome encoding the therapeutic protein HB-EGF (complete soluble form)-DAG1 (native processed alpha DG gene). The 5' to 3' depicted sequence (top) corresponds to SEQ ID NO: 26, and the 3' to 5' depicted sequence (bottom) corresponds to SEQ ID NO: 41.
Figure 14:
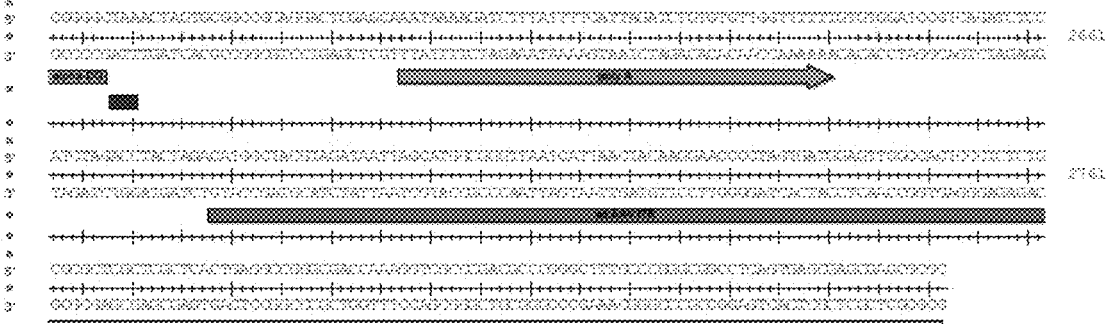

Using the heparin-binding domain and EGF-like domain of soluble HBEGF (sHBEGF) in various exemplary therapeutic proteins described herein provides a dual benefit to patients. Including both domains adds increased muscle membrane stability from the inclusion of the heparin-binding domain along with LAMA2 (G1-5) or DAG1 (a), and then inclusion of the EGF-like domain additionally provides a stimulus for muscle regeneration. FIGS. 10, 11 and 12 show sHBEGF activates an Akt kinase pathway in muscle and increases the expression of muscle regeneration markers. Expression of activated Akt kinase in muscle has previously been shown to stimulate profound muscle growth, akin to what is seen with myostatin inhibitors. The presence of the EGF-like domain of HBEGF in various therapeutic proteins described herein, therefore, adds an additional therapeutic effect for treatment of the diseases described herein.

Figure 9:
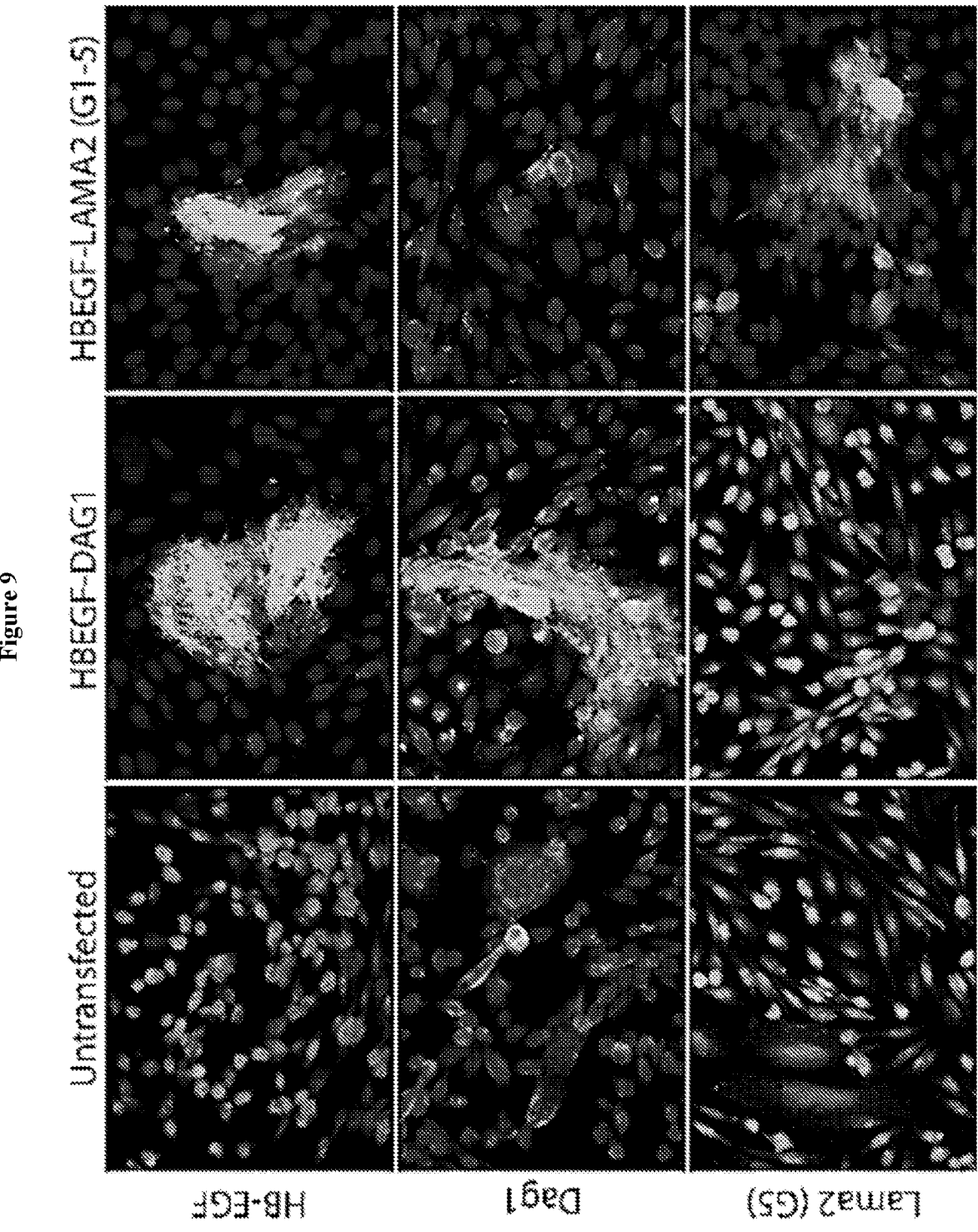
FIG. 9 shows expression of therapeutic proteins described herein by recombinant mammalian host cells.
Figure 9:
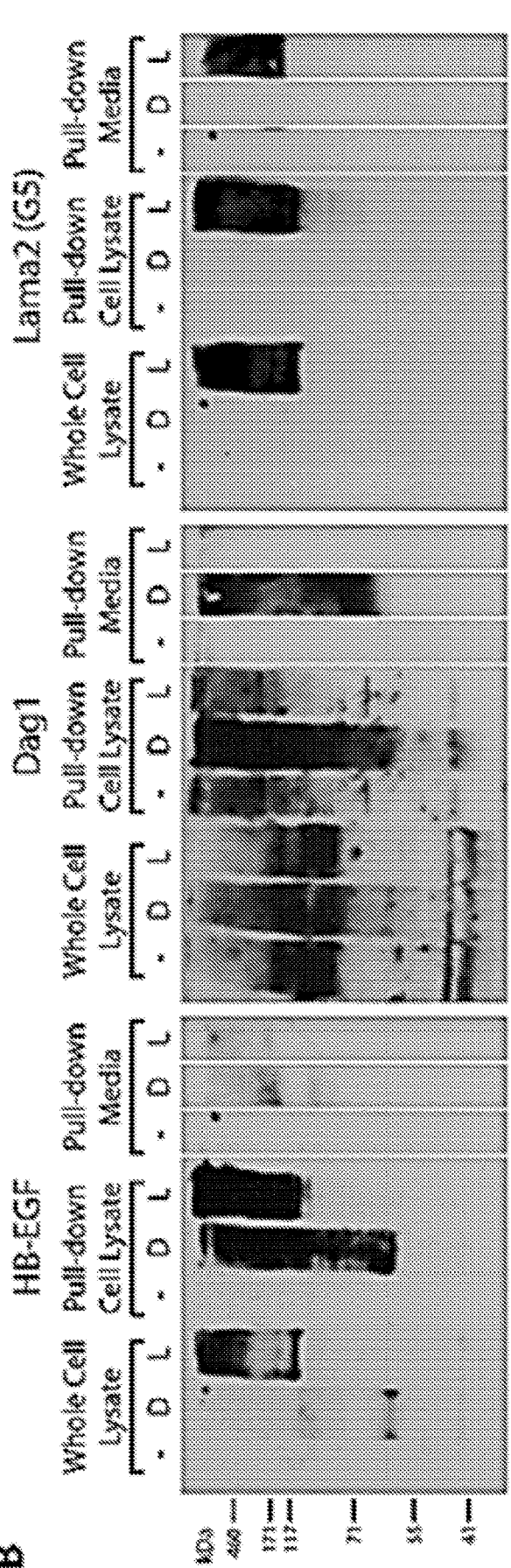

The gastrocnemius muscle on the left side of 5-week-old male C57BL/6J mice was injected with 5×10$^{10}$ vector genomes of r(ds) AAV9.CMV.HB-EGF or r(ds) AAV9.CMV.sHB-EGF in a volume of 50 µL sterile PBS using a 0.3 mL insulin syringe near the midpoint of the muscle. Muscles on the contralateral (right) side of the mouse were mock-injected with an identical volume of sterile PBS. At 4- or 12-weeks post-injection, mice were sacrificed and dissected. Gastrocnemius muscles were embedded in O.C.T. Compound (Fisher Scientific, Pittsburgh, PA) and snap-frozen in liquid nitrogen-cooled isopentane.

sHB-EGF expression was visualized using an antibody that recognizes sHB-EGF and co-stained with either an antibody to Galgt2 protein or the CT glycan. sHB-EGF was expressed along the sarcolemmal membrane of skeletal myofibers in muscles analyzed at 4 weeks post-injection with r(ds) AAV9.CMV.sHB-EGF. FIG. 9 shows that sHB-EGF can be secreted from muscles and stick to the extracellular matrix, supporting its use as a linker protein.

FIG. 10 shows that sHB-EGF induces expression of therapeutic surrogate muscular dystrophy genes.

FIG. 11 shows that sHB-EGF induces Akt tyrosine kinase cascade in skeletal muscle and can stimulate muscle growth and regeneration.

While the present invention has been described in terms of specific embodiments, it is understood that variations and modifications will occur to those skilled in the art. Accordingly, only such limitations as appear in the claims should be placed on the invention.

All documents referred to in this application are hereby incorporated by reference in their entirety.

---

I claim:

1. A polynucleotide comprising a first nucleotide sequence and a second nucleotide sequence, wherein the first nucleotide sequence comprises the nucleotide sequence of SEQ ID NO: 13 or SEQ ID NO: 14, and wherein the second nucleotide sequence comprises the nucleotide sequence of SEQ ID NO: 15 or SEQ ID NO: 16.

2. The polynucleotide of claim 1, wherein the first nucleotide sequence comprises the nucleotide sequence of SEQ ID NO: 13 and the second nucleotide sequence comprises the nucleotide sequence of SEQ ID NO: 15 or the nucleotide sequence of SEQ ID NO: 16.

3. The polynucleotide of claim 1, wherein the first nucleotide sequence comprises the nucleotide sequence of SEQ ID NO: 14 and the second nucleotide sequence comprises the nucleotide sequence of SEQ ID NO: 15 or the nucleotide sequence of SEQ ID NO: 16.

4. The polynucleotide of claim 1, wherein the polynucleotide comprises
   (a) the nucleotide sequence of SEQ ID NO: 1,
   (b) a nucleotide sequence encoding the amino acid sequence of SEQ ID NO: 19,
   (c) the nucleotide sequence of SEQ ID NO: 3,
   (d) a nucleotide sequence encoding the amino acid sequence of SEQ ID NO: 20,
   (e) the nucleotide sequence of SEQ ID NO: 5,
   (f) a nucleotide sequence encoding the amino acid sequence of SEQ ID NO: 21,
   (g) the nucleotide sequence of SEQ ID NO: 7, or
   (h) a nucleotide sequence encoding the amino acid sequence of SEQ ID NO: 22.

5. A recombinant adeno-associated virus (rAAV), wherein the genome of the rAAV comprises
   (a) the polynucleotide sequence of SEQ ID NO: 1,
   (b) the polynucleotide sequence of SEQ ID NO: 3,
   (c) the polynucleotide sequence of SEQ ID NO: 5,
   (d) the polynucleotide sequence of SEQ ID NO: 7,
   (e) nucleotides 3590 to 8215 of SEQ ID NO: 2,
   (f) nucleotides 3590 to 8341 of SEQ ID NO: 4,
   (g) nucleotides 3609 to 6929 of SEQ ID NO: 6,
   (h) nucleotides 3590 to 7036 of SEQ ID NO: 8, or
   (i) the nucleotide sequence set out in SEQ ID NO: 25.

6. The rAAV of claim 5, wherein the genome of the rAAV further comprises a muscle-specific transcriptional control element.

7. A recombinant host cell comprising the polynucleotide of claim 1.

8. A protein encoded by the polynucleotide of claim 1, wherein the protein comprises an amino acid sequence of SEQ ID NO: 19, SEQ ID NO: 20, SEQ ID NO: 21 or SEQ ID NO: 22.

9. A composition comprising the rAAV of claim 5.

* * * * *

SEQUENCE LISTING

```
<160> NUMBER OF SEQ ID NOS: 41

<210> SEQ ID NO 1
<211> LENGTH: 3222
<212> TYPE: DNA
<213> ORGANISM: Artificial Sequence
<220> FEATURE:
<223> OTHER INFORMATION: Synthetic Polynucleotide

<400> SEQUENCE: 1
atgaagctgc tgccgtcggt ggtgctgaag ctctttctgg ctgcagttct ctcggcactg        60
```

```
gtgactggcg agagcctgga gcggcttcgg agagggctag ctgctggaac cagcaacccg      120
gaccctccca ctgtatccac ggaccagctg ctacccctag gaggcggccg ggaccggaaa      180
gtccgtgact tgcaagaggc agatctggac cttttgagag tcactttatc ctccaagcca      240
caagcactgg ccacaccaaa caaggaggag cacgggaaaa gaaagaagaa aggcaagggg      300
ctagggaaga agagggaccc aaaagtatct gtgtcttcag gaggtgactg cattcgaaca      360
tacaaaccag aaatcaagaa aggaagttac aataatattg ttgtcaacgt aaagacagct      420
gttgctgata acctcctctt ttatcttgga agtgccaaat ttattgactt tctggctata      480
gaaatgcgta aaggcaaagt cagcttcctc tgggatgttg gatctggagt tggacgtgta      540
gagtacccag atttgactat tgatgactca tattggtacc gtatcgtagc atcaagaact      600
gggagaaatg gaactatttc tgtgagagcc ctggatggac ccaaagccag cattgtgccc      660
agcacacacc attcgacgtc tcctccaggg tacacgattc tagatgtgga tgcaaatgca      720
atgctgtttg ttggtggcct gactgggaaa ttaaagaagg ctgatgctgt acgtgtgatt      780
acattcactg gctgcatggg agaaacatac tttgacaaca aacctatagg tttgtggaat      840
ttccgagaaa aagaaggtga ctgcaaagga tgcactgtca gtcctcaggt ggaagatagt      900
gaggggacta ttcaatttga tggagaaggt tatgcattgg tcagccgtcc cattcgctgg      960
taccccaaca tctccactgt catgttcaag ttcagaacat tttcttcgag tgctcttctg     1020
atgtatcttg ccacacgaga cctgagagat ttcatgagtg tggagctcac tgatgggcac     1080
ataaaagtca gttacgatct gggctcagga atggcttccg ttgtcagcaa tcaaaaccat     1140
aatgatggga aatggaaatc attcactctg tcaagaattc aaaaacaagc caatatatca     1200
attgtagata tagatactaa tcaggaggag aatatagcaa cttcgtcttc tggaaacaac     1260
tttggtcttg acttgaaagc agatgacaaa atatattttg gtggcctgcc aacgctgaga     1320
aacttgagta tgaaagcaag gccagaagta aatctgaaga aatattccgg ctgcctcaaa     1380
gatattgaaa tttcaagaac tccgtacaat atactcagta gtcccgatta tgttggtgtt     1440
accaaaggat gttccctgga gaatgtttac acagttagct ttcctaagcc tggttttgtg     1500
gagctctccc ctgtgccaat tgatgtagga acagaaatca acctgtcatt cagcaccaag     1560
aatgagtccg gcatcattct tttgggaagt ggagggacac cagcaccacc taggagaaaa     1620
cgaaggcaga ctggacaggc ctattatgta atactcctca acaggggccg tctggaagtg     1680
catctctcca caggggcacg aacaatgagg aaaattgtca tcagaccaga gccgaatctg     1740
tttcatgatg gaagagaaca ttccgttcat gtagagcgaa ctagaggcat ctttacagtt     1800
caagtggatg aaaacagaag atacatgcaa aacctgacag ttgaacagcc tatcgaagtt     1860
aaaaagcttt tcgttggggg tgctccacct gaatttcaac cttccccact cagaaatatt     1920
cctccttttg aaggctgcat atggaatctt gttattaact ctgtccccat ggactttgca     1980
aggcctgtgt ccttcaaaaa tgctgacatt ggtcgctgtg cccatcagaa actccgtgaa     2040
gatgaagatg gagcagctcc agctgaaata gttatccagc ctgagccagt tcccacccca     2100
gcctttccta cgcccacccc agttctgaca catggtcctt gtgctgcaga atcagaacca     2160
gctcttttga tagggagcaa gcagttcggc ctttcaagaa acagtcacat tgcaattgca     2220
tttgatgaca ccaaagttaa aaaccgtctc acaattgagt tggaagtaag aaccgaagct     2280
gaatccggct tgcttttttta catggctcgc atcaatcatg ctgattttgc aacagttcag     2340
ctgagaaatg gattgcccta cttcagctat gacttgggga gtggggacac ccacaccatg     2400
atccccacca aaaatcaatga tggccagtgg cacaagatta agataatgag aagtaagcaa     2460
```

-continued

```
gaaggaattc tttatgtaga tggggcttcc aacagaacca tcagtcccaa aaaagccgac    2520
atcctggatg tcgtgggaat gctgtatgtt ggtgggttac ccatcaacta cactacccga    2580
agaattggtc cagtgaccta tagcattgat ggctgcgtca ggaatctcca catggcagag    2640 gccctgccg atctggaaca acccacctcc agcttccatg ttgggacatg ttttgcaaat    2700
gctcagaggg gaacatattt tgacggaacc ggttttgcca aagcagttgg tggattcaaa    2760
gtgggattgg accttcttgt agaatttgaa ttccgcacaa ctacaacgac tggagttctt    2820
ctggggatca gtagtcaaaa aatggatgga atgggtattg aaatgattga tgaaaagttg    2880
atgtttcatg tggacaatgg tgcgggcaga ttcactgctg tctatgatgc tggggttcca    2940
gggcatttgt gtgatggaca atggcataaa gtcactgcca acaagatcaa acaccgcatt    3000
gagctcacag tcgatgggaa ccaggtggaa gcccaaagcc caaacccagc atctacatca    3060
gctgacacaa atgaccctgt gtttgttgga ggcttcccag atgacctcaa gcagtttggc    3120
ctaacaacca gtattccgtt ccgaggttgc atcagatccc tgaagctcac caaaggcaca    3180
gcaagccact ggaggttaat tttgccaagg ccctggaact ga                       3222
```

```
<210> SEQ ID NO 2
<211> LENGTH: 8269
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: rAAV
<220> FEATURE:
<221> NAME/KEY: misc_feature
<222> LOCATION: (3590)..(3595)
<223> OTHER INFORMATION: n is a, c, g, t or u
<220> FEATURE:
<221> NAME/KEY: misc_feature
<222> LOCATION: (8210)..(8215)
<223> OTHER INFORMATION: n is a, c, g, t or u

<400> SEQUENCE: 2
```

```
gctcttccgc ttggtcgctc actgactcgc tgcgctcggt cgttcggctg cggcgagcgg      60
tatcagctca ctcaaacccg gtaatacggt tatccacaga atcaggggat aacgcaggaa     120
agaacatgtg agcaaaaggc cagcaaaagg ccaggaaccg taaaaaggcc gcgttgctgg     180
cgtttttcca taggctccgc cccctgacg agcatcacaa aaatcgacgc tcaagtcaga     240
ggtggcgaaa cccgacagga ctataaagat accaggcgtt tccccctgga agctccctcg     300
tgcgctctcc tgttccgacc ctgccgctta ccggatacct gtccgccttt ctcccttcgg     360
gaagcgtggc gctttctcat agctcacgct gtaggtatct cagttcggtg taggtcgttc     420
gctccaagct gggctgtgtg cacgaacccc cgttcagccc gaccgctgc gccttatccg     480 gtaactatcg tcttgagtcc aacccggtaa gacacgactt atcgccactg gcagcagcca     540
ctggtaacag gattagcaga gcgaggtatg tacgcggtgc tacagagttc ttgaagtggt     600
ggcctaacta cggctacact agaaggacag tatttggtat ctgcgctctg ctgaagccag     660
ttaccttcgg aaaaagagtt ggtagctctt gatccggcaa acaaaccacc gctggtagcg     720
gtggtttttt tgtttgcaag cagcagatta cgcgcagaaa aaaaggatct caagaagatc     780
ctttgatctt ttctacgggg tctgacgctc agtggaacga aaactcacgt taagggattt     840
tggtcatgag attatcaaaa aggatcttca cctagatcct tttaaattaa aaatgaagtt     900
ttaaatcaat ctaaagtata tatgagtaaa cttggtctga cagttaccaa tgcttaatca     960
```

```
gtgaggcacc tatctcagcg atctgtctat ttcgttcatc catagttgcc tgactccccg      1020
tcgtgtagat aactacgata cgggagggct taccatctgg ccccagtgct gcaatgatac      1080
cgcgagaccc acgctcaccg gctccagatt tatcagcaat aaaccagcca gccggaaggg      1140
ccgagcgcag aagtggtcct gcaactttat ccgcctccat ccagtctatt aattgttgcc      1200
gggaagctag agtaagtagt tcgccagtta atagtttgcg caacgttgtt gccattgcta      1260
caggcatcgt ggtgtcacgc tcgtcgtttg gtatggcttc attcagctcc ggttcccaac      1320
gatcaaggcg agttacatga tcccccatgt tgtgcaaaaa agcggttagc tccttcggtc      1380
ctccgatcgt tgtcagaagt aagttggccg cagtgttatc actcatggtt atggcagcac      1440
tgcataattc tcttactgtc atgccatccg taagatgctt ttctgtgact ggtgagtact      1500
caaccaagtc attctgagaa tagtgtatgc ggcgaccgag ttgctcttgc ccggcgtcaa      1560
tacgggataa taccgcgcca catagcagaa ctttaaaagt gctcatcatt ggaaaacgtt      1620
cttcggggcg aaaactctca aggatcttac cgctgttgag atccagttcg atgtaaccca      1680
ctcgtgcacc caactgatct tcagcatctt ttactttcac cagcgtttct gggtgagcaa      1740
aaacaggaag gcaaaatgcc gcaaaaaagg gaataagggc gacacggaaa tgttgaatac      1800
tcatactctt cctttttcaa tattattgaa gcatttatca gggttattgt ctcatgagcg      1860
gatacatatt tgaatgtatt tagaaaaata aacaaatagg ggttccgcgc acatttcccc      1920
gaaaagtgcc acctgacgtc taagaaacca ttattatcat gacattaacc tataaaaata      1980
ggcgtatcac gaggcccttt cgtctcgcgc gtttcggtga tgacggtgaa aacctctgac      2040
acatgcagct cccggagacg gtcacagctt gtctgtaagc ggatgccggg agcagacaag      2100
cccgtcaggg cgcgtcagcg ggtgttggcg ggtgtcgggg ctggcttaac tatgcggcat      2160
cagagcagat tgtactgaga gtgcaccata tgcggtgtga ataccgcac agatgcgtaa      2220 ggagaaaata ccgcatcagg aacttccaac atccaataaa tcatacaggc aaggcaaaga      2280
attagcaaaa ttaagcaata aagcctcaga gcataaagct aaatcggttg taccaaaaac      2340
attatgaccc tgtaatactt ttgcgggaga agcctttatt tcaacgcaag gataaaaatt      2400
tttagaaccc tcatatattt taaatgcaat gcctgagtaa tgtgtaggta agattcaaa       2460 cgggtgagaa aggccggaga cagtcaaatc accatcaata tgatattcaa ccgttctagc      2520
tgataaattc atgccggaga gggtagctat ttttgagagg tctctacaaa ggctatcagg      2580
tcattgcctg agagtctgga gcaaacaaga gaatcgatga acggtaatcg taaaactagc      2640
atgtcaatca tatgtacccc ggttgataat cagaaaagcc ccaaaaacag gaagattgta      2700
taagcaaata tttaaattgt aaacgttaat attttgttaa aattcgcgtt aaattttttgt      2760 taaatcagct cattttttaa ccaataggcc gaaatcggca aaatccctta taaatcaaaa      2820
gaatagaccg agatagggtt gagtgttgtt ccagtttgga acaagagtcc actattaaag      2880
aacgtggact ccaacgtcaa agggcgaaaa accgtctatc agggcgatgg cccactacgt      2940
gaaccatcac cctaatcaag ttttttgggg tcgaggtgcc gtaaatcact aaatcggaac      3000
cctaaaggga gcccccgatt tagagcttga cggggaaagc cggcgaacgt ggcgagaaag      3060
gaagggaaga aagcgaaagg agcgggcgct agggcgctgg caagtgtagc ggtcacgctg      3120
cgcgtaacca ccacacccgc cgcgcttaat gcgccgctac agggcgcgta ctatggttgc      3180
tttgacgagc acgtataacg tgctttcctc gttagaatca gagcgggagc taaacaggag      3240
gccgattaaa gggattttag acaggaacgg tacgccagaa tcctgagaag tgttttttata      3300
```

```
atcagtgagg ccaccgagta aaagagtctg tccatcacgc aaattaaccg ttgtcgcaat    3360
acttctttga ttagtaataa catcacttgc ctgagtagaa gaactcaaac tatcggcctt    3420
gctggtaata tccagaacaa tattaccgcc agccattgca acaggaaaaa cgctcatgga    3480
aatacctaca ttttgacgct caatcgtctg gaacttccat tcgccattca ggctgcgcaa    3540
ctgttgggaa gggcgatcgg tgcgggcctc ttcgctatta cgccagctgn nnnnngcgcg    3600
ctcgctcgct cactgaggcc gcccgggcaa agcccgggcg tcgggcgacc tttggtcgcc    3660
cggcctcagt gagcgagcga gcgcgcagag agggagtggc caactccatc actaggggtt    3720
ccttgtagtt aatgattaac ccgccatgct aattatctac gtagccatgt ctagggtcgt    3780
tacataactt acggtaaatg gcccgcctgg ctgaccgccc aacgaccccc gcccattgac    3840
gtcaataatg acgtatgttc ccatagtaac gccaataggg actttccatt gacgtcaatg    3900
ggtggagtat ttacggtaaa ctgcccactt ggcagtacat caagtgtatc atatgccaag    3960
tacgccccct attgacgtca atgacggtaa atggcccgcc tggcattatg cccagtacat    4020
gaccttatgg gactttccta cttggcagta catctacgta ttagtcatcg ctattaccat    4080
ggtgatgcgg ttttggcagt acatcaatgg gcgtggatag cggtttgact cacggggatt    4140
tccaagtctc caccccattg acgtcaatgg gagtttgttt tggcaccaaa atcaacggga    4200
ctttccaaaa tgtcgtaaca actccgcccc attgacgcaa atgggcggta ggcgtgtacg    4260
gtgggaggtc tatataagca gagctcgttt agtgaaccgt cagatcgcct ggagacgcca    4320
tccacgctgt tttgacctcc atagaagaca ccgggaccga tccagcctcc ggactctaga    4380
ggatccggta ctcgaggaac tgaaaaacca gaaagttaac tggtaagttt agtctttttg    4440
tcttttattt caggtcccgg atccggtggt ggtgcaaatc aaagaactgc tcctcagtgg    4500
atgttgcctt tacttctagg cctgtacgga agtgttactt ctgctctaaa agctgcggaa    4560
ttgtacccgc ggccgcacca tgaagctgct gccgtcggtg gtgctgaagc tctttctggc    4620
tgcagttctc tcggcactgg tgactggcga gagcctggag cggcttcgga gagggctagc    4680
tgctggaacc agcaacccgg accctcccac tgtatccacg gaccagctgc taccccctagg    4740 aggcggccgg gaccggaaag tccgtgactt gcaagaggca gatctggacc tttttgagagt    4800 cactttatcc tccaagccac aagcactggc cacaccaaac aaggaggagc acgggaaaag    4860
aaagaagaaa ggcaaggggc tagggaagaa gagggaccca aaagtatctg tgtcttcagg    4920
aggtgactgc attcgaacat acaaaccaga aatcaagaaa ggaagttaca ataatattgt    4980
tgtcaacgta aagacagctg ttgctgataa cctcctcttt tatcttggaa gtgccaaatt    5040
tattgacttt ctggctatag aaatgcgtaa aggcaaagtc agcttcctct gggatgttgg    5100
atctggagtt ggacgtgtag agtacccaga tttgactatt gatgactcat attggtaccg    5160
tatcgtagca tcaagaactg ggagaaatgg aactatttct gtgagagccc tggatggacc    5220
caaagccagc attgtgccca gcacacacca ttcgacgtct cctccagggt acacgattct    5280
agatgtggat gcaaatgcaa tgctgtttgt tggtggcctg actgggaaat aaaagaaggc    5340
tgatgctgta cgtgtgatta cattcactgg ctgcatggga gaaacatact ttgacaacaa    5400
acctataggt ttgtggaatt tccgagaaaa agaaggtgac tgcaaaggat gcactgtcag    5460
tcctcaggtg gaagatagtg aggggactat tcaatttgat ggagaaggtt atgcattggt    5520
cagccgtccc attcgctggt accccaacat ctccactgtc atgttcaagt tcagaacatt    5580
ttcttcgagt gctcttctga tgtatcttgc cacacgagac ctgagagatt tcatgagtgt    5640
ggagctcact gatgggcaca taaaagtcag ttacgatctg ggctcaggaa tggcttccgt    5700
```

-continued

```
tgtcagcaat caaaaccata atgatgggaa atggaaatca ttcactctgt caagaattca      5760
aaaacaagcc aatatatcaa ttgtagatat agatactaat caggaggaga atatagcaac      5820
ttcgtcttct ggaaacaact ttggtcttga cttgaaagca gatgacaaaa tatattttgg      5880
tggcctgcca acgctgagaa acttgagtat gaaagcaagg ccagaagtaa atctgaagaa      5940
atattccggc tgcctcaaag atattgaaat ttcaagaact ccgtacaata tactcagtag      6000
tcccgattat gttggtgtta ccaaaggatg ttccctggag aatgtttaca cagttagctt      6060
tcctaagcct ggttttgtgg agctctcccc tgtgccaatt gatgtaggaa cagaaatcaa      6120
cctgtcattc agcaccaaga atgagtccgg catcattctt ttgggaagtg gagggacacc      6180
agcaccacct aggagaaaac gaaggcagac tggacaggcc tattatgtaa tactcctcaa      6240
caggggccgt ctggaagtgc atctctccac aggggcacga acaatgagga aaattgtcat      6300
cagaccagag ccgaatctgt ttcatgatgg aagagaacat tccgttcatg tagagcgaac      6360
tagaggcatc tttacagttc aagtggatga aaacagaaga tacatgcaaa acctgacagt      6420
tgaacagcct atcgaagtta aaaagctttt cgttgggggt gctccacctg aatttcaacc      6480
ttccccactc agaaatattc ctccttttga aggctgcata tggaatcttg ttattaactc      6540
tgtccccatg gactttgcaa ggcctgtgtc cttcaaaaat gctgacattg gtcgctgtgc      6600
ccatcagaaa ctccgtgaag atgaagatgg agcagctcca gctgaaatag ttatccagcc      6660
tgagccagtt cccaccccag cctttcctac gcccacccca gttctgacac atggtccttg      6720
tgctgcagaa tcagaaccag ctcttttgat agggagcaag cagttcgggc tttcaagaaa      6780
cagtcacatt gcaattgcat ttgatgacac caaagttaaa aaccgtctca caattgagtt      6840
ggaagtaaga accgaagctg aatccggctt gcttttttac atggctcgca tcaatcatgc      6900
tgattttgca acagttcagc tgagaaatgg attgccctac ttcagctatg acttggggag      6960
tggggacacc cacaccatga tccccaccaa aatcaatgat ggccagtggc acaagattaa      7020
gataatgaga agtaagcaag aaggaattct ttatgtagat ggggcttcca acagaaccat      7080
cagtcccaaa aaagccgaca tcctggatgt cgtgggaatg ctgtatgttg gtgggttacc      7140
catcaactac actacccgaa gaattggtcc agtgacctat agcattgatg gctgcgtcag      7200
gaatctccac atggcagagg cccctgccga tctggaacaa cccacctcca gcttccatgt      7260
tgggacatgt tttgcaaatg ctcagagggg aacatatttt gacggaaccg gttttgccaa      7320
agcagttggt ggattcaaag tgggattgga ccttcttgta gaatttgaat tccgcacaac      7380
tacaacgact ggagttcttc tggggatcag tagtcaaaaa atggatggaa tgggtattga      7440
aatgattgat gaaaagttga tgtttcatgt ggacaatggt gcgggcagat tcactgctgt      7500
ctatgatgct ggggttccag ggcatttgtg tgatggacaa tggcataaag tcactgccaa      7560
caagatcaaa caccgcattg agctcacagt cgatgggaac caggtggaag cccaaagccc      7620
aaacccagca tctacatcag ctgacacaaa tgaccctgtg tttgttggag cttcccaga       7680 tgacctcaag cagtttggcc taacaaccag tattccgttc cgaggttgca tcagatccct      7740
gaagctcacc aaaggcacag caagccactg gaggttaatt ttgccaaggc cctggaactg      7800
aactagtgcg gccgcgggga tccagacatg ataagataca ttgatgagtt tggacaaacc      7860
acaactagaa tgcagtgaaa aaaatgcttt atttgtgaaa tttgtgatgc tattgcttta      7920
tttgtaacca ttataagctg caataaacaa gttaacaaca caattgcat tcattttatg      7980 tttcaggttc aggggggaggt gtgggaggtt ttttcggatc ctctagagtc gaccacatgg      8040
```

-continued ctacgtagat aattagcatg gcgggttaat cattaactac aaggaacccc tagtgatgga      8100
gttggccact ccctctctgc gcgctcgctc gctcactgag gccgggcgac caaaggtcgc      8160
ccgacgcccg ggctttgccc gggcggcctc agtgagcgag cgagcgcgcn nnnnncagct      8220
gcattaatga atcggccaac gcgcggggag aggcggtttg cgtattggg                 8269

<210> SEQ ID NO 3
<211> LENGTH: 3348
<212> TYPE: DNA
<213> ORGANISM: Artificial Sequence
<220> FEATURE:
<223> OTHER INFORMATION: Synthetic Polynucleotide

<400> SEQUENCE: 3
atgaagctgc tgccgtcggt ggtgctgaag ctctttctgg ctgcagttct ctcggcactg        60
gtgactggcg agagcctgga gcggcttcgg agagggctag ctgctggaac cagcaacccg       120
gaccctccca ctgtatccac ggaccagctg ctacccctag gaggcggccg ggaccggaaa       180
gtccgtgact tgcaagaggc agatctggac cttttgagag tcactttatc ctccaagcca       240
caagcactgg ccacaccaaa caaggaggag cacgggaaaa gaaagaagaa aggcaagggg       300
ctagggaaga agagggaccc atgtcttcgg aaatacaagg acttctgcat ccatggagaa       360
tgcaaatatg tgaaggagct ccgggctccc tcctgcatct gccacccggg ttaccatgga       420
gagaggtgtc atgggctgag cctcccaaaa gtatctgtgt cttcaggagg tgactgcatt       480
cgaacataca aaccagaaat caagaaagga agttacaata atattgttgt caacgtaaag       540
acagctgttg ctgataacct cctctttat cttggaagtg ccaaatttat tgactttctg       600
gctatagaaa tgcgtaaagg caaagtcagc ttcctctggg atgttggatc tggagttgga       660
cgtgtagagt acccagattt gactattgat gactcatatt ggtaccgtat cgtagcatca       720
agaactggga gaaatggaac tatttctgtg agagccctgg atggacccaa agccagcatt       780
gtgcccagca cacaccattc gacgtctcct ccagggtaca cgattctaga gtgtggatgca      840 aatgcaatgc tgtttgttgg tggcctgact gggaaattaa agaaggctga tgctgtacgt       900
gtgattacat tcactggctg catgggagaa acatactttg acaacaaacc tataggtttg       960
tggaatttcc gagaaaaaga aggtgactgc aaaggatgca ctgtcagtcc tcaggtggaa      1020
gatagtgagg ggactattca atttgatgga gaaggttatg cattggtcag ccgtcccatt      1080
cgctggtacc ccaacatctc cactgtcatg ttcaagttca gaacattttc ttcgagtgct      1140
cttctgatgt atcttgccac acgagacctg agagatttca tgagtgtgga gctcactgat      1200
gggcacataa aagtcagtta cgatctgggc tcaggaatgg cttccgttgt cagcaatcaa      1260
aaccataatg atgggaaatg gaatcattc actctgtcaa gaattcaaaa acaagccaat      1320
atatcaattg tagatataga tactaatcag gaggagaata tagcaacttc gtcttctgga      1380
aacaactttg tcttgactt gaaagcagat gacaaaatat attttggtgg cctgccaacg      1440
ctgagaaact tgagtatgaa agcaaggcca gaagtaaatc tgaagaaata ttccggctgc      1500
ctcaaagata ttgaaatttc aagaactccg tacaatatac tcagtagtcc cgattatgtt      1560
ggtgttacca aaggatgttc cctggagaat gtttacacag ttagctttcc taagcctggt      1620
tttgtggagc tctcccctgt gccaattgat gtaggaacag aaatcaacct gtcattcagc      1680
accaagaatg agtccggcat cattcttttg ggaagtggag ggacaccagc accacctagg      1740
agaaaacgaa ggcagactgg acaggcctat tatgtaaac tcctcaacag gggccgtctg      1800
gaagtgcatc tctccacagg ggcacgaaca atgaggaaaa ttgtcatcag accagagccg      1860

-continued

```
aatctgtttc atgatggaag agaacattcc gttcatgtag agcgaactag aggcatcttt      1920
acagttcaag tggatgaaaa cagaagatac atgcaaaacc tgacagttga acagcctatc      1980
gaagttaaaa agcttttcgt tgggggtgct ccacctgaat ttcaaccttc cccactcaga      2040
aatattcctc cttttgaagg ctgcatatgg aatcttgtta ttaactctgt ccccatggac      2100
tttgcaaggc ctgtgtcctt caaaaatgct gacattggtc gctgtgccca tcagaaactc      2160
cgtgaagatg aagatggagc agctccagct gaaatagtta tccagcctga gccagttccc      2220
accccagcct ttcctacgcc caccccagtt ctgacacatg gtccttgtgc tgcagaatca      2280
gaaccagctc ttttgatagg gagcaagcag ttcgggcttt caagaaacag tcacattgca      2340
attgcatttg atgacaccaa agttaaaaac cgtctcacaa ttgagttgga agtaagaacc      2400
gaagctgaat ccggcttgct tttttacatg gctcgcatca atcatgctga ttttgcaaca      2460
gttcagctga gaaatggatt gccctacttc agctatgact tggggagtgg ggacacccac      2520
accatgatcc ccaccaaaat caatgatggc cagtggcaca agattaagat aatgagaagt      2580
aagcaagaag gaattcttta tgtagatggg gcttccaaca gaaccatcag tcccaaaaaa      2640
gccgacatcc tggatgtcgt gggaatgctg tatgttggtg ggttacccat caactacact      2700
acccgaagaa ttggtccagt gacctatagc attgatggc gcgtcaggaa tctccacatg      2760
gcagaggccc ctgccgatct ggaacaaccc acctccagct tccatgttgg gacatgtttt      2820
gcaaatgctc agaggggaac atattttgac ggaaccggtt ttgccaaagc agttggtgga      2880
ttcaaagtgg gattggacct tcttgtagaa tttgaattcc gcacaactac aacgactgga      2940
gttcttctgg ggatcagtag tcaaaaaatg gatggaatgg gtattgaaat gattgatgaa      3000
aagttgatgt ttcatgtgga caatggtgcg ggcagattca ctgctgtcta tgatgctggg      3060
gttccagggc atttgtgtga tggacaatgg cataaagtca ctgccaacaa gatcaaacac      3120
cgcattgagc tcacagtcga tgggaaccag gtggaagccc aaagcccaaa cccagcatct      3180
acatcagctg acacaaatga ccctgtgttt gttggaggct cccagatga cctcaagcag      3240 tttggcctaa caaccagtat tccgttccga ggttgcatca gatccctgaa gctcaccaaa      3300
ggcacagcaa gccactggag gttaattttg ccaaggccct ggaactga               3348
```

<210> SEQ ID NO 4
<211> LENGTH: 8398
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: rAAV
<220> FEATURE:
<221> NAME/KEY: misc_feature
<222> LOCATION: (3590)..(3595)
<223> OTHER INFORMATION: n is a, c, g, t or u
<220> FEATURE:
<221> NAME/KEY: misc_feature
<222> LOCATION: (8336)..(8341)
<223> OTHER INFORMATION: n is a, c, g, t or u

<400> SEQUENCE: 4

```
gctcttccgc ttggtcgctc actgactcgc tgcgctcggt cgttcggctg cggcgagcgg        60
tatcagctca ctcaaacccg gtaatacggt tatccacaga atcaggggat aacgcaggaa       120
agaacatgtg agcaaaaggc cagcaaaagg ccaggaaccg taaaaaggcc gcgttgctgg       180 cgttttttcca taggctccgc cccctgacg agcatcacaa aaatcgacgc tcaagtcaga       240
```

```
ggtggcgaaa cccgacagga ctataaagat accaggcgtt tccccctgga agctccctcg   300
tgcgctctcc tgttccgacc ctgccgctta ccggatacct gtccgccttt ctcccttcgg   360
gaagcgtggc gctttctcat agctcacgct gtaggtatct cagttcggtg taggtcgttc   420
gctccaagct gggctgtgtg cacgaacccc ccgttcagcc cgaccgctgc gccttatccg   480
gtaactatcg tcttgagtcc aacccggtaa gacacgactt atcgccactg gcagcagcca   540
ctggtaacag gattagcaga gcgaggtatg tacgcggtgc tacagagttc ttgaagtggt   600
ggcctaacta cggctacact agaaggacag tatttggtat ctgcgctctg ctgaagccag   660
ttaccttcgg aaaaagagtt ggtagctctt gatccggcaa acaaaccacc gctggtagcg   720
gtggtttttt tgtttgcaag cagcagatta cgcgcagaaa aaaaggatct caagaagatc   780
ctttgatctt ttctacgggg tctgacgctc agtggaacga aaactcacgt taagggattt   840
tggtcatgag attatcaaaa aggatcttca cctagatcct tttaaattaa aaatgaagtt   900
ttaaatcaat ctaaagtata tatgagtaaa cttggtctga cagttaccaa tgcttaatca   960
gtgaggcacc tatctcagcg atctgtctat ttcgttcatc catagttgcc tgactccccg  1020
tcgtgtagat aactacgata cgggagggct taccatctgg ccccagtgct gcaatgatac  1080
cgcgagaccc acgctcaccg gctccagatt tatcagcaat aaaccagcca gccggaaggg  1140
ccgagcgcag aagtggtcct gcaactttat ccgcctccat ccagtctatt aattgttgcc  1200
gggaagctag agtaagtagt tcgccagtta atagtttgcg caacgttgtt gccattgcta  1260
caggcatcgt ggtgtcacgc tcgtcgtttg gtatggcttc attcagctcc ggttcccaac  1320
gatcaaggcg agttacatga tcccccatgt tgtgcaaaaa agcggttagc tccttcggtc  1380
ctccgatcgt tgtcagaagt aagttggccg cagtgttatc actcatggtt atggcagcac  1440
tgcataattc tcttactgtc atgccatccg taagatgctt ttctgtgact ggtgagtact  1500
caaccaagtc attctgagaa tagtgtatgc ggcgaccgag ttgctcttgc ccggcgtcaa  1560
tacgggataa taccgcgcca catagcagaa ctttaaaagt gctcatcatt ggaaaacgtt  1620
cttcggggcg aaaactctca aggatcttac cgctgttgag atccagttcg atgtaaccca  1680
ctcgtgcacc caactgatct tcagcatctt ttactttcac cagcgtttct gggtgagcaa  1740
aaacaggaag gcaaaatgcc gcaaaaaagg gaataagggc gacacggaaa tgttgaatac  1800
tcatactctt cctttttcaa tattattgaa gcatttatca gggttattgt ctcatgagcg  1860
gatacatatt tgaatgtatt tagaaaaata aacaaatagg ggttccgcgc acatttcccc  1920
gaaaagtgcc acctgacgtc taagaaacca ttattatcat gacattaacc tataaaaata  1980
ggcgtatcac gaggcccttt cgtctcgcgc gtttcggtga tgacggtgaa aacctctgac  2040
acatgcagct cccggagacg gtcacagctt gtctgtaagc ggatgccggg agcagacaag  2100
cccgtcaggg cgcgtcagcg ggtgttggcg ggtgtcgggg ctggcttaac tatgcggcat  2160
cagagcagat tgtactgaga gtgcaccata tgcggtgtga ataccgcac agatgcgtaa   2220 ggagaaaata ccgcatcagg aacttccaac atccaataaa tcatacaggc aaggcaaaga  2280
attagcaaaa ttaagcaata aagcctcaga gcataaagct aaatcggttg taccaaaaac  2340
attatgaccc tgtaatactt ttgcgggaga agcctttatt tcaacgcaag ataaaaatt   2400 tttagaaccc tcatatattt taaatgcaat gcctgagtaa tgtgtaggta agattcaaa   2460 cgggtgagaa aggccggaga cagtcaaatc accatcaata tgatattcaa ccgttctagc  2520
tgataaattc atgccggaga gggtagctat ttttgagagg tctctacaaa ggctatcagg  2580
```

-continued

```
tcattgcctg agagtctgga gcaaacaaga gaatcgatga acggtaatcg taaaactagc    2640
atgtcaatca tatgtacccc ggttgataat cagaaaagcc ccaaaaacag gaagattgta    2700
taagcaaata tttaaattgt aaacgttaat attttgttaa aattcgcgtt aaattttttgt   2760 taaatcagct catttttttaa ccaataggcc gaaatcggca aaatccctta taaatcaaaa    2820
gaatagaccg agatagggtt gagtgttgtt ccagtttgga acaagagtcc actattaaag    2880
aacgtggact ccaacgtcaa agggcgaaaa accgtctatc agggcgatgg cccactacgt    2940
gaaccatcac cctaatcaag ttttttgggg tcgaggtgcc gtaaatcact aaatcggaac    3000
cctaaaggga gccccccgatt tagagcttga cggggaaagc cggcgaacgt ggcgagaaag    3060
gaagggaaga aagcgaaagg agcgggcgct agggcgctgg caagtgtagc ggtcacgctg    3120
cgcgtaacca ccacccccgc cgcgcttaat gcgccgctac agggcgcgta ctatggttgc    3180
tttgacgagc acgtataacg tgctttcctc gttagaatca gagcgggagc taaacaggag    3240
gccgattaaa gggattttag acaggaacgg tacgccagaa tcctgagaag tgttttttata   3300 atcagtgagg ccaccgagta aaagagtctg tccatcacgc aaattaaccg ttgtcgcaat    3360
acttctttga ttagtaataa catcacttgc ctgagtagaa gaactcaaac tatcggcctt    3420
gctggtaata tccagaacaa tattaccgcc agccattgca acaggaaaaa cgctcatgga    3480
aatacctaca ttttgacgct caatcgtctg gaacttccat tcgccattca ggctgcgcaa    3540
ctgttgggaa gggcgatcgg tgcgggcctc ttcgctatta cgccagctgn nnnnngcgcg    3600
ctcgctcgct cactgaggcc gcccgggcaa agcccgggcg tcgggcgacc tttggtcgcc    3660
cggcctcagt gagcgagcga gcgcgcagag agggagtggc caactccatc actaggggtt    3720
ccttgtagtt aatgattaac ccgccatgct aattatctac gtagccatgt ctagggtcgt    3780
tacataactt acggtaaatg gcccgcctgg ctgaccgccc aacgacccc gcccattgac      3840 gtcaataatg acgtatgttc ccatagtaac gccaataggg actttccatt gacgtcaatg    3900
ggtggagtat ttacggtaaa ctgcccactt ggcagtacat caagtgtatc atatgccaag    3960
tacgccccct attgacgtca atgacggtaa atggcccgcc tggcattatg cccagtacat    4020
gaccttatgg gactttccta cttggcagta catctacgta ttagtcatcg ctattaccat    4080
ggtgatgcgg ttttggcagt acatcaatgg gcgtggatag cggtttgact cacggggatt    4140
tccaagtctc cacccccattg acgtcaatgg gagtttgttt tggcaccaaa atcaacggga    4200
ctttccaaaa tgtcgtaaca actccgcccc attgacgcaa atgggcggta ggcgtgtacg    4260
gtgggaggtc tatataagca gagctcgttt agtgaaccgt cagatcgcct ggagacgcca    4320
tccacgctgt tttgacctcc atagaagaca ccgggaccga tccagcctcc ggactctaga    4380
ggatccggta ctcgaggaac tgaaaaacca gaaagttaac tggtaagttt agtcttttttg   4440 tcttttatttt caggtcccgg atccggtggt ggtgcaaatc aaagaactgc tcctcagtgg    4500
atgttgcctt tacttctagg cctgtacgga agtgttactt ctgctctaaa agctgcggaa    4560
ttgtacccgc ggccgcacca tgaagctgct gccgtcggtg gtgctgaagc tctttctggc    4620
tgcagttctc tcggcactgg tgactggcga gagcctggag cggcttcgga gagggctagc    4680
tgctggaacc agcaacccgg accctcccac tgtatccacg gaccagctgc tacccctagg    4740
aggcggccgg gaccggaaag tccgtgactt gcaagaggca gatctggacc ttttgagagt    4800
cactttatcc tccaagccac aagcactggc cacaccaaac aaggaggagc acgggaaaag    4860
aaagaagaaa ggcaagggg tagggaagaa gaggggaccccc tgtcttcgga aatacaagga    4920
cttctgcatc catggagaat gcaaatatgt gaaggagctc cgggctccct cctgcatctg    4980
```

```
ccacccgggt taccatggag agaggtgtca tgggctgagc ctcccaaaag tatctgtgtc      5040
ttcaggaggt gactgcattc gaacatacaa accagaaatc aagaaaggaa gttacaataa      5100
tattgttgtc aacgtaaaga cagctgttgc tgataacctc ctcttttatc ttggaagtgc      5160
caaatttatt gactttctgg ctatagaaat gcgtaaaggc aaagtcagct tcctctggga      5220
tgttggatct ggagttggac gtgtagagta cccagatttg actattgatg actcatattg      5280
gtaccgtatc gtagcatcaa gaactgggag aaatggaact atttctgtga gagccctgga      5340
tggacccaaa gccagcattg tgcccagcac acaccattcg acgtctcctc cagggtacac      5400
gattctagat gtggatgcaa atgcaatgct gtttgttggt ggcctgactg ggaaattaaa      5460
gaaggctgat gctgtacgtg tgattacatt cactggctgc atgggagaaa catactttga      5520
caacaaacct ataggtttgt ggaatttccg agaaaaagaa ggtgactgca aaggatgcac      5580
tgtcagtcct caggtggaag atagtgaggg gactattcaa tttgatggag aaggttatgc      5640
attggtcagc cgtcccattc gctggtaccc aacatctcc actgtcatgt tcaagttcag      5700
aacattttct tcgagtgctc ttctgatgta tcttgccaca cgagacctga gagatttcat      5760
gagtgtggag ctcactgatg ggcacataaa agtcagttac gatctgggct caggaatggc      5820
ttccgttgtc agcaatcaaa accataatga tgggaaatgg aaatcattca ctctgtcaag      5880
aattcaaaaa caagccaata tatcaattgt agatatagat actaatcagg aggagaatat      5940
agcaacttcg tcttctggaa caactttgg tcttgacttg aaagcagatg acaaaatata      6000
ttttggtggc ctgccaacgc tgagaaactt gagtatgaaa gcaaggccag aagtaaatct      6060
gaagaaatat tccggctgcc tcaaagatat tgaaatttca agaactccgt acaatatact      6120
cagtagtccc gattatgttg gtgttaccaa aggatgttcc ctggagaatg tttacacagt      6180
tagctttcct aagcctggtt ttgtggagct ctccctgtg ccaattgatg taggaacaga      6240
aatcaacctg tcattcagca ccaagaatga gtccggcatc attcttttgg gaagtggagg      6300
gacaccagca ccacctagga gaaaacgaag gcagactgga caggcctatt atgtaatact      6360
cctcaacagg ggccgtctgg aagtgcatct ctccacaggg gcacgaacaa tgaggaaaat      6420
tgtcatcaga ccagagccga atctgtttca tgatggaaga gaacattccg ttcatgtaga      6480
gcgaactaga ggcatcttta cagttcaagt ggatgaaaac agaagataca tgcaaaacct      6540
gacagttgaa cagcctatcg aagttaaaaa gcttttcgtt gggggtgctc cacctgaatt      6600
tcaaccttcc ccactcagaa atattcctcc ttttgaaggc tgcatatgga atcttgttat      6660
taactctgtc cccatggact ttgcaaggcc tgtgtccttc aaaaatgctg acattggtcg      6720
ctgtgcccat cagaaactcc gtgaagatga agatggagca gctccagctg aaatagttat      6780
ccagcctgag ccagttccca ccccagcctt tcctacgccc acccagttc tgacacatgg      6840 tccttgtgct gcagaatcag aaccagctct tttgataggg agcaagcagt cgggctttc      6900 aagaaacagt cacattgcaa ttgcatttga tgacaccaaa gttaaaaacc gtctcacaat      6960
tgagttggaa gtaagaaccg aagctgaatc cggcttgctt ttttacatgg ctcgcatcaa      7020
tcatgctgat tttgcaacag ttcagctgag aaatggattg ccctacttca gctatgactt      7080
ggggagtggg gacacccaca ccatgatccc caccaaaatc aatgatggcc agtggcacaa      7140
gattaagata atgagaagta agcaagaagg aattctttat gtagatgggg cttccaacag      7200
aaccatcagt cccaaaaaag ccgacatcct ggatgtcgtg ggaatgctgt atgttggtgg      7260
gttacccatc aactacacta cccgaagaat tggtccagtg acctatagca ttgatggctg      7320
```

-continued

```
cgtcaggaat ctccacatgg cagaggcccc tgccgatctg gaacaaccca cctccagctt      7380
ccatgttggg acatgttttg caaatgctca gaggggaaca tattttgacg gaaccggttt      7440
tgccaaagca gttggtggat tcaaagtggg attggacctt cttgtagaat ttgaattccg      7500
cacaactaca acgactggag ttcttctggg gatcagtagt caaaaaatgg atggaatggg      7560
tattgaaatg attgatgaaa agttgatgtt tcatgtggac aatggtgcgg gcagattcac      7620
tgctgtctat gatgctgggg ttccaggca tttgtgtgat ggacaatggc ataaagtcac       7680
tgccaacaag atcaaacacc gcattgagct cacagtcgat gggaaccagg tggaagccca      7740
aagcccaaac ccagcatcta catcagctga cacaaatgac cctgtgtttg ttggaggctt      7800
cccagatgac ctcaagcagt ttggcctaac aaccagtatt ccgttccgag gttgcatcag      7860
atccctgaag ctcaccaaag gcacagcaag ccactggagg ttaattttgc caaggccctg      7920
gaactgaact agtgcggccg cggggatcca gacatgataa gatacattga tgagtttgga      7980
caaaccacaa ctagaatgca gtgaaaaaaa tgctttattt gtgaaatttg tgatgctatt      8040
gctttatttg taaccattat aagctgcaat aaacaagtta acaacaacaa ttgcattcat      8100
tttatgtttc aggttcaggg ggaggtgtgg gaggtttttt cggatcctct agagtcgacc      8160
acatggctac gtagataatt agcatggcgg gttaatcatt aactacaagg aacccctagt      8220
gatggagttg gccactccct ctctgcgcgc tcgctcgctc actgaggccg ggcgaccaaa      8280
ggtcgcccga cgcccgggct ttgcccgggc ggcctcagtg agcgagcgag cgcgcnnnnn      8340
ncagctgcat taatgaatcg gccaacgcgc ggggagaggc ggtttgcgta ttgggcmg       8398
```

<210> SEQ ID NO 5
<211> LENGTH: 1917
<212> TYPE: DNA
<213> ORGANISM: Artificial Sequence
<220> FEATURE:
<223> OTHER INFORMATION: Synthetic Polynucleotide

<400> SEQUENCE: 5

```
atgaagctgc tgccgtcggt ggtgctgaag ctctttctgg ctgcagttct ctcggcactg        60
gtgactggcg agagcctgga gcggcttcgg agagggctag ctgctggaac cagcaacccg       120
gaccctccca ctgtatccac ggaccagctg ctaccctag gaggcggccg ggaccggaaa        180
gtccgtgact tgcaagaggc agatctggac ctttttgagag tcactttatc ctccaagcca       240
caagcactgg ccacaccaaa caaggaggag cacgggaaaa gaaagaagaa aggcaagggg       300
ctagggaaga agagggaccc acagactgga caggcctatt atgtaatact cctcaacagg       360
ggccgtctgg aagtgcatct ctccacaggg gcacgaacaa tgaggaaaat tgtcatcaga       420
ccagagccga atctgtttca tgatggaaga aacattccg ttcatgtaga gcgaactaga        480
ggcatcttta cagttcaagt ggatgaaaac agaagataca tgcaaaacct gacagttgaa       540
cagcctatcg aagttaaaaa gctttcgtt gggggtgctc cacctgaatt tcaaccttcc        600
ccactcagaa atattcctcc ttttgaaggc tgcatatgga tcttgttat taactctgtc        660 cccatggact ttgcaaggcc tgtgtccttc aaaaatgctg acattggtcg ctgtgcccat       720
cagaaactcc gtgaagatga agatggagca gctccagctg aaatagttat ccagcctgag       780
ccagttccca ccccagcctt tcctacgccc accccagttc tgacacatgg tccttgtgct       840
gcagaatcag aaccagctct tttgataggg agcaagcagt tcgggctttc aagaaacagt       900
cacattgcaa ttgcatttga tgacaccaaa gttaaaaacc gtctcacaat tgagttggaa       960
gtaagaaccg aagctgaatc cggcttgctt ttttacatgg ctcgcatcaa tcatgctgat      1020
```

```
tttgcaacag ttcagctgag aaatggattg ccctacttca gctatgactt ggggagtggg    1080
gacacccaca ccatgatccc caccaaaatc aatgatggcc agtggcacaa gattaagata    1140
atgagaagta agcaagaagg aattctttat gtagatgggg cttccaacag aaccatcagt    1200
cccaaaaaag ccgacatcct ggatgtcgtg ggaatgctgt atgttggtgg gttacccatc    1260
aactacacta cccgaagaat tggtccagtg acctatagca ttgatggctg cgtcaggaat    1320
ctccacatgg cagaggcccc tgccgatctg gaacaaccca cctccagctt ccatgttggg    1380
acatgttttg caaatgctca gaggggaaca tattttgacg gaaccggttt tgccaaagca    1440
gttggtggat tcaaagtggg attggacctt cttgtagaat ttgaattccg cacaactaca    1500
acgactggag ttcttctggg gatcagtagt caaaaaatgg atggaatggg tattgaaatg    1560
attgatgaaa agttgatgtt tcatgtggac aatggtgcgg gcagattcac tgctgtctat    1620
gatgctgggg ttccagggca tttgtgtgat ggacaatggc ataaagtcac tgccaacaag    1680
atcaaacacc gcattgagct cacagtcgat gggaaccagg tggaagccca aagcccaaac    1740
ccagcatcta catcagctga cacaaatgac cctgtgtttg ttggaggctt cccagatgac    1800
ctcaagcagt ttggcctaac aaccagtatt ccgttccgag gttgcatcag atccctgaag    1860
ctcaccaaag gcacagcaag ccactggagg ttaatttttgc caaggccctg gaactga       1917
```

```
<210> SEQ ID NO 6
<211> LENGTH: 6984
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: rAAV
<220> FEATURE:
<221> NAME/KEY: misc_feature
<222> LOCATION: (3609)..(3614)
<223> OTHER INFORMATION: n is a, c, g, t or u
<220> FEATURE:
<221> NAME/KEY: misc_feature
<222> LOCATION: (6924)..(6929)
<223> OTHER INFORMATION: n is a, c, g, t or u

<400> SEQUENCE: 6
```

```
gctcttccgc ttggtcgctc actgactcgc tgcgctcggt cgttcggctg cggcgagcgg      60
tatcagctca ctcaaacccg gtaatacggt tatccacaga atcaggggat aacgcaggaa     120
agaacatgtg agcaaaaggc cagcaaaagg ccaggaaccg taaaaaggcc gcgttgctgg     180 cgttttttcca taggctccgc ccccctgacg agcatcacaa aaatcgacgc tcaagtcaga     240
ggtggcgaaa cccgacagga ctataaagat accaggcgtt ccccctggaa gctccctcg      300 tgcgctctcc tgttccgacc ctgccgctta ccggatacct gtccgccttt ctcccttcgg     360
gaagcgtggc gctttctcat agctcacgct gtaggtatct cagttcggtg taggtcgttc     420
gctccaagct gggctgtgtg cacgaacccc cgttcagcc cgaccgctgc gccttatccg      480
gtaactatcg tcttgagtcc aacccggtaa gacacgactt atcgccactg gcagcagcca     540
ctggtaacag gattagcaga gcgaggtatg tacgcggtgc tacagagttc ttgaagtggt     600
ggcctaacta cggctacact agaaggacag tatttggtat ctgcgctctg ctgaagccag     660
ttaccttcgg aaaaagagtt ggtagctctt gatccggcaa acaaaccacc gctggtagcg     720
gtggtttttt tgtttgcaag cagcagatta cgcgcagaaa aaaaggatct caagaagatc     780
ctttgatctt ttctacgggg tctgacgctc agtggaacga aaactcacgt taagggattt     840
```

-continued

```
tggtcatgag attatcaaaa aggatcttca cctagatcct tttaaattaa aaatgaagtt    900
ttaaatcaat ctaaagtata tatgagtaaa cttggtctga cagttaccaa tgcttaatca    960
gtgaggcacc tatctcagcg atctgtctat ttcgttcatc catagttgcc tgactccccg   1020
tcgtgtagat aactacgata cgggagggct taccatctgg ccccagtgct gcaatgatac   1080
cgcgagaccc acgctcaccg gctccagatt tatcagcaat aaaccagcca gccggaaggg   1140
ccgagcgcag aagtggtcct gcaactttat ccgcctccat ccagtctatt aattgttgcc   1200
gggaagctag agtaagtagt tcgccagtta atagtttgcg caacgttgtt gccattgcta   1260
caggcatcgt ggtgtcacgc tcgtcgtttg gtatggcttc attcagctcc ggttcccaac   1320
gatcaaggcg agttacatga tcccccatgt tgtgcaaaaa agcggttagc tccttcggtc   1380
ctccgatcgt tgtcagaagt aagttggccg cagtgttatc actcatggtt atggcagcac   1440
tgcataattc tcttactgtc atgccatccg taagatgctt ttctgtgact ggtgagtact   1500
caaccaagtc attctgagaa tagtgtatgc ggcgaccgag ttgctcttgc ccggcgtcaa   1560
tacgggataa taccgcgcca catagcagaa ctttaaaagt gctcatcatt ggaaaacgtt   1620
cttcggggcg aaaactctca aggatcttac cgctgttgag atccagttcg atgtaaccca   1680
ctcgtgcacc caactgatct tcagcatctt ttactttcac cagcgtttct gggtgagcaa   1740
aaacaggaag gcaaaatgcc gcaaaaaagg gaataagggc gacacggaaa tgttgaatac   1800
tcatactctt cctttttcaa tattattgaa gcatttatca gggttattgt ctcatgagcg   1860
gatacatatt tgaatgtatt tagaaaaata aacaaatagg ggttccgcgc acatttcccc   1920
gaaaagtgcc acctgacgtc taagaaacca tcgttacata acttacggta tattatcatg   1980
acattaacct ataaaaatag gcgtatcacg aggccctttc gtctcgcgcg tttcggtgat   2040
gacggtgaaa acctctgaca catgcagctc ccggagacgg tcacagcttg tctgtaagcg   2100
gatgccggga gcagacaagc ccgtcagggc gcgtcagcgg gtgttggcgg gtgtcggggc   2160
tggcttaact atgcggcatc agagcagatt gtactgagag tgcaccatat gcggtgtgaa   2220
ataccgcaca gatgcgtaag gagaaaatac cgcatcagga acttccaaca tccaataaat   2280
catacaggca aggcaaagaa ttagcaaaat taagcaataa agcctcagag cataaagcta   2340
aatcggttgt accaaaaaca ttatgaccct gtaatacttt tgcgggagaa gcctttattt   2400
caacgcaagg ataaaaattt ttagaaccct catatatttt aaatgcaatg cctgagtaat   2460
gtgtaggtaa agattcaaac gggtgagaaa ggccggagac agtcaaatca ccatcaatat   2520
gatattcaac cgttctagct gataaattca tgccggagag ggtagctatt tttgagaggt   2580
ctctacaaag gctatcaggt cattgcctga gagtctggag caaacaagag aatcgatgaa   2640
cggtaatcgt aaaactagca tgtcaatcat atgtaccccg gttgataatc agaaaagccc   2700
caaaaacagg aagattgtat aagcaaatat ttaaattgta aacgttaata ttttgttaaa   2760
attcgcgtta aattttttgtt aaatcagctc attttttaac caataggccg aaatcggcaa   2820
aatcccttat aaatcaaaag aatagaccga gatagggttg agtgttgttc cagtttggaa   2880
caagagtcca ctattaaaga acgtggactc caacgtcaaa gggcgaaaaa ccgtctatca   2940
gggcgatggc ccactacgtg aaccatcacc ctaatcaagt tttttggggt cgaggtgccg   3000
taaatcacta atcggaacc ctaaagggag cccccgattt agagcttgac ggggaaagcc   3060
ggcgaacgtg cgagaaagg aagggaagaa agcgaaagga gcgggcgcta gggcgctggc   3120
aagtgtagcg gtcacgctgc gcgtaaccac cacacccgcc gcgcttaatg cgccgctaca   3180
```

```
gggcgcgtac tatggttgct ttgacgagca cgtataacgt gctttcctcg ttagaatcag    3240
agcgggagct aaacaggagg ccgattaaag ggattttaga caggaacggt acgccagaat    3300
cctgagaagt gtttttataa tcagtgaggc caccgagtaa aagagtctgt ccatcacgca    3360
aattaaccgt tgtcgcaata cttctttgat tagtaataac atcacttgcc tgagtagaag    3420
aactcaaact atcggccttg ctggtaatat ccagaacaat attaccgcca gccattgcaa    3480
caggaaaaac gctcatggaa atacctacat tttgacgctc aatcgtctgg aacttccatt    3540
cgccattcag gctgcgcaac tgttgggaag ggcgatcggt gcgggcctct cgctattac    3600 gccagctgnn nnnngcgcgc tcgctcgctc actgaggccg cccgggcaaa gcccgggcgt    3660
cgggcgacct ttggtcgccc ggcctcagtg agcgagcgag cgcgcagaga gggagtggcc    3720
aactccatca ctaggggttc cttgtagtta atgattaacc cgccatgcta attatctacg    3780
tagccatgtc tagggtcgtt acataactta cggtaaatgg cccgcctggc tgaccgccca    3840 acgaccccg cccattgacg tcaataatga cgtatgttcc catagtaacg ccaatagggac    3900 ctttccattg acgtcaatgg gtggagtatt tacggtaaac tgcccacttg gcagtacatc    3960
aagtgtatca tatgccaagt acgcccccta ttgacgtcaa tgacggtaaa tggcccgcct    4020
ggcattatgc ccagtacatg accttatggg actttcctac ttggcagtac atctacgtat    4080
tagtcatcgc tattaccatg gtgatgcggt tttggcagta catcaatggg cgtggatagc    4140
ggtttgactc acggggattt ccaagtctcc accccattga cgtcaatggg agtttgtttt    4200
ggcaccaaaa tcaacgggac tttccaaaat gtcgtaacaa ctccgcccca ttgacgcaaa    4260
tgggcggtag cgcgtgtacgg tgggaggtct atataagcag agctcgttta gtgaaccgtc    4320
agatcgcctg gagacgccat ccacgctgtt ttgacctcca tagaagacac cgggaccgat    4380
ccagcctccg gactctagag gatccggtac tcgaggaact gaaaaaccag aaagttaact    4440
ggtaagttta gtcttttttgt cttttatttc aggtcccgga tccggtggtg gtgcaaatca    4500
aagaactgct cctcagtgga tgttgccttt acttctaggc ctgtacggaa gtgttacttc    4560
tgctctaaaa gctgcggaat tgtacccgcg gccgcaccat gaagctgctg ccgtcggtgg    4620
tgctgaagct ctttctggct gcagttctct cggcactggt gactggcgag agcctggagc    4680
ggcttcggag agggctagct gctggaacca gcaacccgga ccctcccact gtatccacgg    4740
accagctgct accctagga ggcggccggg accggaaagt ccgtgacttg caagaggcag    4800
atctggacct tttgagagtc actttatcct ccaagccaca agcactggcc acaccaaaca    4860
aggaggagca cgggaaaaga aagaagaaag gcaaggggct agggaagaag agggacccac    4920
agactggaca ggcctattat gtaatactcc tcaacagggg ccgtctggaa gtgcatctct    4980
ccacaggggc acgaacaatg aggaaaattg tcatcagacc agagccgaat ctgtttcatg    5040
atggaagaga acattccgtt catgtagagc gaactagagg catctttaca gttcaagtgg    5100
atgaaaacag aagatacatg caaaacctga cagttgaaca gcctatcgaa gttaaaaagc    5160
ttttcgttgg gggtgctcca cctgaatttc aaccttcccc actcagaaat attcctcctt    5220
ttgaaggctg catatggaat cttgttatta ctctgtccc catggacttt gcaaggcctg    5280
tgtccttcaa aaatgctgac attggtcgct gtgcccatca gaaactccgt gaagatgaag    5340
atggagcagc tccagctgaa atagttatcc agcctgagcc agttcccacc ccagcctttc    5400
ctacgcccac cccagttctg acacatggtc cttgtgctgc agaatcagaa ccagctcttt    5460 tgataggag caagcagttc gggctttcaa gaaacagtca cattgcaatt gcatttgatg    5520
acaccaaagt taaaaaccgt ctcacaattg agttggaagt aagaaccgaa gctgaatccg    5580
```

-continued

```
gcttgctttt ttacatggct cgcatcaatc atgctgattt tgcaacagtt cagctgagaa     5640
atggattgcc ctacttcagc tatgacttgg ggagtgggga cacccacacc atgatcccca     5700
ccaaaatcaa tgatggccag tggcacaaga ttaagataat gagaagtaag caagaaggaa     5760
ttctttatgt agatggggct tccaacagaa ccatcagtcc caaaaaagcc gacatcctgg     5820
atgtcgtggg aatgctgtat gttggtgggt tacccatcaa ctacactacc cgaagaattg     5880
gtccagtgac ctatagcatt gatggctgcg tcaggaatct ccacatggca gaggcccctg     5940
ccgatctgga acaacccacc tccagcttcc atgttgggac atgttttgca aatgctcaga     6000
ggggaacata ttttgacgga accggttttg ccaaagcagt tggtggattc aaagtgggat     6060
tggaccttct tgtagaattt gaattccgca caactacaac gactggagtt cttctgggga     6120
tcagtagtca aaaaatggat ggaatgggta ttgaaatgat tgatgaaaag ttgatgtttc     6180
atgtggacaa tggtgcgggc agattcactg ctgtctatga tgctggggtt ccagggcatt     6240
tgtgtgatgg acaatggcat aaagtcactg ccaacaagat caaacaccgc attgagctca     6300
cagtcgatgg gaaccaggtg gaagcccaaa gcccaaaccc agcatctaca tcagctgaca     6360
caaatgaccc tgtgtttgtt ggaggcttcc cagatgacct caagcagttt ggcctaacaa     6420
ccagtattcc gttccgaggt tgcatcagat ccctgaagct caccaaaggc acagcaagcc     6480
actggaggtt aattttgcca aggccctgga actgaactag tgcggccgcg gggatccaga     6540
catgataaga tacattgatg agtttggaca aaccacaact agaatgcagt gaaaaaaatg     6600
ctttatttgt gaaatttgtg atgctattgc tttatttgta accattataa gctgcaataa     6660
acaagttaac aacaacaatt gcattcattt tatgtttcag gttcaggggg aggtgtggga     6720
ggttttttcg gatcctctag agtcgaccac atggctacgt agataattag catggcgggt     6780
taatcattaa ctacaaggaa cccctagtga tggagttggc cactccctct ctgcgcgctc     6840
gctcgctcac tgaggccggg cgaccaaagg tcgcccgacg cccgggcttt gcccgggcgg     6900
cctcagtgag cgagcgagcg cgcnnnnnnc agctgcatta atgaatcggc caacgcgcgg     6960
ggagaggcgg tttgcgtatt gggc                                           6984
```

```
<210> SEQ ID NO 7
<211> LENGTH: 2043
<212> TYPE: DNA
<213> ORGANISM: Artificial Sequence
<220> FEATURE:
<223> OTHER INFORMATION: Synthetic Polynucleotide

<400> SEQUENCE: 7
atgaagctgc tgccgtcggt ggtgctgaag ctctttctgg ctgcagttct ctcggcactg      60
gtgactggcg agagcctgga gcggcttcgg agagggctag ctgctggaac cagcaacccg     120
gaccctccca ctgtatccac ggaccagctg ctacccctag gaggcggccg ggaccggaaa     180
gtccgtgact tgcaagaggc agatctggac cttttgagag tcactttatc ctccaagcca     240
caagcactgg ccacaccaaa caaggaggag cacgggaaaa gaaagaagaa aggcaagggg     300
ctagggaaga gagggacccc atgtcttcgg aaatacaagg acttctgcat ccatggagaa     360
tgcaaatatg tgaaggagct ccgggctccc tcctgcatct gccacccggg ttaccatgga     420
gagaggtgtc atgggctgag cctcccacag actggacagg cctattatgt aatactcctc     480 aacagggcc gtctggaagt gcatctctcc acagggcac gaacaatgag gaaaattgtc     540
atcagaccag agccgaatct gtttcatgat ggaagagaac attccgttca tgtagagcga     600
```

-continued

```
actagaggca tctttacagt tcaagtggat gaaaacagaa gatacatgca aaacctgaca      660
gttgaacagc ctatcgaagt taaaaagctt ttcgttgggg gtgctccacc tgaatttcaa      720
ccttccccac tcagaaatat tcctcctttt gaaggctgca tatggaatct tgttattaac      780
tctgtcccca tggactttgc aaggcctgtg tccttcaaaa atgctgacat tggtcgctgt      840
gcccatcaga aactccgtga agatgaagat ggagcagctc cagctgaaat agttatccag      900
cctgagccag ttcccacccc agcctttcct acgcccaccc cagttctgac acatggtcct      960
tgtgctgcag aatcagaacc agctcttttg atagggagca agcagttcgg gctttcaaga     1020
aacagtcaca ttgcaattgc atttgatgac accaaagtta aaaaccgtct cacaattgag     1080
ttggaagtaa gaaccgaagc tgaatccggc ttgcttttt acatggctcg catcaatcat     1140
gctgattttg caacagttca gctgagaaat ggattgccct acttcagcta tgacttgggg     1200
agtggggaca cccacaccat gatccccacc aaaatcaatg atggccagtg gcacaagatt     1260
aagataatga gaagtaagca agaaggaatt ctttatgtag atggggcttc caacagaacc     1320
atcagtccca aaaagccga catcctggat gtcgtgggaa tgctgtatgt tggtgggtta     1380
cccatcaact acactacccg aagaattggt ccagtgacct atagcattga tggctgcgtc     1440
aggaatctcc acatggcaga ggcccctgcc gatctggaac aacccacctc cagcttccat     1500
gttgggacat gttttgcaaa tgctcagagg ggaacatatt ttgacggaac cggttttgcc     1560
aaagcagttg gtggattcaa agtgggattg gaccttcttg tagaatttga attccgcaca     1620
actacaacga ctggagttct tctggggatc agtagtcaaa aaatggatgg aatgggtatt     1680
gaaatgattg atgaaaagtt gatgtttcat gtggacaatg gtgcgggcag attcactgct     1740
gtctatgatg ctggggttcc agggcatttg tgtgatggac aatggcataa agtcactgcc     1800
aacaagatca aacaccgcat tgagctcaca gtcgatggga accaggtgga gcccaaagc     1860 ccaaacccag catctacatc agctgacaca aatgaccctg tgtttgttgg aggcttccca     1920
gatgacctca gcagtttgg cctaacaacc agtattccgt tccgaggttg catcagatcc     1980
ctgaagctca ccaaaggcac agcaagccac tggaggttaa ttttgccaag gccctggaac     2040
tga                                                                    2043
```

```
<210> SEQ ID NO 8
<211> LENGTH: 7091
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: rAAV
<220> FEATURE:
<221> NAME/KEY: misc_feature
<222> LOCATION: (3590)..(3595)
<223> OTHER INFORMATION: n is a, c, g, t or u
<220> FEATURE:
<221> NAME/KEY: misc_feature
<222> LOCATION: (7031)..(7036)
<223> OTHER INFORMATION: n is a, c, g, t or u

<400> SEQUENCE: 8
```

```
gctcttccgc ttggtcgctc actgactcgc tgcgctcggt cgttcggctg cggcgagcgg       60
tatcagctca ctcaaacccg gtaatacggt tatccacaga atcaggggat aacgcaggaa      120
agaacatgtg agcaaaaggc cagcaaaagg ccaggaaccg taaaaaggcc gcgttgctgg      180
cgtttttcca taggctccgc cccctgacg agcatcacaa aaatcgacgc tcaagtcaga      240
```

-continued

```
ggtggcgaaa cccgacagga ctataaagat accaggcgtt tccccctgga agctccctcg       300
tgcgctctcc tgttccgacc ctgccgctta ccggatacct gtccgccttt ctcccttcgg       360
gaagcgtggc gctttctcat agctcacgct gtaggtatct cagttcggtg taggtcgttc       420
gctccaagct gggctgtgtg cacgaacccc ccgttcagcc cgaccgctgc gccttatccg       480
gtaactatcg tcttgagtcc aacccggtaa gacacgactt atcgccactg gcagcagcca       540
ctggtaacag gattagcaga gcgaggtatg tacgcggtgc tacagagttc ttgaagtggt       600
ggcctaacta cggctacact agaaggacag tatttggtat ctgcgctctg ctgaagccag       660
ttaccttcgg aaaaagagtt ggtagctctt gatccggcaa acaaaccacc gctggtagcg       720
gtggtttttt tgtttgcaag cagcagatta cgcgcagaaa aaaaggatct caagaagatc       780
ctttgatctt ttctacgggg tctgacgctc agtggaacga aaactcacgt taagggattt       840
tggtcatgag attatcaaaa aggatcttca cctagatcct tttaaattaa aaatgaagtt       900
ttaaatcaat ctaaagtata tatgagtaaa cttggtctga cagttaccaa tgcttaatca       960
gtgaggcacc tatctcagcg atctgtctat ttcgttcatc catagttgcc tgactccccg      1020
tcgtgtagat aactacgata cgggagggct taccatctgg ccccagtgct gcaatgatac      1080
cgcgagaccc acgctcaccg gctccagatt tatcagcaat aaaccagcca gccggaaggg      1140
ccgagcgcag aagtggtcct gcaactttat ccgcctccat ccagtctatt aattgttgcc      1200
gggaagctag agtaagtagt tcgccagtta atagtttgcg caacgttgtt gccattgcta      1260
caggcatcgt ggtgtcacgc tcgtcgtttg gtatggcttc attcagctcc ggttcccaac      1320
gatcaaggcg agtacatga tccccatgt tgtgcaaaaa agcggttagc tccttcggtc      1380
ctccgatcgt tgtcagaagt aagttggccg cagtgttatc actcatggtt atggcagcac      1440
tgcataattc tcttactgtc atgccatccg taagatgctt ttctgtgact ggtgagtact      1500
caaccaagtc attctgagaa tagtgtatgc ggcgaccgag ttgctcttgc ccggcgtcaa      1560
tacgggataa taccgcgcca catagcagaa ctttaaaagt gctcatcatt ggaaaacgtt      1620
cttcggggcg aaaactctca aggatcttac cgctgttgag atccagttcg atgtaaccca      1680
ctcgtgcacc caactgatct tcagcatctt ttactttcac cagcgtttct gggtgagcaa      1740
aaacaggaag gcaaaatgcc gcaaaaaagg gaataagggc gacacggaaa tgttgaatac      1800
tcatactctt cctttttcaa tattattgaa gcatttatca gggttattgt ctcatgagcg      1860
gatacatatt tgaatgtatt tagaaaaata aacaaatagg ggttccgcgc acatttcccc      1920
gaaaagtgcc acctgacgtc taagaaacca ttattatcat gacattaacc tataaaaata      1980
ggcgtatcac gaggcccttt cgtctcgcgc gtttcggtga tgacggtgaa aacctctgac      2040
acatgcagct cccggagacg gtcacagctt gtctgtaagc ggatgccggg agcagacaag      2100
cccgtcaggg cgcgtcagcg ggtgttggcg ggtgtcgggg ctggcttaac tatgcggcat      2160
cagagcagat tgtactgaga gtgcaccata tgcggtgtga ataccgcac agatgcgtaa      2220 ggagaaaata ccgcatcagg aacttccaac atccaataaa tcatacaggc aaggcaaaga      2280
attagcaaaa ttaagcaata aagcctcaga gcataaagct aaatcggttg taccaaaaac      2340
attatgaccc tgtaatactt ttgcgggaga gcctttatt tcaacgcaag gataaaaatt      2400
tttagaaccc tcatatattt taaatgcaat gcctgagtaa tgtgtaggta agattcaaa      2460 cgggtgagaa aggccggaga cagtcaaatc accatcaata tgatattcaa ccgttctagc      2520
tgataaattc atgccggaga gggtagctat ttttgagagg tctctacaaa ggctatcagg      2580
tcattgcctg agagtctgga gcaaacaaga gaatcgatga acggtaatcg taaaactagc      2640
```

```
atgtcaatca tatgtacccc ggttgataat cagaaaagcc ccaaaaacag gaagattgta      2700
taagcaaata tttaaattgt aaacgttaat attttgttaa aattcgcgtt aaatttttgt      2760
taaatcagct cattttttaa ccaataggcc gaaatcggca aaatccctta taaatcaaaa      2820
gaatagaccg agatagggtt gagtgttgtt ccagtttgga acaagagtcc actattaaag      2880
aacgtggact ccaacgtcaa agggcgaaaa accgtctatc agggcgatgg cccactacgt      2940
gaaccatcac cctaatcaag ttttttgggg tcgaggtgcc gtaaatcact aaatcggaac      3000
cctaaaggga gcccccgatt tagagcttga cggggaaagc cggcgaacgt ggcgagaaag      3060
gaagggaaga aagcgaaagg agcgggcgct agggcgctgg caagtgtagc ggtcacgctg      3120
cgcgtaacca ccacacccgc cgcgcttaat gcgccgctac agggcgcgta ctatggttgc      3180
tttgacgagc acgtataacg tgctttcctc gttagaatca gagcgggagc taaacaggag      3240
gccgattaaa gggattttag acaggaacgg tacgccagaa tcctgagaag tgttttttata     3300 atcagtgagg ccaccgagta aaagagtctg tccatcacgc aaattaaccg ttgtcgcaat      3360
acttctttga ttagtaataa catcacttgc ctgagtagaa gaactcaaac tatcggcctt      3420
gctggtaata tccagaacaa tattaccgcc agccattgca acaggaaaaa cgctcatgga      3480
aatacctaca ttttgacgct caatcgtctg gaacttccat tcgccattca ggctgcgcaa      3540
ctgttgggaa gggcgatcgg tgcgggcctc ttcgctatta cgccagctgn nnnnngcgcg      3600
ctcgctcgct cactgaggcc gcccgggcaa agcccgggcg tcgggcgacc tttggtcgcc      3660
cggcctcagt gagcgagcga gcgcgcagag agggagtggc caactccatc actaggggtt      3720
ccttgtagtt aatgattaac cgccatgct aattatctac gtagccatgt ctagggtcgt       3780
tacataactt acggtaaatg gcccgcctgg ctgaccgcc aacgacccc gcccattgac         3840 gtcaataatg acgtatgttc ccatagtaac gccaataggg actttccatt gacgtcaatg      3900
ggtggagtat ttacggtaaa ctgcccactt ggcagtacat caagtgtatc atatgccaag      3960 tacgcccct attgacgtca atgacggtaa atggcccgcc tggcattatg cccagtacat        4020
gaccttatgg gactttccta cttggcagta catctacgta ttagtcatcg ctattaccat      4080
ggtgatgcgg ttttggcagt acatcaatgg gcgtggatag cggtttgact cacggggatt      4140
tccaagtctc cacccattg acgtcaatgg gagtttgttt tggcaccaaa atcaacggga       4200
ctttccaaaa tgtcgtaaca actccgcccc attgacgcaa atgggcggta ggcgtgtacg      4260
gtgggaggtc tatataagca gagctcgttt agtgaaccgt cagatcgcct ggagacgcca      4320
tccacgctgt tttgacctcc atagaagaca ccgggaccga tccagcctcc ggactctaga      4380
ggatccggta ctcgaggaac tgaaaaacca gaaagttaac tggtaagttt agtctttttg      4440
tcttttattt caggtcccgg atccggtggt ggtgcaaatc aaagaactgc tcctcagtgg      4500
atgttgcctt tacttctagg cctgtacgga agtgttactt ctgctctaaa agctgcggaa      4560
ttgtacccgc ggccgcacca tgaagctgct gccgtcggtg gtgctgaagc tctttctggc      4620
tgcagttctc tcggcactgg tgactggcga gagcctggag cggcttcgga gagggctagc      4680
tgctggaacc agcaacccgg accctcccac tgtatccacg gaccagctgc tacccctagg      4740
aggcggccgg gaccggaaag tccgtgactt gcaagaggca gatctggacc ttttgagagt      4800
cactttatcc tccaagccac aagcactggc cacaccaaac aaggaggagc acgggaaaag      4860
aaagaagaaa ggcaaggggc tagggaagaa gagggaccca tgtcttcgga aatacaagga     4920
cttctgcatc catggagaat gcaaatatgt gaaggagctc cgggctccct cctgcatctg      4980
```

-continued

```
ccacccgggt taccatggag agaggtgtca tgggctgagc ctcccacaga ctggacaggc      5040
ctattatgta atactcctca acaggggccg tctggaagtg catctctcca caggggcacg      5100
aacaatgagg aaaattgtca tcagaccaga gccgaatctg tttcatgatg gaagagaaca      5160
ttccgttcat gtagagcgaa ctagaggcat ctttacagtt caagtggatg aaaacagaag      5220
atacatgcaa aacctgacag ttgaacagcc tatcgaagtt aaaaagcttt tcgttggggg      5280
tgctccacct gaatttcaac cttccccact cagaaatatt cctccttttg aaggctgcat      5340
atggaatctt gttattaact ctgtccccat ggactttgca aggcctgtgt ccttcaaaaa      5400
tgctgacatt ggtcgctgtg cccatcagaa actccgtgaa gatgaagatg gagcagctcc      5460
agctgaaata gttatccagc ctgagccagt tcccacccca gcctttccta cgcccacccc      5520
agttctgaca catggtcctt gtgctgcaga atcagaacca gctcttttga tagggagcaa      5580
gcagttcggg ctttcaagaa acagtcacat tgcaattgca tttgatgaca ccaaagttaa      5640
aaaccgtctc acaattgagt tggaagtaag aaccgaagct gaatccggct tgctttttta      5700
catggctcgc atcaatcatg ctgattttgc aacagttcag ctgagaaatg gattgcccta      5760
cttcagctat gacttgggga gtggggacac ccacaccatg atccccacca aaatcaatga      5820
tggccagtgg cacaagatta agataatgag aagtaagcaa gaaggaattc tttatgtaga      5880
tggggcttcc aacagaacca tcagtcccaa aaaagccgac atcctggatg tcgtgggaat      5940
gctgtatgtt ggtgggttac ccatcaacta cactacccga agaattggtc cagtgaccta      6000
tagcattgat ggctgcgtca ggaatctcca catggcagag gcccctgccg atctggaaca      6060
acccacctcc agcttccatg ttgggacatg ttttgcaaat gctcagaggg gaacatattt      6120
tgacggaacc ggttttgcca aagcagttgg tggattcaaa gtgggattgg accttcttgt      6180
agaatttgaa ttccgcacaa ctacaacgac tggagttctt ctggggatca gtagtcaaaa      6240
aatggatgga atgggtattg aaatgattga tgaaaagttg atgtttcatg tggacaatgg      6300
tgcgggcaga ttcactgctg tctatgatgc tggggttcca gggcatttgt gtgatggaca      6360
atggcataaa gtcactgcca acaagatcaa acaccgcatt gagctcacag tcgatgggaa      6420
ccaggtggaa gcccaaagcc caaacccagc atctacatca gctgacacaa atgaccctgt      6480
gtttgttgga ggcttcccag atgacctcaa gcagtttggc ctaacaacca gtattccgtt      6540
ccgaggttgc atcagatccc tgaagctcac caaaggcaca gcaagccact ggaggttaat      6600
tttgccaagg ccctggaact gaactagtgc ggccgcgggg atccagacat gataagatac      6660
attgatgagt ttggacaaac cacaactaga atgcagtgaa aaaaatgctt tatttgtgaa      6720
atttgtgatg ctattgcttt atttgtaacc attataagct gcaataaaca agttaacaac      6780
aacaattgca ttcattttat gtttcaggtt caggggggagg tgtgggaggt tttttcggat      6840
cctctagagt cgaccacatg ctacgtagaa taattagcat ggcgggttaa tcattaacta      6900
caaggaaccc ctagtgatgg agttggccac tccctctctg cgcgctcgct cgctcactga      6960
ggccgggcga ccaaaggtcg cccgacgccc gggctttgcc cggcggccct cagtgagcga      7020
gcgagcgcgc nnnnnncagc tgcattaatg aatcggccaa cgcgcgggga gaggcggttt      7080
gcgtattggg c                                                          7091
```

<210> SEQ ID NO 9
<211> LENGTH: 1347
<212> TYPE: DNA
<213> ORGANISM: Artificial Sequence
<220> FEATURE:
<223> OTHER INFORMATION: Synthetic Polynucleotide -continued

```
<400> SEQUENCE: 9
atgaagctgc tgccgtcggt ggtgctgaag ctctttctgg ctgcagttct ctcggcactg      60
gtgactggcg agagcctgga gcggcttcgg agagggctag ctgctggaac cagcaacccg     120
gaccctccca ctgtatccac ggaccagctg ctacccctag gaggcggccg ggaccggaaa     180
gtccgtgact tgcaagaggc agatctggac cttttgagag tcactttatc ctccaagcca     240
caagcactgg ccacaccaaa caaggaggag cacgggaaaa gaaagaagaa aggcaagggg     300
ctagggaaga agagggaccc acagatccat gctacaccca cacctgtcac tgccattggg     360
cccccaacca cggctatcca ggagccccca tccaggatcg tgccaacccc cacatctcca     420
gccattgctc ctccaacaga gaccatggct cctccagtca gggatcctgt tcctgggaaa     480
cccacggtca ccatccggac tcgaggcgcc attattcaaa ccccaacccct aggccccatc    540 cagcctactc gggtgtcaga agctggcacc acagttcctg gccagattcg cccaacgatg     600
accattcctg ctatgtggaa gcctactgca gttgctaccc ctcccacaac caccaccaag     660
aagccacgag tatccacacc aaaaccagca acgccttcaa ctgactccac caccaccacg     720
actcgcaggc caaccaagaa accacggaca ccccggccag tgccccgggt caccaccaaa     780
gtttccatca ccagattgga aactgcctca ccgcctactc gtattcgcac caccaccagt     840
ggagtgcccc gtggcggaga acccaaccag cgcccagagc tcaagaacca tattgacagg     900
gtagatgcct gggttggcac ctactttgag gtgaagatcc cgtcagacac tttctatgac     960
catgaggaca ccaccactga caagctgaag ctgaccctga aactgcggga gcagcagctg    1020
gtgggcgaga gtcctgggt acagttcaac agcaacagcc agctcatgta tggccttccc     1080
gacagcagcc acgtgggcaa acacgagtat ttcatgcatg ccacagacaa ggggggcctg    1140
tcggctgtgg atgccttcga gatccacgtc cacaggcgcc cccaagggga tagggctcct    1200
gcaaggttca aggccaagtt tgtgggtgac ccggcactgg tgttgaatga catccacaag    1260
aagattgcct tggtaaagaa actggccttc gcctttggag accgaaactg tagcaccatc    1320
accctgcaga atatcacccg gggctaa                                       1347

<210> SEQ ID NO 10
<211> LENGTH: 6395
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: rAAV
<220> FEATURE:
<221> NAME/KEY: misc_feature
<222> LOCATION: (3590)..(3595)
<223> OTHER INFORMATION: n is a, c, g, t or u
<220> FEATURE:
<221> NAME/KEY: misc_feature
<222> LOCATION: (6335)..(6340)
<223> OTHER INFORMATION: n is a, c, g, t or u

<400> SEQUENCE: 10
gctcttccgc ttggtcgctc actgactcgc tgcgctcggt cgttcggctg cggcgagcgg      60
tatcagctca ctcaaacccg gtaatacggt tatccacaga atcaggggat aacgcaggaa     120
agaacatgtg agcaaaaggc cagcaaaagg ccaggaaccg taaaaaggcc gcgttgctgg     180
cgtttttcca taggctccgc cccccgacg agcatcacaa aaatcgacgc tcaagtcaga     240
ggtggcgaaa cccgacagga ctataaagat accaggcgtt cccccctgga agctccctcg     300
```

-continued

```
tgcgctctcc tgttccgacc ctgccgctta ccggatacct gtccgccttt ctcccttcgg      360
gaagcgtggc gctttctcat agctcacgct gtaggtatct cagttcggtg taggtcgttc      420
gctccaagct gggctgtgtg cacgaacccc ccgttcagcc cgaccgctgc gccttatccg      480
gtaactatcg tcttgagtcc aacccggtaa gacacgactt atcgccactg gcagcagcca      540
ctggtaacag gattagcaga gcgaggtatg tacgcggtgc tacagagttc ttgaagtggt      600
ggcctaacta cggctacact agaaggacag tatttggtat ctgcgctctg ctgaagccag      660
ttaccttcgg aaaaagagtt ggtagctctt gatccggcaa acaaaccacc gctggtagcg      720
gtggtttttt tgtttgcaag cagcagatta cgcgcagaaa aaaaggatct caagaagatc      780
ctttgatctt ttctacgggg tctgacgctc agtggaacga aaactcacgt taagggattt      840
tggtcatgag attatcaaaa aggatcttca cctagatcct tttaaattaa aaatgaagtt      900
ttaaatcaat ctaaagtata tatgagtaaa cttggtctga cagttaccaa tgcttaatca      960
gtgaggcacc tatctcagcg atctgtctat ttcgttcatc catagttgcc tgactccccg     1020
tcgtgtagat aactacgata cgggagggct taccatctgg ccccagtgct gcaatgatac     1080
cgcgagaccc acgctcaccg gctccagatt tatcagcaat aaaccagcca gccggaaggg     1140
ccgagcgcag aagtggtcct gcaactttat ccgcctccat ccagtctatt aattgttgcc     1200
gggaagctag agtaagtagt tcgccagtta atagtttgcg caacgttgtt gccattgcta     1260
caggcatcgt ggtgtcacgc tcgtcgtttg gtatggcttc attcagctcc ggttcccaac     1320
gatcaaggcg agttacatga tcccccatgt tgtgcaaaaa agcggttagc tccttcggtc     1380
ctccgatcgt tgtcagaagt aagttggccg cagtgttatc actcatggtt atggcagcac     1440
tgcataattc tcttactgtc atgccatccg taagatgctt ttctgtgact ggtgagtact     1500
caaccaagtc attctgagaa tagtgtatgc ggcgaccgag ttgctcttgc ccggcgtcaa     1560
tacgggataa taccgcgcca catagcagaa ctttaaaagt gctcatcatt ggaaaacgtt     1620
cttcggggcg aaaactctca aggatcttac cgctgttgag atccagttcg atgtaaccca     1680
ctcgtgcacc caactgatct tcagcatctt ttactttcac cagcgtttct gggtgagcaa     1740
aaacaggaag gcaaaatgcc gcaaaaaagg gaataagggc gacacggaaa tgttgaatac     1800
tcatactctt cctttttcaa tattattgaa gcatttatca gggttattgt ctcatgagcg     1860
gatacatatt tgaatgtatt tagaaaaata aacaaatagg ggttccgcgc acatttcccc     1920
gaaaagtgcc acctgacgtc taagaaacca ttattatcat gacattaacc tataaaaata     1980
ggcgtatcac gaggcccttt cgtctcgcgc gtttcggtga tgacggtgaa aacctctgac     2040
acatgcagct cccggagacg gtcacagctt gtctgtaagc ggatgccggg agcagacaag     2100
cccgtcaggc gcgtcagcg ggtgttggcg ggtgtcgggg ctggcttaac tatgcggcat     2160
cagagcagat tgtactgaga gtgcaccata tgcggtgtga ataccgcac agatgcgtaa     2220 ggagaaaata ccgcatcagg aacttccaac atccaataaa tcatacaggc aaggcaaaga     2280
attagcaaaa ttaagcaata aagcctcaga gcataaagct aaatcggttg taccaaaaac     2340
attatgaccc tgtaatactt ttgcgggaga agcctttatt tcaacgcaag gataaaaatt     2400
tttagaaccc tcatatattt taaatgcaat gcctgagtaa tgtgtaggta agattcaaa     2460 cgggtgagaa aggccggaga cagtcaaatc accatcaata tgatattcaa ccgttctagc     2520
tgataaattc atgccggaga gggtagctat ttttgagagg tctctacaaa ggctatcagg     2580
tcattgcctg agagtctgga gcaaacaaga gaatcgatga acggtaatcg taaaactagc     2640
```

-continued

```
atgtcaatca tatgtacccc ggttgataat cagaaaagcc ccaaaaacag gaagattgta   2700
taagcaaata tttaaattgt aaacgttaat attttgttaa aattcgcgtt aaattttgt    2760 taaatcagct cattttttaa ccaataggcc gaaatcggca aaatccctta taaatcaaaa   2820
gaatagaccg agatagggtt gagtgttgtt ccagtttgga acaagagtcc actattaaag   2880
aacgtggact ccaacgtcaa agggcgaaaa accgtctatc agggcgatgg cccactacgt   2940
gaaccatcac cctaatcaag tttttggg tcgaggtgcc gtaaatcact aaatcggaac     3000
cctaaaggga gcccccgatt tagagcttga cggggaaagc cggcgaacgt ggcgagaaag    3060
gaagggaaga aagcgaaagg agcgggcgct agggcgctgg caagtgtagc ggtcacgctg    3120
cgcgtaacca ccacacccgc cgcgcttaat gcgccgctac agggcgcgta ctatggttgc    3180
tttgacgagc acgtataacg tgctttcctc gttagaatca gagcgggagc taaacaggag    3240
gccgattaaa gggattttag acaggaacgg tacgccagaa tcctgagaag tgttttttata   3300 atcagtgagg ccaccgagta aaagagtctg tccatcacgc aaattaaccg ttgtcgcaat    3360
acttctttga ttagtaataa catcacttgc ctgagtagaa gaactcaaac tatcggcctt    3420
gctggtaata tccagaacaa tattaccgcc agccattgca acaggaaaaa cgctcatgga    3480
aatacctaca ttttgacgct caatcgtctg gaacttccat tcgccattca ggctgcgcaa    3540
ctgttgggaa gggcgatcgg tgcgggcctc ttcgctatta cgccagctgn nnnnngcgcg    3600
ctcgctcgct cactgaggcc gcccgggcaa agcccgggcg tcgggcgacc tttggtcgcc    3660
cggcctcagt gagcgagcga gcgcgcagag agggagtggc caactccatc actaggggtt    3720
ccttgtagtt aatgattaac ccgccatgct aattatctac gtagccatgt ctagggtcgt    3780
tacataactt acggtaaatg gcccgcctgg ctgaccgccc aacgaccccc gcccattgac    3840
gtcaataatg acgtatgttc ccatagtaac gccaataggg actttccatt gacgtcaatg    3900
ggtggagtat ttacggtaaa ctgcccactt ggcagtacat caagtgtatc atatgccaag    3960
tacgccccct attgacgtca atgacggtaa atggcccgcc tggcattatg cccagtacat    4020
gaccttatgg gactttccta cttggcagta catctacgta ttagtcatcg ctattaccat    4080
ggtgatgcgg ttttggcagt acatcaatgg gcgtggatag cggtttgact cacggggatt    4140
tccaagtctc caccccattg acgtcaatgg gagtttgttt tggcaccaaa atcaacggga    4200
ctttccaaaa tgtcgtaaca actccgcccc attgacgcaa atgggcggta ggcgtgtacg    4260
gtgggaggtc tatataagca gagctcgttt agtgaaccgt cagatcgcct ggagacgcca    4320
tccacgctgt tttgacctcc atagaagaca ccgggaccga tccagcctcc ggactctaga    4380
ggatccggta ctcgaggaac tgaaaaacca gaaagttaac tggtaagttt agtctttttg    4440
tcttttattt caggtcccgg atccggtggt ggtgcaaatc aaagaactgc tcctcagtgg    4500
atgttgcctt tacttctagg cctgtacgga agtgttactt ctgctctaaa agctgcggaa    4560
ttgtacccgc ggccgcacca tgaagctgct gccgtcggtg gtgctgaagc tcttctggc     4620 tgcagttctc tcggcactgg tgactggcga gagcctggag cggcttcgga gagggctagc    4680
tgctggaacc agcaacccgg accctccac tgtatccacg gaccagctgc tacccctagg     4740
aggcggccgg gaccggaaag tccgtgactt gcaagaggca gatctggacc ttttgagagt    4800
cactttatcc tccaagccac aagcactggc cacaccaaac aaggaggagc acgggaaaag    4860
aaagaagaaa ggcaagggc tagggaagaa gagggaccca cagatccatg ctacacccac      4920
acctgtcact gccattgggc ccccaaccac ggctatccag gagcccccat ccaggatcgt    4980
gccaaccccc acatctccag ccattgctcc tccaacagag accatggctc ctccagtcag    5040
```

```
ggatcctgtt cctgggaaac ccacggtcac catccggact cgaggcgcca ttattcaaac    5100
cccaacccta ggccccatcc agcctactcg ggtgtcagaa gctggcacca cagttcctgg    5160
ccagattcgc ccaacgatga ccattcctgg ctatgtggag cctactgcag ttgctacccc    5220
tcccacaacc accaccaaga agccacgagt atccacacca aaaccagcaa cgccttcaac    5280
tgactccacc accaccacga ctcgcaggcc aaccagaaa ccacggacac cccggccagt    5340
gccccgggtc accaccaaag tttccatcac cagattggaa actgcctcac cgcctactcg    5400
tattcgcacc accaccagtg gagtgccccg tggcggagaa cccaaccagc gcccagagct    5460
caagaaccat attgacaggg tagatgcctg ggttggcacc tactttgagg tgaagatccc    5520
gtcagacact ttctatgacc atgaggacac caccactgac aagctgaagc tgaccctgaa    5580
actgcgggag cagcagctgg tgggcgagaa gtcctgggta cagttcaaca gcaacagcca    5640
gctcatgtat ggccttcccg acagcagcca cgtgggcaaa cacgagtatt tcatgcatgc    5700
cacagacaag gggggcctgt cggctgtgga tgccttcgag atccacgtcc acaggcgccc    5760
ccaaggggat agggctcctg caaggttcaa ggccaagttt gtgggtgacc cggcactggt    5820
gttgaatgac atccacaaga agattgcctt ggtaaagaaa ctggccttcg cctttggaga    5880
ccgaaactgt agcaccatca ccctgcagaa tatcacccgg ggctaaacta gtgcggccgc    5940
ggggatccag acatgataag atacattgat gagtttggac aaaccacaac tagaatgcag    6000
tgaaaaaaat gctttatttg tgaaatttgt gatgctattg ctttatttgt aaccattata    6060
agctgcaata aacaagttaa caacaacaat tgcattcatt ttatgtttca ggttcagggg    6120
gaggtgtggg aggttttttc ggatcctcta gagtcgacca catggctacg tagataatta    6180
gcatggcggg ttaatcatta actacaagga cccctagtg atggagttgg ccactccctc     6240
tctgcgcgct cgctcgctca ctgaggccgg gcgaccaaag gtcgcccgac gcccgggctt    6300 tgccgggcg gcctcagtga gcgagcgagc gcgcnnnnn cagctgcatt aatgaatcgg    6360
ccaacgcgcg gggagaggcg gtttgcgtat tgggc                              6395
```

```
<210> SEQ ID NO 11
<211> LENGTH: 1473
<212> TYPE: DNA
<213> ORGANISM: Artificial Sequence
<220> FEATURE:
<223> OTHER INFORMATION: Synthetic Polynucleotide

<400> SEQUENCE: 11
atgaagctgc tgccgtcggt ggtgctgaag ctctttctgg ctgcagttct ctcggcactg      60
gtgactggcg agagcctgga gcggcttcgg agagggctag ctgctggaac cagcaacccg     120
gaccctccca ctgtatccac ggaccagctg ctacccctag gaggcggccg ggaccggaaa     180
gtccgtgact tgcaagaggc agatctggac ctttttgagag tcactttatc ctccaagcca     240
caagcactgg cccacccaaa caaggaggag cacgggaaaa gaaagaagaa aggcaagggg     300
ctagggaaga gagggacccc atgtcttcgg aaatacaagg acttctgcat ccatggagaa     360
tgcaaatatg tgaaggagct ccgggctccc tcctgcatct gccacccggg ttaccatgga     420
gagaggtgtc atgggctgag cctcccacag atccatgcta cacccacacc tgtcactgcc     480
attgggcccc caaccacggc tatccaggag cccccatcca ggatcgtgcc aaccccccaca     540 tctccagcca ttgctcctcc aacagagacc atggctcctc cagtcaggga tcctgttcct     600
gggaaaccca cggtcaccat ccggactcga ggcgccatta ttcaaacccc aaccctaggc     660
```

-continued

```
cccatccagc ctactcgggt gtcagaagct ggcaccacag ttcctggcca gattcgccca          720
acgatgacca ttcctggcta tgtggagcct actgcagttg ctacccctcc cacaaccacc          780
accaagaagc cacgagtatc cacaccaaaa ccagcaacgc cttcaactga ctccaccacc          840
accacgactc gcaggccaac caagaaacca cggacacccc ggccagtgcc ccgggtcacc          900
accaaagttt ccatcaccag attggaaact gcctcaccgc ctactcgtat tcgcaccacc          960
accagtggag tgccccgtgg cggagaaccc aaccagcgcc cagagctcaa gaaccatatt         1020
gacagggtag atgcctgggt tggcacctac tttgaggtga agatcccgtc agacactttc         1080
tatgaccatg aggacaccac cactgacaag ctgaagctga ccctgaaact gcgggagcag         1140
cagctggtgg gcgagaagtc ctgggtacag ttcaacagca cagccagct catgtatggc          1200 cttcccgaca gcagccacgt gggcaaaac gagtatttca tgcatgccac agacaagggg          1260
ggcctgtcgg ctgtggatgc cttcgagatc cacgtccaca ggcgcccca aggggatagg          1320 gctcctgcaa ggttcaaggc caagtttgtg ggtgacccgg cactggtgtt gaatgacatc         1380
cacaagaaga ttgccttggt aaagaaactg gccttcgcct ttggagaccg aaactgtagc         1440
accatcaccc tgcagaatat cacccgggggc taa                                    1473
```

```
<210> SEQ ID NO 12
<211> LENGTH: 6521
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: rAAV
<220> FEATURE:
<221> NAME/KEY: misc_feature
<222> LOCATION: (3590)..(3595)
<223> OTHER INFORMATION: n is a, c, g, t or u
<220> FEATURE:
<221> NAME/KEY: misc_feature
<222> LOCATION: (6461)..(6466)
<223> OTHER INFORMATION: n is a, c, g, t or u

<400> SEQUENCE: 12
```

```
gctcttccgc ttggtcgctc actgactcgc tgcgctcggt cgttcggctg cggcgagcgg           60
tatcagctca ctcaaacccg gtaatacggt tatccacaga atcaggggat aacgcaggaa          120
agaacatgtg agcaaaaggc cagcaaaagg ccaggaaccg taaaaaggcc gcgttgctgg          180
cgtttttcca taggctccgc cccccctgacg agcatcacaa aaatcgacgc tcaagtcaga         240
ggtggcgaaa cccgacagga ctataaagat accaggcgtt ccccctggaa gctccctcg          300 tgcgctctcc tgttccgacc ctgccgctta ccggatacct gtccgccttt ctcccttcgg          360
gaagcgtggc gctttctcat agctcacgct gtaggtatc cagttcggtg taggtcgttc          420
gctccaagct gggctgtgtg cacgaacccc ccgttcagcc cgaccgctgc gccttatccg          480
gtaactatcg tcttgagtcc aacccggtaa gacacgactt atcgccactg gcagcagcca          540
ctggtaacag gattagcaga gcgaggtatg tacgcggtgc tacagagttc ttgaagtggt          600
ggcctaacta cggctacact agaaggacag tatttggtat ctgcgctctg ctgaagccag          660
ttaccttcgg aaaaagagtt ggtagctctt gatccggcaa acaaaccacc gctggtagcg          720
gtggtttttt tgtttgcaag cagcagatta cgcgcagaaa aaaggatct caagaagatc          780 ctttgatctt ttctacgggg tctgacgctc agtggaacga aaactcacgt taagggattt          840
tggtcatgag attatcaaaa aggatcttca cctagatcct tttaaattaa aaatgaagtt          900
```

-continued

```
ttaaatcaat ctaaagtata tatgagtaaa cttggtctga cagttaccaa tgcttaatca    960
gtgaggcacc tatctcagcg atctgtctat ttcgttcatc catagttgcc tgactccccg   1020
tcgtgtagat aactacgata cgggagggct taccatctgg ccccagtgct gcaatgatac   1080
cgcgagaccc acgctcaccg gctccagatt tatcagcaat aaaccagcca gccggaaggg   1140
ccgagcgcag aagtggtcct gcaactttat ccgcctccat ccagtctatt aattgttgcc   1200
gggaagctag agtaagtagt tcgccagtta atagtttgcg caacgttgtt gccattgcta   1260
caggcatcgt ggtgtcacgc tcgtcgtttg gtatggcttc attcagctcc ggttcccaac   1320
gatcaaggcg agttacatga tcccccatgt tgtgcaaaaa agcggttagc tccttcggtc   1380
ctccgatcgt tgtcagaagt aagttggccg cagtgttatc actcatggtt atggcagcac   1440
tgcataattc tcttactgtc atgccatccg taagatgctt ttctgtgact ggtgagtact   1500
caaccaagtc attctgagaa tagtgtatgc ggcgaccgag ttgctcttgc ccggcgtcaa   1560
tacgggataa taccgcgcca catagcagaa ctttaaaagt gctcatcatt ggaaaacgtt   1620
cttcggggcg aaaactctca aggatcttac cgctgttgag atccagttcg atgtaaccca   1680
ctcgtgcacc caactgatct tcagcatctt ttactttcac cagcgtttct gggtgagcaa   1740
aaacaggaag gcaaaatgcc gcaaaaaagg gaataagggc gacacggaaa tgttgaatac   1800
tcatactctt cctttttcaa tattattgaa gcatttatca gggttattgt ctcatgagcg   1860
gatacatatt tgaatgtatt tagaaaaata aacaaatagg ggttccgcgc acatttcccc   1920
gaaaagtgcc acctgacgtc taagaaacca ttattatcat gacattaacc tataaaaata   1980
ggcgtatcac gaggcccttt cgtctcgcgc gtttcggtga tgacggtgaa aacctctgac   2040
acatgcagct cccggagacg gtcacagctt gtctgtaagc ggatgccggg agcagacaag   2100
cccgtcaggc gcgtcagcg ggtgttggcg ggtgtcgggg ctggcttaac tatgcggcat   2160
cagagcagat tgtactgaga gtgcaccata tgcggtgtga ataccgcac agatgcgtaa   2220 ggagaaaata ccgcatcagg aacttccaac atccaataaa tcatacaggc aaggcaaaga   2280
attagcaaaa ttaagcaata aagcctcaga gcataaagct aaatcggttg taccaaaaac   2340
attatgaccc tgtaatactt ttgcgggaga agcctttatt tcaacgcaag ataaaaatt   2400 tttagaaccc tcatatattt taaatgcaat gcctgagtaa tgtgtaggta aagattcaaa   2460
cgggtgagaa aggccggaga cagtcaaatc accatcaata tgatattcaa ccgttctagc   2520
tgataaattc atgccggaga gggtagctat ttttgagagg tctctacaaa ggctatcagg   2580
tcattgcctg agagtctgga gcaaacaaga gaatcgatga acggtaatcg taaaactagc   2640
atgtcaatca tatgtaccccc ggttgataat cagaaaagcc ccaaaaacag gaagattgta   2700
taagcaaata tttaaattgt aaacgttaat attttgttaa aattcgcgtt aaatttttgt   2760
taaatcagct cattttttaa ccaataggcc gaaatcggca aaatcccta taaatcaaaa   2820 gaatagaccg agatagggtt gagtgttgtt ccagtttgga acaagagtcc actattaaag   2880
aacgtggact ccaacgtcaa agggcgaaaa accgtctatc agggcgatgg cccactacgt   2940
gaaccatcac cctaatcaag ttttttgggg tcgaggtgcc gtaaatcact aaatcggaac   3000
cctaaaggga gcccccgatt tagagcttga cggggaaagc cggcgaacgt ggcgagaaag   3060
gaagggaaga aagcgaaagg agcgggcgct agggcgctgg caagtgtagc ggtcacgctg   3120
cgcgtaacca ccacacccgc cgcgcttaat gcgccgctac agggcgcgta ctatggttgc   3180
tttgacgagc acgtataacg tgctttcctc gttagaatca gagcgggagc taaacaggag   3240
gccgattaaa gggattttag acaggaacgg tacgccagaa tcctgagaag tgtttttata   3300
```

-continued

```
atcagtgagg ccaccgagta aaagagtctg tccatcacgc aaattaaccg ttgtcgcaat    3360
acttctttga ttagtaataa catcacttgc ctgagtagaa gaactcaaac tatcggcctt    3420
gctggtaata tccagaacaa tattaccgcc agccattgca acaggaaaaa cgctcatgga    3480
aatacctaca ttttgacgct caatcgtctg gaacttccat tcgccattca ggctgcgcaa    3540
ctgttgggaa gggcgatcgg tgcgggcctc ttcgctatta cgccagctgn nnnnngcgcg    3600
ctcgctcgct cactgaggcc gcccgggcaa agcccgggcg tcgggcgacc tttggtcgcc    3660
cggcctcagt gagcgagcga gcgcgcagag agggagtggc caactccatc actaggggtt    3720
ccttgtagtt aatgattaac ccgccatgct aattatctac gtagccatgt ctagggtcgt    3780
tacataactt acggtaaatg gcccgcctgg ctgaccgccc aacgacccc gcccattgac    3840 gtcaataatg acgtatgttc ccatagtaac gccaataggg actttccatt gacgtcaatg    3900
ggtggagtat ttacggtaaa ctgcccactt ggcagtacat caagtgtatc atatgccaag    3960 tacgcccct attgacgtca atgacggtaa atggcccgcc tggcattatg cccagtacat    4020
gaccttatgg gactttccta cttggcagta catctacgta ttagtcatcg ctattaccat    4080
ggtgatgcgg ttttggcagt acatcaatgg gcgtggatag cggtttgact cacggggatt    4140
tccaagtctc caccccattg acgtcaatgg gagtttgttt tggcaccaaa atcaacggga    4200
ctttccaaaa tgtcgtaaca actccgcccc attgacgcaa atgggcggta ggcgtgtacg    4260
gtgggaggtc tatataagca gagctcgttt agtgaaccgt cagatcgcct ggagacgcca    4320
tccacgctgt tttgacctcc atagaagaca ccgggaccga tccagcctcc ggactctaga    4380
ggatccggta ctcgaggaac tgaaaaacca gaaagttaac tggtaagttt agtctttttg    4440
tcttttattt caggtcccgg atccggtggt ggtgcaaatc aaagaactgc tcctcagtgg    4500
atgttgcctt tacttctagg cctgtacgga agtgttactt ctgctctaaa agctgcggaa    4560
ttgtacccgc ggccgcacca tgaagctgct gccgtcggtg gtgctgaagc tctttctggc    4620
tgcagttctc tcggcactgg tgactggcga gagcctggag cggcttcgga gagggctagc    4680
tgctggaacc agcaacccgg accctcccac tgtatccacg gaccagctgc taccctagg    4740 aggcggccgg gaccggaaag tccgtgactt gcaagaggca gatctggacc ttttgagagt    4800
cactttatcc tccaagccac aagcactggc cacaccaaac aaggaggagc acgggaaaag    4860
aaagaagaaa ggcaaggggc tagggaagaa gagggaccca tgtcttcgga aatacaagga    4920
cttctgcatc catggagaat gcaaatatgt gaaggagctc cgggctccct cctgcatctg    4980
ccacccgggt taccatggag agaggtgtca tgggctgagc ctcccacaga tccatgctac    5040
acccacacct gtcactgcca ttgggcccc aaccacggct atccaggagc ccccatccag    5100
gatcgtgcca accccacat ctccagccat tgctcctcca acagagacca tggctcctcc    5160
agtcagggat cctgttcctg ggaaacccac ggtcaccatc cggactcgag gcgccattat    5220
tcaaacccca accctaggcc ccatccagcc tactcgggtg tcagaagctg gcaccacagt    5280
tcctggccag attcgcccaa cgatgaccat tcctggctat gtggagccta ctgcagttgc    5340
tacccctccc acaaccacca ccaagaagcc acgagtatcc acaccaaaac cagcaacgcc    5400
ttcaactgac tccaccacca ccacgactcg caggccaacc aagaaaccac ggacaccccg    5460
gccagtgccc cgggtcacca ccaaagtttc catcaccaga ttggaaactg cctcaccgcc    5520
tactcgtatt cgcaccacca ccagtggagt gccccgtggc ggagaaccca accagcgccc    5580
agagctcaag aaccatattg acagggtaga tgcctgggtt ggcacctact ttgaggtgaa    5640
```

-continued

```
gatcccgtca gacactttct atgaccatga ggacaccacc actgacaagc tgaagctgac    5700
cctgaaactg cgggagcagc agctggtggg cgagaagtcc tgggtacagt tcaacagcaa    5760
cagccagctc atgtatggcc ttcccgacag cagccacgtg ggcaaacacg agtatttcat    5820
gcatgccaca gacaaggggg gcctgtcggc tgtggatgcc ttcgagatcc acgtccacag    5880
gcgcccccaa ggggataggg ctcctgcaag gttcaaggcc aagtttgtgg gtgacccggc    5940
actggtgttg aatgacatcc acaagaagat tgccttggta aagaaactgg ccttcgcctt    6000
tggagaccga aactgtagca ccatcaccct gcagaatatc acccggggct aaactagtgc    6060
ggccgcgggg atccagacat gataagatac attgatgagt ttggacaaac cacaactaga    6120
atgcagtgaa aaaaatgctt tatttgtgaa atttgtgatg ctattgcttt atttgtaacc    6180
attataagct gcaataaaca agttaacaac aacaattgca ttcattttat gtttcaggtt    6240 caggggggagg tgtgggaggt tttttcggat cctctagagt cgaccacatg gctacgtaga    6300
taattagcat ggcgggttaa tcattaacta caaggaaccc ctagtgatgg agttggccac    6360
tccctctctg cgcgctcgct cgctcactga ggccgggcga ccaaaggtcg cccgacgccc    6420
gggctttgcc cggcggcct cagtgagcga gcgagcgcgc nnnnnncagc tgcattaatg    6480
aatcggccaa cgcgcgggga gaggcggttt gcgtattggg c                        6521
```

```
<210> SEQ ID NO 13
<211> LENGTH: 321
<212> TYPE: DNA
<213> ORGANISM: Artificial Sequence
<220> FEATURE:
<223> OTHER INFORMATION: Synthetic Polynucleotide

<400> SEQUENCE: 13
atgaagctgc tgccgtcggt ggtgctgaag ctctttctgg ctgcagttct ctcggcactg     60
gtgactggcg agagcctgga gcggcttcgg agagggctag ctgctggaac cagcaacccg    120
gaccctccca ctgtatccac ggaccagctg ctacccctag gaggcggccg ggaccggaaa    180
gtccgtgact tgcaagaggc agatctggac cttttgagag tcactttatc ctccaagcca    240
caagcactgg ccacaccaaa caaggaggag cacgggaaaa gaaagaagaa aggcaagggg    300
ctagggaaga agagggaccc a                                              321
```

```
<210> SEQ ID NO 14
<211> LENGTH: 447
<212> TYPE: DNA
<213> ORGANISM: Artificial Sequence
<220> FEATURE:
<223> OTHER INFORMATION: Synthetic Polynucleotide

<400> SEQUENCE: 14
atgaagctgc tgccgtcggt ggtgctgaag ctctttctgg ctgcagttct ctcggcactg     60
gtgactggcg agagcctgga gcggcttcgg agagggctag ctgctggaac cagcaacccg    120
gaccctccca ctgtatccac ggaccagctg ctacccctag gaggcggccg ggaccggaaa    180
gtccgtgact tgcaagaggc agatctggac cttttgagag tcactttatc ctccaagcca    240
caagcactgg ccacaccaaa caaggaggag cacgggaaaa gaaagaagaa aggcaagggg    300
ctagggaaga agagggaccc atgtcttcgg aaatacaagg acttctgcat ccatggagaa    360
tgcaaatatg tgaaggagct ccgggctccc tcctgcatct gccacccggg ttaccatgga    420
gagaggtgtc atgggctgag cctccca                                        447
```

-continued

<210> SEQ ID NO 15
<211> LENGTH: 2901
<212> TYPE: DNA
<213> ORGANISM: Artificial Sequence
<220> FEATURE:
<223> OTHER INFORMATION: Synthetic Polynucleotide

<400> SEQUENCE: 15
aaagtatctg tgtcttcagg aggtgactgc attcgaacat acaaaccaga aatcaagaaa        60
ggaagttaca ataatattgt tgtcaacgta aagacagctg ttgctgataa cctcctcttt       120
tatcttggaa gtgccaaatt tattgacttt ctggctatag aaatgcgtaa aggcaaagtc       180
agcttcctct gggatgttgg atctggagtt ggacgtgtag agtacccaga tttgactatt       240
gatgactcat attggtaccg tatcgtagca tcaagaactg ggagaaatgg aactatttct       300
gtgagagccc tggatggacc caaagccagc attgtgccca gcacacacca ttcgacgtct       360
cctccagggt acacgattct agatgtggat gcaaatgcaa tgctgtttgt tggtggcctg       420
actgggaaat aaagaaggc tgatgctgta cgtgtgatta cattcactgg ctgcatggga       480
gaaacatact ttgacaacaa acctataggt ttgtggaatt ccgagaaaa agaaggtgac       540 tgcaaaggat gcactgtcag tcctcaggtg aagatagtg aggggactat tcaatttgat       600
ggagaaggtt atgcattggt cagccgtccc attcgctggt accccaacat ctccactgtc       660
atgttcaagt tcagaacatt ttcttcgagt gctcttctga tgtatcttgc cacacgagac       720
ctgagagatt tcatgagtgt ggagctcact gatgggcaca taaaagtcag ttacgatctg       780
ggctcaggaa tggcttccgt tgtcagcaat caaaaccata atgatgggaa atggaaatca       840
ttcactctgt caagaattca aaaacaagcc aatatatcaa ttgtagatat agatactaat       900
caggaggaga atatagcaac ttcgtcttct ggaaacaact ttggtcttga cttgaaagca       960
gatgacaaaa tatattttgg tggcctgcca acgctgagaa acttgagtat gaaagcaagg      1020
ccagaagtaa atctgaagaa atattccggc tgcctcaaag atattgaaat ttcaagaact      1080
ccgtacaata tactcagtag tcccgattat gttggtgtta ccaaaggatg ttccctggag      1140
aatgtttaca cagttagctt tcctaagcct ggttttgtgg agctctcccc tgtgccaatt      1200
gatgtaggaa cagaaatcaa cctgtcattc agcaccaaga tgagtccgg catcattctt      1260 ttgggaagtg gagggacacc agcaccacct aggagaaaac gaaggcagac tggacaggcc      1320
tattatgtaa tactcctcaa caggggccgt ctggaagtgc atctctccac aggggcacga      1380
acaatgagga aaattgtcat cagaccagag ccgaatctgt ttcatgatgg aagagaacat      1440
tccgttcatg tagagcgaac tagaggcatc tttacagttc aagtggatga aaacagaaga      1500
tacatgcaaa acctgacagt tgaacagcct atcgaagtta aaaagctttt cgttgggggt      1560
gctccacctg aatttcaacc ttccccactc agaaatattc ctccttttga aggctgcata      1620
tggaatcttg ttattaactc tgtccccatg gactttgcaa ggcctgtgtc cttcaaaaat      1680
gctgacattg tcgctgtgc ccatcagaaa ctccgtgaag atgaagatgg agcagctcca      1740
gctgaaatag ttatccagcc tgagccagtt cccaccccag cctttcctac gcccacccca      1800
gttctgacac atggtccttg tgctgcagaa tcagaaccag ctctttttgat agggagcaag      1860 cagttcgggc tttcaagaaa cagtcacatt gcaattgcat ttgatgacac caaagttaaa      1920
aaccgtctca caattgagtt ggaagtaaga accgaagctg aatccggctt gctttttttac      1980 atggctcgca tcaatcatgc tgattttgca acagttcagc tgagaaatgg attgccctac      2040
ttcagctatg acttggggag tggggacacc cacaccatga tccccaccaa aatcaatgat      2100

-continued

```
ggccagtggc acaagattaa gataatgaga agtaagcaag aaggaattct ttatgtagat    2160 gggcttcca  acagaaccat cagtcccaaa aaagccgaca tcctggatgt cgtgggaatg    2220
ctgtatgttg gtgggttacc catcaactac actacccgaa gaattggtcc agtgacctat    2280
agcattgatg gctgcgtcag gaatctccac atggcagagg cccctgccga tctggaacaa    2340
cccacctcca gcttccatgt tgggacatgt tttgcaaatg ctcagagggg aacatatttt    2400
gacggaaccg gttttgccaa agcagttggt ggattcaaag tgggattgga ccttcttgta    2460
gaatttgaat tccgcacaac tacaacgact ggagttcttc tggggatcag tagtcaaaaa    2520
atggatggaa tgggtattga aatgattgat gaaaagttga tgtttcatgt ggacaatggt    2580
gcgggcagat tcactgctgt ctatgatgct ggggttccag ggcatttgtg tgatggacaa    2640
tggcataaag tcactgccaa caagatcaaa caccgcattg agctcacagt cgatgggaac    2700
caggtggaag cccaaagccc aaacccagca tctacatcag ctgacacaaa tgaccctgtg    2760
tttgttggag gcttcccaga tgacctcaag cagtttggcc taacaaccag tattccgttc    2820
cgaggttgca tcagatccct gaagctcacc aaaggcacag caagccactg gaggttaatt    2880
ttgccaaggc cctggaactg a                                             2901

<210> SEQ ID NO 16
<211> LENGTH: 1332
<212> TYPE: DNA
<213> ORGANISM: Artificial Sequence
<220> FEATURE:
<223> OTHER INFORMATION: Synthetic Polynucleotide

<400> SEQUENCE: 16
cagactggac aggcctatta tgtaatactc ctcaacaggg gccgtctgga agtgcatctc      60
tccacagggg cacgaacaat gaggaaaatt gtcatcagac cagagccgaa tctgtttcat     120
gatggaagag aacattccgt tcatgtagag cgaactagag gcatctttac agttcaagtg     180
gatgaaaaca gaagatacat gcaaaacctg acagttgaac agcctatcga agttaaaaag     240
cttttcgttg ggggtgctcc acctgaattt caaccttccc cactcagaaa tattcctcct     300
tttgaaggct gcatatggaa tcttgttatt aactctgtcc ccatggactt tgcaaggcct     360
gtgtccttca aaaatgctga cattggtcgc tgtgcccatc agaaactccg tgaagatgaa     420
gatggagcag ctccagctga aatagttatc cagcctgagc cagttcccac cccagccttt     480
cctacgccca ccccagttct gacacatggt ccttgtgctg cagaatcaga accagctctt     540
ttgataggga gcaagcagtt cgggctttca agaaacagtc acattgcaat tgcatttgat     600
gacaccaaag ttaaaaaccg tctcacaatt gagttggaag taagaaccga agctgaatcc     660
ggcttgcttt tttacatggc tcgcatcaat catgctgatt ttgcaacagt tcagctgaga     720
aatggattgc cctacttcag ctatgacttg gggagtgggg acacccacac catgatcccc     780
accaaaatca atgatggcca gtggcacaag attaagataa tgagaagtaa gcaagaagga     840
attctttatg tagatgggc ttccaacaga accatcagtc ccaaaaaagc cgacatcctg     900
gatgtcgtgg gaatgctgta tgttggtggg ttacccatca actacactac ccgaagaatt     960
ggtccagtga cctatagcat tgatggctgc gtcaggaatc tccacatggc agaggccccct    1020 gccgatctgg aacaacccac ctccagcttc catgttggga catgtttttgc aaatgctcag    1080 aggggaacat attttgacgg aaccggtttt gccaaagcag ttggtggatt caaagtggga    1140
ttggaccttc ttgtagaatt tgaattccgc acaactacaa cgactggagt tcttctgggg    1200
atcagtagtc aaaaaatgga tggaatgggt attgaaatga ttgatgaaaa gttgatgttt    1260
```

-continued

```
catgtggaca atggtgcggg cagattcact gctgtctatg atgctggggt tccagggcat    1320
ttgtgtgatg ga                                                        1332

<210> SEQ ID NO 17
<211> LENGTH: 1023
<212> TYPE: DNA
<213> ORGANISM: Artificial Sequence
<220> FEATURE:
<223> OTHER INFORMATION: Synthetic Polynucleotide

<400> SEQUENCE: 17
cagatccatg ctacacccac acctgtcact gccattgggc ccccaaccac ggctatccag      60
gagcccccat ccaggatcgt gccaaccccc acatctccag ccattgctcc tccaacagag     120
accatggctc ctccagtcag ggatcctgtt cctgggaaac ccacggtcac catccggact     180
cgaggcgcca ttattcaaac cccaacccta ggccccatcc agcctactcg ggtgtcagaa     240
gctggcacca cagttcctgg ccagattcgc ccaacgatga ccattcctgg ctatgtggag     300
cctactgcag ttgctacccc tcccacaacc accaccaaga agccacgagt atccacacca     360
aaaccagcaa cgccttcaac tgactccacc accaccacga ctcgcaggcc aaccaagaaa     420
ccacggacac cccggccagt gccccgggtc accaccaaag tttccatcac cagattggaa     480
actgcctcac cgcctactcg tattcgcacc accaccagtg gagtgccccg tggcggagaa     540
cccaaccagc gcccagagct caagaaccat attgacaggg tagatgcctg ggttggcacc     600
tactttgagg tgaagatccc gtcagacact ttctatgacc atgaggacac caccactgac     660
aagctgaagc tgaccctgaa actgcgggag cagcagctgg tgggcgagaa gtcctgggta     720
cagttcaaca gcaacagcca gctcatgtat ggccttcccg acagcagcca cgtgggcaaa     780
cacgagtatt tcatgcatgc cacagacaag gggggcctgt cggctgtgga tgccttcgag     840
atccacgtcc acaggcgccc ccaaggggat agggctcctg caaggttcaa ggccaagttt     900
gtgggtgacc cggcactggt gttgaatgac atccacaaga agattgcctt ggtaaagaaa     960
ctggccttcg cctttggaga ccgaaactgt agcaccatca ccctgcagaa tatcacccgg    1020
ggc                                                                  1023

<210> SEQ ID NO 18
<211> LENGTH: 529
<212> TYPE: DNA
<213> ORGANISM: Artificial Sequence
<220> FEATURE:
<223> OTHER INFORMATION: Synthetic Polynucleotide

<400> SEQUENCE: 18
cgttacataa cttacggtaa atggcccgcc tggctgaccg cccaacgacc cccgcccatt      60
gacgtcaata atgacgtatg ttcccatagt aacgccaata gggactttcc attgacgtca     120
atgggtggag tatttacggt aaactgccca cttggcagta tcaagtgt atcatatgcc     180 aagtacgccc cctattgacg tcaatgacgg taaatggccc gcctggcatt atgcccagta     240
catgacctta tgggactttc ctacttggca gtacatctac gtattagtca tcgctattac     300
catggtgatg cggttttggc agtacatcaa tgggcgtgga tagcggtttg actcacgggg     360
atttccaagt ctccacccca ttgacgtcaa tgggagtttg ttttggcacc aaaatcaacg     420
ggactttcca aaatgtcgta acaactccgc cccattgacg caaatgggcg gtaggcgtgt     480
acggtgggag gtctatataa gcagagctcg tttagtgaac cgtcagatc                529
```

<210> SEQ ID NO 19
<211> LENGTH: 1073
<212> TYPE: PRT
<213> ORGANISM: Artificial Sequence
<220> FEATURE:
<223> OTHER INFORMATION: Synthetic Polypeptide

<400> SEQUENCE: 19

Met Lys Leu Leu Pro Ser Val Val Leu Lys Leu Phe Leu Ala Ala Val
1               5                   10                  15

Leu Ser Ala Leu Val Thr Gly Glu Ser Leu Glu Arg Leu Arg Arg Gly
            20                  25                  30

Leu Ala Ala Gly Thr Ser Asn Pro Asp Pro Thr Val Ser Thr Asp
            35                  40                  45

Gln Leu Leu Pro Leu Gly Gly Gly Arg Asp Arg Lys Val Arg Asp Leu
    50                  55                  60

Gln Glu Ala Asp Leu Asp Leu Leu Arg Val Thr Leu Ser Ser Lys Pro
65                  70                  75                  80

Gln Ala Leu Ala Thr Pro Asn Lys Glu Glu His Gly Lys Arg Lys Lys
                85                  90                  95

Lys Gly Lys Gly Leu Gly Lys Lys Arg Asp Pro Lys Val Ser Val Ser
            100                 105                 110

Ser Gly Gly Asp Cys Ile Arg Thr Tyr Lys Pro Glu Ile Lys Lys Gly
            115                 120                 125

Ser Tyr Asn Asn Ile Val Val Asn Val Lys Thr Ala Val Ala Asp Asn
    130                 135                 140

Leu Leu Phe Tyr Leu Gly Ser Ala Lys Phe Ile Asp Phe Leu Ala Ile
145                 150                 155                 160

Glu Met Arg Lys Gly Lys Val Ser Phe Leu Trp Asp Val Gly Ser Gly
                165                 170                 175

Val Gly Arg Val Glu Tyr Pro Asp Leu Thr Ile Asp Asp Ser Tyr Trp
            180                 185                 190

Tyr Arg Ile Val Ala Ser Arg Thr Gly Arg Asn Gly Thr Ile Ser Val
            195                 200                 205

Arg Ala Leu Asp Gly Pro Lys Ala Ser Ile Val Pro Ser Thr His His
    210                 215                 220

Ser Thr Ser Pro Pro Gly Tyr Thr Ile Leu Asp Val Asp Ala Asn Ala
225                 230                 235                 240

Met Leu Phe Val Gly Gly Leu Thr Gly Lys Leu Lys Lys Ala Asp Ala
                245                 250                 255

Val Arg Val Ile Thr Phe Thr Gly Cys Met Gly Glu Thr Tyr Phe Asp
            260                 265                 270

Asn Lys Pro Ile Gly Leu Trp Asn Phe Arg Glu Lys Glu Gly Asp Cys
            275                 280                 285

Lys Gly Cys Thr Val Ser Pro Gln Val Glu Asp Ser Glu Gly Thr Ile
    290                 295                 300

Gln Phe Asp Gly Glu Gly Tyr Ala Leu Val Ser Arg Pro Ile Arg Trp
305                 310                 315                 320

Tyr Pro Asn Ile Ser Thr Val Met Phe Lys Phe Arg Thr Phe Ser Ser
                325                 330                 335

Ser Ala Leu Leu Met Tyr Leu Ala Thr Arg Asp Leu Arg Asp Phe Met
            340                 345                 350

Ser Val Glu Leu Thr Asp Gly His Ile Lys Val Ser Tyr Asp Leu Gly
            355                 360                 365

```
Ser Gly Met Ala Ser Val Val Ser Asn Gln Asn His Asn Asp Gly Lys
    370             375             380
```

```
Trp Lys Ser Phe Thr Leu Ser Arg Ile Gln Lys Gln Ala Asn Ile Ser
385             390             395             400
```

```
Ile Val Asp Ile Asp Thr Asn Gln Glu Glu Asn Ile Ala Thr Ser Ser
            405             410             415
```

```
Ser Gly Asn Asn Phe Gly Leu Asp Leu Lys Ala Asp Asp Lys Ile Tyr
            420             425             430
```

```
Phe Gly Gly Leu Pro Thr Leu Arg Asn Leu Ser Met Lys Ala Arg Pro
            435             440             445
```

```
Glu Val Asn Leu Lys Lys Tyr Ser Gly Cys Leu Lys Asp Ile Glu Ile
    450             455             460
```

```
Ser Arg Thr Pro Tyr Asn Ile Leu Ser Ser Pro Asp Tyr Val Gly Val
465             470             475             480
```

```
Thr Lys Gly Cys Ser Leu Glu Asn Val Tyr Thr Val Ser Phe Pro Lys
            485             490             495
```

```
Pro Gly Phe Val Glu Leu Ser Pro Val Pro Ile Asp Val Gly Thr Glu
            500             505             510
```

```
Ile Asn Leu Ser Phe Ser Thr Lys Asn Glu Ser Gly Ile Ile Leu Leu
            515             520             525
```

```
Gly Ser Gly Gly Thr Pro Ala Pro Pro Arg Arg Lys Arg Arg Gln Thr
    530             535             540
```

```
Gly Gln Ala Tyr Tyr Val Ile Leu Leu Asn Arg Gly Arg Leu Glu Val
545             550             555             560
```

```
His Leu Ser Thr Gly Ala Arg Thr Met Arg Lys Ile Val Ile Arg Pro
            565             570             575
```

```
Glu Pro Asn Leu Phe His Asp Gly Arg Glu His Ser Val His Val Glu
            580             585             590
```

```
Arg Thr Arg Gly Ile Phe Thr Val Gln Val Asp Glu Asn Arg Arg Tyr
            595             600             605
```

```
Met Gln Asn Leu Thr Val Glu Gln Pro Ile Glu Val Lys Lys Leu Phe
            610             615             620
```

```
Val Gly Gly Ala Pro Pro Glu Phe Gln Pro Ser Pro Leu Arg Asn Ile
625             630             635             640
```

```
Pro Pro Phe Glu Gly Cys Ile Trp Asn Leu Val Ile Asn Ser Val Pro
            645             650             655
```

```
Met Asp Phe Ala Arg Pro Val Ser Phe Lys Asn Ala Asp Ile Gly Arg
            660             665             670
```

```
Cys Ala His Gln Lys Leu Arg Glu Asp Glu Asp Gly Ala Ala Pro Ala
            675             680             685
```

```
Glu Ile Val Ile Gln Pro Glu Pro Val Pro Thr Pro Ala Phe Pro Thr
    690             695             700
```

```
Pro Thr Pro Val Leu Thr His Gly Pro Cys Ala Ala Glu Ser Glu Pro
705             710             715             720
```

```
Ala Leu Leu Ile Gly Ser Lys Gln Phe Gly Leu Ser Arg Asn Ser His
            725             730             735
```

```
Ile Ala Ile Ala Phe Asp Asp Thr Lys Val Lys Asn Arg Leu Thr Ile
            740             745             750
```

```
Glu Leu Glu Val Arg Thr Glu Ala Glu Ser Gly Leu Leu Phe Tyr Met
            755             760             765
```

```
Ala Arg Ile Asn His Ala Asp Phe Ala Thr Val Gln Leu Arg Asn Gly
    770             775             780
```

```
Leu Pro Tyr Phe Ser Tyr Asp Leu Gly Ser Gly Asp Thr His Thr Met
```

-continued

```
785                 790                 795                 800
Ile Pro Thr Lys Ile Asn Asp Gly Gln Trp His Lys Ile Lys Ile Met
                805                 810                 815
Arg Ser Lys Gln Glu Gly Ile Leu Tyr Val Asp Gly Ala Ser Asn Arg
            820                 825                 830
Thr Ile Ser Pro Lys Lys Ala Asp Ile Leu Asp Val Val Gly Met Leu
            835                 840                 845
Tyr Val Gly Gly Leu Pro Ile Asn Tyr Thr Thr Arg Arg Ile Gly Pro
        850                 855                 860
Val Thr Tyr Ser Ile Asp Gly Cys Val Arg Asn Leu His Met Ala Glu
865                 870                 875                 880
Ala Pro Ala Asp Leu Glu Gln Pro Thr Ser Ser Phe His Val Gly Thr
                885                 890                 895
Cys Phe Ala Asn Ala Gln Arg Gly Thr Tyr Phe Asp Gly Thr Gly Phe
            900                 905                 910
Ala Lys Ala Val Gly Gly Phe Lys Val Gly Leu Asp Leu Leu Val Glu
            915                 920                 925
Phe Glu Phe Arg Thr Thr Thr Thr Thr Gly Val Leu Leu Gly Ile Ser
        930                 935                 940
Ser Gln Lys Met Asp Gly Met Gly Ile Glu Met Ile Asp Glu Lys Leu
945                 950                 955                 960
Met Phe His Val Asp Asn Gly Ala Gly Arg Phe Thr Ala Val Tyr Asp
                965                 970                 975
Ala Gly Val Pro Gly His Leu Cys Asp Gly Gln Trp His Lys Val Thr
            980                 985                 990
Ala Asn Lys Ile Lys His Arg Ile  Glu Leu Thr Val Asp  Gly Asn Gln
        995                 1000                1005
Val Glu  Ala Gln Ser Pro Asn  Pro Ala Ser Thr Ser  Ala Asp Thr
    1010                1015                1020
Asn Asp  Pro Val Phe Val Gly  Gly Phe Pro Asp Asp  Leu Lys Gln
    1025                1030                1035
Phe Gly  Leu Thr Thr Ser Ile  Pro Phe Arg Gly Cys  Ile Arg Ser
    1040                1045                1050
Leu Lys  Leu Thr Lys Gly Thr  Ala Ser His Trp Arg  Leu Ile Leu
    1055                1060                1065
Pro Arg  Pro Trp Asn
    1070
```

```
<210> SEQ ID NO 20
<211> LENGTH: 1115
<212> TYPE: PRT
<213> ORGANISM: Artificial Sequence
<220> FEATURE:
<223> OTHER INFORMATION: Synthetic Polypeptide

<400> SEQUENCE: 20

Met Lys Leu Leu Pro Ser Val Val Leu Lys Leu Phe Leu Ala Ala Val
1               5                   10                  15
Leu Ser Ala Leu Val Thr Gly Glu Ser Leu Glu Arg Leu Arg Arg Gly
            20                  25                  30
Leu Ala Ala Gly Thr Ser Asn Pro Asp Pro Pro Thr Val Ser Thr Asp
            35                  40                  45
Gln Leu Leu Pro Leu Gly Gly Gly Arg Asp Arg Lys Val Arg Asp Leu
        50                  55                  60
Gln Glu Ala Asp Leu Asp Leu Leu Arg Val Thr Leu Ser Ser Lys Pro
```

-continued

```
65                  70                  75                  80

Gln Ala Leu Ala Thr Pro Asn Lys Glu Glu His Gly Lys Arg Lys Lys
                85                  90                  95

Lys Gly Lys Gly Leu Gly Lys Lys Arg Asp Pro Cys Leu Arg Lys Tyr
            100                 105                 110

Lys Asp Phe Cys Ile His Gly Glu Cys Lys Tyr Val Lys Glu Leu Arg
            115                 120                 125

Ala Pro Ser Cys Ile Cys His Pro Gly Tyr His Gly Glu Arg Cys His
        130                 135                 140

Gly Leu Ser Leu Pro Lys Val Ser Val Ser Ser Gly Gly Asp Cys Ile
145                 150                 155                 160

Arg Thr Tyr Lys Pro Glu Ile Lys Lys Gly Ser Tyr Asn Asn Ile Val
                165                 170                 175

Val Asn Val Lys Thr Ala Val Ala Asp Asn Leu Leu Phe Tyr Leu Gly
            180                 185                 190

Ser Ala Lys Phe Ile Asp Phe Leu Ala Ile Glu Met Arg Lys Gly Lys
            195                 200                 205

Val Ser Phe Leu Trp Asp Val Gly Ser Gly Val Gly Arg Val Glu Tyr
        210                 215                 220

Pro Asp Leu Thr Ile Asp Asp Ser Tyr Trp Tyr Arg Ile Val Ala Ser
225                 230                 235                 240

Arg Thr Gly Arg Asn Gly Thr Ile Ser Val Arg Ala Leu Asp Gly Pro
                245                 250                 255

Lys Ala Ser Ile Val Pro Ser Thr His His Ser Thr Ser Pro Pro Gly
            260                 265                 270

Tyr Thr Ile Leu Asp Val Asp Ala Asn Ala Met Leu Phe Val Gly Gly
            275                 280                 285

Leu Thr Gly Lys Leu Lys Lys Ala Asp Ala Val Arg Val Ile Thr Phe
        290                 295                 300

Thr Gly Cys Met Gly Glu Thr Tyr Phe Asp Asn Lys Pro Ile Gly Leu
305                 310                 315                 320

Trp Asn Phe Arg Glu Lys Glu Gly Asp Cys Lys Gly Cys Thr Val Ser
                325                 330                 335

Pro Gln Val Glu Asp Ser Glu Gly Thr Ile Gln Phe Asp Gly Glu Gly
            340                 345                 350

Tyr Ala Leu Val Ser Arg Pro Ile Arg Trp Tyr Pro Asn Ile Ser Thr
            355                 360                 365

Val Met Phe Lys Phe Arg Thr Phe Ser Ser Ser Ala Leu Leu Met Tyr
        370                 375                 380

Leu Ala Thr Arg Asp Leu Arg Asp Phe Met Ser Val Glu Leu Thr Asp
385                 390                 395                 400

Gly His Ile Lys Val Ser Tyr Asp Leu Gly Ser Gly Met Ala Ser Val
            405                 410                 415

Val Ser Asn Gln Asn His Asn Asp Gly Lys Trp Lys Ser Phe Thr Leu
            420                 425                 430

Ser Arg Ile Gln Lys Gln Ala Asn Ile Ser Ile Val Asp Ile Asp Thr
            435                 440                 445

Asn Gln Glu Glu Asn Ile Ala Thr Ser Ser Ser Gly Asn Asn Phe Gly
        450                 455                 460

Leu Asp Leu Lys Ala Asp Asp Lys Ile Tyr Phe Gly Gly Leu Pro Thr
465                 470                 475                 480

Leu Arg Asn Leu Ser Met Lys Ala Arg Pro Glu Val Asn Leu Lys Lys
                485                 490                 495
```

Tyr Ser Gly Cys Leu Lys Asp Ile Glu Ile Ser Arg Thr Pro Tyr Asn
            500                 505                 510

Ile Leu Ser Ser Pro Asp Tyr Val Gly Val Thr Lys Gly Cys Ser Leu
            515                 520                 525

Glu Asn Val Tyr Thr Val Ser Phe Pro Lys Pro Gly Phe Val Glu Leu
            530                 535                 540

Ser Pro Val Pro Ile Asp Val Gly Thr Glu Ile Asn Leu Ser Phe Ser
545                 550                 555                 560

Thr Lys Asn Glu Ser Gly Ile Ile Leu Leu Gly Ser Gly Gly Thr Pro
            565                 570                 575

Ala Pro Pro Arg Arg Lys Arg Gln Thr Gly Gln Ala Tyr Tyr Val
            580                 585                 590

Ile Leu Leu Asn Arg Gly Arg Leu Glu Val His Leu Ser Thr Gly Ala
            595                 600                 605

Arg Thr Met Arg Lys Ile Val Ile Arg Pro Glu Pro Asn Leu Phe His
            610                 615                 620

Asp Gly Arg Glu His Ser Val His Val Glu Arg Thr Arg Gly Ile Phe
625                 630                 635                 640

Thr Val Gln Val Asp Glu Asn Arg Arg Tyr Met Gln Asn Leu Thr Val
            645                 650                 655

Glu Gln Pro Ile Glu Val Lys Lys Leu Phe Val Gly Gly Ala Pro Pro
            660                 665                 670

Glu Phe Gln Pro Ser Pro Leu Arg Asn Ile Pro Pro Phe Glu Gly Cys
            675                 680                 685

Ile Trp Asn Leu Val Ile Asn Ser Val Pro Met Asp Phe Ala Arg Pro
            690                 695                 700

Val Ser Phe Lys Asn Ala Asp Ile Gly Arg Cys Ala His Gln Lys Leu
705                 710                 715                 720

Arg Glu Asp Glu Asp Gly Ala Ala Pro Ala Glu Ile Val Ile Gln Pro
            725                 730                 735

Glu Pro Val Pro Thr Pro Ala Phe Pro Thr Pro Thr Pro Val Leu Thr
            740                 745                 750

His Gly Pro Cys Ala Ala Glu Ser Glu Pro Ala Leu Leu Ile Gly Ser
            755                 760                 765

Lys Gln Phe Gly Leu Ser Arg Asn Ser His Ile Ala Ile Ala Phe Asp
            770                 775                 780

Asp Thr Lys Val Lys Asn Arg Leu Thr Ile Glu Leu Glu Val Arg Thr
785                 790                 795                 800

Glu Ala Glu Ser Gly Leu Leu Phe Tyr Met Ala Arg Ile Asn His Ala
            805                 810                 815

Asp Phe Ala Thr Val Gln Leu Arg Asn Gly Leu Pro Tyr Phe Ser Tyr
            820                 825                 830

Asp Leu Gly Ser Gly Asp Thr His Thr Met Ile Pro Thr Lys Ile Asn
            835                 840                 845

Asp Gly Gln Trp His Lys Ile Lys Ile Met Arg Ser Lys Gln Glu Gly
            850                 855                 860

Ile Leu Tyr Val Asp Gly Ala Ser Asn Arg Thr Ile Ser Pro Lys Lys
865                 870                 875                 880

Ala Asp Ile Leu Asp Val Val Gly Met Leu Tyr Val Gly Gly Leu Pro
            885                 890                 895

Ile Asn Tyr Thr Thr Arg Arg Ile Gly Pro Val Thr Tyr Ser Ile Asp
            900                 905                 910

-continued

```
Gly Cys Val Arg Asn Leu His Met Ala Glu Ala Pro Ala Asp Leu Glu
        915                 920                 925

Gln Pro Thr Ser Ser Phe His Val Gly Thr Cys Phe Ala Asn Ala Gln
        930                 935                 940

Arg Gly Thr Tyr Phe Asp Gly Thr Gly Phe Ala Lys Ala Val Gly Gly
945                 950                 955                 960

Phe Lys Val Gly Leu Asp Leu Leu Val Glu Phe Glu Phe Arg Thr Thr
                965                 970                 975

Thr Thr Thr Gly Val Leu Leu Gly Ile Ser Ser Gln Lys Met Asp Gly
                980                 985                 990

Met Gly Ile Glu Met Ile Asp Glu  Lys Leu Met Phe His  Val Asp Asn
        995                 1000                 1005

Gly Ala  Gly Arg Phe Thr Ala  Val Tyr Asp Ala Gly  Val Pro Gly
        1010                1015                1020

His Leu  Cys Asp Gly Gln Trp  His Lys Val Thr Ala  Asn Lys Ile
        1025                1030                1035

Lys His  Arg Ile Glu Leu Thr  Val Asp Gly Asn Gln  Val Glu Ala
        1040                1045                1050

Gln Ser  Pro Asn Pro Ala Ser  Thr Ser Ala Asp Thr  Asn Asp Pro
        1055                1060                1065

Val Phe  Val Gly Gly Phe Pro  Asp Asp Leu Lys Gln  Phe Gly Leu
        1070                1075                1080

Thr Thr  Ser Ile Pro Phe Arg  Gly Cys Ile Arg Ser  Leu Lys Leu
        1085                1090                1095

Thr Lys  Gly Thr Ala Ser His  Trp Arg Leu Ile Leu  Pro Arg Pro
        1100                1105                1110

Trp Asn
        1115
```

```
<210> SEQ ID NO 21
<211> LENGTH: 680
<212> TYPE: PRT
<213> ORGANISM: Artificial Sequence
<220> FEATURE:
<223> OTHER INFORMATION: Synthetic Polypeptide

<400> SEQUENCE: 21

Met Lys Leu Leu Pro Ser Val Val Leu Lys Leu Phe Leu Ala Ala Val
1               5                   10                  15

Leu Ser Ala Leu Val Thr Gly Glu Ser Leu Glu Arg Leu Arg Arg Gly
                20                  25                  30

Leu Ala Ala Gly Thr Ser Asn Pro Asp Pro Pro Thr Val Ser Thr Asp
            35                  40                  45

Gln Leu Leu Pro Leu Gly Gly Gly Arg Asp Arg Lys Val Arg Asp Leu
    50                  55                  60

Gln Glu Ala Asp Leu Asp Leu Leu Arg Val Thr Leu Ser Ser Lys Pro
65                  70                  75                  80

Gln Ala Leu Ala Thr Pro Asn Lys Glu Glu His Gly Lys Arg Lys Lys
                85                  90                  95

Lys Gly Lys Gly Leu Gly Lys Lys Arg Asp Pro Cys Leu Arg Lys Tyr
            100                 105                 110

Lys Asp Phe Cys Ile His Gly Glu Cys Lys Tyr Val Lys Glu Leu Arg
        115                 120                 125

Ala Pro Ser Cys Ile Cys His Pro Gly Tyr His Gly Glu Arg Cys His
        130                 135                 140
```

-continued

```
Gly Leu Ser Leu Pro Gln Thr Gly Gln Ala Tyr Tyr Val Ile Leu Leu
145                 150                 155                 160

Asn Arg Gly Arg Leu Glu Val His Leu Ser Thr Gly Ala Arg Thr Met
                165                 170                 175

Arg Lys Ile Val Ile Arg Pro Glu Pro Asn Leu Phe His Asp Gly Arg
            180                 185                 190

Glu His Ser Val His Val Glu Arg Thr Arg Gly Ile Phe Thr Val Gln
        195                 200                 205

Val Asp Glu Asn Arg Arg Tyr Met Gln Asn Leu Thr Val Glu Gln Pro
    210                 215                 220

Ile Glu Val Lys Lys Leu Phe Val Gly Gly Ala Pro Pro Glu Phe Gln
225                 230                 235                 240

Pro Ser Pro Leu Arg Asn Ile Pro Pro Phe Glu Gly Cys Ile Trp Asn
                245                 250                 255

Leu Val Ile Asn Ser Val Pro Met Asp Phe Ala Arg Pro Val Ser Phe
                260                 265                 270

Lys Asn Ala Asp Ile Gly Arg Cys Ala His Gln Lys Leu Arg Glu Asp
            275                 280                 285

Glu Asp Gly Ala Ala Pro Ala Glu Ile Val Ile Gln Pro Glu Pro Val
    290                 295                 300

Pro Thr Pro Ala Phe Pro Thr Pro Thr Pro Val Leu Thr His Gly Pro
305                 310                 315                 320

Cys Ala Ala Glu Ser Glu Pro Ala Leu Leu Ile Gly Ser Lys Gln Phe
                325                 330                 335

Gly Leu Ser Arg Asn Ser His Ile Ala Ile Ala Phe Asp Asp Thr Lys
            340                 345                 350

Val Lys Asn Arg Leu Thr Ile Glu Leu Glu Val Arg Thr Glu Ala Glu
            355                 360                 365

Ser Gly Leu Leu Phe Tyr Met Ala Arg Ile Asn His Ala Asp Phe Ala
    370                 375                 380

Thr Val Gln Leu Arg Asn Gly Leu Pro Tyr Phe Ser Tyr Asp Leu Gly
385                 390                 395                 400

Ser Gly Asp Thr His Thr Met Ile Pro Thr Lys Ile Asn Asp Gly Gln
                405                 410                 415

Trp His Lys Ile Lys Ile Met Arg Ser Lys Gln Glu Gly Ile Leu Tyr
            420                 425                 430

Val Asp Gly Ala Ser Asn Arg Thr Ile Ser Pro Lys Lys Ala Asp Ile
        435                 440                 445

Leu Asp Val Val Gly Met Leu Tyr Val Gly Gly Leu Pro Ile Asn Tyr
    450                 455                 460

Thr Thr Arg Arg Ile Gly Pro Val Thr Tyr Ser Ile Asp Gly Cys Val
465                 470                 475                 480

Arg Asn Leu His Met Ala Glu Ala Pro Ala Asp Leu Glu Gln Pro Thr
                485                 490                 495

Ser Ser Phe His Val Gly Thr Cys Phe Ala Asn Ala Gln Arg Gly Thr
                500                 505                 510

Tyr Phe Asp Gly Thr Gly Phe Ala Lys Ala Val Gly Gly Phe Lys Val
            515                 520                 525

Gly Leu Asp Leu Leu Val Glu Phe Glu Phe Arg Thr Thr Thr Thr Thr
    530                 535                 540

Gly Val Leu Leu Gly Ile Ser Ser Gln Lys Met Asp Gly Met Gly Ile
545                 550                 555                 560

Glu Met Ile Asp Glu Lys Leu Met Phe His Val Asp Asn Gly Ala Gly
```

-continued

```
                   565                 570                 575

Arg Phe Thr Ala Val Tyr Asp Ala Gly Val Pro Gly His Leu Cys Asp
            580                 585                 590

Gly Gln Trp His Lys Val Thr Ala Asn Lys Ile Lys His Arg Ile Glu
        595                 600                 605

Leu Thr Val Asp Gly Asn Gln Val Glu Ala Gln Ser Pro Asn Pro Ala
        610                 615                 620

Ser Thr Ser Ala Asp Thr Asn Asp Pro Val Phe Val Gly Gly Phe Pro
625                 630                 635                 640

Asp Asp Leu Lys Gln Phe Gly Leu Thr Thr Ser Ile Pro Phe Arg Gly
                645                 650                 655

Cys Ile Arg Ser Leu Lys Leu Thr Lys Gly Thr Ala Ser His Trp Arg
                660                 665                 670

Leu Ile Leu Pro Arg Pro Trp Asn
                675                 680

<210> SEQ ID NO 22
<211> LENGTH: 680
<212> TYPE: PRT
<213> ORGANISM: Artificial Sequence
<220> FEATURE:
<223> OTHER INFORMATION: Synthetic Polypeptide

<400> SEQUENCE: 22

Met Lys Leu Leu Pro Ser Val Val Leu Lys Leu Phe Leu Ala Ala Val
1               5                   10                  15

Leu Ser Ala Leu Val Thr Gly Glu Ser Leu Glu Arg Leu Arg Arg Gly
            20                  25                  30

Leu Ala Ala Gly Thr Ser Asn Pro Asp Pro Thr Val Ser Thr Asp
        35                  40                  45

Gln Leu Leu Pro Leu Gly Gly Gly Arg Asp Arg Lys Val Arg Asp Leu
    50                  55                  60

Gln Glu Ala Asp Leu Asp Leu Leu Arg Val Thr Leu Ser Ser Lys Pro
65                  70                  75                  80

Gln Ala Leu Ala Thr Pro Asn Lys Glu Glu His Gly Lys Arg Lys Lys
            85                  90                  95

Lys Gly Lys Gly Leu Gly Lys Lys Arg Asp Pro Cys Leu Arg Lys Tyr
            100                 105                 110

Lys Asp Phe Cys Ile His Gly Glu Cys Lys Tyr Val Lys Glu Leu Arg
        115                 120                 125

Ala Pro Ser Cys Ile Cys His Pro Gly Tyr His Gly Glu Arg Cys His
    130                 135                 140

Gly Leu Ser Leu Pro Gln Thr Gly Gln Ala Tyr Tyr Val Ile Leu Leu
145                 150                 155                 160

Asn Arg Gly Arg Leu Glu Val His Leu Ser Thr Gly Ala Arg Thr Met
                165                 170                 175

Arg Lys Ile Val Ile Arg Pro Glu Pro Asn Leu Phe His Asp Gly Arg
            180                 185                 190

Glu His Ser Val His Val Glu Arg Thr Arg Gly Ile Phe Thr Val Gln
        195                 200                 205

Val Asp Glu Asn Arg Arg Tyr Met Gln Asn Leu Thr Val Glu Gln Pro
    210                 215                 220

Ile Glu Val Lys Lys Leu Phe Val Gly Gly Ala Pro Pro Glu Phe Gln
225                 230                 235                 240

Pro Ser Pro Leu Arg Asn Ile Pro Pro Phe Glu Gly Cys Ile Trp Asn
```

-continued

```
                245                250                255
Leu Val Ile Asn Ser Val Pro Met Asp Phe Ala Arg Pro Val Ser Phe
            260                265                270
Lys Asn Ala Asp Ile Gly Arg Cys Ala His Gln Lys Leu Arg Glu Asp
            275                280                285
Glu Asp Gly Ala Ala Pro Ala Glu Ile Val Ile Gln Pro Glu Pro Val
            290                295                300
Pro Thr Pro Ala Phe Pro Thr Pro Thr Pro Val Leu Thr His Gly Pro
305                310                315                320
Cys Ala Ala Glu Ser Glu Pro Ala Leu Leu Ile Gly Ser Lys Gln Phe
                325                330                335
Gly Leu Ser Arg Asn Ser His Ile Ala Ile Ala Phe Asp Asp Thr Lys
            340                345                350
Val Lys Asn Arg Leu Thr Ile Glu Leu Glu Val Arg Thr Glu Ala Glu
            355                360                365
Ser Gly Leu Leu Phe Tyr Met Ala Arg Ile Asn His Ala Asp Phe Ala
            370                375                380
Thr Val Gln Leu Arg Asn Gly Leu Pro Tyr Phe Ser Tyr Asp Leu Gly
385                390                395                400
Ser Gly Asp Thr His Thr Met Ile Pro Thr Lys Ile Asn Asp Gly Gln
                405                410                415
Trp His Lys Ile Lys Ile Met Arg Ser Lys Gln Glu Gly Ile Leu Tyr
                420                425                430
Val Asp Gly Ala Ser Asn Arg Thr Ile Ser Pro Lys Lys Ala Asp Ile
            435                440                445
Leu Asp Val Val Gly Met Leu Tyr Val Gly Gly Leu Pro Ile Asn Tyr
            450                455                460
Thr Thr Arg Arg Ile Gly Pro Val Thr Tyr Ser Ile Asp Gly Cys Val
465                470                475                480
Arg Asn Leu His Met Ala Glu Ala Pro Ala Asp Leu Glu Gln Pro Thr
                485                490                495
Ser Ser Phe His Val Gly Thr Cys Phe Ala Asn Ala Gln Arg Gly Thr
                500                505                510
Tyr Phe Asp Gly Thr Gly Phe Ala Lys Ala Val Gly Gly Phe Lys Val
            515                520                525
Gly Leu Asp Leu Leu Val Glu Phe Glu Phe Arg Thr Thr Thr Thr Thr
530                535                540
Gly Val Leu Leu Gly Ile Ser Ser Gln Lys Met Asp Gly Met Gly Ile
545                550                555                560
Glu Met Ile Asp Glu Lys Leu Met Phe His Val Asp Asn Gly Ala Gly
                565                570                575
Arg Phe Thr Ala Val Tyr Asp Ala Gly Val Pro Gly His Leu Cys Asp
            580                585                590
Gly Gln Trp His Lys Val Thr Ala Asn Lys Ile Lys His Arg Ile Glu
            595                600                605
Leu Thr Val Asp Gly Asn Gln Val Glu Ala Gln Ser Pro Asn Pro Ala
            610                615                620
Ser Thr Ser Ala Asp Thr Asn Asp Pro Val Phe Val Gly Gly Phe Pro
625                630                635                640
Asp Asp Leu Lys Gln Phe Gly Leu Thr Thr Ser Ile Pro Phe Arg Gly
                645                650                655
Cys Ile Arg Ser Leu Lys Leu Thr Lys Gly Thr Ala Ser His Trp Arg
            660                665                670
```

-continued

```
Leu Ile Leu Pro Arg Pro Trp Asn
        675                 680

<210> SEQ ID NO 23
<211> LENGTH: 448
<212> TYPE: PRT
<213> ORGANISM: Artificial Sequence
<220> FEATURE:
<223> OTHER INFORMATION: Synthetic Polypeptide

<400> SEQUENCE: 23

Met Lys Leu Leu Pro Ser Val Val Leu Lys Leu Phe Leu Ala Ala Val
1               5                   10                  15

Leu Ser Ala Leu Val Thr Gly Glu Ser Leu Glu Arg Leu Arg Arg Gly
            20                  25                  30

Leu Ala Ala Gly Thr Ser Asn Pro Asp Pro Pro Thr Val Ser Thr Asp
            35                  40                  45

Gln Leu Leu Pro Leu Gly Gly Gly Arg Asp Arg Lys Val Arg Asp Leu
        50                  55                  60

Gln Glu Ala Asp Leu Asp Leu Leu Arg Val Thr Leu Ser Ser Lys Pro
65                  70                  75                  80

Gln Ala Leu Ala Thr Pro Asn Lys Glu Glu His Gly Lys Arg Lys Lys
                85                  90                  95

Lys Gly Lys Gly Leu Gly Lys Lys Arg Asp Pro Gln Ile His Ala Thr
            100                 105                 110

Pro Thr Pro Val Thr Ala Ile Gly Pro Pro Thr Thr Ala Ile Gln Glu
            115                 120                 125

Pro Pro Ser Arg Ile Val Pro Thr Pro Thr Ser Pro Ala Ile Ala Pro
        130                 135                 140

Pro Thr Glu Thr Met Ala Pro Pro Val Arg Asp Pro Val Pro Gly Lys
145                 150                 155                 160

Pro Thr Val Thr Ile Arg Thr Arg Gly Ala Ile Ile Gln Thr Pro Thr
                165                 170                 175

Leu Gly Pro Ile Gln Pro Thr Arg Val Ser Glu Ala Gly Thr Thr Val
                180                 185                 190

Pro Gly Gln Ile Arg Pro Thr Met Thr Ile Pro Gly Tyr Val Glu Pro
            195                 200                 205

Thr Ala Val Ala Thr Pro Pro Thr Thr Thr Lys Lys Pro Arg Val
        210                 215                 220

Ser Thr Pro Lys Pro Ala Thr Pro Ser Thr Asp Ser Thr Thr Thr Thr
225                 230                 235                 240

Thr Arg Arg Pro Thr Lys Lys Pro Arg Thr Pro Arg Pro Val Pro Arg
                245                 250                 255

Val Thr Thr Lys Val Ser Ile Thr Arg Leu Glu Thr Ala Ser Pro Pro
                260                 265                 270

Thr Arg Ile Arg Thr Thr Thr Ser Gly Val Pro Arg Gly Gly Glu Pro
            275                 280                 285

Asn Gln Arg Pro Glu Leu Lys Asn His Ile Asp Arg Val Asp Ala Trp
        290                 295                 300

Val Gly Thr Tyr Phe Glu Val Lys Ile Pro Ser Asp Thr Phe Tyr Asp
305                 310                 315                 320

His Glu Asp Thr Thr Thr Asp Lys Leu Lys Leu Thr Leu Lys Leu Arg
                325                 330                 335

Glu Gln Gln Leu Val Gly Glu Lys Ser Trp Val Gln Phe Asn Ser Asn
            340                 345                 350
```

```
Ser Gln Leu Met Tyr Gly Leu Pro Asp Ser Ser His Val Gly Lys His
        355             360             365

Glu Tyr Phe Met His Ala Thr Asp Lys Gly Gly Leu Ser Ala Val Asp
    370             375             380

Ala Phe Glu Ile His Val His Arg Arg Pro Gln Gly Asp Arg Ala Pro
385             390             395             400

Ala Arg Phe Lys Ala Lys Phe Val Gly Asp Pro Ala Leu Val Leu Asn
            405             410             415

Asp Ile His Lys Lys Ile Ala Leu Val Lys Lys Leu Ala Phe Ala Phe
            420             425             430

Gly Asp Arg Asn Cys Ser Thr Ile Thr Leu Gln Asn Ile Thr Arg Gly
        435             440             445
```

<210> SEQ ID NO 24
<211> LENGTH: 490
<212> TYPE: PRT
<213> ORGANISM: Artificial Sequence
<220> FEATURE:
<223> OTHER INFORMATION: Synthetic Polypeptide

<400> SEQUENCE: 24

```
Met Lys Leu Leu Pro Ser Val Val Leu Lys Leu Phe Leu Ala Ala Val
1               5               10              15

Leu Ser Ala Leu Val Thr Gly Glu Ser Leu Glu Arg Leu Arg Arg Gly
            20              25              30

Leu Ala Ala Gly Thr Ser Asn Pro Asp Pro Thr Val Ser Thr Asp
        35              40              45

Gln Leu Leu Pro Leu Gly Gly Gly Arg Asp Arg Lys Val Arg Asp Leu
    50              55              60

Gln Glu Ala Asp Leu Asp Leu Leu Arg Val Thr Leu Ser Ser Lys Pro
65              70              75              80

Gln Ala Leu Ala Thr Pro Asn Lys Glu Glu His Gly Lys Arg Lys Lys
            85              90              95

Lys Gly Lys Gly Leu Gly Lys Lys Arg Asp Pro Cys Leu Arg Lys Tyr
            100             105             110

Lys Asp Phe Cys Ile His Gly Glu Cys Lys Tyr Val Lys Glu Leu Arg
            115             120             125

Ala Pro Ser Cys Ile Cys His Pro Gly Tyr His Gly Glu Arg Cys His
    130             135             140

Gly Leu Ser Leu Pro Gln Ile His Ala Thr Pro Thr Pro Val Thr Ala
145             150             155             160

Ile Gly Pro Pro Thr Thr Ala Ile Gln Glu Pro Pro Ser Arg Ile Val
            165             170             175

Pro Thr Pro Thr Ser Pro Ala Ile Ala Pro Pro Thr Glu Thr Met Ala
            180             185             190

Pro Pro Val Arg Asp Pro Val Pro Gly Lys Pro Thr Val Thr Ile Arg
            195             200             205

Thr Arg Gly Ala Ile Ile Gln Thr Pro Thr Leu Gly Pro Ile Gln Pro
    210             215             220

Thr Arg Val Ser Glu Ala Gly Thr Thr Val Pro Gly Gln Ile Arg Pro
225             230             235             240

Thr Met Thr Ile Pro Gly Tyr Val Glu Pro Thr Ala Val Ala Thr Pro
            245             250             255

Pro Thr Thr Thr Thr Lys Lys Pro Arg Val Ser Thr Pro Lys Pro Ala
            260             265             270
```

```
Thr Pro Ser Thr Asp Ser Thr Thr Thr Thr Thr Arg Arg Pro Thr Lys
        275                 280                 285

Lys Pro Arg Thr Pro Arg Pro Val Pro Arg Val Thr Thr Lys Val Ser
    290                 295                 300

Ile Thr Arg Leu Glu Thr Ala Ser Pro Pro Thr Arg Ile Arg Thr Thr
305                 310                 315                 320

Thr Ser Gly Val Pro Arg Gly Gly Glu Pro Asn Gln Arg Pro Glu Leu
                325                 330                 335

Lys Asn His Ile Asp Arg Val Asp Ala Trp Val Gly Thr Tyr Phe Glu
            340                 345                 350

Val Lys Ile Pro Ser Asp Thr Phe Tyr Asp His Glu Asp Thr Thr Thr
        355                 360                 365

Asp Lys Leu Lys Leu Thr Leu Lys Leu Arg Glu Gln Gln Leu Val Gly
    370                 375                 380

Glu Lys Ser Trp Val Gln Phe Asn Ser Asn Ser Gln Leu Met Tyr Gly
385                 390                 395                 400

Leu Pro Asp Ser Ser His Val Gly Lys His Glu Tyr Phe Met His Ala
                405                 410                 415

Thr Asp Lys Gly Gly Leu Ser Ala Val Asp Ala Phe Glu Ile His Val
            420                 425                 430

His Arg Arg Pro Gln Gly Asp Arg Ala Pro Ala Arg Phe Lys Ala Lys
        435                 440                 445

Phe Val Gly Asp Pro Ala Leu Val Leu Asn Asp Ile His Lys Lys Ile
    450                 455                 460

Ala Leu Val Lys Lys Leu Ala Phe Ala Phe Gly Asp Arg Asn Cys Ser
465                 470                 475                 480

Thr Ile Thr Leu Gln Asn Ile Thr Arg Gly
                485                 490
```

```
<210> SEQ ID NO 25
<211> LENGTH: 4637
<212> TYPE: DNA
<213> ORGANISM: Artificial Sequence
<220> FEATURE:
<223> OTHER INFORMATION: Synthetic Polynucleotide

<400> SEQUENCE: 25
```

```
gcgcgctcgc tcgctcactg aggccgcccg ggcaaagccc gggcgtcggg cgacctttgg      60
tcgcccggcc tcagtgagcg agcgagcgcg cagagaggga gtggccaact ccatcactag     120
gggttccttg tagttaatga ttaacccgcc atgctaatta tctacgtagc catgtctagg     180
gtcgttacat aacttacggt aaatggcccg cctggctgac cgcccaacga cccccgccca     240
ttgacgtcaa taatgacgta tgttcccata gtaacgccaa tagggacttt ccattgacgt     300
caatgggtgg agtatttacg gtaaactgcc cacttggcag tacatcaagt gtatcatatg     360
ccaagtacgc cccctattga cgtcaatgac ggtaaatggc ccgcctggca ttatgcccag     420
tacatgacct tatgggactt tcctacttgg cagtacatct acgtattagt catcgctatt     480
accatggtga tgcggttttg gcagtacatc aatgggcgtg atagcggttt gactcacgg      540 ggatttccaa gtctccaccc cattgacgtc aatgggagtt tgttttggca ccaaaatcaa     600
cgggactttc caaaatgtcg taacaactcc gccccattga cgcaaatggg cggtaggcgt     660
gtacggtggg aggtctatat aagcagagct cgtttagtga accgtcagat cgcctggaga     720
cgccatccac gctgttttga cctccataga agacaccggg accgatccag cctccggact     780
```

-continued

```
ctagaggatc cggtactcga ggaactgaaa aaccagaaag ttaactggta agtttagtct      840
ttttgtcttt tatttcaggt cccggatccg gtggtggtgc aaatcaaaga actgctcctc      900
agtggatgtt gcctttactt ctaggcctgt acggaagtgt tacttctgct ctaaaagctg      960
cggaattgta cccgcggccg caccatgaag ctgctgccgt cggtggtgct gaagctcttt     1020
ctggctgcag ttctctcggc actggtgact ggcgagagcc tggagcggct tcggagaggg     1080
ctagctgctg gaaccagcaa cccggaccct cccactgtat ccacggacca gctgctaccc     1140
ctaggaggcg gccgggaccg gaaagtccgt gacttgcaag aggcagatct ggaccttttg     1200
agagtcactt tatcctccaa gccacaagca ctggccacac caaacaagga ggagcacggg     1260
aaaagaaaga agaaaggcaa ggggctaggg aagaagaggg acccaaaagt atctgtgtct     1320
tcaggaggtg actgcattcg aacatacaaa ccagtttccc gtgctcctcc ttgtttgaaa     1380
tcaagaaagg aagttacaat aatattgttg tcaacgtaaa gacagctgtt gctgataacc     1440
tcctctttta tcttggaagt gccaaattta ttgactttct ggctatagaa atgcgtaaag     1500
gcaaagtcag cttcctctgg gatgttggat ctggagttgg acgtgtagag tacccagatt     1560
tgactattga tgactcatat tggtaccgta tcgtagcatc aagaactggg agaaatggaa     1620
ctatttctgt gagagccctg gatggaccca aagccagctg tgtgcccagc acacaccatt     1680
cgacgtctcc tccagggtac acgattctag atgtggatgc aaatgcaatg ctgtttgttg     1740
gtggcctgac tgggaaatta aagaaggctg atgctgtacg tgtgattaca ttcactggct     1800
gcatgggaga aacatacttt gacaacaaac ctataggttt gtggaatttc cgagaaaaag     1860
aaggtgactg caaaggatgc actgtcagtc ctcaggtgga agatagtgag gggactattc     1920
aatttgatgg agaaggttat gcattggtca gccgtcccat tcgctggtac cccaacatct     1980
ccactgtcat gttcaagttc agaacatttt cttcgagtgc tcttctgatg tatcttgcca     2040
cacgagacct gagagatttc atgagtgtgg agctcactga tgggcacata aaagtcagtt     2100
acgatctggg ctcaggaatg gcttccgttg tcagcaatca aaaccataat gatgggaaat     2160
ggaaatcatt cactctgtca agaattcaaa aacaagccaa tatatcaatt gtagatatag     2220
atactaatca ggaggagaat atagcaactt cgtcttctgg aaacaacttt ggtcttgact     2280
tgaaagcaga tgacaaaata tattttggtg gcctgccaac gctgagaaac ttgagtatga     2340
aagcaaggcc agaagtaaat ctgaagaaat attccggctg cctcaaagat attgaaattt     2400
caagaactcc gtacaatata ctcagtagtc ccgattatgt tggtgttacc aaaggatgtt     2460
ccctggagaa tgtttacaca gttagctttc ctaagcctgg ttttgtggag ctctcccctg     2520
tgccaattga tgtaggaaca gaaatcaacc tgtcattcag caccaagaat gagtccggca     2580
tcattctttt gggaagtgga gggacaccag caccacctag gagaaaacga aggcagactg     2640
gacaggccta ttatgtaata ctcctcaaca ggggccgtct ggaagtgcat ctctccacag     2700
gggcacgaac aatgaggaaa attgtcatca gaccagagcc gaatctgttt catgatggaa     2760
gagaacattc cgttcatgta gagcgaacta gaggcatctt tacagttcaa gtggatgaaa     2820
acagaagata catgcaaaac ctgacagttg aacagcctat cgaagttaaa aagcttttcg     2880
ttgggggtgc tccacctgaa tttcaacctt ccccactcag aaatattcct ccttttgaag     2940
gctgcatatg gaatcttgtt attaactctg tccccatgga ctttgcaagg cctgtgtcct     3000
tcaaaaatgc tgacattggt cgctgtgccc atcagaaact ccgtgaagat gaagatggag     3060
cagctccagc tgaaatagtt atccagcctg agccagttcc caccccagcc tttcctacgc     3120 ccacccagt tctgacacat ggtccttgtg ctgcagaatc agaaccagct cttttgatag     3180
```

-continued

```
ggagcaagca gttcgggctt tcaagaaaca gtcacattgc aattgcattt gatgacacca    3240
aagttaaaaa ccgtctcaca attgagttgg aagtaagaac cgaagctgaa tccggcttgc    3300
ttttttacat ggctcgcatc aatcatgctg attttgcaac agttcagctg agaaatggat    3360
tgccctactt cagctatgac ttggggagtg gggacaccca caccatgatc cccaccaaaa    3420
tcaatgatgg ccagtggcac aagattaaga taatgagaag taagcaagaa ggaattcttt    3480
atgtagatgg ggcttccaac agaaccatca gtcccaaaaa agccgacatc ctggatgtcg    3540
tgggaatgct gtatgttggt gggttaccca tcaactacac tacccgaaga attggtccag    3600
tgacctatag cattgatggc tgcgtcagga atctccacat ggcagaggcc cctgccgatc    3660
tggaacaacc cacctccagc ttccatgttg ggacatgttt tgcaaatgct cagaggggaa    3720
catattttga cggaaccggt tttgccaaag cagttggtgg attcaaagtg ggattggacc    3780
ttcttgtaga atttgaattc cgcacaacta caacgactgg agttcttctg gggatcagta    3840
gtcaaaaaat ggatggaatg ggtattgaaa tgattgatga aaagttgatg tttcatgtgg    3900
acaatggtgc gggcagattc actgctgtct atgatgctgg ggttccaggg catttgtgtg    3960
atggacaatg gcataaagtc actgccaaca agatcaaaca ccgcattgag ctcacagtcg    4020
atgggaacca ggtggaagcc caaagcccaa acccagcatc tacatcagct gacacaaatg    4080
accctgtgtt tgttggaggc ttcccagatg acctcaagca gtttggccta acaaccagta    4140
ttccgttccg aggttgcatc agatccctga gctcaccaa aggcacagca agccactgga    4200
ggttaatttt gccaaggccc tggaactgaa ctagtgcggc cgcggggatc cagacatgat    4260
aagatacatt gatgagtttg gacaaaccac aactagaatg cagtgaaaaa aatgctttat    4320
ttgtgaaatt tgtgatgcta ttgctttatt tgtaaccatt ataagctgca ataaacaagt    4380
taacaacaac aattgcattc attttatgtt tcaggttcag ggggaggtgt gggaggtttt    4440
ttcggatcct ctagagtcga ccacatggct acgtagataa ttagcatggc gggttaatca    4500
ttaactacaa ggaacccta gtgatggagt tggccactcc ctctctgcgc gctcgctcgc    4560
tcactgaggc cgggcgacca aaggtcgccc gacgcccggg ctttgcccgg gcggcctcag    4620
tgagcgagcg agcgcgc                                                    4637
```

```
<210> SEQ ID NO 26
<211> LENGTH: 2739
<212> TYPE: DNA
<213> ORGANISM: Artificial Sequence
<220> FEATURE:
<223> OTHER INFORMATION: Synthetic Polynucleotide

<400> SEQUENCE: 26
gcgcgctcgc tcgctcactg aggccgcccg ggcaaagccc gggcgtcggg cgacctttgg      60
tcgcccggcc tcagtgagcg agcgagcgcg cagagaggga gtggccaact ccatcactag     120
gggttccttg tagttaatga ttaacccgcc atgctaatta tctacgtagc catgtctagg     180
gtcgttacat aacttacggt aaatggcccg cctggctgac cgcccaacga ccccgccca     240 ttgacgtcaa taatgacgta tgttcccata gtaacgccaa tagggacttt ccattgacgt     300
caatgggtgg agtatttacg gtaaactgcc cacttggcag tacatcaagt gtatcatatg     360
ccaagtacgc ccctattga cgtcaatgac ggtaaatggc ccgcctggca ttatgcccag     420
tacatgacct tatgggactt tcctacttgg cagtacatct acgtattagt catcgctatt     480
accatggtga tgcggttttg gcagtacatc aatgggcgtg atagcggttt tgactcacgg     540
```

```
ggatttccaa gtctccaccc cattgacgtc aatgggagtt tgttttggca ccaaaatcaa      600
cgggactttc caaaatgtcg taacaactcc gccccattga cgcaaatggg cggtaggcgt      660
gtacggtggg aggtctatat aagcagagct cgtttagtga accgtcagat cgcctggaga      720
cgccatccac gctgttttga cctccataga agacaccggg accgatccag cctccggact      780
ctagaggatc cggtactcga ggaactgaaa aaccagaaag ttaactggta agtttagtct      840
ttttgtcttt tatttcaggt cccggatccg gtggtggtgc aaatcaaaga actgctcctc      900
agtggatgtt gcctttactt ctaggcctgt acggaagtgt tacttctgct ctaaaagctg      960
cggaattgta cccgcggccg caccatgaag ctgctgccgt cggtggtgct gaagctcttt     1020
ctggctgcag ttctctcggc actggtgact ggcgagagcc tggagcggct tcggagaggg     1080
ctagctgctg gaaccagcaa cccgaccct cccactgtat ccacggacca gctgctaccc     1140
ctaggaggcg gccgggaccg gaaagtccgt gacttgcaag aggcagatct ggacctttg      1200 agagtcactt tatcctccaa gccacaagca ctggccacac caaacaagga ggagcacggg     1260
aaaagaaaga agaaaggcaa ggggctaggg aagaagaggg acccacagat ccatgctaca     1320
cccacacctg tcactgccat tgggcccca accacggcta tccaggagcc cccatccagg      1380
atcgtgccaa cccccacatc tccagccatt gctcctccaa cagagaccat ggctcctcca     1440
gtcagggatc ctgttcctgg gaaacccacg gtcaccatcc ggactcgagg cgccattatt     1500
caaaccccaa ccctaggccc catccagcct actcgggtgt cagaagctgg caccacagtt     1560
cctggccaga ttcgcccaac gatgaccatt cctggctatg tggagcctac tgcagttgct     1620 accctccca caaccaccac caagaagcca cgagtatcca caccaaaacc agcaacgcct      1680
tcaactgact ccaccaccac cacgactcgc aggccaacca agaaaccacg gacaccccgg     1740
ccagtgcccc gggtcaccac caaagtttcc atcaccagat tggaaactgc ctcaccgcct     1800
actcgtattc gcaccaccac cagtggagtg ccccgtggcg gagaacccaa ccagcgccca     1860
gagctcaaga accatattga cagggtagat gcctgggttg gcacctactt tgaggtgaag     1920
atcccgtcag acactttcta tgaccatgag gacaccacca ctgacaagct gaagctgacc     1980
ctgaaactgc gggagcagca gctggtgggc gagaagtcct gggtacagtt caacagcaac     2040
agccagctca tgtatggcct tcccgacagc agccacgtgg gcaaacacga gtatttcatg     2100
catgccacag acaaggggg cctgtcggct gtggatgcct tcgagatcca cgtccacagg     2160
cgcccccaag gggatagggc tcctgcaagg ttcaaggcca agtttgtggg tgacccggca     2220
ctggtgttga atgacatcca caagaagatt gccttggtaa agaaactggc cttcgccttt     2280
ggagaccgaa actgtagcac catcaccctg cagaatatca cccgggggcta aactagtgcg     2340 gccgcgggga tccagacatg ataagataca ttgatgagtt tggacaaacc acaactagaa     2400
tgcagtgaaa aaaatgcttt atttgtgaaa tttgtgatgc tattgcttta tttgtaacca     2460
ttataagctg caataaacaa gttaacaaca caattgcat tcattttatg tttcaggttc      2520
agggggaggt gtgggaggtt ttttcggatc ctctagagtc gaccacatgg ctacgtagat     2580
aattagcatg gcgggttaat cattaactac aaggaacccc tagtgatgga gttggccact     2640
ccctctctgc gcgctcgctc gctcactgag gccgggcgac caaaggtcgc ccgacgcccg     2700
ggctttgccc gggcggcctc agtgagcgag cgagcgcgc                           2739
```

<210> SEQ ID NO 27
<211> LENGTH: 3251
<212> TYPE: DNA
<213> ORGANISM: Artificial Sequence -continued

```
<220> FEATURE:
<223> OTHER INFORMATION: Synthetic Polynucleotide

<400> SEQUENCE: 27
aagcggccgc accatgaagc tgctgccgtc ggtggtgctg aagctctttc tggctgcagt      60
tctctcggca ctggtgactg gcgagagcct ggagcggctt cggagagggc tagctgctgg     120
aaccagcaac ccggaccctc ccactgtatc cacggaccag ctgctacccc taggaggcgg     180
ccgggaccgg aaagtccgtg acttgcaaga ggcagatctg gaccttttga gagtcacttt     240
atcctccaag ccacaagcac tggccacacc aaacaaggag gagcacggga aaagaaagaa     300
gaaaggcaag gggctaggga agaagaggga cccaaaagta tctgtgtctt caggaggtga     360
ctgcattcga acatacaaac cagaaatcaa gaaaggaagt tacaataata ttgttgtcaa     420
cgtaaagaca gctgttgctg ataacctcct cttttatctt ggaagtgcca aatttattga     480
ctttctggct atagaaatgc gtaaaggcaa agtcagcttc ctctgggatg ttggatctgg     540
agttggacgt gtagagtacc cagatttgac tattgatgac tcatattggt accgtatcgt     600
agcatcaaga actgggagaa atggaactat ttctgtgaga gccctggatg acccaaagc      660 cagcattgtg cccagcacac accattcgac gtctcctcca gggtacacga ttctagatgt     720
ggatgcaaat gcaatgctgt ttgttggtgg cctgactggg aaattaaaga aggctgatgc     780
tgtacgtgtg attacattca ctggctgcat gggagaaaca tactttgaca acaaacctat     840
aggtttgtgg aatttccgag aaaaagaagg tgactgcaaa ggatgcactg tcagtcctca     900
ggtggaagat agtgagggga ctattcaatt tgatggagaa ggttatgcat ggtcagccg      960 tcccattcgc tggtacccca acatctccac tgtcatgttc aagttcagaa cattttcttc    1020
gagtgctctt ctgatgtatc ttgccacacg agacctgaga gatttcatga gtgtggagct    1080
cactgatggg cacataaaag tcagttacga tctgggctca ggaatggctt ccgttgtcag    1140
caatcaaaac cataatgatg ggaaatggaa atcattcact ctgtcaagaa ttcaaaaaca    1200
agccaatata tcaattgtag atatagatac taatcaggag gagaatatag caacttcgtc    1260
ttctggaaac aactttggtc ttgacttgaa agcagatgac aaaatatatt ttggtggcct    1320
gccaacgctg agaaacttga gtatgaaagc aaggccagaa gtaaatctga agaaatattc    1380
cggctgcctc aaagatattg aaatttcaag aactccgtac aatatactca gtagtcccga    1440
ttatgttggt gttaccaaag gatgttccct ggagaatgtt tacacagtta gctttcctaa    1500
gcctggtttt gtggagctct cccctgtgcc aattgatgta ggaacagaaa tcaacctgtc    1560
attcagcacc aagaatgagt ccggcatcat tctttggga agtggaggga caccagcacc    1620
acctaggaga aaacgaaggc agactggaca ggcctattat gtaatactcc tcaacagggg    1680
ccgtctggaa gtgcatctct ccacagggc acgaacaatg aggaaaattg tcatcagacc    1740
agagccgaat ctgtttcatg atggaagaga acattccgtt catgtagagc gaactagagg    1800
catctttaca gttcaagtgg atgaaaacag aagatacatg caaaacctga cagttgaaca    1860
gcctatcgaa gttaaaaagc ttttcgttgg gggtgctcca cctgaatttc aaccttcccc    1920
actcagaaat attcctcctt ttgaaggctg catatggaat cttgttatta actctgtccc    1980
catggacttt gcaaggcctg tgtccttcaa aaatgctgac attggtcgct gtgcccatca    2040
gaaactccgt gaagatgaag atggagcagc tccagctgaa atagttatcc agcctgagcc    2100
agttcccacc ccagcctttc ctacgcccac cccagttctg acacatggtc cttgtgctgc    2160
agaatcagaa ccagctcttt tgatagggag caagcagttc gggctttcaa gaaacagtca    2220
```

-continued

```
cattgcaatt gcatttgatg acaccaaagt taaaaaccgt ctcacaattg agttggaagt      2280
aagaaccgaa gctgaatccg gcttgctttt ttacatggct cgcatcaatc atgctgattt      2340
tgcaacagtt cagctgagaa atggattgcc ctacttcagc tatgacttgg ggagtgggga      2400
cacccacacc atgatcccca ccaaaatcaa tgatggccag tggcacaaga ttaagataat      2460
gagaagtaag caagaaggaa ttctttatgt agatggggct tccaacagaa ccatcagtcc      2520
caaaaaagcc gacatcctgg atgtcgtggg aatgctgtat gttggtgggt tacccatcaa      2580
ctacactacc cgaagaattg gtccagtgac ctatagcatt gatggctgcg tcaggaatct      2640
ccacatggca gaggcccctg ccgatctgga acaacccacc tccagcttcc atgttgggac      2700
atgttttgca aatgctcaga ggggaacata ttttgacgga accggttttg ccaaagcagt      2760
tggtggattc aaagtgggat tggaccttct tgtagaattt gaattccgca caactacaac      2820
gactggagtt cttctgggga tcagtagtca aaaaatggat ggaatgggta ttgaaatgat      2880
tgatgaaaag ttgatgtttc atgtggacaa tggtgcgggc agattcactg ctgtctatga      2940 tgctgggggtt ccagggcatt tgtgtgatgg acaatggcat aaagtcactg ccaacaagat      3000
caaacaccgc attgagctca cagtcgatgg gaaccaggtg gaagcccaaa gcccaaaccc      3060
agcatctaca tcagctgaca caaatgaccc tgtgtttgtt ggaggcttcc cagatgacct      3120
caagcagttt ggcctaacaa ccagtattcc gttccgaggt tgcatcagat ccctgaagct      3180
caccaaaggc acagcaagcc actggaggtt aattttgcca aggccctgga actgaactag      3240
tgcggccgca a                                                           3251
```

<210> SEQ ID NO 28
<211> LENGTH: 3377
<212> TYPE: DNA
<213> ORGANISM: Artificial Sequence
<220> FEATURE:
<223> OTHER INFORMATION: Synthetic Polynucleotide

<400> SEQUENCE: 28

```
aagcggccgc accatgaagc tgctgccgtc ggtggtgctg aagctctttc tggctgcagt        60
tctctcggca ctggtgactg gcgagagcct ggagcggctt cggagagggc tagctgctgg       120
aaccagcaac ccggacccctc ccactgtatc cacggaccag ctgctacccc taggaggcgg       180
ccgggaccgg aaagtccgtg acttgcaaga ggcagatctg gacctttttga gagtcacttt       240 atcctccaag ccacaagcac tggccacacc aaacaaggag gagcacggga aaagaaagaa       300
gaaaggcaag gggctaggga agaagaggga cccatgtctt cggaaataca aggacttctg       360
catccatgga gaatgcaaat atgtgaagga gctccgggct ccctcctgca tctgccaccc       420
gggttaccat ggagagaggt gtcatgggct gagcctccca aaagtatctg tgtcttcagg       480
aggtgactgc attcgaacat acaaaccaga aatcaagaaa ggaagttaca ataatattgt       540
tgtcaacgta aagacagctg ttgctgataa cctcctcttt tatcttggaa gtgccaaatt       600
tattgacttt ctggctatag aaatgcgtaa aggcaaagtc agcttcctct gggatgttgg       660
atctggagtt ggacgtgtag agtacccaga tttgactatt gatgactcat attggtaccg       720
tatcgtagca tcaagaactg ggagaaatgg aactatttct gtgagagccc tggatggacc       780
caaagccagc attgtgccca gcacacacca ttcgacgtct cctccagggt acacgattct       840
agatgtggat gcaaatgcaa tgctgtttgt tggtggcctg actgggaaat taaagaaggc       900
tgatgctgta cgtgtgatta cattcactgg ctgcatggga gaaacatact ttgacaacaa       960
acctataggt ttgtggaatt ccgagaaaa agaaggtgac tgcaaaggat gcactgtcag      1020
```

-continued

```
tcctcaggtg gaagatagtg aggggactat tcaatttgat ggagaaggtt atgcattggt   1080
cagccgtccc attcgctggt accccaacat ctccactgtc atgttcaagt tcagaacatt   1140
ttcttcgagt gctcttctga tgtatcttgc cacacgagac ctgagagatt tcatgagtgt   1200
ggagctcact gatgggcaca taaaagtcag ttacgatctg ggctcaggaa tggcttccgt   1260
tgtcagcaat caaaaccata atgatgggaa atggaaatca ttcactctgt caagaattca   1320
aaaacaagcc aatatatcaa ttgtagatat agatactaat caggaggaga atatagcaac   1380
ttcgtcttct ggaaacaact ttggtcttga cttgaaagca gatgacaaaa tatattttgg   1440
tggcctgcca acgctgagaa acttgagtat gaaagcaagg ccagaagtaa atctgaagaa   1500
atattccggc tgcctcaaag atattgaaat ttcaagaact ccgtacaata tactcagtag   1560
tcccgattat gttggtgtta ccaaaggatg ttccctggag aatgtttaca cagttagctt   1620
tcctaagcct ggttttgtgg agctctcccc tgtgccaatt gatgtaggaa cagaaatcaa   1680
cctgtcattc agcaccaaga atgagtccgg catcattctt ttgggaagtg gagggacacc   1740
agcaccacct aggagaaaac gaaggcagac tggacaggcc tattatgtaa tactcctcaa   1800
caggggccgt ctggaagtgc atctctccac aggggcacga acaatgagga aaattgtcat   1860
cagaccagag ccgaatctgt ttcatgatgg aagagaacat tccgttcatg tagagcgaac   1920
tagaggcatc tttacagttc aagtggatga aaacagaaga tacatgcaaa acctgacagt   1980
tgaacagcct atcgaagtta aaaagctttt cgttgggggt gctccacctg aatttcaacc   2040
ttccccactc agaaatattc ctccttttga aggctgcata tggaatcttg ttattaactc   2100
tgtccccatg gactttgcaa ggcctgtgtc cttcaaaaat gctgacattg gtcgctgtgc   2160
ccatcagaaa ctccgtgaag atgaagatgg agcagctcca gctgaaatag ttatccagcc   2220
tgagccagtt cccaccccag cctttcctac gcccacccca gttctgacac atggtccttg   2280
tgctgcagaa tcagaaccag ctcttttgat agggagcaag cagttcgggc tttcaagaaa   2340
cagtcacatt gcaattgcat ttgatgacac caaagttaaa aaccgtctca caattgagtt   2400
ggaagtaaga accgaagctg aatccggctt gctttttttac atggctcgca tcaatcatgc   2460
tgattttgca acagttcagc tgagaaatgg attgccctac ttcagctatg acttggggag   2520
tggggacacc cacaccatga tccccaccaa aatcaatgat ggccagtggc acaagattaa   2580
gataatgaga agtaagcaag aaggaattct ttatgtagat ggggcttcca acagaaccat   2640
cagtcccaaa aaagccgaca tcctggatgt cgtgggaatg ctgtatgttg gtgggttacc   2700
catcaactac actacccgaa gaattggtcc agtgacctat agcattgatg gctgcgtcag   2760
gaatctccac atggcagagg cccctgccga tctggaacaa cccacctcca gcttccatgt   2820
tgggacatgt tttgcaaatg ctcagagggg aacatatttt gacggaaccg gttttgccaa   2880
agcagttggt ggattcaaag tgggattgga ccttcttgta gaatttgaat ccgcacaac   2940 tacaacgact ggagttcttc tggggatcag tagtcaaaaa atggatggaa tgggtattga   3000
aatgattgat gaaaagttga tgtttcatgt ggacaatggt gcgggcagat tcactgctgt   3060
ctatgatgct ggggttccag ggcatttgtg tgatggacaa tggcataaag tcactgccaa   3120
caagatcaaa caccgcattg agctcacagt cgatgggaac caggtggaag cccaaagccc   3180
aaacccagca tctacatcag ctgacacaaa tgaccctgtg tttgttggag gcttccaga   3240 tgacctcaag cagtttggcc taacaaccag tattccgttc cgaggttgca tcagatccct   3300
gaagctcacc aaaggcacag caagccactg gaggttaatt ttgccaaggc cctggaactg   3360
```

-continued

```
aactagtgcg gccgcaa                                                          3377

<210> SEQ ID NO 29
<211> LENGTH: 1946
<212> TYPE: DNA
<213> ORGANISM: Artificial Sequence
<220> FEATURE:
<223> OTHER INFORMATION: Synthetic Polynucleotide

<400> SEQUENCE: 29
aagcggccgc accatgaagc tgctgccgtc ggtggtgctg aagctctttc tggctgcagt      60
tctctcggca ctggtgactg gcgagagcct ggagcggctt cggagagggc tagctgctgg     120
aaccagcaac ccggaccctc ccactgtatc cacggaccag ctgctacccc taggaggcgg     180
ccgggaccgg aaagtccgtg acttgcaaga ggcagatctg gaccttttga gagtcacttt     240
atcctccaag ccacaagcac tggccacacc aaacaaggag gagcacggga aaagaaagaa     300
gaaaggcaag gggctaggga agaagaggga cccacagact ggacaggcct attatgtaat     360
actcctcaac aggggccgtc tggaagtgca tctctccaca ggggcacgaa caatgaggaa     420
aattgtcatc agaccagagc cgaatctgtt tcatgatgga agagaacatt ccgttcatgt     480
agagcgaact agaggcatct ttacagttca agtggatgaa aacagaagat acatgcaaaa     540
cctgacagtt gaacagccta tcgaagttaa aaagcttttc gttgggggtg ctccacctga     600
atttcaacct tccccactca gaaatattcc tccttttgaa ggctgcatat ggaatcttgt     660
tattaactct gtccccatgg actttgcaag gcctgtgtcc ttcaaaaatg ctgacattgg     720
tcgctgtgcc catcagaaac tccgtgaaga tgaagatgga gcagctccag ctgaaatagt     780
tatccagcct gagccagttc ccaccccagc ctttcctacg cccaccccag ttctgacaca     840
tggtccttgt gctgcagaat cagaaccagc tcttttgata gggagcaagc agttcgggct     900
ttcaagaaac agtcacattg caattgcatt tgatgacacc aaagttaaaa accgtctcac     960
aattgagttg gaagtaagaa ccgaagctga atccggcttg cttttttaca tggctcgcat    1020
caatcatgct gattttgcaa cagttcagct gagaaatgga ttgccctact tcagctatga    1080
cttggggagt ggggacaccc acaccatgat ccccaccaaa atcaatgatg ccagtggca    1140 caagattaag ataatgagaa gtaagcaaga aggaattctt tatgtagatg gggcttccaa    1200
cagaaccatc agtcccaaaa aagccgacat cctggatgtc gtgggaatgc tgtatgttgg    1260
tgggttaccc atcaactaca ctacccgaag aattggtcca gtgacctata gcattgatgg    1320
ctgcgtcagg aatctccaca tggcagaggc ccctgccgat ctggaacaac ccacctccag    1380
cttccatgtt gggacatgtt ttgcaaatgc tcagaggga acatattttg acggaaccgg    1440
ttttgccaaa gcagttggtg gattcaaagt gggattggac cttcttgtag aatttgaatt    1500
ccgcacaact acaacgactg gagttcttct ggggatcagt agtcaaaaaa tggatggaat    1560
gggtattgaa atgattgatg aaaagttgat gtttcatgtg gacaatggtg cgggcagatt    1620
cactgctgtc tatgatgctg gggttccagg gcatttgtgt gatggacaat ggcataaagt    1680
cactgccaac aagatcaaac accgcattga gctcacagtc gatgggaacc aggtggaagc    1740
ccaaagccca aacccagcat ctacatcagc tgacacaaat gaccctgtgt ttgttggagg    1800
cttcccagat gacctcaagc agtttggcct aacaaccagt attccgttcc gaggttgcat    1860
cagatccctg aagctcacca aaggcacagc aagccactgg aggttaattt tgccaaggcc    1920
ctggaactga actagtgcgg ccgcaa                                          1946
```

```
<210> SEQ ID NO 30
<211> LENGTH: 2072
<212> TYPE: DNA
<213> ORGANISM: Artificial Sequence
<220> FEATURE:
<223> OTHER INFORMATION: Synthetic Polynucleotide

<400> SEQUENCE: 30
aagcggccgc accatgaagc tgctgccgtc ggtggtgctg aagctctttc tggctgcagt        60
tctctcggca ctggtgactg gcgagagcct ggagcggctt cggagagggc tagctgctgg       120
aaccagcaac ccggaccctc ccactgtatc cacggaccag ctgctacccc taggaggcgg       180
ccgggaccgg aaagtccgtg acttgcaaga ggcagatctg gaccttttga gagtcacttt       240
atcctccaag ccacaagcac tggccacacc aaacaaggag gagcacggga aaagaaagaa       300
gaaaggcaag gggctaggga agaagaggga cccatgtctt cggaaataca aggacttctg       360
catccatgga gaatgcaaat atgtgaagga gctccgggct ccctcctgca tctgccaccc       420
gggttaccat ggagagaggt gtcatgggct gagcctccca cagactggac aggcctatta       480
tgtaatactc ctcaacaggg gccgtctgga agtgcatctc tccacagggg cacgaacaat       540
gaggaaaatt gtcatcagac cagagccgaa tctgtttcat gatggaagag aacattccgt       600
tcatgtagag cgaactagag gcatctttac agttcaagtg gatgaaaaca gaagatacat       660
gcaaaacctg acagttgaac agcctatcga agttaaaaag cttttcgttg ggggtgctcc       720
acctgaattt caaccttccc cactcagaaa tattcctcct tttgaaggct gcatatggaa       780
tcttgttatt aactctgtcc ccatggactt tgcaaggcct gtgtccttca aaaatgctga       840
cattggtcgc tgtgcccatc agaaactccg tgaagatgaa gatggagcag ctccagctga       900
aatagttatc cagcctgagc cagttcccac cccagccttt cctacgccca ccccagttct       960
gacacatggt ccttgtgctg cagaatcaga accagctctt ttgatataggga gcaagcagtt      1020 cgggctttca agaaacagtc acattgcaat tgcatttgat gacaccaaag ttaaaaaccg      1080
tctcacaatt gagttggaag taagaaccga agctgaatcc ggcttgcttt tttacatggc      1140
tcgcatcaat catgctgatt ttgcaacagt tcagctgaga aatggattgc cctacttcag      1200
ctatgacttg gggagtgggg acacccacac catgatcccc accaaaatca atgatggcca      1260
gtggcacaag attaagataa tgagaagtaa gcaagaagga attctttatg tagatgggc      1320 ttccaacaga accatcagtc ccaaaaaagc cgacatcctg gatgtcgtgg gaatgctgta      1380
tgttggtggg ttacccatca actacactac ccgaagaatt ggtccagtga cctatagcat      1440
tgatggctgc gtcaggaatc tccacatggc agaggcccct gccgatctgg aacaacccac      1500
ctccagcttc catgttggga catgtttttgc aaatgctcag aggggaacat attttgacgg      1560
aaccggtttt gccaaagcag ttggtggatt caaagtggga ttggaccttc ttgtagaatt      1620
tgaattccgc acaactacaa cgactggagt tcttctgggg atcagtagtc aaaaaatgga      1680
tggaatgggt attgaaatga ttgatgaaaa gttgatgttt catgtggaca atggtgcggg      1740
cagattcact gctgtctatg atgctgggg tccagggcat ttgtgtgatg gacaatggca      1800
taaagtcact gccaacaaga tcaaacaccg cattgagctc acagtcgatg ggaaccaggt      1860
ggaagcccaa agcccaaacc cagcatctac atcagctgac acaaatgacc ctgtgtttgt      1920
tggaggcttc ccagatgacc tcaagcagtt tggcctaaca accagtattc cgttccgagg      1980
ttgcatcaga tccctgaagc tcaccaaagg cacagcaagc cactggaggt taattttgcc      2040
aaggccctgg aactgaacta gtgcggccgc aa                                     2072
```

```
<210> SEQ ID NO 31
<211> LENGTH: 1376
<212> TYPE: DNA
<213> ORGANISM: Artificial Sequence
<220> FEATURE:
<223> OTHER INFORMATION: Synthetic Polynucleotide

<400> SEQUENCE: 31
aagcggccgc accatgaagc tgctgccgtc ggtggtgctg aagctctttc tggctgcagt        60
tctctcggca ctggtgactg gcgagagcct ggagcggctt cggagagggc tagctgctgg       120
aaccagcaac ccggaccctc ccactgtatc cacggaccag ctgctacccc taggaggcgg       180
ccgggaccgg aaagtccgtg acttgcaaga ggcagatctg gaccttttga gagtcacttt       240
atcctccaag ccacaagcac tggccacacc aaacaaggag gagcacggga aaagaaagaa       300
gaaaggcaag gggctaggga agaagaggga cccacagatc catgctacac ccacacctgt       360
cactgccatt gggcccccaa ccacggctat ccaggagccc ccatccagga tcgtgccaac       420
ccccacatct ccagccattg ctcctccaac agagaccatg gctcctccag tcagggatcc       480
tgttcctggg aaacccacgg tcaccatccg gactcgaggc gccattattc aaaccccaac       540
cctaggcccc atccagccta ctcgggtgtc agaagctggc accacagttc ctggccagat       600
tcgcccaacg atgaccattc ctggctatgt ggagcctact gcagttgcta cccctcccac       660
aaccaccacc aagaagccac gagtatccac accaaaacca gcaacgcctt caactgactc       720
caccaccacc acgactcgca ggccaaccaa gaaaccacgg acaccccggc cagtgccccg       780
ggtcaccacc aaagtttcca tcaccagatt ggaaactgcc tcaccgccta ctcgtattcg       840
caccaccacc agtggagtgc cccgtggcgg agaacccaac cagcgccag agctcaagaa       900 ccatattgac agggtagatg cctgggttgg cacctacttt gaggtgaaga tcccgtcaga       960
cactttctat gaccatgagg acaccaccac tgacaagctg aagctgaccc tgaaactgcg      1020
ggagcagcag ctggtgggcg agaagtcctg ggtacagttc aacagcaaca gccagctcat      1080
gtatggcctt cccgacagca gccacgtggg caaacacgag tatttcatgc atgccacaga      1140 caagggggc ctgtcggctg tggatgcctt cgagatccac gtccacaggc gcccccaagg      1200
ggatagggct cctgcaaggt tcaaggccaa gtttgtgggt gacccggcac tggtgttgaa      1260
tgacatccac aagaagattg ccttggtaaa gaaactggcc ttcgcctttg agaccgaaa      1320 ctgtagcacc atcaccctgc agaatatcac ccggggctaa actagtgcgg ccgcaa          1376

<210> SEQ ID NO 32
<211> LENGTH: 1502
<212> TYPE: DNA
<213> ORGANISM: Artificial Sequence
<220> FEATURE:
<223> OTHER INFORMATION: Synthetic Polynucleotide

<400> SEQUENCE: 32
aagcggccgc accatgaagc tgctgccgtc ggtggtgctg aagctctttc tggctgcagt        60
tctctcggca ctggtgactg gcgagagcct ggagcggctt cggagagggc tagctgctgg       120
aaccagcaac ccggaccctc ccactgtatc cacggaccag ctgctacccc taggaggcgg       180
ccgggaccgg aaagtccgtg acttgcaaga ggcagatctg gaccttttga gagtcacttt       240
atcctccaag ccacaagcac tggccacacc aaacaaggag gagcacggga aaagaaagaa       300
gaaaggcaag gggctaggga agaagaggga cccatgtctt cggaaataca aggacttctg       360
catccatgga gaatgcaaat atgtgaagga gctccgggct ccctcctgca tctgccaccc       420
```

-continued

```
gggttaccat ggagagaggt gtcatgggct gagcctccca cagatccatg ctacacccac      480
acctgtcact gccattgggc ccccaaccac ggctatccag gagcccccat ccaggatcgt      540 gccaacccc  acatctccag ccattgctcc tccaacagag accatggctc ctccagtcag      600
ggatcctgtt cctgggaaac ccacggtcac catcccggact cgaggcgcca ttattcaaac      660
cccaacccta ggccccatcc agcctactcg ggtgtcagaa gctggcacca cagttcctgg      720
ccagattcgc ccaacgatga ccattcctgg ctatgtggag cctactgcag ttgctacccc      780
tcccacaacc accaccaaga agccacgagt atccacacca aaaccagcaa cgccttcaac      840
tgactccacc accaccacga ctcgcaggcc aaccaagaaa ccacggacac cccggccagt      900
gccccgggtc accaccaaag tttccatcac cagattggaa actgcctcac cgcctactcg      960
tattcgcacc accaccagtg gagtgccccg tggcggagaa cccaaccagc gcccagagct     1020
caagaaccat attgacaggg tagatgcctg ggttggcacc tactttgagg tgaagatccc     1080
gtcagacact ttctatgacc atgaggacac caccactgac aagctgaagc tgaccctgaa     1140
actgcgggag cagcagctgg tgggcgagaa gtcctgggta cagttcaaca gcaacagcca     1200
gctcatgtat ggccttcccg acagcagcca cgtgggcaaa cacgagtatt tcatgcatgc     1260
cacagacaag ggggggcctgt cggctgtgga tgccttcgag atccacgtcc acaggcgccc     1320 ccaagggggat agggctcctg caaggttcaa ggccaagttt gtgggtgacc cggcactggt     1380
gttgaatgac atccacaaga agattgcctt ggtaaagaaa ctggccttcg cctttggaga     1440
ccgaaactgt agcaccatca ccctgcagaa tatcacccgg ggctaaacta gtgcggccgc     1500
aa                                                                   1502
```

```
<210> SEQ ID NO 33
<211> LENGTH: 1077
<212> TYPE: PRT
<213> ORGANISM: Artificial Sequence
<220> FEATURE:
<223> OTHER INFORMATION: Synthetic Polypeptide

<400> SEQUENCE: 33

Ser Gly Arg Thr Met Lys Leu Leu Pro Ser Val Val Leu Lys Leu Phe
1               5                   10                  15

Leu Ala Ala Val Leu Ser Ala Leu Val Thr Gly Glu Ser Leu Glu Arg
            20                  25                  30

Leu Arg Arg Gly Leu Ala Ala Gly Thr Ser Asn Pro Asp Pro Pro Thr
        35                  40                  45

Val Ser Thr Asp Gln Leu Leu Pro Leu Gly Gly Gly Arg Asp Arg Lys
    50                  55                  60

Val Arg Asp Leu Gln Glu Ala Asp Leu Asp Leu Leu Arg Val Thr Leu
65                  70                  75                  80

Ser Ser Lys Pro Gln Ala Leu Ala Thr Pro Asn Lys Glu Glu His Gly
            85                  90                  95

Lys Arg Lys Lys Lys Gly Lys Gly Leu Gly Lys Lys Arg Asp Pro Lys
            100                 105                 110

Val Ser Val Ser Ser Gly Gly Asp Cys Ile Arg Thr Tyr Lys Pro Glu
        115                 120                 125

Ile Lys Lys Gly Ser Tyr Asn Asn Ile Val Val Asn Val Lys Thr Ala
    130                 135                 140

Val Ala Asp Asn Leu Leu Phe Tyr Leu Gly Ser Ala Lys Phe Ile Asp
145                 150                 155                 160
```

-continued

Phe Leu Ala Ile Glu Met Arg Lys Gly Lys Val Ser Phe Leu Trp Asp
165                     170                 175

Val Gly Ser Gly Val Gly Arg Val Glu Tyr Pro Asp Leu Thr Ile Asp
            180                 185                 190

Asp Ser Tyr Trp Tyr Arg Ile Val Ala Ser Arg Thr Gly Arg Asn Gly
            195                 200                 205

Thr Ile Ser Val Arg Ala Leu Asp Gly Pro Lys Ala Ser Ile Val Pro
    210                 215                 220

Ser Thr His His Ser Thr Ser Pro Pro Gly Tyr Thr Ile Leu Asp Val
225                 230                 235                 240

Asp Ala Asn Ala Met Leu Phe Val Gly Gly Leu Thr Gly Lys Leu Lys
            245                 250                 255

Lys Ala Asp Ala Val Arg Val Ile Thr Phe Thr Gly Cys Met Gly Glu
            260                 265                 270

Thr Tyr Phe Asp Asn Lys Pro Ile Gly Leu Trp Asn Phe Arg Glu Lys
            275                 280                 285

Glu Gly Asp Cys Lys Gly Cys Thr Val Ser Pro Gln Val Glu Asp Ser
    290                 295                 300

Glu Gly Thr Ile Gln Phe Asp Gly Glu Gly Tyr Ala Leu Val Ser Arg
305                 310                 315                 320

Pro Ile Arg Trp Tyr Pro Asn Ile Ser Thr Val Met Phe Lys Phe Arg
            325                 330                 335

Thr Phe Ser Ser Ser Ala Leu Leu Met Tyr Leu Ala Thr Arg Asp Leu
            340                 345                 350

Arg Asp Phe Met Ser Val Glu Leu Thr Asp Gly His Ile Lys Val Ser
            355                 360                 365

Tyr Asp Leu Gly Ser Gly Met Ala Ser Val Val Ser Asn Gln Asn His
    370                 375                 380

Asn Asp Gly Lys Trp Lys Ser Phe Thr Leu Ser Arg Ile Gln Lys Gln
385                 390                 395                 400

Ala Asn Ile Ser Ile Val Asp Ile Asp Thr Asn Gln Glu Glu Asn Ile
            405                 410                 415

Ala Thr Ser Ser Ser Gly Asn Asn Phe Gly Leu Asp Leu Lys Ala Asp
            420                 425                 430

Asp Lys Ile Tyr Phe Gly Gly Leu Pro Thr Leu Arg Asn Leu Ser Met
            435                 440                 445

Lys Ala Arg Pro Glu Val Asn Leu Lys Lys Tyr Ser Gly Cys Leu Lys
    450                 455                 460

Asp Ile Glu Ile Ser Arg Thr Pro Tyr Asn Ile Leu Ser Ser Pro Asp
465                 470                 475                 480

Tyr Val Gly Val Thr Lys Gly Cys Ser Leu Glu Asn Val Tyr Thr Val
            485                 490                 495

Ser Phe Pro Lys Pro Gly Phe Val Glu Leu Ser Pro Val Pro Ile Asp
            500                 505                 510

Val Gly Thr Glu Ile Asn Leu Ser Phe Ser Thr Lys Asn Glu Ser Gly
            515                 520                 525

Ile Ile Leu Leu Gly Ser Gly Gly Thr Pro Ala Pro Pro Arg Arg Lys
    530                 535                 540

Arg Arg Gln Thr Gly Gln Ala Tyr Tyr Val Ile Leu Leu Asn Arg Gly
545                 550                 555                 560

Arg Leu Glu Val His Leu Ser Thr Gly Ala Arg Thr Met Arg Lys Ile
            565                 570                 575

Val Ile Arg Pro Glu Pro Asn Leu Phe His Asp Gly Arg Glu His Ser

-continued

```
                580                 585                 590

Val His Val Glu Arg Thr Arg Gly Ile Phe Thr Val Gln Val Asp Glu
        595                 600                 605

Asn Arg Arg Tyr Met Gln Asn Leu Thr Val Glu Gln Pro Ile Glu Val
        610                 615                 620

Lys Lys Leu Phe Val Gly Gly Ala Pro Pro Glu Phe Gln Pro Ser Pro
625                 630                 635                 640

Leu Arg Asn Ile Pro Pro Phe Glu Gly Cys Ile Trp Asn Leu Val Ile
                645                 650                 655

Asn Ser Val Pro Met Asp Phe Ala Arg Pro Val Ser Phe Lys Asn Ala
                660                 665                 670

Asp Ile Gly Arg Cys Ala His Gln Lys Leu Arg Glu Asp Glu Asp Gly
                675                 680                 685

Ala Ala Pro Ala Glu Ile Val Ile Gln Pro Glu Pro Val Pro Thr Pro
        690                 695                 700

Ala Phe Pro Thr Pro Thr Pro Val Leu Thr His Gly Pro Cys Ala Ala
705                 710                 715                 720

Glu Ser Glu Pro Ala Leu Leu Ile Gly Ser Lys Gln Phe Gly Leu Ser
                725                 730                 735

Arg Asn Ser His Ile Ala Ile Ala Phe Asp Asp Thr Lys Val Lys Asn
                740                 745                 750

Arg Leu Thr Ile Glu Leu Glu Val Arg Thr Glu Ala Glu Ser Gly Leu
                755                 760                 765

Leu Phe Tyr Met Ala Arg Ile Asn His Ala Asp Phe Ala Thr Val Gln
        770                 775                 780

Leu Arg Asn Gly Leu Pro Tyr Phe Ser Tyr Asp Leu Gly Ser Gly Asp
785                 790                 795                 800

Thr His Thr Met Ile Pro Thr Lys Ile Asn Asp Gly Gln Trp His Lys
                805                 810                 815

Ile Lys Ile Met Arg Ser Lys Gln Glu Gly Ile Leu Tyr Val Asp Gly
                820                 825                 830

Ala Ser Asn Arg Thr Ile Ser Pro Lys Lys Ala Asp Ile Leu Asp Val
        835                 840                 845

Val Gly Met Leu Tyr Val Gly Gly Leu Pro Ile Asn Tyr Thr Thr Arg
        850                 855                 860

Arg Ile Gly Pro Val Thr Tyr Ser Ile Asp Gly Cys Val Arg Asn Leu
865                 870                 875                 880

His Met Ala Glu Ala Pro Ala Asp Leu Glu Gln Pro Thr Ser Ser Phe
                885                 890                 895

His Val Gly Thr Cys Phe Ala Asn Ala Gln Arg Gly Thr Tyr Phe Asp
                900                 905                 910

Gly Thr Gly Phe Ala Lys Ala Val Gly Gly Phe Lys Val Gly Leu Asp
        915                 920                 925

Leu Leu Val Glu Phe Glu Phe Arg Thr Thr Thr Thr Thr Gly Val Leu
        930                 935                 940

Leu Gly Ile Ser Ser Gln Lys Met Asp Gly Met Gly Ile Glu Met Ile
945                 950                 955                 960

Asp Glu Lys Leu Met Phe His Val Asp Asn Gly Ala Gly Arg Phe Thr
                965                 970                 975

Ala Val Tyr Asp Ala Gly Val Pro Gly His Leu Cys Asp Gly Gln Trp
                980                 985                 990

His Lys Val Thr Ala Asn Lys Ile  Lys His Arg Ile Glu  Leu Thr Val
        995                 1000                1005
```

```
Asp Gly  Asn Gln Val Glu Ala  Gln Ser Pro Asn Pro  Ala Ser Thr
    1010             1015             1020

Ser Ala  Asp Thr Asn Asp Pro  Val Phe Val Gly Gly  Phe Pro Asp
    1025             1030             1035

Asp Leu  Lys Gln Phe Gly Leu  Thr Thr Ser Ile Pro  Phe Arg Gly
    1040             1045             1050

Cys Ile  Arg Ser Leu Lys Leu  Thr Lys Gly Thr Ala  Ser His Trp
    1055             1060             1065

Arg Leu  Ile Leu Pro Arg Pro  Trp Asn
    1070             1075
```

```
<210> SEQ ID NO 34
<211> LENGTH: 1119
<212> TYPE: PRT
<213> ORGANISM: Artificial Sequence
<220> FEATURE:
<223> OTHER INFORMATION: Synthetic Polypeptide

<400> SEQUENCE: 34
```

```
Ser Gly Arg Thr Met Lys Leu Leu Pro Ser Val Val Leu Lys Leu Phe
1               5               10              15

Leu Ala Ala Val Leu Ser Ala Leu Val Thr Gly Glu Ser Leu Glu Arg
            20              25              30

Leu Arg Arg Gly Leu Ala Ala Gly Thr Ser Asn Pro Asp Pro Pro Thr
        35              40              45

Val Ser Thr Asp Gln Leu Leu Pro Leu Gly Gly Gly Arg Asp Arg Lys
    50              55              60

Val Arg Asp Leu Gln Glu Ala Asp Leu Asp Leu Leu Arg Val Thr Leu
65              70              75              80

Ser Ser Lys Pro Gln Ala Leu Ala Thr Pro Asn Lys Glu Glu His Gly
            85              90              95

Lys Arg Lys Lys Lys Gly Lys Gly Leu Gly Lys Lys Arg Asp Pro Cys
        100             105             110

Leu Arg Lys Tyr Lys Asp Phe Cys Ile His Gly Glu Cys Lys Tyr Val
        115             120             125

Lys Glu Leu Arg Ala Pro Ser Cys Ile Cys His Pro Gly Tyr His Gly
    130             135             140

Glu Arg Cys His Gly Leu Ser Leu Pro Lys Val Ser Val Ser Ser Gly
145             150             155             160

Gly Asp Cys Ile Arg Thr Tyr Lys Pro Glu Ile Lys Lys Gly Ser Tyr
            165             170             175

Asn Asn Ile Val Val Asn Val Lys Thr Ala Val Ala Asp Asn Leu Leu
            180             185             190

Phe Tyr Leu Gly Ser Ala Lys Phe Ile Asp Phe Leu Ala Ile Glu Met
        195             200             205

Arg Lys Gly Lys Val Ser Phe Leu Trp Asp Val Gly Ser Gly Val Gly
    210             215             220

Arg Val Glu Tyr Pro Asp Leu Thr Ile Asp Asp Ser Tyr Trp Tyr Arg
225             230             235             240

Ile Val Ala Ser Arg Thr Gly Arg Asn Gly Thr Ile Ser Val Arg Ala
            245             250             255

Leu Asp Gly Pro Lys Ala Ser Ile Val Pro Ser Thr His His Ser Thr
            260             265             270

Ser Pro Pro Gly Tyr Thr Ile Leu Asp Val Asp Ala Asn Ala Met Leu
        275             280             285
```

```
Phe Val Gly Gly Leu Thr Gly Lys Leu Lys Lys Ala Asp Ala Val Arg
    290             295             300

Val Ile Thr Phe Thr Gly Cys Met Gly Glu Thr Tyr Phe Asp Asn Lys
305             310             315             320

Pro Ile Gly Leu Trp Asn Phe Arg Glu Lys Glu Gly Asp Cys Lys Gly
                325             330             335

Cys Thr Val Ser Pro Gln Val Glu Asp Ser Glu Gly Thr Ile Gln Phe
            340             345             350

Asp Gly Glu Gly Tyr Ala Leu Val Ser Arg Pro Ile Arg Trp Tyr Pro
        355             360             365

Asn Ile Ser Thr Val Met Phe Lys Phe Arg Thr Phe Ser Ser Ser Ala
    370             375             380

Leu Leu Met Tyr Leu Ala Thr Arg Asp Leu Arg Asp Phe Met Ser Val
385             390             395             400

Glu Leu Thr Asp Gly His Ile Lys Val Ser Tyr Asp Leu Gly Ser Gly
            405             410             415

Met Ala Ser Val Val Ser Asn Gln Asn His Asn Asp Gly Lys Trp Lys
            420             425             430

Ser Phe Thr Leu Ser Arg Ile Gln Lys Gln Ala Asn Ile Ser Ile Val
            435             440             445

Asp Ile Asp Thr Asn Gln Glu Glu Asn Ile Ala Thr Ser Ser Ser Gly
    450             455             460

Asn Asn Phe Gly Leu Asp Leu Lys Ala Asp Asp Lys Ile Tyr Phe Gly
465             470             475             480

Gly Leu Pro Thr Leu Arg Asn Leu Ser Met Lys Ala Arg Pro Glu Val
                485             490             495

Asn Leu Lys Lys Tyr Ser Gly Cys Leu Lys Asp Ile Glu Ile Ser Arg
            500             505             510

Thr Pro Tyr Asn Ile Leu Ser Ser Pro Asp Tyr Val Gly Val Thr Lys
            515             520             525

Gly Cys Ser Leu Glu Asn Val Tyr Thr Val Ser Phe Pro Lys Pro Gly
    530             535             540

Phe Val Glu Leu Ser Pro Val Pro Ile Asp Val Gly Thr Glu Ile Asn
545             550             555             560

Leu Ser Phe Ser Thr Lys Asn Glu Ser Gly Ile Ile Leu Leu Gly Ser
            565             570             575

Gly Gly Thr Pro Ala Pro Pro Arg Arg Lys Arg Arg Gln Thr Gly Gln
            580             585             590

Ala Tyr Tyr Val Ile Leu Leu Asn Arg Gly Arg Leu Glu Val His Leu
        595             600             605

Ser Thr Gly Ala Arg Thr Met Arg Lys Ile Val Ile Arg Pro Glu Pro
    610             615             620

Asn Leu Phe His Asp Gly Arg Glu His Ser Val His Val Glu Arg Thr
625             630             635             640

Arg Gly Ile Phe Thr Val Gln Val Asp Glu Asn Arg Arg Tyr Met Gln
                645             650             655

Asn Leu Thr Val Glu Gln Pro Ile Glu Val Lys Lys Leu Phe Val Gly
            660             665             670

Gly Ala Pro Pro Glu Phe Gln Pro Ser Pro Leu Arg Asn Ile Pro Pro
            675             680             685

Phe Glu Gly Cys Ile Trp Asn Leu Val Ile Asn Ser Val Pro Met Asp
    690             695             700
```

-continued

```
Phe Ala Arg Pro Val Ser Phe Lys Asn Ala Asp Ile Gly Arg Cys Ala
705                 710                 715                 720

His Gln Lys Leu Arg Glu Asp Glu Asp Gly Ala Ala Pro Ala Glu Ile
                725                 730                 735

Val Ile Gln Pro Glu Pro Val Pro Thr Pro Ala Phe Pro Thr Pro Thr
                740                 745                 750

Pro Val Leu Thr His Gly Pro Cys Ala Ala Glu Ser Glu Pro Ala Leu
                755                 760                 765

Leu Ile Gly Ser Lys Gln Phe Gly Leu Ser Arg Asn Ser His Ile Ala
            770                 775                 780

Ile Ala Phe Asp Asp Thr Lys Val Lys Asn Arg Leu Thr Ile Glu Leu
785                 790                 795                 800

Glu Val Arg Thr Glu Ala Glu Ser Gly Leu Leu Phe Tyr Met Ala Arg
                805                 810                 815

Ile Asn His Ala Asp Phe Ala Thr Val Gln Leu Arg Asn Gly Leu Pro
                820                 825                 830

Tyr Phe Ser Tyr Asp Leu Gly Ser Gly Asp Thr His Thr Met Ile Pro
                835                 840                 845

Thr Lys Ile Asn Asp Gly Gln Trp His Lys Ile Lys Ile Met Arg Ser
            850                 855                 860

Lys Gln Glu Gly Ile Leu Tyr Val Asp Gly Ala Ser Asn Arg Thr Ile
865                 870                 875                 880

Ser Pro Lys Lys Ala Asp Ile Leu Asp Val Val Gly Met Leu Tyr Val
                885                 890                 895

Gly Gly Leu Pro Ile Asn Tyr Thr Thr Arg Arg Ile Gly Pro Val Thr
                900                 905                 910

Tyr Ser Ile Asp Gly Cys Val Arg Asn Leu His Met Ala Glu Ala Pro
                915                 920                 925

Ala Asp Leu Glu Gln Pro Thr Ser Ser Phe His Val Gly Thr Cys Phe
            930                 935                 940

Ala Asn Ala Gln Arg Gly Thr Tyr Phe Asp Gly Thr Gly Phe Ala Lys
945                 950                 955                 960

Ala Val Gly Gly Phe Lys Val Gly Leu Asp Leu Leu Val Glu Phe Glu
                965                 970                 975

Phe Arg Thr Thr Thr Thr Thr Gly Val Leu Leu Gly Ile Ser Ser Gln
                980                 985                 990

Lys Met Asp Gly Met Gly Ile Glu  Met Ile Asp Glu Lys  Leu Met Phe
            995                 1000                 1005

His Val Asp Asn Gly Ala Gly  Arg Phe Thr Ala Val  Tyr Asp Ala
    1010                 1015                 1020

Gly Val Pro Gly His Leu Cys  Asp Gly Gln Trp His  Lys Val Thr
    1025                 1030                 1035

Ala Asn Lys Ile Lys His Arg  Ile Glu Leu Thr Val  Asp Gly Asn
    1040                 1045                 1050

Gln Val Glu Ala Gln Ser Pro  Asn Pro Ala Ser Thr  Ser Ala Asp
    1055                 1060                 1065

Thr Asn Asp Pro Val Phe Val  Gly Gly Phe Pro Asp  Asp Leu Lys
    1070                 1075                 1080

Gln Phe Gly Leu Thr Thr Ser  Ile Pro Phe Arg Gly  Cys Ile Arg
    1085                 1090                 1095

Ser Leu Lys Leu Thr Lys Gly  Thr Ala Ser His Trp  Arg Leu Ile
    1100                 1105                 1110

Leu Pro  Arg Pro Trp Asn
```

```
       1115
```

<210> SEQ ID NO 35
<211> LENGTH: 684
<212> TYPE: PRT
<213> ORGANISM: Artificial Sequence
<220> FEATURE:
<223> OTHER INFORMATION: Synthetic Polypeptide

<400> SEQUENCE: 35

Ser Gly Arg Thr Met Lys Leu Leu Pro Ser Val Val Leu Lys Leu Phe
1               5                   10                  15

Leu Ala Ala Val Leu Ser Ala Leu Val Thr Gly Glu Ser Leu Glu Arg
            20                  25                  30

Leu Arg Arg Gly Leu Ala Ala Gly Thr Ser Asn Pro Asp Pro Pro Thr
        35                  40                  45

Val Ser Thr Asp Gln Leu Leu Pro Leu Gly Gly Gly Arg Asp Arg Lys
    50                  55                  60

Val Arg Asp Leu Gln Glu Ala Asp Leu Asp Leu Leu Arg Val Thr Leu
65                  70                  75                  80

Ser Ser Lys Pro Gln Ala Leu Ala Thr Pro Asn Lys Glu Glu His Gly
                85                  90                  95

Lys Arg Lys Lys Lys Gly Lys Gly Leu Gly Lys Lys Arg Asp Pro Cys
            100                 105                 110

Leu Arg Lys Tyr Lys Asp Phe Cys Ile His Gly Glu Cys Lys Tyr Val
            115                 120                 125

Lys Glu Leu Arg Ala Pro Ser Cys Ile Cys His Pro Gly Tyr His Gly
        130                 135                 140

Glu Arg Cys His Gly Leu Ser Leu Pro Gln Thr Gly Gln Ala Tyr Tyr
145                 150                 155                 160

Val Ile Leu Leu Asn Arg Gly Arg Leu Glu Val His Leu Ser Thr Gly
                165                 170                 175

Ala Arg Thr Met Arg Lys Ile Val Ile Arg Pro Glu Pro Asn Leu Phe
            180                 185                 190

His Asp Gly Arg Glu His Ser Val His Val Glu Arg Thr Arg Gly Ile
            195                 200                 205

Phe Thr Val Gln Val Asp Glu Asn Arg Arg Tyr Met Gln Asn Leu Thr
    210                 215                 220

Val Glu Gln Pro Ile Glu Val Lys Lys Leu Phe Val Gly Gly Ala Pro
225                 230                 235                 240

Pro Glu Phe Gln Pro Ser Pro Leu Arg Asn Ile Pro Pro Phe Glu Gly
                245                 250                 255

Cys Ile Trp Asn Leu Val Ile Asn Ser Val Pro Met Asp Phe Ala Arg
            260                 265                 270

Pro Val Ser Phe Lys Asn Ala Asp Ile Gly Arg Cys Ala His Gln Lys
        275                 280                 285

Leu Arg Glu Asp Glu Asp Gly Ala Ala Pro Ala Glu Ile Val Ile Gln
    290                 295                 300

Pro Glu Pro Val Pro Thr Pro Ala Phe Pro Thr Pro Thr Pro Val Leu
305                 310                 315                 320

Thr His Gly Pro Cys Ala Ala Glu Ser Glu Pro Ala Leu Leu Ile Gly
                325                 330                 335

Ser Lys Gln Phe Gly Leu Ser Arg Asn Ser His Ile Ala Ile Ala Phe
            340                 345                 350

Asp Asp Thr Lys Val Lys Asn Arg Leu Thr Ile Glu Leu Glu Val Arg

-continued

```
             355                  360                  365
Thr Glu Ala Glu Ser Gly Leu Leu Phe Tyr Met Ala Arg Ile Asn His
    370                  375                  380

Ala Asp Phe Ala Thr Val Gln Leu Arg Asn Gly Leu Pro Tyr Phe Ser
385                  390                  395                  400

Tyr Asp Leu Gly Ser Gly Asp Thr His Thr Met Ile Pro Thr Lys Ile
                405                  410                  415

Asn Asp Gly Gln Trp His Lys Ile Lys Ile Met Arg Ser Lys Gln Glu
                420                  425                  430

Gly Ile Leu Tyr Val Asp Gly Ala Ser Asn Arg Thr Ile Ser Pro Lys
            435                  440                  445

Lys Ala Asp Ile Leu Asp Val Val Gly Met Leu Tyr Val Gly Gly Leu
    450                  455                  460

Pro Ile Asn Tyr Thr Thr Arg Arg Ile Gly Pro Val Thr Tyr Ser Ile
465                  470                  475                  480

Asp Gly Cys Val Arg Asn Leu His Met Ala Glu Ala Pro Ala Asp Leu
                485                  490                  495

Glu Gln Pro Thr Ser Ser Phe His Val Gly Thr Cys Phe Ala Asn Ala
                500                  505                  510

Gln Arg Gly Thr Tyr Phe Asp Gly Thr Gly Phe Ala Lys Ala Val Gly
            515                  520                  525

Gly Phe Lys Val Gly Leu Asp Leu Leu Val Glu Phe Glu Phe Arg Thr
    530                  535                  540

Thr Thr Thr Thr Gly Val Leu Leu Gly Ile Ser Ser Gln Lys Met Asp
545                  550                  555                  560

Gly Met Gly Ile Glu Met Ile Asp Glu Lys Leu Met Phe His Val Asp
                565                  570                  575

Asn Gly Ala Gly Arg Phe Thr Ala Val Tyr Asp Ala Gly Val Pro Gly
                580                  585                  590

His Leu Cys Asp Gly Gln Trp His Lys Val Thr Ala Asn Lys Ile Lys
            595                  600                  605

His Arg Ile Glu Leu Thr Val Asp Gly Asn Gln Val Glu Ala Gln Ser
    610                  615                  620

Pro Asn Pro Ala Ser Thr Ser Ala Asp Thr Asn Asp Pro Val Phe Val
625                  630                  635                  640

Gly Gly Phe Pro Asp Asp Leu Lys Gln Phe Gly Leu Thr Thr Ser Ile
                645                  650                  655

Pro Phe Arg Gly Cys Ile Arg Ser Leu Lys Leu Thr Lys Gly Thr Ala
                660                  665                  670

Ser His Trp Arg Leu Ile Leu Pro Arg Pro Trp Asn
    675                  680
```

```
<210> SEQ ID NO 36
<211> LENGTH: 684
<212> TYPE: PRT
<213> ORGANISM: Artificial Sequence
<220> FEATURE:
<223> OTHER INFORMATION: Synthetic Polypeptide

<400> SEQUENCE: 36

Ser Gly Arg Thr Met Lys Leu Leu Pro Ser Val Val Leu Lys Leu Phe
1                5                   10                  15

Leu Ala Ala Val Leu Ser Ala Leu Val Thr Gly Glu Ser Leu Glu Arg
                20                  25                  30

Leu Arg Arg Gly Leu Ala Ala Gly Thr Ser Asn Pro Asp Pro Pro Thr
```

-continued

```
            35                  40                  45
Val Ser Thr Asp Gln Leu Leu Pro Leu Gly Gly Gly Arg Asp Arg Lys
    50                  55                  60

Val Arg Asp Leu Gln Glu Ala Asp Leu Asp Leu Leu Arg Val Thr Leu
65                  70                  75                  80

Ser Ser Lys Pro Gln Ala Leu Ala Thr Pro Asn Lys Glu Glu His Gly
                85                  90                  95

Lys Arg Lys Lys Lys Gly Lys Gly Leu Gly Lys Lys Arg Asp Pro Cys
            100                 105                 110

Leu Arg Lys Tyr Lys Asp Phe Cys Ile His Gly Glu Cys Lys Tyr Val
            115                 120                 125

Lys Glu Leu Arg Ala Pro Ser Cys Ile Cys His Pro Gly Tyr His Gly
    130                 135                 140

Glu Arg Cys His Gly Leu Ser Leu Pro Gln Thr Gly Gln Ala Tyr Tyr
145                 150                 155                 160

Val Ile Leu Leu Asn Arg Gly Arg Leu Glu Val His Leu Ser Thr Gly
                165                 170                 175

Ala Arg Thr Met Arg Lys Ile Val Ile Arg Pro Glu Pro Asn Leu Phe
            180                 185                 190

His Asp Gly Arg Glu His Ser Val His Val Glu Arg Thr Arg Gly Ile
            195                 200                 205

Phe Thr Val Gln Val Asp Glu Asn Arg Arg Tyr Met Gln Asn Leu Thr
    210                 215                 220

Val Glu Gln Pro Ile Glu Val Lys Lys Leu Phe Val Gly Gly Ala Pro
225                 230                 235                 240

Pro Glu Phe Gln Pro Ser Pro Leu Arg Asn Ile Pro Pro Phe Glu Gly
                245                 250                 255

Cys Ile Trp Asn Leu Val Ile Asn Ser Val Pro Met Asp Phe Ala Arg
            260                 265                 270

Pro Val Ser Phe Lys Asn Ala Asp Ile Gly Arg Cys Ala His Gln Lys
            275                 280                 285

Leu Arg Glu Asp Glu Asp Gly Ala Ala Pro Ala Glu Ile Val Ile Gln
    290                 295                 300

Pro Glu Pro Val Pro Thr Pro Ala Phe Pro Thr Pro Thr Pro Val Leu
305                 310                 315                 320

Thr His Gly Pro Cys Ala Ala Glu Ser Glu Pro Ala Leu Leu Ile Gly
            325                 330                 335

Ser Lys Gln Phe Gly Leu Ser Arg Asn Ser His Ile Ala Ile Ala Phe
            340                 345                 350

Asp Asp Thr Lys Val Lys Asn Arg Leu Thr Ile Glu Leu Glu Val Arg
            355                 360                 365

Thr Glu Ala Glu Ser Gly Leu Leu Phe Tyr Met Ala Arg Ile Asn His
    370                 375                 380

Ala Asp Phe Ala Thr Val Gln Leu Arg Asn Gly Leu Pro Tyr Phe Ser
385                 390                 395                 400

Tyr Asp Leu Gly Ser Gly Asp Thr His Thr Met Ile Pro Thr Lys Ile
                405                 410                 415

Asn Asp Gly Gln Trp His Lys Ile Lys Ile Met Arg Ser Lys Gln Glu
            420                 425                 430

Gly Ile Leu Tyr Val Asp Gly Ala Ser Asn Arg Thr Ile Ser Pro Lys
            435                 440                 445

Lys Ala Asp Ile Leu Asp Val Val Gly Met Leu Tyr Val Gly Gly Leu
    450                 455                 460
```

```
Pro Ile Asn Tyr Thr Thr Arg Arg Ile Gly Pro Val Thr Tyr Ser Ile
465                 470                 475                 480

Asp Gly Cys Val Arg Asn Leu His Met Ala Glu Ala Pro Ala Asp Leu
                485                 490                 495

Glu Gln Pro Thr Ser Ser Phe His Val Gly Thr Cys Phe Ala Asn Ala
            500                 505                 510

Gln Arg Gly Thr Tyr Phe Asp Gly Thr Gly Phe Ala Lys Ala Val Gly
        515                 520                 525

Gly Phe Lys Val Gly Leu Asp Leu Leu Val Glu Phe Glu Phe Arg Thr
    530                 535                 540

Thr Thr Thr Thr Gly Val Leu Leu Gly Ile Ser Ser Gln Lys Met Asp
545                 550                 555                 560

Gly Met Gly Ile Glu Met Ile Asp Glu Lys Leu Met Phe His Val Asp
            565                 570                 575

Asn Gly Ala Gly Arg Phe Thr Ala Val Tyr Asp Ala Gly Val Pro Gly
            580                 585                 590

His Leu Cys Asp Gly Gln Trp His Lys Val Thr Ala Asn Lys Ile Lys
        595                 600                 605

His Arg Ile Glu Leu Thr Val Asp Gly Asn Gln Val Glu Ala Gln Ser
    610                 615                 620

Pro Asn Pro Ala Ser Thr Ser Ala Asp Thr Asn Asp Pro Val Phe Val
625                 630                 635                 640

Gly Gly Phe Pro Asp Asp Leu Lys Gln Phe Gly Leu Thr Thr Ser Ile
            645                 650                 655

Pro Phe Arg Gly Cys Ile Arg Ser Leu Lys Leu Thr Lys Gly Thr Ala
        660                 665                 670

Ser His Trp Arg Leu Ile Leu Pro Arg Pro Trp Asn
    675                 680
```

```
<210> SEQ ID NO 37
<211> LENGTH: 452
<212> TYPE: PRT
<213> ORGANISM: Artificial Sequence
<220> FEATURE:
<223> OTHER INFORMATION: Synthetic Polypeptide

<400> SEQUENCE: 37
```

```
Ser Gly Arg Thr Met Lys Leu Leu Pro Ser Val Val Leu Lys Leu Phe
1               5                   10                  15

Leu Ala Ala Val Leu Ser Ala Leu Val Thr Gly Glu Ser Leu Glu Arg
            20                  25                  30

Leu Arg Arg Gly Leu Ala Ala Gly Thr Ser Asn Pro Asp Pro Pro Thr
        35                  40                  45

Val Ser Thr Asp Gln Leu Leu Pro Leu Gly Gly Gly Arg Asp Arg Lys
    50                  55                  60

Val Arg Asp Leu Gln Glu Ala Asp Leu Asp Leu Leu Arg Val Thr Leu
65                  70                  75                  80

Ser Ser Lys Pro Gln Ala Leu Ala Thr Pro Asn Lys Glu Glu His Gly
                85                  90                  95

Lys Arg Lys Lys Lys Gly Lys Gly Leu Gly Lys Lys Arg Asp Pro Gln
            100                 105                 110

Ile His Ala Thr Pro Thr Pro Val Thr Ala Ile Gly Pro Pro Thr Thr
        115                 120                 125

Ala Ile Gln Glu Pro Pro Ser Arg Ile Val Pro Thr Pro Thr Ser Pro
    130                 135                 140
```

-continued

```
Ala Ile Ala Pro Pro Thr Glu Thr Met Ala Pro Pro Val Arg Asp Pro
145                 150                 155                 160

Val Pro Gly Lys Pro Thr Val Thr Ile Arg Thr Arg Gly Ala Ile Ile
                165                 170                 175

Gln Thr Pro Thr Leu Gly Pro Ile Gln Pro Thr Arg Val Ser Glu Ala
            180                 185                 190

Gly Thr Thr Val Pro Gly Gln Ile Arg Pro Thr Met Thr Ile Pro Gly
            195                 200                 205

Tyr Val Glu Pro Thr Ala Val Ala Thr Pro Pro Thr Thr Thr Thr Lys
    210                 215                 220

Lys Pro Arg Val Ser Thr Pro Lys Pro Ala Thr Pro Ser Thr Asp Ser
225                 230                 235                 240

Thr Thr Thr Thr Thr Arg Arg Pro Thr Lys Lys Pro Arg Thr Pro Arg
                245                 250                 255

Pro Val Pro Arg Val Thr Thr Lys Val Ser Ile Thr Arg Leu Glu Thr
                260                 265                 270

Ala Ser Pro Pro Thr Arg Ile Arg Thr Thr Thr Ser Gly Val Pro Arg
            275                 280                 285

Gly Gly Glu Pro Asn Gln Arg Pro Glu Leu Lys Asn His Ile Asp Arg
    290                 295                 300

Val Asp Ala Trp Val Gly Thr Tyr Phe Glu Val Lys Ile Pro Ser Asp
305                 310                 315                 320

Thr Phe Tyr Asp His Glu Asp Thr Thr Thr Asp Lys Leu Lys Leu Thr
                325                 330                 335

Leu Lys Leu Arg Glu Gln Gln Leu Val Gly Glu Lys Ser Trp Val Gln
            340                 345                 350

Phe Asn Ser Asn Ser Gln Leu Met Tyr Gly Leu Pro Asp Ser Ser His
            355                 360                 365

Val Gly Lys His Glu Tyr Phe Met His Ala Thr Asp Lys Gly Gly Leu
    370                 375                 380

Ser Ala Val Asp Ala Phe Glu Ile His Val His Arg Arg Pro Gln Gly
385                 390                 395                 400

Asp Arg Ala Pro Ala Arg Phe Lys Ala Lys Phe Val Gly Asp Pro Ala
                405                 410                 415

Leu Val Leu Asn Asp Ile His Lys Lys Ile Ala Leu Val Lys Lys Leu
                420                 425                 430

Ala Phe Ala Phe Gly Asp Arg Asn Cys Ser Thr Ile Thr Leu Gln Asn
            435                 440                 445

Ile Thr Arg Gly
    450
```

```
<210> SEQ ID NO 38
<211> LENGTH: 494
<212> TYPE: PRT
<213> ORGANISM: Artificial Sequence
<220> FEATURE:
<223> OTHER INFORMATION: Synthetic Polypeptide

<400> SEQUENCE: 38
```

```
Ser Gly Arg Thr Met Lys Leu Leu Pro Ser Val Val Leu Lys Leu Phe
1               5                   10                  15

Leu Ala Ala Val Leu Ser Ala Leu Val Thr Gly Glu Ser Leu Glu Arg
                20                  25                  30

Leu Arg Arg Gly Leu Ala Ala Gly Thr Ser Asn Pro Asp Pro Pro Thr
        35                  40                  45
```

```
Val Ser Thr Asp Gln Leu Leu Pro Leu Gly Gly Gly Arg Asp Arg Lys
    50              55              60

Val Arg Asp Leu Gln Glu Ala Asp Leu Asp Leu Leu Arg Val Thr Leu
65              70              75              80

Ser Ser Lys Pro Gln Ala Leu Ala Thr Pro Asn Lys Glu Glu His Gly
                85              90              95

Lys Arg Lys Lys Lys Gly Lys Gly Leu Gly Lys Lys Arg Asp Pro Cys
            100             105             110

Leu Arg Lys Tyr Lys Asp Phe Cys Ile His Gly Glu Cys Lys Tyr Val
        115             120             125

Lys Glu Leu Arg Ala Pro Ser Cys Ile Cys His Pro Gly Tyr His Gly
    130             135             140

Glu Arg Cys His Gly Leu Ser Leu Pro Gln Ile His Ala Thr Pro Thr
145             150             155             160

Pro Val Thr Ala Ile Gly Pro Pro Thr Thr Ala Ile Gln Glu Pro Pro
            165             170             175

Ser Arg Ile Val Pro Thr Pro Thr Ser Pro Ala Ile Ala Pro Pro Thr
            180             185             190

Glu Thr Met Ala Pro Pro Val Arg Asp Pro Val Pro Gly Lys Pro Thr
            195             200             205

Val Thr Ile Arg Thr Arg Gly Ala Ile Ile Gln Thr Pro Thr Leu Gly
    210             215             220

Pro Ile Gln Pro Thr Arg Val Ser Glu Ala Gly Thr Thr Val Pro Gly
225             230             235             240

Gln Ile Arg Pro Thr Met Thr Ile Pro Gly Tyr Val Glu Pro Thr Ala
            245             250             255

Val Ala Thr Pro Pro Thr Thr Thr Thr Lys Lys Pro Arg Val Ser Thr
            260             265             270

Pro Lys Pro Ala Thr Pro Ser Thr Asp Ser Thr Thr Thr Thr Thr Arg
    275             280             285

Arg Pro Thr Lys Lys Pro Arg Thr Pro Arg Pro Val Pro Arg Val Thr
    290             295             300

Thr Lys Val Ser Ile Thr Arg Leu Glu Thr Ala Ser Pro Pro Thr Arg
305             310             315             320

Ile Arg Thr Thr Thr Ser Gly Val Pro Arg Gly Gly Glu Pro Asn Gln
            325             330             335

Arg Pro Glu Leu Lys Asn His Ile Asp Arg Val Asp Ala Trp Val Gly
            340             345             350

Thr Tyr Phe Glu Val Lys Ile Pro Ser Asp Thr Phe Tyr Asp His Glu
            355             360             365

Asp Thr Thr Thr Asp Lys Leu Lys Leu Thr Leu Lys Leu Arg Glu Gln
    370             375             380

Gln Leu Val Gly Glu Lys Ser Trp Val Gln Phe Asn Ser Asn Ser Gln
385             390             395             400

Leu Met Tyr Gly Leu Pro Asp Ser Ser His Val Gly Lys His Glu Tyr
            405             410             415

Phe Met His Ala Thr Asp Lys Gly Gly Leu Ser Ala Val Asp Ala Phe
            420             425             430

Glu Ile His Val His Arg Arg Pro Gln Gly Asp Arg Ala Pro Ala Arg
        435             440             445

Phe Lys Ala Lys Phe Val Gly Asp Pro Ala Leu Val Leu Asn Asp Ile
    450             455             460
```

```
His Lys Lys Ile Ala Leu Val Lys Lys Leu Ala Phe Ala Phe Gly Asp
465                 470                 475                 480

Arg Asn Cys Ser Thr Ile Thr Leu Gln Asn Ile Thr Arg Gly
                485                 490

<210> SEQ ID NO 39
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 39

Thr Ser Ala Ala Ala
1               5

<210> SEQ ID NO 40
<211> LENGTH: 4637
<212> TYPE: DNA
<213> ORGANISM: Artificial Sequence
<220> FEATURE:
<223> OTHER INFORMATION: Synthetic Polynucleotide

<400> SEQUENCE: 40
gcgcgctcgc tcgctcactg aggccgcccg ggcaaagccc gggcgtcggg cgacctttgg      60
tcgcccggcc tcagtgagcg agcgagcgcg cagagaggga gtggccaact ccatcactag     120
gggttccttg tagttaatga ttaacccgcc atgctaatta tctacgtagc catgtggtcg     180
actctagagg atccgaaaaa acctcccaca cctcccctg aacctgaaac ataaaatgaa      240
tgcaattgtt gttgttaact tgtttattgc agcttataat ggttacaaat aaagcaatag     300
catcacaaat ttcacaaata aagcattttt ttcactgcat tctagttgtg tttgtccaa      360 actcatcaat gtatcttatc atgtctggat ccccgcggcc gcactagttc agttccaggg     420
ccttggcaaa attaacctcc agtggcttgc tgtgcctttg gtgagcttca gggatctgat     480
gcaacctcgg aacggaatac tggttgttag gccaaactgc ttgaggtcat ctgggaagcc     540
tccaacaaac acagggtcat ttgtgtcagc tgatgtagat gctgggtttg ggctttgggc     600
ttccacctgg ttcccatcga ctgtgagctc aatgcggtgt ttgatcttgt tggcagtgac     660
tttatgccat tgtccatcac acaaatgccc tggaacccca gcatcataga cagcagtgaa     720
tctgcccgca ccattgtcca catgaaacat caacttttca tcaatcattt caatacccat     780
tccatccatt ttttgactac tgatccccag aagaactcca gtcgttgtag ttgtgcggaa     840
ttcaaattct acaagaaggt ccaatcccac tttgaatcca ccaactgctt tggcaaaacc     900
ggttccgtca aaatatgttc ccctctgagc atttgcaaaa catgtcccaa catggaagct     960
ggaggtgggt tgttccagat cggcaggggc ctctgccatg tggagattcc tgacgcagcc    1020
atcaatgcta taggtcactg gaccaattct tcgggtagtg tagttgatgg gtaacccacc    1080
aacatacagc attcccacga catccaggat gtcggctttt ttgggactga tggttctgtt    1140
ggaagcccca tctacataaa gaattccttc ttgcttactt ctcattatct taatcttgtg    1200
ccactggcca tcattgattt tggtggggat catggtgtgg gtgtccccac tccccaagtc    1260
atagctgaag tagggcaatc catttctcag ctgaactgtt gcaaatcag catgattgat     1320 gcgagccatg taaaaaagca agccggattc agcttcggtt cttacttcca actcaattgt    1380
gagacggttt ttaactttgg tgtcatcaaa tgcaattgca atgtgactgt ttcttgaaag    1440
cccgaactgc ttgctcccta tcaaaagagc tggttctgat tctgcagcac aaggaccatg    1500
```

-continued

```
tgtcagaact ggggtgggcg taggaaaggc tggggtggga actggctcag gctggataac    1560
tatttcagct ggagctgctc catcttcatc ttcacggagt ttctgatggg cacagcgacc    1620
aatgtcagca tttttgaagg acacaggcct tgcaaagtcc atggggacag agttaataac    1680
aagattccat atgcagcctt caaaaggagg aatatttctg agtggggaag gttgaaattc    1740
aggtggagca cccccaacga aaagcttttt aacttcgata ggctgttcaa ctgtcaggtt    1800
ttgcatgtat cttctgtttt catccacttg aactgtaaag atgcctctag ttcgctctac    1860
atgaacggaa tgttctcttc catcatgaaa cagattcggc tctggtctga tgacaatttt    1920
cctcattgtt cgtgcccctg tggagagatg cacttccaga cggcccctgt tgaggagtat    1980
tacataatag gcctgtccag tctgccttcg ttttctccta ggtggtgctg gtgtccctcc    2040
acttcccaaa agaatgatgc cggactcatt cttggtgctg aatgacaggt tgatttctgt    2100
tcctacatca attggcacag gggagagctc cacaaaacca ggcttaggaa agctaactgt    2160
gtaaacattc tccagggaac atcctttggt aacaccaaca taatcgggac tactgagtat    2220
attgtacgga gttcttgaaa tttcaatatc tttgaggcag ccggaatatt tcttcagatt    2280
tacttctggc cttgctttca tactcaagtt tctcagcgtt ggcaggccac caaaatatat    2340
tttgtcatct gctttcaagt caagaccaaa gttgtttcca gaagacgaag ttgctatatt    2400
ctcctcctga ttagtatcta tatctacaat tgatatattg gcttgttttt gaattcttga    2460
cagagtgaat gatttccatt tcccatcatt atggttttga ttgctgacaa cggaagccat    2520
tcctgagccc agatcgtaac tgacttttat gtgcccatca gtgagctcca cactcatgaa    2580
atctctcagg tctcgtgtgg caagatacat cagaagagca ctcgaagaaa atgttctgaa    2640
cttgaacatg acagtggaga tgttggggta ccagcgaatg ggacggctga ccaatgcata    2700
accttctcca tcaaattgaa tagtcccctc actatcttcc acctgaggac tgacagtgca    2760
tcctttgcag tcaccttctt tttctcggaa attccacaaa cctataggtt tgttgtcaaa    2820
gtatgtttct cccatgcagc cagtgaatgt aatcacacgt acagcatcag ccttctttaa    2880
tttcccagtc aggccaccaa caaacagcat tgcatttgca tccacatcta gaatcgtgta    2940
ccctggagga gacgtcgaat ggtgtgtgct gggcacaatg ctggctttgg gtccatccag    3000
ggctctcaca gaaatagttc catttctccc agttcttgat gctacgatac ggtaccaata    3060
tgagtcatca atagtcaaat ctgggtactc tacacgtcca actccagatc caacatccca    3120
gaggaagctg actttgcctt tacgcatttc tatagccaga aagtcaataa atttggcact    3180
tccaagataa aagaggaggt tatcagcaac agctgtcttt acgttgacaa caatattatt    3240
gtaacttcct ttcttgattt caaacaagga ggagcacggg aaactggttt gtatgttcga    3300
atgcagtcac ctcctgaaga cacagatact tttgggtccc tcttcttccc tagcccttg     3360 cctttcttct ttcttttccc gtgctcctcc ttgtttggtg tggccagtgc ttgtggcttg    3420
gaggataaag tgactctcaa aaggtccaga tctgcctctt gcaagtcacg gactttccgg    3480
tcccggccgc ctcctagggg tagcagctgg tccgtggata cagtgggagg gtccgggttg    3540
ctggttccag cagctagccc tctccgaagc cgctccaggc tctcgccagt caccagtgcc    3600
gagagaactg cagccagaaa gagcttcagc accaccgacg gcagcagctt catggtgcgg    3660
ccgcgggtac aattccgcag cttttagagc agaagtaaca cttccgtaca ggcctagaag    3720
taaaggcaac atccactgag gagcagttct ttgatttgca ccaccaccgg atccgggacc    3780
tgaaataaaa gacaaaaaga ctaaacttac cagttaactt tctggttttt cagttcctcg    3840
agtaccggat cctctagagt ccggaggctg gatcggtccc ggtgtcttct atggaggtca    3900
```

-continued

```
aaacagcgtg gatggcgtct ccaggcgatc tgacggttca ctaaacgagc tctgcttata      3960
tagacctccc accgtacacg cctaccgccc atttgcgtca atggggcgga gttgttacga      4020
cattttggaa agtcccgttg attttggtgc caaaacaaac tcccattgac gtcaatgggg      4080
tggagacttg gaaatccccg tgagtcaaac cgctatccac gcccattgat gtactgccaa      4140
aaccgcatca ccatggtaat agcgatgact aatacgtaga tgtactgcca agtaggaaag      4200
tcccataagg tcatgtactg ggcataatgc caggcgggcc atttaccgtc attgacgtca      4260
atagggggcg tacttggcat atgatacact tgatgtactg ccaagtgggc agtttaccgt      4320
aaatactcca cccattgacg tcaatggaaa gtccctattg gcgttactat gggaacatac      4380
gtcattattg acgtcaatgg gcgggggtcg ttgggcggtc agccaggcgg gccatttacc      4440
gtaagttatg taacgaccct agacatggct acgtagataa ttagcatggc gggttaatca      4500
ttaactacaa ggaaccccta gtgatggagt tggccactcc ctctctgcgc gctcgctcgc      4560
tcactgaggc cggcgacca aaggtcgccc gacgcccggg ctttgcccgg gcggcctcag      4620
tgagcgagcg agcgcgc                                                      4637
```

<210> SEQ ID NO 41
<211> LENGTH: 2739
<212> TYPE: DNA
<213> ORGANISM: Artificial Sequence
<220> FEATURE:
<223> OTHER INFORMATION: Synthetic Polynucleotide

<400> SEQUENCE: 41

```
gcgcgctcgc tcgctcactg aggccgcccg ggcaaagccc gggcgtcggg cgacctttgg        60
tcgcccggcc tcagtgagcg agcgagcgcg cagagaggga gtggccaact ccatcactag       120
gggttccttg tagttaatga ttaacccgcc atgctaatta tctacgtagc catgtggtcg       180
actctagagg atccgaaaaa acctcccaca cctcccctg aacctgaaac ataaaatgaa        240
tgcaattgtt gttgttaact gtttattgc agcttataat ggttacaaat aaagcaatag       300
catcacaaat ttcacaaata aagcattttt ttcactgcat tctagttgtg gtttgtccaa       360
actcatcaat gtatcttatc atgtctggat ccccgcggcc gcactagttt agccccgggt       420
gatattctgc agggtgatgg tgctacagtt tcggtctcca aaggcgaagg ccagtttctt       480
taccaaggca atcttcttgt ggatgtcatt caacaccagt gccgggtcac ccacaaactt       540
ggccttgaac cttgcaggag ccctatcccc ttggggggcgc ctgtggacgt ggatctcgaa       600
ggcatccaca gccgacaggc ccccccttgtc tgtggcatgc atgaaatact cgtgtttgcc       660
cacgtggctg ctgtcgggaa ggccatacat gagctggctg ttgctgttga actgtaccca       720
ggacttctcg cccaccagct gctgctcccg cagtttcagg gtcagcttca gcttgtcagt       780
ggtggtgtcc tcatggtcat agaaagtgtc tgacgggatc ttcacctcaa agtaggtgcc       840
aacccaggca tctaccctgt caatatggtt cttgagctct gggcgctggt tgggttctcc       900
gccacggggc actccactgg tggtggtgcg aatacgagta ggcggtgagg cagtttccaa       960
tctggtgatg gaaactttgg tggtgacccg gggcactggc cggggtgtcc gtggtttctt      1020
ggttggcctg cgagtcgtgg tggtggtgga tcagttgaa ggcgttgctg gttttggtgt       1080
ggatactcgt ggcttcttgg tggtggttgt gggaggggta gcaactgcag taggctccac      1140
atagccagga atggtcatcg ttgggcgaat ctggccagga actgtggtgc cagcttctga      1200
cacccgagta ggctggatgg ggcctagggt tgggtttga ataatggcgc ctcgagtccg       1260
```

-continued

```
gatggtgacc gtgggtttcc caggaacagg atccctgact ggaggagcca tggtctctgt   1320
tggaggagca atggctggag atgtgggggt tggcacgatc ctggatgggg gctcctggat   1380
agccgtggtt gggggcccaa tggcagtgac aggtgtgggt gtagcatgga tctgtgggtc   1440
cctcttcttc cctagcccct tgcctttctt ctttcttttc ccgtgctcct ccttgtttgg   1500
tgtggccagt gcttgtggct tggaggataa agtgactctc aaaaggtcca gatctgcctc   1560
ttgcaagtca cggactttcc ggtcccggcc gcctcctagg ggtagcagct ggtccgtgga   1620
tacagtggga gggtccgggt tgctggttcc agcagctagc cctctccgaa gccgctccag   1680
gctctcgcca gtcaccagtg ccgagagaac tgcagccaga aagagcttca gcaccaccga   1740
cggcagcagc ttcatggtgc ggccgcgggt acaattccgc agcttttaga gcagaagtaa   1800
cacttccgta caggcctaga agtaaaggca acatccactg aggagcagtt ctttgatttg   1860
caccaccacc ggatccggga cctgaaataa aagacaaaaa gactaaactt accagttaac   1920
tttctggttt ttcagttcct cgagtaccgg atcctctaga gtccggaggc tggatcggtc   1980
ccggtgtctt ctatggaggt caaaacagcg tggatggcgt ctccaggcga tctgacggtt   2040
cactaaacga gctctgctta tatagacctc ccaccgtaca cgcctaccgc ccatttgcgt   2100
caatggggcg gagttgttac gacattttgg aaagtcccgt tgattttggt gccaaaacaa   2160
actcccattg acgtcaatgg ggtggagact tggaaatccc cgtgagtcaa accgctatcc   2220
acgcccattg atgtactgcc aaaaccgcat caccatggta atagcgatga ctaatacgta   2280
gatgtactgc caagtaggaa agtcccataa ggtcatgtac tgggcataat gccaggcggg   2340
ccatttaccg tcattgacgt caatagggg cgtacttggc atatgataca cttgatgtac   2400
tgccaagtgg gcagtttacc gtaaatactc cacccattga cgtcaatgga aagtccctat   2460
tggcgttact atgggaacat acgtcattat tgacgtcaat gggcgggggt cgttgggcgg   2520
tcagccaggc gggccattta ccgtaagtta tgtaacgacc ctagacatgg ctacgtagat   2580
aattagcatg gcgggttaat cattaactac aaggaacccc tagtgatgga gttggccact   2640
ccctctctgc gcgctcgctc gctcactgag gccgggcgac caaaggtcgc ccgacgcccg   2700
ggctttgccc gggcggcctc agtgagcgag cgagcgcgc                         2739
```